(12) United States Patent
Chen et al.

(10) Patent No.: US 12,213,971 B2
(45) Date of Patent: Feb. 4, 2025

(54) HISTONE DEACETYLASE INHIBITORS FOR IMMUNOMODULATION IN TUMOR MICROENVIRONMENT

(71) Applicant: GREAT NOVEL THERAPEUTICS BIOTECH & MEDICALS CORPORATION, Taipei (TW)

(72) Inventors: Jia-Shiong Chen, Taipei (TW); Mu-Hsuan Yang, Taipei (TW); Yi-Hong Wu, Taipei (TW); Sz-Hao Chu, Taipei (TW); Cheng-Han Chou, Taipei (TW); Ye-Su Chao, Taipei (TW); Chia-Nan Chen, Taipei (TW)

(73) Assignee: GREAT NOVEL THERAPEUTICS BIOTECH & MEDICALS CORPORATION, Taipei (TW)

( * ) Notice: Subject to any disclaimer, the term of this patent is extended or adjusted under 35 U.S.C. 154(b) by 113 days.

(21) Appl. No.: 18/310,387

(22) Filed: May 1, 2023

(65) Prior Publication Data

US 2023/0263790 A1 Aug. 24, 2023

Related U.S. Application Data

(62) Division of application No. 17/243,378, filed on Apr. 28, 2021, now Pat. No. 11,672,788.

(60) Provisional application No. 63/018,427, filed on Apr. 30, 2020.

(51) Int. Cl.
| | | |
|---|---|---|
| *A61K 31/444* | (2006.01) | |
| *A61K 31/44* | (2006.01) | |
| *A61K 31/4406* | (2006.01) | |
| *A61P 35/00* | (2006.01) | |
| *C07D 213/56* | (2006.01) | |
| *C07D 401/12* | (2006.01) | |

(52) U.S. Cl.
CPC ............ *A61K 31/444* (2013.01); *A61K 31/44* (2013.01); *A61K 31/4406* (2013.01); *A61P 35/00* (2018.01); *C07D 213/56* (2013.01); *C07D 401/12* (2013.01)

(58) Field of Classification Search
None
See application file for complete search history.

(56) References Cited

U.S. PATENT DOCUMENTS 11,840,570 B2   12/2023   Chen et al.

FOREIGN PATENT DOCUMENTS

| CN | 106916100 A | 7/2017 |
|---|---|---|
| CN | 106916101 A | 7/2017 |
| EP | 0847992 A1 | 6/1998 |
| TW | 201934143 A | 9/2019 |
| WO | 2004058234 A2 | 7/2004 |
| WO | 2005055928 A2 | 6/2005 |
| WO | 2009047615 A2 | 4/2009 |

OTHER PUBLICATIONS

Office Action issued on Mar. 12, 2024 in Taiwan Patent Application No. 110115446.
Supplemental Search Report for EP Patent Application No. 21796395.8 mailed on Jan. 27, 2023.
Dong, Guoqiang et al., Small Molecule Inhibitors Simultaneously Targeting Cancer Metabolism and Epigenetics: Discovery of Novel Nicotinamide Phosphoribosyltransferase (NAMPT) and Histone Deacetylase (HDAC) Dual Inhibitors. Journal of Medicinal Chemistry Sep. 8, 2017 (Sep. 8, 2017) No. 19 col. 60 ISSN: 1250-4804 pp. 7965-7983.
International Search Report and Written Opinion issued on Jul. 29, 2021 in International Patent Application No. PCT/CN2021/090718.

*Primary Examiner* — Zinna Northington Davis
(74) *Attorney, Agent, or Firm* — Prosyla Group PC

(57) ABSTRACT

The present disclosure generally relates to compounds class I HDAC inhibitors, their production and applications. The compounds possess epigenetic immunomodulatory activities in the tumor microenvironment (TME) and thus inhibit growth of tumor cells.

21 Claims, 68 Drawing Sheets

GNTbm-01    M+Na =>   405+23=428

GNTbm-02    M+Na =>   405+23=428

GNTbm-03   M+H   => 404+1=405

Entinostat (12.5 µM), 3h

Entinostat (12.5 µM), 0

GNTbm-02 (12.5 µM) 3d

GNTbm-02 (12.5 µM) 2d

GNTbm-02 (12.5 μM) 1d

GNTbm-02 (12.5 μM) 6h

GNTbm-02 (12.5 μM) 3h

GNTbm-02 (12.5 μM) 0

GNTbm-02 1.56 µM  GNTbm-02 0.78 µM

GNTbm-02 0.39 µM  GNTbm-02 0 µM

Entinostat (6.25 μM), 3d

Entinostat (6.25 μM), 2d

Entinostat (6.25 μM), 1d

Entinostat (6.25 μM), 6h

GNTbm-02 (6.25 μM), 1d

GNTbm-02 (6.25 μM), 6h

GNTbm-02 (6.25 μM), 3h

GNTbm-02 (6.25 μM), 0

Entinostat 25 µM

Entinostat 12.5 µM

Entinostat 6.25 µM

Entinostat 3.125 µM

Entinostat 1.625 μM

Entinostat 0 μM

GNTbm-02 25.0 μM

GNTbm-02 12.5 μM

Entinostat (12.5 μM), 3d

Entinostat (12.5 μM), 2d

Entinostat (12.5 μM), 1d

Entinostat (12.5 μM), 6h

Entinostat (12.5 μM), 3h    Entinostat (12.5 μM), 0

GNTbm-02 (12.5 μM), 3d    GNTbm-02 (12.5 μM), 2d

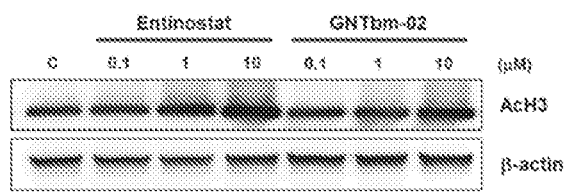
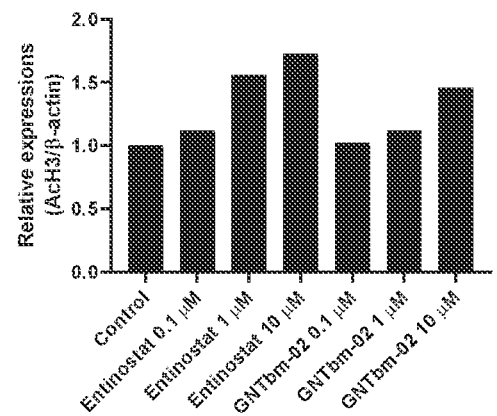
FIG. 10A
FIG. 10B
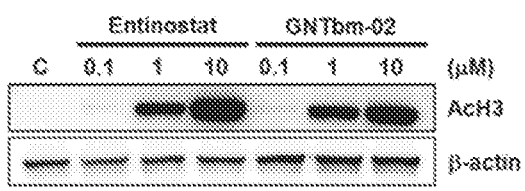
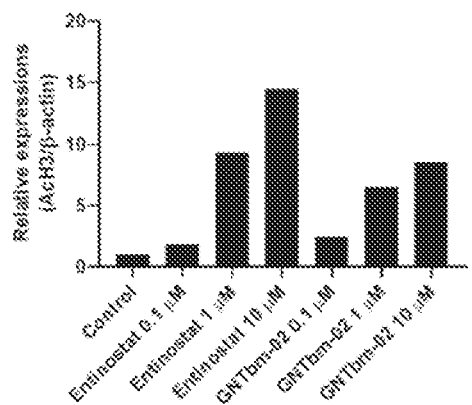
FIG. 10C
FIG. 10D

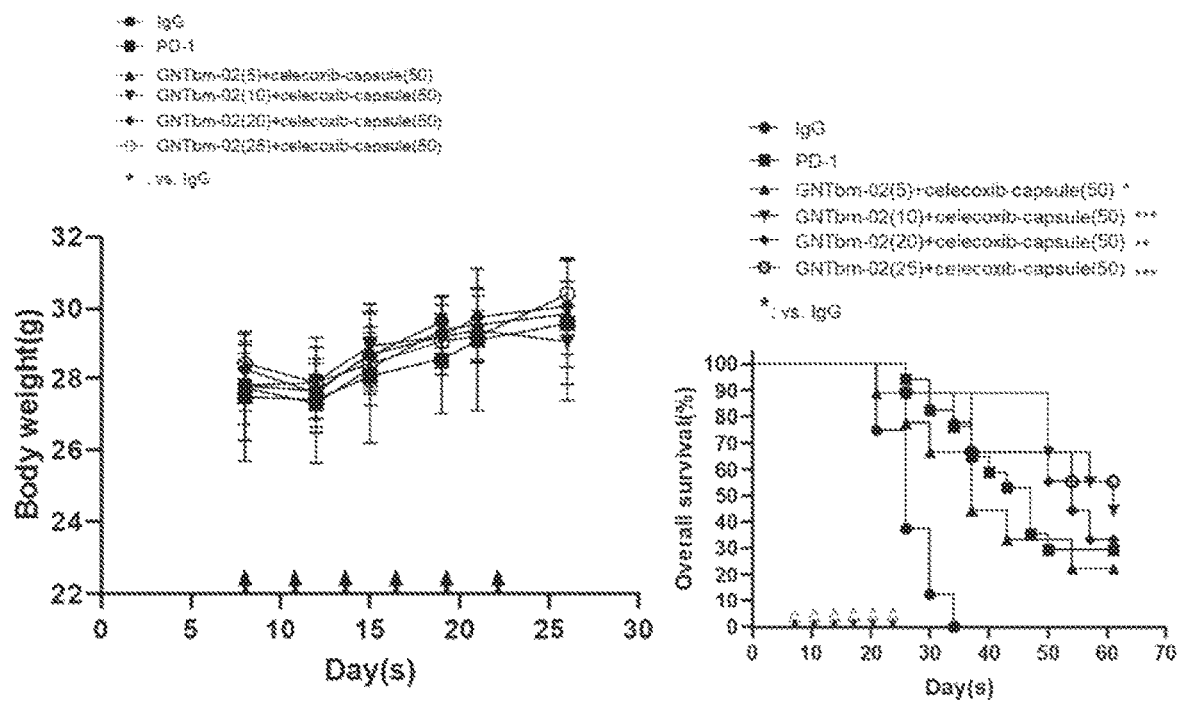
FIG. 14D
FIG. 14E
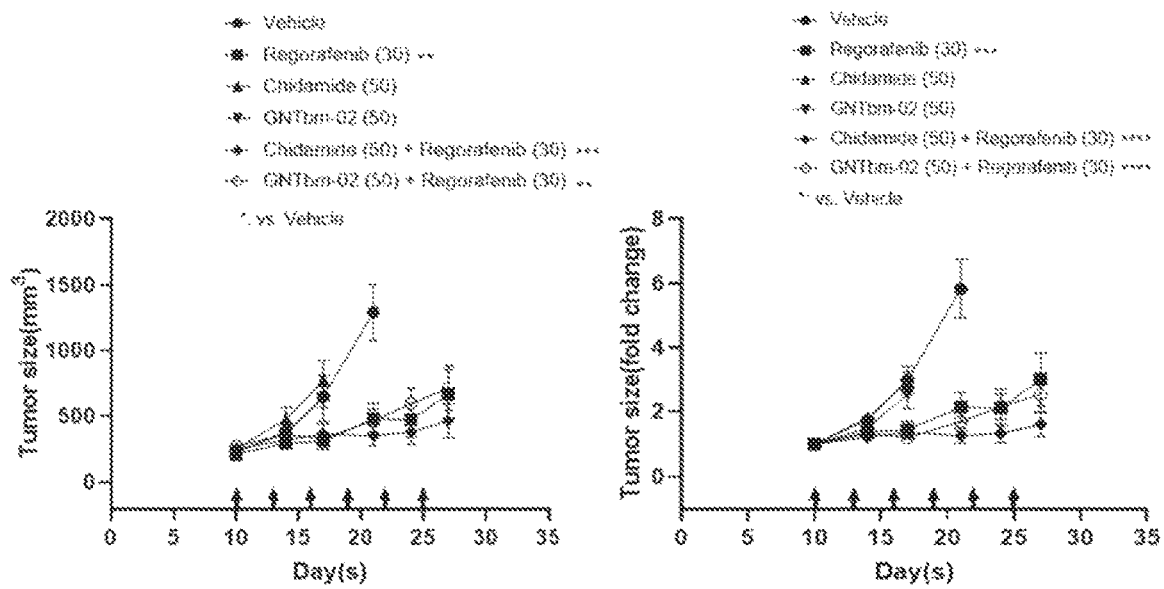
FIG. 14F

Treatment Group:
1. Anti-IgG (2.5 mg/kg)
2. Anti-PD-1 (2.5 mg/kg)
3. Anti-PD-1 (2.5 mg/kg) + GNTbm-02 (10 mg/kg) + celecoxib (50 mg/kg; from capsule)
4. GNTbm-02 (10 mg/kg) + celecoxib (50 mg/kg; from capsule)

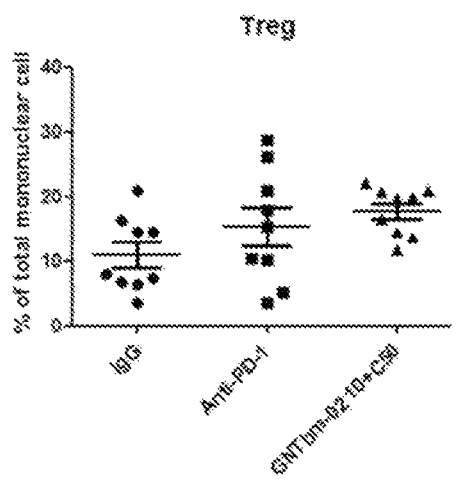
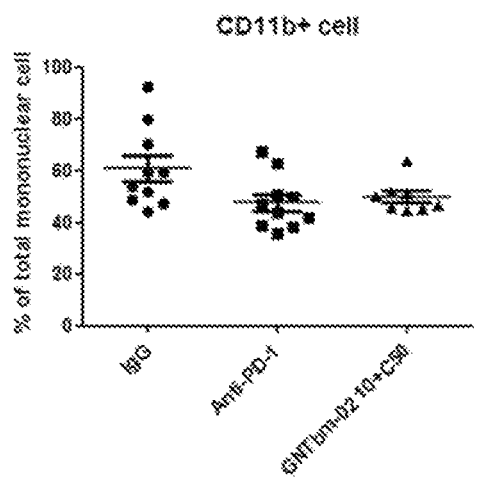
FIG. 17G	FIG. 17H
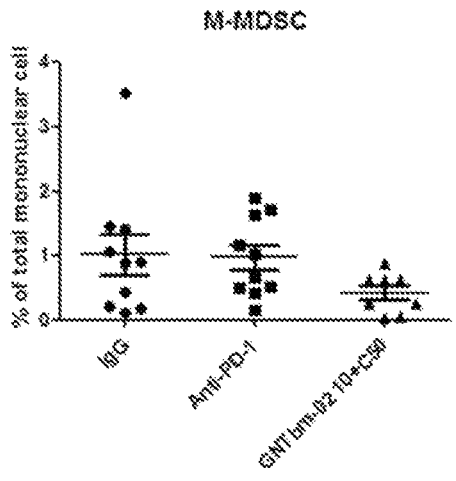
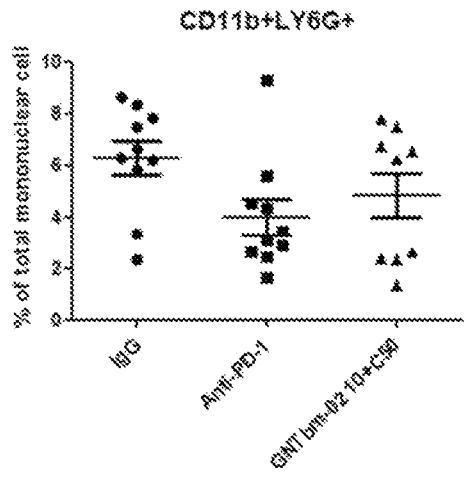
FIG. 17I	FIG. 17J
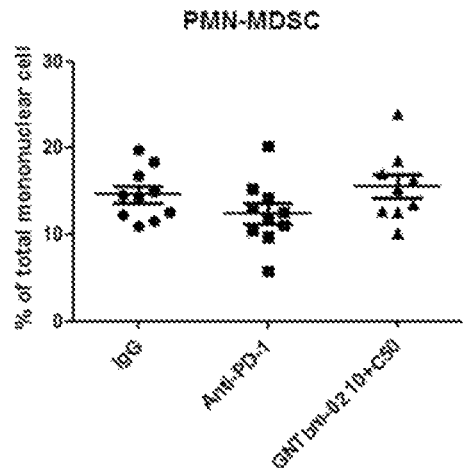
FIG. 17K

HISTONE DEACETYLASE INHIBITORS FOR IMMUNOMODULATION IN TUMOR MICROENVIRONMENT

PRIORITY DATA INFORMATION

The subject application is a divisional of U.S. patent application Ser. No. 17/243,378, filed Apr. 28, 2021, which claims benefit to and priority of U.S. Provisional Patent Application No. 63/018,427, filed Apr. 30, 2020, the contents of which are incorporated herein in their entirety.

FIELD OF THE INVENTION

The present disclosure generally relates to compounds of class I histone deacetylase (HDAC) inhibitors, their production, and applications. Particularly, the compounds possess epigenetic immunomodulatory activities in the tumor microenvironment (TME) and thus inhibit growth of tumor cells.

BACKGROUND OF THE INVENTION

Immunotherapy has become standard of care for the treatment of several advanced cancers. The breakthrough in immunotherapy is the development and clinical application of immune checkpoint inhibitors (ICIs) such as anti-PD-1/anti-PD-L1/anti-CTLA-4 antibody. However, ICIs can cause immune-related adverse events and more importantly, only a small fraction of patients obtain therapeutic benefit (low response rate). The dynamic and complex tumor microenvironment (TME) is a key factor for determining the immune response to tumors. The composition of TME includes cancer cells and many different immune cells interwoven with normal tissue cells. Many growth factors, cytokines and chemokines are secreted by different cells in the TME.

CTLs (Cytotoxic T lymphocytes) are the primary immune cells of adaptive immunity specific for direct killing of cancer cells. CTLs are susceptible to multiple immunosuppressive cells infiltrating into the TME which cause CTL inactivation. Well-known immunosuppressive cells include Treg (regulatory T cells), M-MDSC (monocytic-myeloid-derived suppressor cells), PMN-MDSC (polymorphonuclear-myeloid-derived suppressor cells), and TAM (Tumor-associated macrophages). These immunosuppressive cells contribute to the inhibition of the cytotoxic effect of killing cancer cells mediated by CTLs. There are different mechanisms executed by these immunosuppressive cells which lead to the dysfunction of CTLs.

Although ICI therapies have been shown to be effective in increasing immune activation to eradicate cancer, these therapies still face the unsolved issues of primary and acquired drug resistance. The intrinsic factors driving primary and acquired resistance to these immune therapies include genetic and epigenetic mechanisms, which, through processes such as immunoediting, often cause downregulation of MHC I or loss of antigen expression, resulting in an overall loss of antigen presentation. Therefore, there is a need for development of compounds with immunomodulatory activities in the TME to stimulate anti-tumor immunity by upregulation of antigen processing and presentation machinery.

SUMMARY OF THE INVENTION

In brief, embodiments of the present disclosure provide class I HDAC inhibitor compounds, including a pharmaceutically acceptable salt, hydrate, stereoisomer, solvate or prodrug thereof, which are capable of epigenetically immunomodulating in TME. Methods for use of such compounds for treatment of various diseases or conditions, such as cancer, are also provided.

In one embodiment, the present disclosure provides a compound of formula (I):

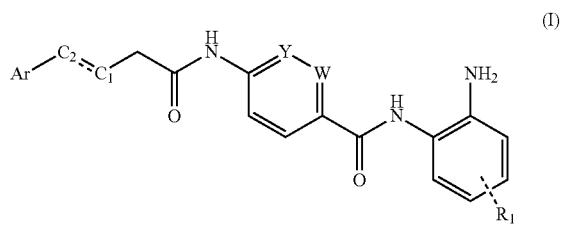

wherein W and Y are each independently selected from CH and N;

$R_1$ is independently selected from hydrogen, halogen, $C_1$-$C_3$ alkyl and halogenated $C_1$-$C_3$ alkyl, and can be mono-, di-, tri- or tetra-substitution;

$C_1$ and $C_2$ are C atoms linked by a single bond or a double bond;

Ar is selected from the group consisting of the following:

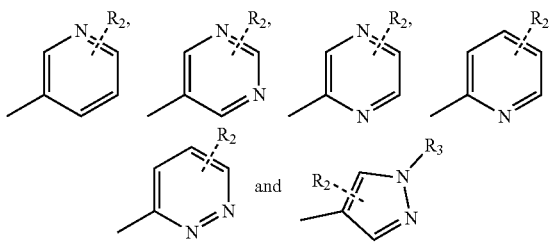

wherein Ar is linked to $C_2$ via the solid line;

$R_2$ has the same meaning as described for $R_1$; and $R_3$ is hydrogen or $C_1$-$C_3$ alkyl;

or a pharmaceutically acceptable salt, hydrate, stereoisomer, solvate or prodrug thereof.

In one embodiment, the compound of formula (I) is 6-((E)-4-(6-methylpyridin-3-yl)but-3-enamido)-N-(2-amino-4-fluorophenyl) pyridine-3-carboxamide, named after GNTbm-01. In one embodiment, the compound of formula (I) is 5-((E)-4-(6-methylpyridin-3-yl)but-3-enamido)-N-(2-amino-4-fluorophenyl) pyridine-2-carboxamide, named after GNTbm-02. In one embodiment, the compound of formula (I) is 4-((E)-4-(6-methylpyridin-3-yl)but-3-enamido)-N-(2-amino-4-fluorophenyl) benzamide, named after GNTbm-03. In one embodiment, the compound of formula (I) is 5-((E)-4-(pyridin-3-yl)but-3-enamido)-N-(2-amino-4-fluorophenyl)pyridine-2-carboxamide, named after GNTbm-04. In one embodiment, the compound of formula (I) is 5-((E)-4-(pyridin-3-yl)but-3-enamido)-N-(2-aminophenyl)pyridine-2-carboxamide, named after GNTbm-05. In one embodiment, the compound of formula (I) is 5-((E)-4-(6-methylpyridin-3-yl)but-3-enamido)-N-(2-aminophenyl)pyridine-2-carboxamide, named after GNTbm-06. In one embodiment, the compound of formula (I) is 5-(4-(6-methylpyridin-3-yl)butanamido)-N-(2-amino-4-fluorophenyl)pyridine-2-carboxamide, named after GNTbm-08. In one embodiment, the compound of formula (I) is 5-((E)-4-

(pyridin-3-yl)but-3-enamido)-N-(2-amino-4-(trifluoromethyl)phenyl)pyridine-2-carboxamide, named after GNTbm-11. In one embodiment, the compound of formula (I) is 5-((E)-4-(6-methylpyridin-3-yl)but-3-enamido)-N-(2-amino-4-(trifluoromethyl)phenyl)pyridine-2-carboxamide, named after GNTbm-12. In one embodiment, the compound of formula (I) is 5-(4-(6-methylpyridin-3-yl)butanamido)-N-(2-aminophenyl)pyridine-2-carboxamide, named after GNTbm-19. In one embodiment, the compound of formula (I) is 5-(4-(6-methylpyridin-3-yl)butanamido)-N-(2-amino-4-(trifluoromethyl)phenyl)pyridine-2-carboxamide, named after GNTbm-25. In one embodiment, the compound of formula (I) is 4-((E)-4-(pyridin-3-yl)but-3-enamido)-N-(2-amino-4-(trifluoromethyl)phenyl)benzamide, named after GNTbm-33. In one embodiment, the compound of formula (I) is 4-(4-(pyridin-3-yl)butanamido)-N-(2-amino-4-fluorophenyl)benzamide, named after GNTbm-37. In one embodiment, the compound of formula (I) is 4-((E)-4-(pyridin-3-yl)but-3-enamido)-N-(2-aminophenyl)benzamide, named after GNTbm-38. In one embodiment, the compound of formula (I) is 4-((E)-4-(pyridin-3-yl)but-3-enamido)-N-(2-amino-4-fluorophenyl)benzamide, named after GNTbm-39.

In other embodiments, the present disclosure provides a pharmaceutical composition or combination comprising a compound described herein.

In other embodiments, the present disclosure provides a method for epigenetic immunomodulation of TME and/or treatment of cancer, the method comprising administering an effective amount of a pharmaceutical composition or combination comprising any one or more of the compounds of formula (I) or a pharmaceutically acceptable salt, hydrate, stereoisomer, solvate or prodrug thereof to a subject in need thereof.

In some embodiments, the method is for inducing cell cycle arrest of tumor cells, for inducing apoptosis of tumor cells, for inducing histone H3 acetylation, for inducing immune memory, for activating CTL, for decreasing immunosuppressive cells.

In other embodiments, the present disclosure provides use of an effective amount of the compound or a pharmaceutically acceptable salt, hydrate, stereoisomer, solvate or prodrug thereof or the pharmaceutical composition or combination in the manufacture of a medicament for epigenetic immunomodulation of TME and/or treatment of cancer in a subject in need thereof.

In some embodiments, the medicament is for inducing cell cycle arrest of tumor cells, for inducing apoptosis of tumor cells, for inducing histone H3 acetylation, for inducing immune memory, for activating CTL, for decreasing immunosuppressive cells.

In other embodiments, the present disclosure provides a method of treating or preventing the disease associated with class I HDAC in a subject, which comprises administering an effective amount of a compound or a pharmaceutically acceptable salt, hydrate, stereoisomer, solvate or prodrug thereof or a pharmaceutical composition or combination to a subject in need thereof.

In other embodiments, the present disclosure provides use of an effective amount of the compound or a pharmaceutically acceptable salt, hydrate, stereoisomer, solvate or prodrug thereof or the pharmaceutical composition or combination in the manufacture of a medicament for treating or preventing the disease associated with class I HDAC in a subject in need thereof.

BRIEF DESCRIPTION OF THE DRAWINGS

(FIG. 2A) $^1$H-NMR spectroscopic data of compound GNTbm-01, (FIG. 2B) $^1$H-NMR spectroscopic data of compound GNTbm-02, (FIG. 2C) $^1$H-NMR spectroscopic data of compound GNTbm-03, (FIG. 2D) high-resolution MS spectroscopic data of compound GNTbm-01, (FIG. 2E) high-resolution MS spectroscopic data of compound GNTbm-02, (FIG. 2F) high-resolution MS spectroscopic data of compound GNTbm-03.

(FIG. 3A) MDA-MB-231 cells, (FIG. 3B) SW48 cells, (FIG. 3C) M10 cells.

(FIG. 4A) & (FIG. 4B) dose-dependent manner. (FIG. 4C) & (FIG. 4D) time-dependent manner.

(FIG. 5A) & (FIG. 5B) dose-dependent manner. (FIG. 5C) & (FIG. 5D) time-dependent manner.

(FIG. 6A) & (FIG. 6B) dose-dependent manner. (FIG. 6C) & (FIG. D) time-dependent manner.

(FIG. 7A) & (FIG. 7B) dose-dependent manner. (FIG. 7C) & (FIG. 7D) time-dependent manner.

(FIG. 8A) & (FIG. 8B) dose-dependent manner. (FIG. 8C) & (FIG. 8D) time-dependent manner.

(FIG. 9A) & (FIG. 9B) dose-dependent manner. (FIG. 9C) & (FIG. 9D) time-dependent manner.

FIGS. 10A-10D show results of Western Blot analysis of acetylation level of histone H3 in cells treated with GNTbm-02 and Entinostat: representative immunoblot analysis of acetyl histone H3, β-actin in MDA-MB-231 or SW48 cells. Cells were treated with the indicated concentrations of GNTbm-02 and Entinostat for 24 hours. Control cells were incubated with a vehicle. (FIG. 10A) (FIG. 10C) Extracts of MDA-MB-231 or SW48 cells treated with GNTbm-02 or Entinostat as indicated were resolved by SDS-PAGE, followed by western blotting and immunostaining after detection with an antibody to histone H3 acetylation (AcH3). (FIG. 10B) (FIG. 10D) Quantification of the AcH3 protein expression level was normalized to β-actin, shown as fold change.

(FIG. 11A) (FIG. 11C) Extracts of MDA-MB-231 or SW48 cells treated with GNTbm-02 as indicated were resolved by SDS-PAGE, followed by western blotting and immunostaining after detection with an antibody to histone H3 acetylation (AcH3). (FIG. 11B) (FIG. 11D) Quantification of the AcH3 protein expression level was normalized to β-actin, shown as fold change.

(FIG. 12A) Extracts of SW48 cells treated with GNTbm-04, GNTbm-05, GNTbm-11 and Chidamide as indicated were resolved by SDS-PAGE, followed by western blotting and immunostaining after detection with an antibody to histone H3 acetylation (AcH3). (FIG. 12B) Extracts of SW48 cells treated with GNTbm-04, GNTbm-05, GNTbm-06 and Chidamide as indicated were resolved by SDS-PAGE, followed by western blotting and immunostaining after detection with an antibody to histone H3 acetylation (AcH3). (FIG. 12C) Extracts of SW48 cells treated with GNTbm-04, GNTbm-05, GNTbm-38, GNTbm-39 and Chidamide as indicated were resolved by SDS-PAGE, followed by western blotting and immunostaining after detection with an antibody to histone H3 acetylation (AcH3). All these data represented the quantification of the AcH3 protein expression level normalized to β-actin, shown as fold change.

(FIG. 15A) Scheme of subcutaneous injection of CT26 tumors and different treatment groups (n=6 mice per group). (FIG. 15B) Total tumor volumes. (FIG. 15C) Tumor volume folds change. (FIG. 15D) Mice body weight. (FIG. 15E) Individual tumor volumes. CT26 tumor bearing nude mice were treated as indicated and euthanized when tumor volume reached 3000 mm³ after tumor implantation.

(FIG. 16A) Assessment was performed after incubation of 2 μM of GNTbm-02, Chidamide or Entinostat with HDAC3 enzyme (including assay buffer) for 20 min, 40 min and 60 min. GNTbm-02 was shown to bind with HDAC3 and inhibit HDAC3 stronger than Entinostat. (FIG. 16B) Assessment was performed after incubation of 2 μM of GNTbm-02, GNTbm-03 or GNTbm-01 with HDAC3 enzyme (including assay buffer) for 20 min, 40 min and 60 min. GNTbm-02 was shown to bind with HDAC3 and inhibit HDAC3 stronger than GNTbm-03 and GNTbm-01.

FIGS. 17A-17K show GNTbm-02 (10 mg/kg) plus Celecoxib (50 mg/kg) modulate mononuclear cell and T cell response in the CT26-bearing models: BALB/c mice bearing CT26 tumors were treated with the indicated therapeutic modalities, followed by FACS analyses to assess circulating immune cells. Means and SDs are shown, with P values indicated. Blood samples were isolated at day 16 after treatment in CT26-bearing mice. (FIG. 17A) FACS result for circulating lymphocyte cells. (FIG. 17B) FACS result for circulating monocyte cells. (FIG. 17C) FACS result for circulating granulocyte cells. (FIG. 17D) FACS result for circulating $CD3^+$ T cells. (FIG. 17E) FACS result for circulating $CD4^+$ T cells. (FIG. 17F) FACS result for circulating $CD8^+$ T cells. (FIG. 17G) FACS result for circulating Treg cells. (FIG. 17H) FACS result for circulating $CD11b^+$ cells. (FIG. 17I) FACS result for circulating M-MDSC ($CD11b^+Ly6C^+$) cells. (FIG. 17J) FACS result for circulating $CD11b^+Ly6G^+Ly6C^+$ cells. (FIG. 17K) FACS result for circulating PMN-MDSC ($CD11b^+Ly6G^+Ly6C^-$) cells. Mean±SD is shown for n=8-12 mice per group. One way ANOVA and Dunnett's Multiple Comparison Test (*p<0.05, p<0.01, *p<0.001 vs. IgG control).

DETAILED DESCRIPTION OF THE INVENTION

Definitions

Figure 1:
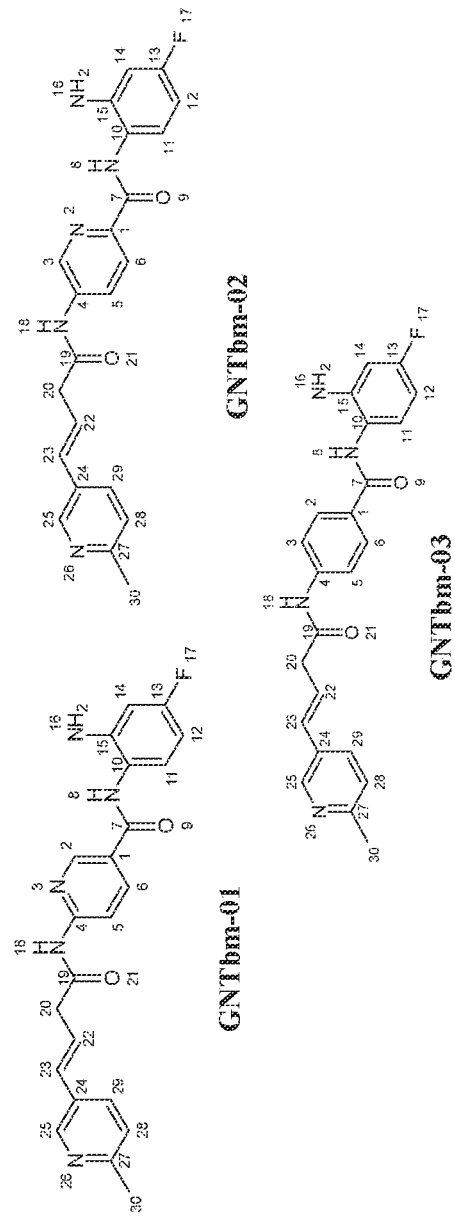
FIG. 1 shows the structures of compounds GNTbm-01, GNTbm-02, and GNTbm-03.
Figure 2A:
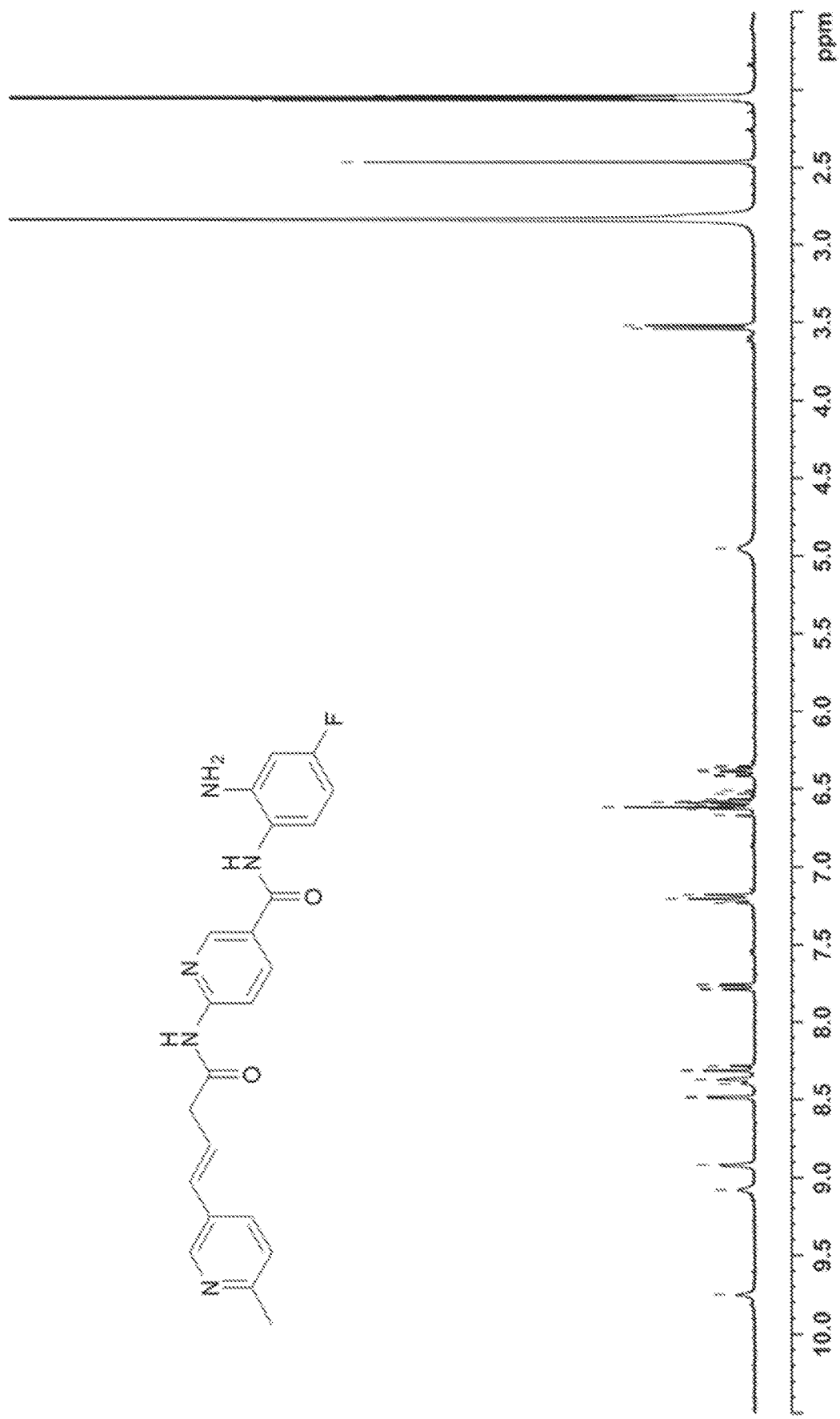
FIGS. 2A-2F show NMR and high-resolution MS spectra.
Figure 2B:
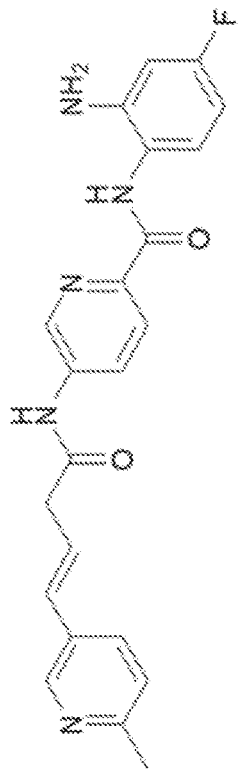
Figure 2B:
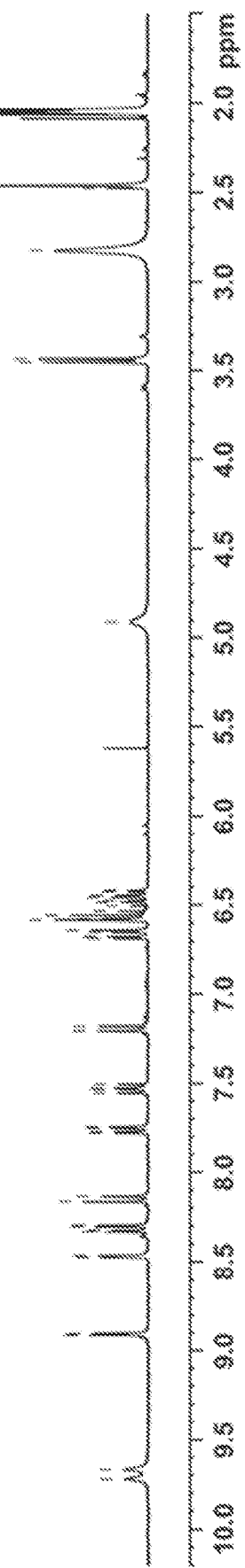
Figure 2C:
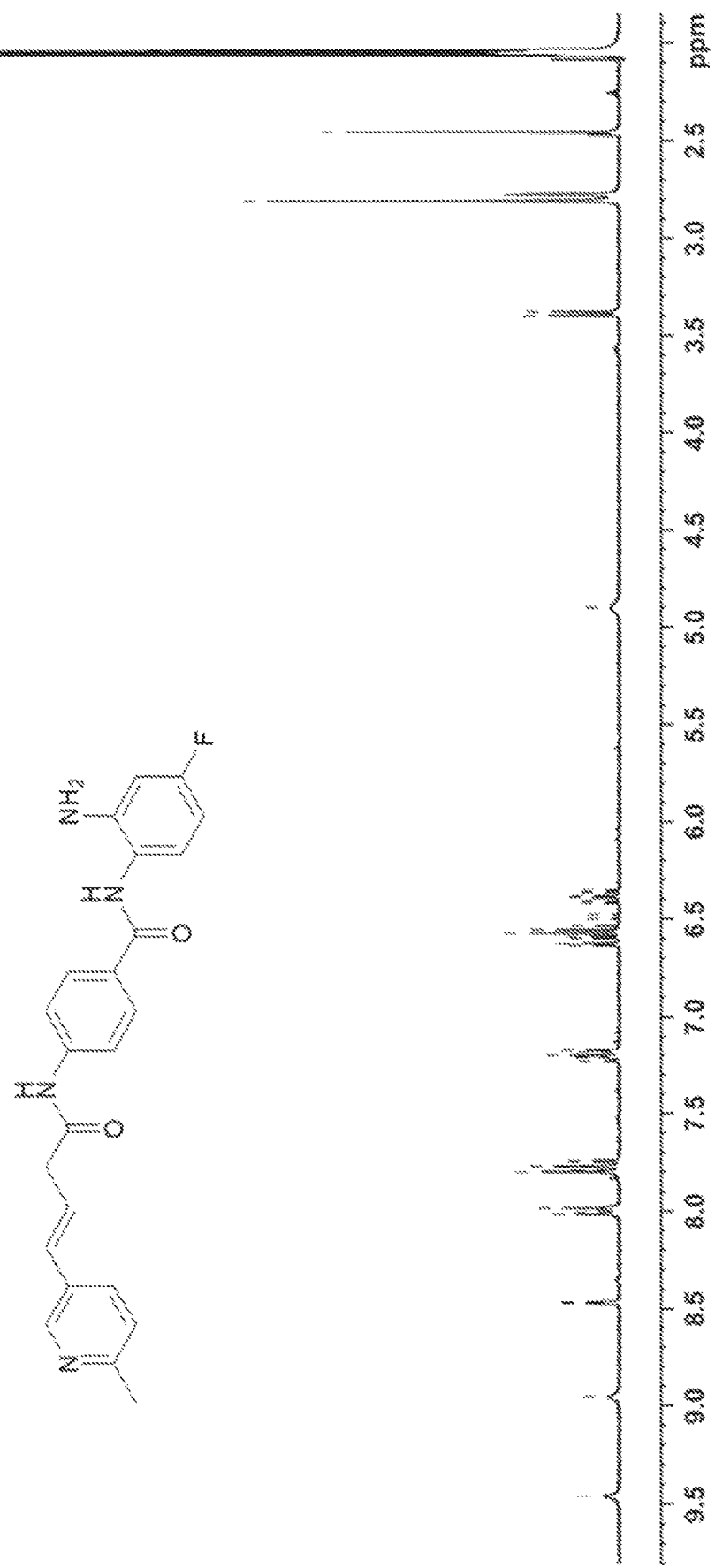
Figure 2D:
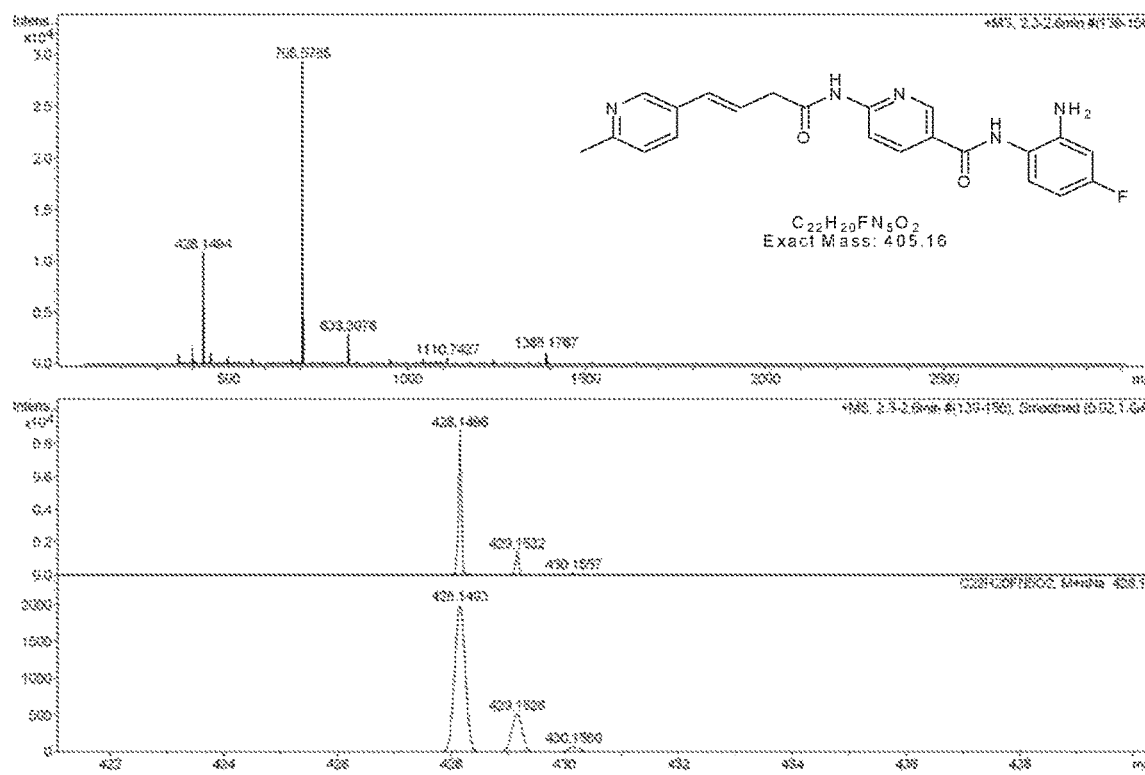
Figure 2E:
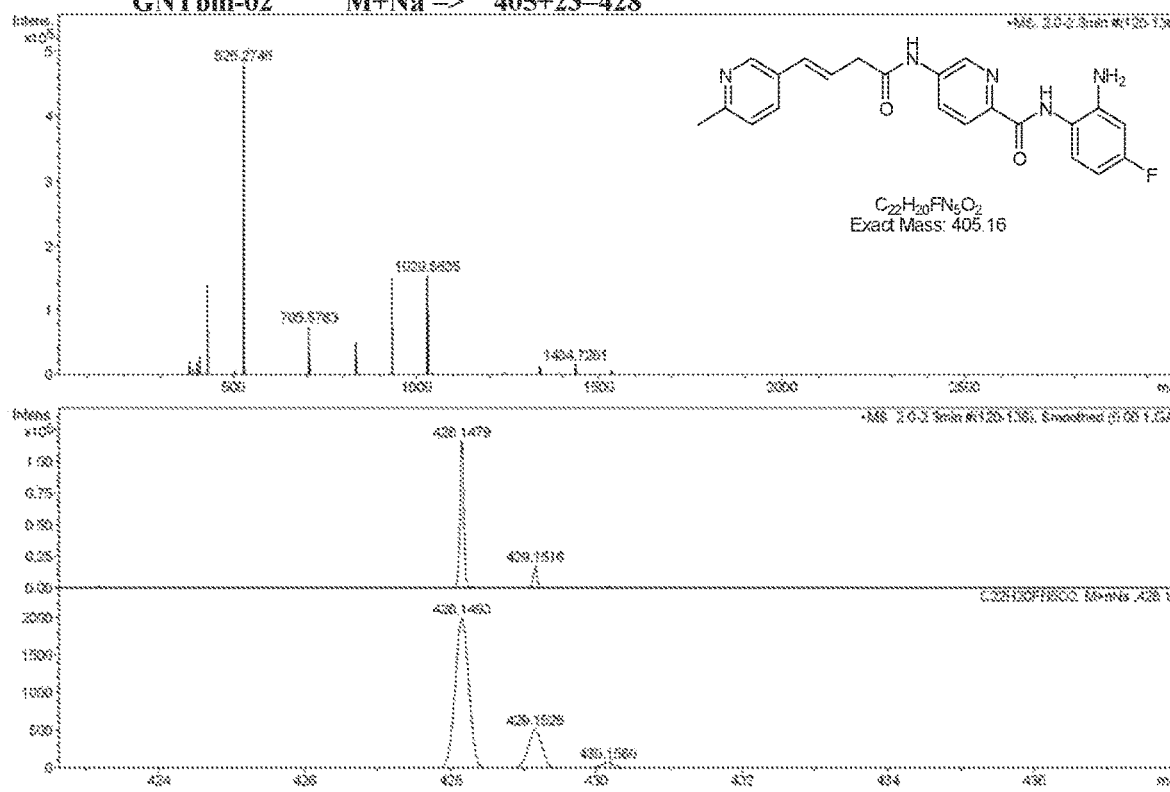
Figure 2F:
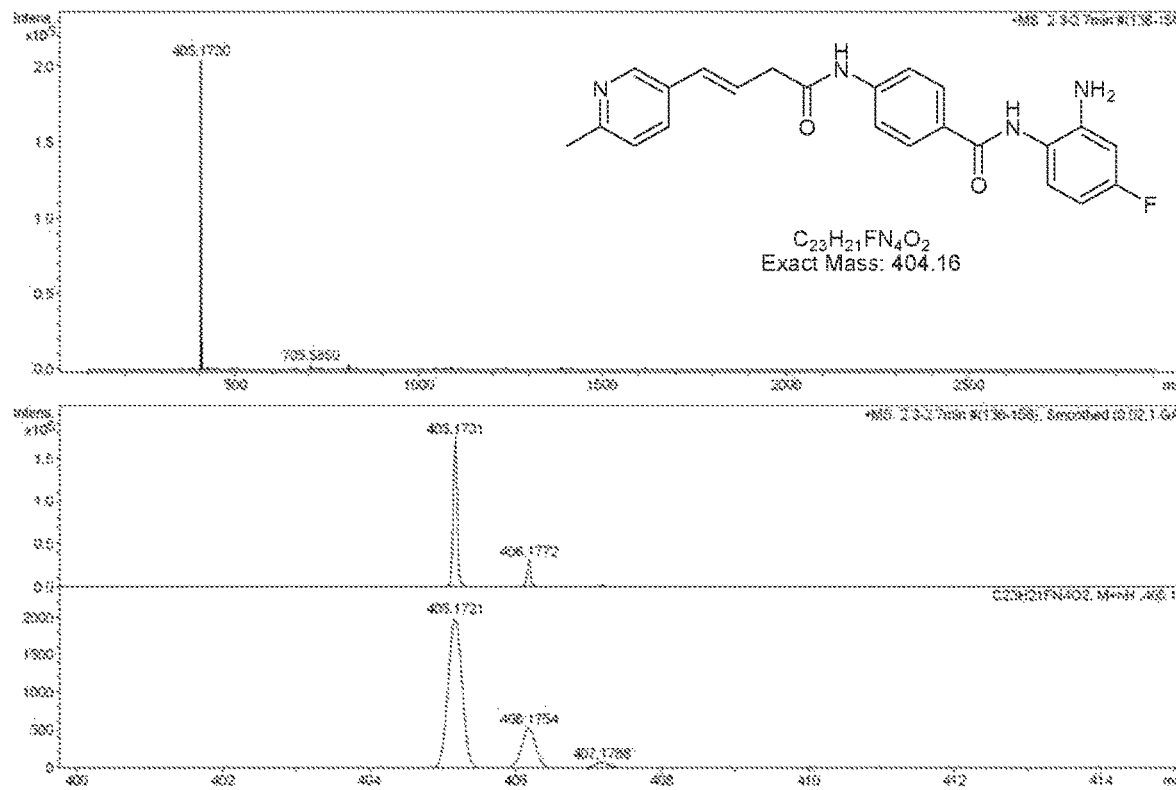

Unless otherwise defined, all technical and scientific terms used herein have the same meaning as commonly understood by one of ordinary skill in the art to which this invention belongs, applying the terms in context to their use in describing the present disclosure. The terminology used in the description is for describing particular embodiments only and is not intended to limit the invention.

Where a range of values is provided, it is understood that each intervening value, to the tenth of the unit of the lower limit—unless the context clearly dictates otherwise (such as in the case of a group containing a number of carbon atoms in which case each carbon atom number falling within the range is provided)—is between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

The articles "a" and "an" as used herein and in the appended claims are used to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The terms "halo" and "halogen," as used herein, refer to an atom selected from fluorine, chlorine, bromine and iodine.

The term "alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless specifically stated otherwise in the specification, an alkyl group is optionally substituted by one or more of substituents. The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkoxy" refers to a radical bonded through an oxygen atom of the formula —O-alkyl, where alkyl is an alkyl chain as defined above.

The term "alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless specifically stated otherwise in the specification, an alkenyl group is optionally substituted by one or more substituents.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but are not limited to, cyclopropyl, cyclobutyl, cyclopentyl, cyclohexyl, cyclopentyl and cyclooctyl.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one of the ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heterocycloalkyl," as used herein, refers to a non-aromatic 3-, 4-, 5-, 6- or 7-membered ring or a bi- or tri-cyclic group fused of non-fused system, where (i) at least one ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present disclosure include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formate, fumarate, gluceptate, glucoheptanoate, gluconate, glutamate, glycerophosphate, glycollylarsanilate, hemisulfate, heptanoate, hexanoate, hexylresorcinate, hydrabamate, hydrobromide, hydrochloride, 2-hydroxyethanesulfonate, hydroxynaphthoate, hydroiodide, iodide, isonicotinate, isothionate, lactate, lactobionate, laurate, malate, maleate, mandelate, mesylate, methylnitrate, methylsulfate, methanesulfonate, mucate, 2-naphthalenesulfonate, napsylate, nicotinate, nitrate, oleate, oxalate, pamoate (embonate), palmitate, pantothenate, pectinate, persulfate, phosphate/diphosphate, pimelate, phenylpropanoate, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also included are the basic nitrogen-containing groups that may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredients of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "prevent," "prevention" or "preventing" means inhibition or averting of symptoms associated with the target disease.

The phrase "therapeutically effective amount" refers to that amount of a compound, material, or composition comprising a compound of the present disclosure which is effective for producing a desired therapeutic effect, at a reasonable benefit/risk ratio applicable to any medical treatment.

Class I HDAC Inhibitor Compounds

Epigenetic therapies for cancer such as histone deacetylase inhibitors can stimulate anti-tumor immunity by upregulation of antigen processing and presentation machinery. The epigenetic modifications play an important role in controlling the initiation and progression of tumors. The epigenetic regulation is accomplished mainly through two main mechanisms affecting gene expression: DNA methylation/demethylation that occurs by the addition/removal of a methyl group to DNA, and histone acetylation/deacetylation that occurs by the enzymatic addition/removal of acetyl group to histone proteins wrapped by DNA. Histone deacetylase inhibitors (HDACis) have been thought to be promising targets for new drug development. The fundamental mechanism for HDACs to play a crucial role in cancer is by control of the degree of acetylation in histones or non-histone proteins, which are involved in the regulation of cell cycle, differentiation, apoptosis, DNA-damage response, angiogenesis, metastasis, and other cellular processes.

Class I HDACs are primarily located in the nucleus and expressed ubiquitously in human tissues and play an important role to control cell proliferation, differentiation, and cell cycle progression. Class I HDACs were highly expressed in certain cancers. For example, HDAC1 is highly expressed in prostate, gastric, colon, breast, lung, and esophageal cancers; HDAC2 was highly expressed in gastric, cervical, and colorectal malignancies; HDAC3 was highly expressed in colon and breast cancers. Uncontrolled expression of HDACs will cause silence of many genes which inhibit cell growth, and therefore loss monitoring of cell growth and control of cell differentiation, cell cycle arrest and apoptosis. The dysregulation of HDAC overexpression was significantly correlated with tumor malignancy and poor prognosis. Many class I HDAC inhibitors possess epigenetic immunomodulatory properties.

The mechanisms of immunomodulation by HDAC inhibitors in the TME have been reported to involve components of both soluble factors and immune cells. The expression of varieties of genes and proteins through epigenetic regulation of HDAC inhibitors by inhibiting specific HDAC isoforms are changed in such way that the status of TME would be switched into a mode favoring the killing of cancer cells as an outcome. From previously published studies it was demonstrated that some HDAC inhibitors possessed immunomodulatory properties which would control the secretion of cytokines/chemokines, antigen-presenting cells, reduce the number or function of Treg, and trigger the activation of NK cells. Other studies showed mechanisms which would enhance the expression of cancer antigens, and modulate the activities of immunosuppressive cells like MDSCs. Selective class I HDAC inhibitors can increase PD-L1 and MHC I expression on cancer cells. Moreover, class I HDAC inhibitors downregulate myeloid-derived suppressor cells (MDSCs) infiltrating the tumor microenvironment.

In one aspect, the present disclosure provides a compound of formula (I):

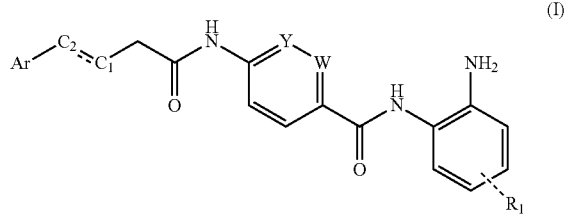

wherein W and Y are each independently selected from CH and N;

$R_1$ is each independently selected from hydrogen, halogen, $C_1$-$C_3$ alkyl and halogenated $C_1$-$C_3$ alkyl, and can be mono-, di-, tri- or tetra-substitution;

$C_1$ and $C_2$ are C atoms linked by a single bond or a double bond;

Ar is selected from the group consisting of the following:

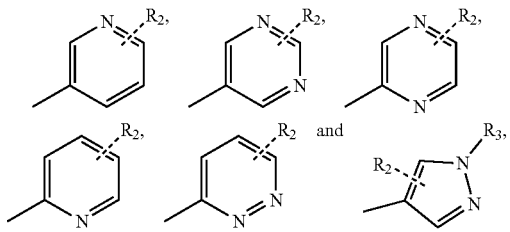

wherein Ar is linked to $C_2$ via the solid line;

$R_2$ has the same meaning as described for $R_1$; and $R_3$ is hydrogen or $C_1$-$C_3$ alkyl;

or a pharmaceutically acceptable salt, hydrate, stereoisomer, solvate or prodrug thereof.

In one embodiment, the compound of formula (I) has the following formula (Ia):

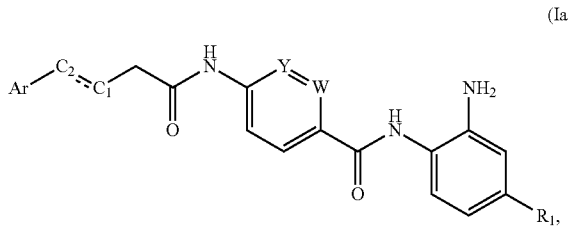

wherein W, Y, $R_1$, $C_1$, $C_2$ and Ar have the same meaning as described; or a pharmaceutically acceptable salt, hydrate, stereoisomer, solvate or prodrug thereof.

In one embodiment, Ar is selected from the six-membered rings. In one embodiment, $R_2$ and the atom of Ar linked to $C_2$ are at para-positions.

In one embodiment, Ar is selected from the group consisting of the following:

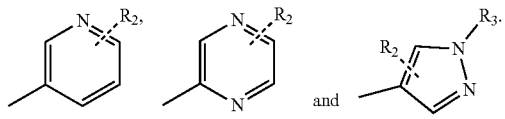

In one embodiment, W and Y are selected from the following combinations: (1) W is N and Y is CH, (2) W is CH and Y is N, and (3) W and Y are CH. In preferred embodiments, W is N or CH and Y is CH.

In one embodiment, $R_1$ is F or fluronated $C_1$-$C_3$ alkyl. In one embodiment, fluronated $C_1$-$C_3$ alkyl is $CF_3$.

In one embodiment, $R_1$ is hydrogen.

In one embodiment, $C_1$ and $C_2$ are C atoms linked by a double bond. In another embodiment, $C_1$ and $C_2$ are C atoms linked by a single bond.

In one embodiment, $R_2$ is $C_1$-$C_3$ alkyl or fluorinated $C_1$-$C_3$ alkyl. In one embodiment, $C_1$-$C_3$ alkyl is $CH_3$. In one embodiment, fluronated $C_1$-$C_3$ alkyl is $CF_3$.

In one embodiment, $R_2$ is hydrogen.

In one embodiment, Ar is

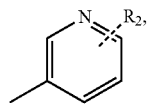

$R_2$ and the atom of Ar linked to $C_2$ are at para-positions, and $C_1$ and $C_2$ are C atoms linked by a double bond.

In one embodiment, Ar is

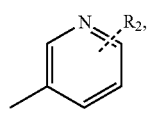

$R_2$ and the atom of Ar linked to $C_2$ are at para-positions, and $R_1$ is hydrogen or F.

In one embodiment, Ar is

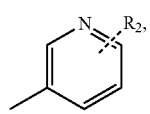

$R_2$ and the atom of Ar linked to $C_2$ are at para-positions, and $R_2$ is hydrogen or $CH_3$.

In one embodiment, $R_1$ is hydrogen or F, and $R_2$ is hydrogen or $CH_3$.

In one embodiment, $R_1$ is hydrogen or F, $R_2$ is hydrogen or $CH_3$, and $C_1$ and $C_2$ are C atoms linked by a double bond.

In one embodiment, Ar is

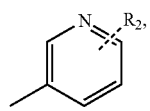

$R_2$ and the atom of Ar linked to $C_2$ are at para-positions, $R_1$ is hydrogen or F, $R_2$ is hydrogen or $CH_3$, and $C_1$ and $C_2$ are C atoms linked by a double bond.

In one embodiment, the compound of formula (I) can be the following compounds:
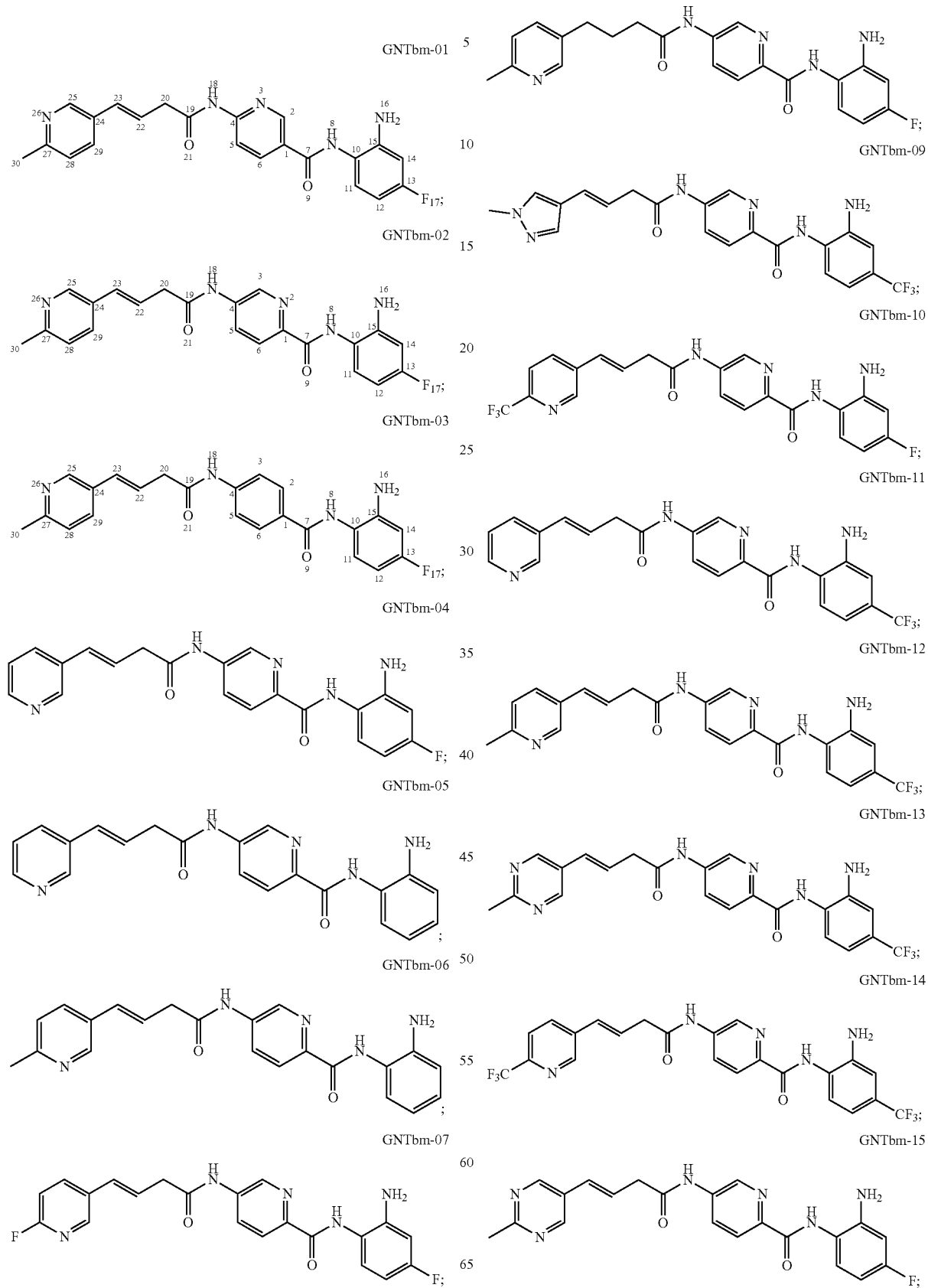

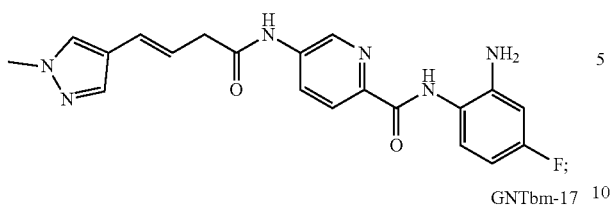
GNTbm-16
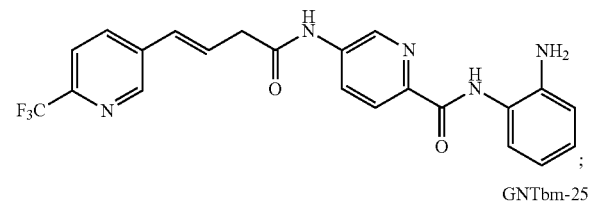
GNTbm-24
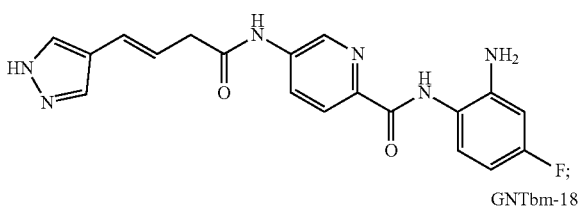
GNTbm-17
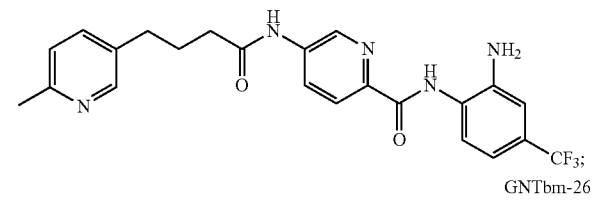
GNTbm-25
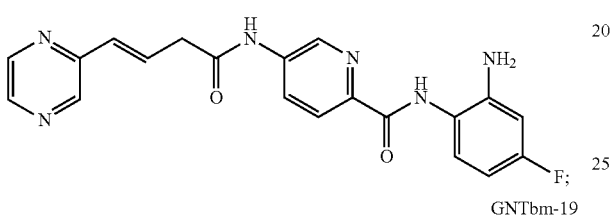
GNTbm-18
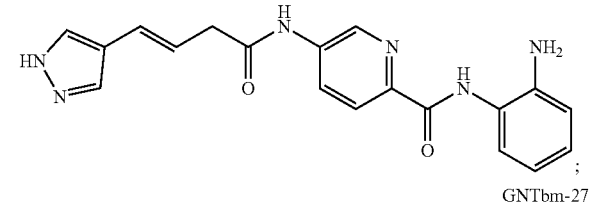
GNTbm-26
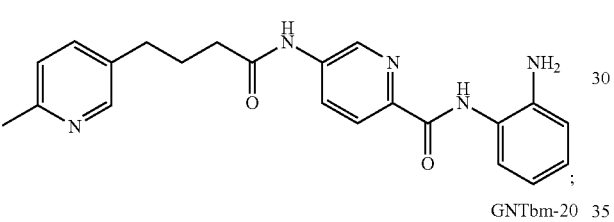
GNTbm-19
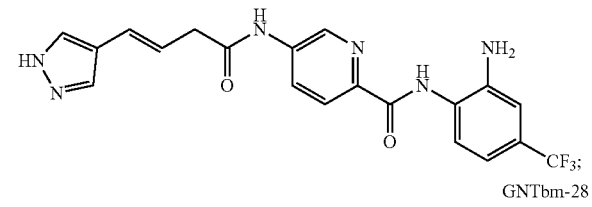
GNTbm-27
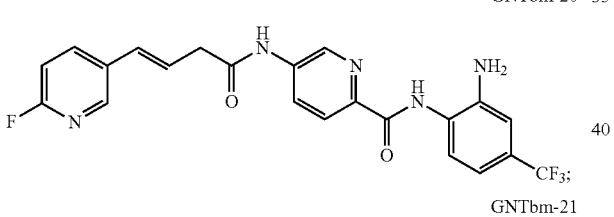
GNTbm-20
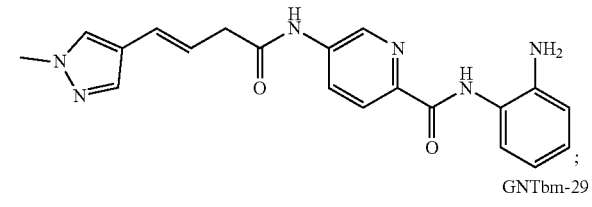
GNTbm-28
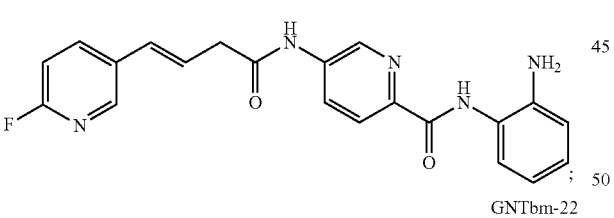
GNTbm-21
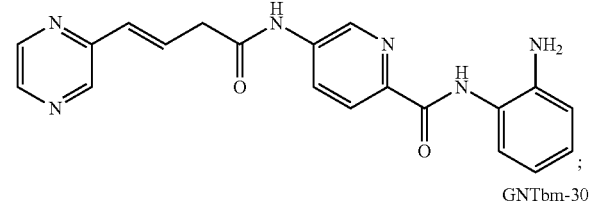
GNTbm-29
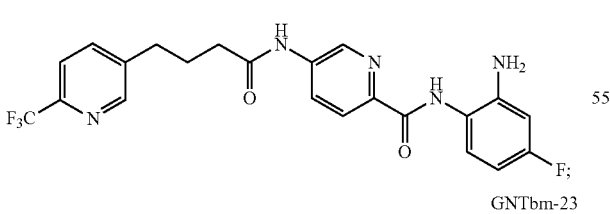
GNTbm-22
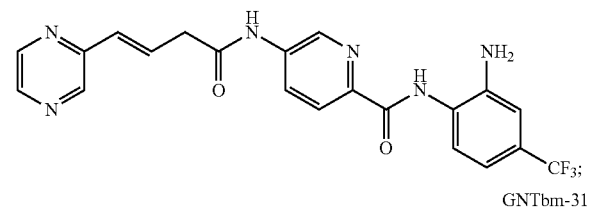
GNTbm-30
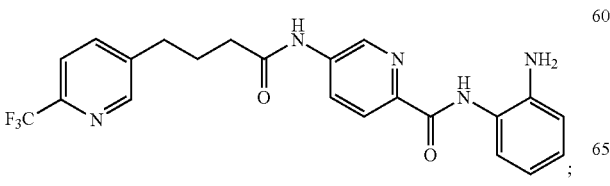
GNTbm-23
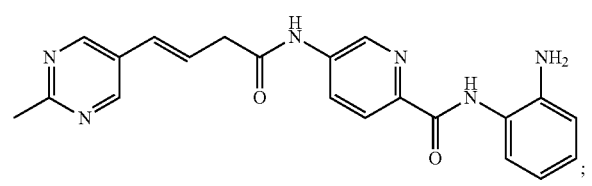
GNTbm-31

-continued

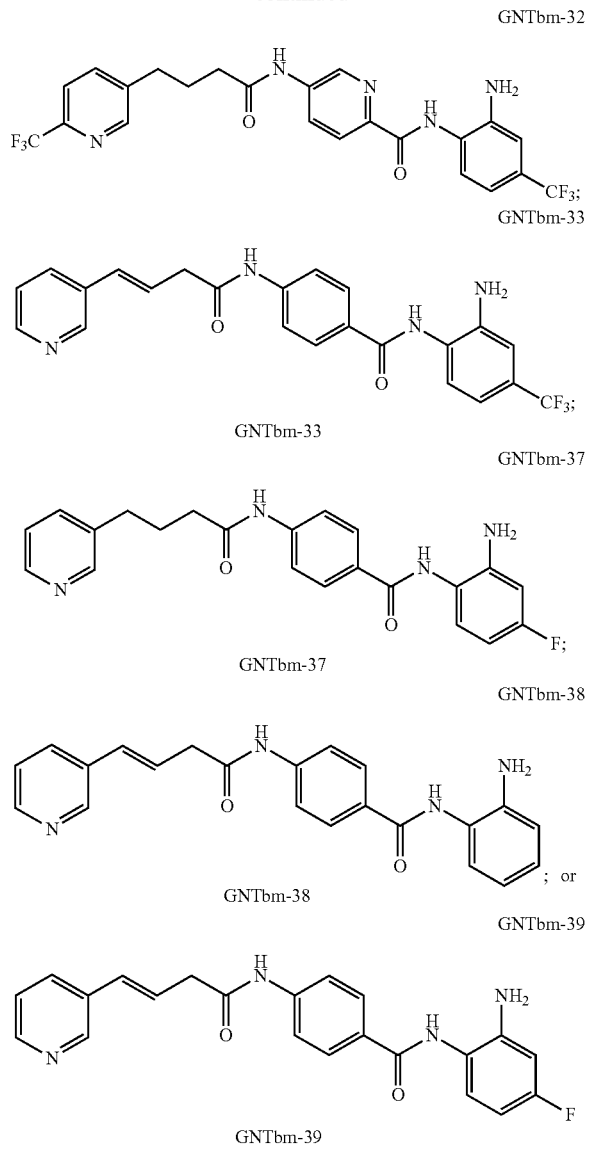

or a pharmaceutically acceptable salt, hydrate, stereoisomer, solvate or prodrug thereof.

The present disclosure encompasses all stereoisomeric forms of the compounds of formula (I). Centers of asymmetry that are present in the compounds of formula (I) can all independently of one another have (R) configuration or (S) configuration. When bonds to the chiral carbon are depicted as straight lines in the structural formulae of the invention, it is understood that both the (R) and (S) are configurations of the chiral carbon, and hence both enantiomers and mixtures thereof, are embraced within the formulae. When a particular configuration is depicted, that enantiomer (either (R) or (S), at that center)) is intended. Similarly, when a compound name is recited without a chiral designation for a chiral carbon, it is understood that both the (R) and (S) are configurations of the chiral carbon, and hence individual enantiomers and mixtures thereof, are embraced by the name.

The invention includes all possible enantiomers, regioisomers, and diastereomers and mixtures of two or more stereoisomers, for example, mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both cis form and trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of formula (I) or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present disclosure includes all such isomers, as well as salts, solvates (including hydrates) and solvated salts of such racemates, enantiomers, diastereomers and tautomers and mixtures thereof.

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); M (micromolar); Hz (Hertz); MHz (mega hertz); mmol (millimoles); hr or hrs (hours); min (minutes); MS (mass spectrometry); ESI (electrospray ionization); TLC (thin layer chromatography); and HPLC (high pressure liquid chromatography). For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

The compounds of formula (I) of the present disclosure are prepared according to general chemical synthetic procedures. An exemplified synthetic route is shown below:

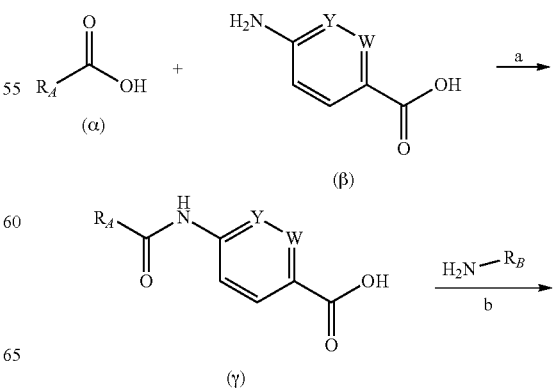

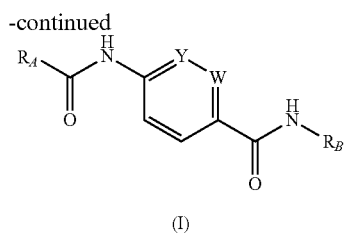

wherein $R_A$ corresponds to the —C—$C_1$=$C_2$—Ar moiety and $R_B$ corresponds to the

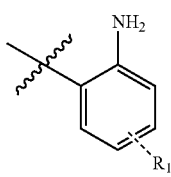

moiety in formula (I).

In this route, N,N'-dicyclohexylcarbodiimide (DCC) and dichloromethane (DCM) may be used in condition a, and 1-ethyl-3-(3-dimethylaminopropyl)carbodiimide (EDC), hydroxybenzotriazole (HOBt) and N,N-Dimethylformamide (DMF) may be used in condition b.

Other proper modifications on the process, e.g., using suitable protection/deprotection agents to groups susceptible to certain reaction conditions during the synthesis, isolating and purifying intermediates for subsequent reactions, selecting proper solvents, etc., can also be introduced by a skilled person in the art based on need. For example, the —OH group of Compound (β) in the route depicted above may be protected before reacting with Compound (α), and the resulting product can be deprotected to give Compound (γ), etc.

Pharmaceutical Compositions/Combinations

In another aspect, the invention provides a pharmaceutical composition/combination comprising a compound of any of formulae (I), or a pharmaceutically acceptable salt, hydrate, stereoisomer, solvate or prodrug thereof, together with a pharmaceutically acceptable carrier.

The pharmaceutical composition/combination can further comprise one or more second agents. In one embodiment, the second agent is an immune checkpoint inhibitor, an NSAID, a tyrosine kinase inhibitor (TKI) or an anti-cancer agent. In a further embodiment, the pharmaceutical composition/combination comprises a compound described herein and an immune checkpoint inhibitor and/or an NSAID or optionally a tyrosine kinase inhibitor (TKI).

In one embodiment, the immune checkpoint inhibitor can be used in combination with the pharmaceutical combination described herein to stimulate an immune system against cancer cells and to treat a cancer. The immune checkpoint inhibitor is an anti-cytotoxic T-lymphocyte antigen-4 (CTLA-4) antibody or agent, anti-programmed cell death protein 1 (PD-1) antibody or agent, an anti-programmed death-ligand 1 (PD-L1) antibody or agent, an anti-T-cell immunoglobulin and mucin domain-3 (TIM-3) antibody or agent, anti-B- and T-lymphocyte attenuator (BTLA) antibody or agent, anti-V-domain Ig containing suppressor of T-cell activation (VISTA) antibody or agent, an anti-lymphocyte activation gene-3 (LAG-3) antibody or agent, KIR (killer-cell immunoglobulin-like receptor) inhibitor or antibody, A2AR (adenosine A2A receptor) inhibitor or antibody, CD276 inhibitor or antibody, or VTCN1 inhibitor or antibody. More preferably, the immune checkpoint inhibitor is pembrolizumab, lambrolizumab, pidilizumab, nivolumab, durvalumab, avelumab, or atezolizumab. Examples of PD-1 or PD-L1 inhibitors include, without limitation, humanized antibodies blocking human PD-1 such as lambrolizumab (anti-PD-1 Ab, trade name Keytruda) or pidilizumab (anti-PD-1 Ab), Bavencio (anti-PD-L1 Ab, avelumab), Imfinzi (anti-PD-L1 Ab, durvalumab), and Tecentriq (anti-PD-L1 Ab, atezolizumab) as well as fully human antibodies such as nivolumab (anti-PD-1 Ab, trade name Opdivo) and cemiplimab-rwlc (anti-PD-1 Ab, trade name Libtayo). Other PD-1 inhibitors may include presentations of soluble PD-1 ligand including, without limitation, PD-L2 Fc fusion protein also known as B7-DC-Ig or AMP-244 and other PD-1 inhibitors presently under investigation and/or development for use in therapy. In addition, immune checkpoint inhibitors may include, without limitation, humanized or fully human antibodies blocking PD-L1 such as durvalumab and MIH1 (anti-CD274 (PD-L1, B7-H1) monoclonal antibody) and other PD-L1 inhibitors presently under investigation.

NSAID is a class of drugs that reduce pain, decrease fever, and, in higher doses, decrease inflammation. Most NSAIDs inhibit the activity of cyclooxygenase-1 (COX-1) and cyclooxygenase-2 (COX-2), and thereby the synthesis of thromboxanes and prostaglandins. It is thought that inhibiting COX-2 leads to anti-inflammatory, analgesic and antipyretic effects, whereas those NSAIDs also inhibiting COX-1, particularly aspirin, may cause gastrointestinal bleeding and ulcers in large doses. COX-2 inhibitors are widely used to treat autoimmune and inflammatory diseases. Cyclooxygenase (COX), which has two isoforms, COX-1 and COX-2, is the enzyme responsible for the rate-determining step in the synthesis of bioactive lipids of prostanoids consisting of prostaglandin D2 (PGD2), PGE2, PGF2α, prostacyclin PGI2 and thromboxane TXA2. COX-1 is constitutively expressed in body tissues to maintain homeostatic prostanoids and is involved in several biological functions such as angiogenesis, vasodilation, and tissue maintenance. However, COX-2 is expressed in low levels in normal conditions. COX-2 is rapidly induced by stimuli such as infection, injury and pain to initiate pro-inflammatory processes. Selective COX-2 inhibitors are a type of nonsteroidal anti-inflammatory drugs (NSAIDs). In some embodiments, the NSAID includes, but is not limited to, aspirin, ibuprofen, indomethacin, naproxen and a COX-2 inhibitor. In some embodiments of the present disclosure, the NSAID is a COX2 inhibitor. In some embodiments, the COX2 inhibitor includes, but is not limited to, Celebrex (generic name is celecoxib), Rofecoxib, Imrecoxib and Etoricoxib. Preferably, the COX2 inhibitor is Celecoxib.

The tyrosine kinase inhibitors (TKIs) are a family of small molecules with the activity to inhibit either cytosolic or receptor tyrosine kinases. TKIs inhibit these growth factor signaling pathways by various mechanisms. They compete with ATP, substrate, or for sites for dimerization, and could also act allosterically. The inhibition of cytosolic or receptor tyrosine kinase was demonstrated by several different classes of TKIs, such as through direct competition for ATP binding to the tyrosine kinase, allosteric inhibition of the tyrosine kinase, and inhibition of ligand binding to receptor tyrosine kinases. TKIs are playing an increasingly significant role in treating cancers, especially VEGFR inhibitors such as Axitinib, Lenvatinib, Cabozantinib and Regorafenib. In some embodiments of the disclosure, the TKI is an inhibitor of receptor tyrosine kinases. Preferably, the TKI is an inhibitor of vascular endothelial growth factor receptor (VEGFR). More preferably, the TKI is Cabozantinib, Regorafenib, Axitinib, Afatinib, Ninetedanib, Crizotinib, Alectinib, Trametinib, Dabrafenib, Sunitinib, Ruxolitinib, Vemurafenib, Sorafenib, Ponatinib, Encorafenib, Brigatinib, Pazopanib, Dasatinib, Imatinib, Lenvatinib, Vandetanib, surufatinib or Sitravatinib.

The additional anti-cancer agent is any anti-cancer agent described herein or known in the art. In one embodiment, the additional anti-cancer agent is chemotherapy or platinum-based doublet chemotherapy. In certain embodiments, the additional anti-cancer agent is a tyrosine kinase inhibitor (TKI). In one embodiment, the additional anti-cancer agent is an anti-VEGF or anti-VEGFR antibody or compound. In other embodiments, the anti-cancer agent is a platinum agent (e.g., cisplatin, carboplatin), a mitotic inhibitor (e.g., paclitaxel, albumin-bound paclitaxel, docetaxel, taxotere, docecad), a fluorinated *Vinca* alkaloid (e.g., vinflunine, javlor), vinorelbine, vinblastine, etoposide, or pemetrexed gemcitabin. In one embodiment, the additional anti-cancer agent is 5-flurouracil (5-FU). In certain embodiments, the additional anti-cancer agent is any other anti-cancer agent known in the art.

To prepare the pharmaceutical compositions/combinations of this invention, one or more compounds of the present disclosure as the active ingredient is thoroughly admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gel caps and tablets, suitable carriers and additives include starches, sugars, diluents, granulating agents, lubricants, binders, disintegrating agents and the like. Because of their ease in administration, tablets and capsules represent the most advantageous oral dosage unit form, in which case, solid pharmaceutical carriers are obviously employed. If desired, tablets may be sugar-coated or enteric-coated by standard techniques. For parenterals, the carrier will usually comprise sterile water, though other ingredients, for example, for purposes such as aiding solubility or for preservation, may be included. Injectable suspensions may also be prepared, in which case, appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The liquid forms in which the novel compositions of the present disclosure may be incorporated for administration orally or by injection include: aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include: synthetic and natural gums such as tragacanth, acacia, alginate, dextran, sodium carboxymethylcellulose, methylcellulose, polyvinyl-pyrrolidone or gelatin.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g., polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilizing by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspension in the sterile vehicle. Advantageously, a surfactant or wetting agent can be included in the composition to facilitate uniform distribution of the compound of the application.

Pharmaceutical preparation for administration by inhalation can be delivered from an insufflator or a nebulizer pressurized pack.

Therapeutic Applications

In another aspect, the present disclosure provides a method for epigenetic immunomodulation of TME, comprising administering an effective amount of a compound or a pharmaceutical composition/combination described herein to a subject in need thereof.

In another aspect, the present disclosure provides a method of treating or preventing the disease associated with class I HDAC in a subject, which comprises administering an effective amount of a compound or a pharmaceutical composition/combination described herein to a subject in need thereof.

In one embodiment, the methods comprise further administering one or more second agents. In some embodiments, the second agent is an immune checkpoint inhibitor, an NSAID, a TKI or an anti-cancer agent. In a further embodiment, the pharmaceutical composition/combination comprises a compound described herein and an immune checkpoint inhibitor and/or an NSAID or optionally a TKI. Embodiments of the immune checkpoint inhibitor, NSAID, TKI or anti-cancer agent are those described herein.

The compounds of the invention are useful for treating or preventing any disease and/or condition, wherein inhibition of class I HDAC is desired. Particularly, the compounds of the invention possess epigenetic immunomodulation of TME, hereby improving immunotherapies. Inhibition of the HDAC enzyme activity can lead to attenuation of tumor growth. Thus, the invention provides methods for the treatment or prevention of tumors or cancers.

Examples of cancer which can be treated in accordance with the present teachings include, but are not limited to, invasive breast carcinoma, adenocarcinoma, lung cancer (non-small cell, squamous cell carcinoma, adenocarcinoma, and large cell lung cancer), liver cancer, colorectal cancer, brain, head and neck cancer (e.g., neuro/glioblastoma), breast cancer, ovarian cancer, transitional cell carcinoma of the bladder, prostate cancer, oral squamous cell carcinoma, bone sarcoma, adrenocortical cancer, gastrointestinal tumors including colorectal cancer, biliary tract cancer such as gallbladder carcinoma (GBC), bladder cancer, esophageal cancer, gastric cancer, cervical cancer, salivary gland cancer, diarrhea benign neoplasm, ductal carcinoma in situ, paronychia, cholangiocarcinoma, kidney cancer, pancreatic cancer, medulloblastoma, glioblastoma, luminal, HER2-positive and triple negative mammary tumors, hematologic malignancies and leukemia (acute myelogenous leukemia (AML), B-precursor cell acute lymphoblastic leukemia (ALL), a fraction of T-cell ALL, and chronic myelogenous leukemia (CML)).

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

The invention having now been described by way of written description, those of skill in the art will recognize that the invention can be practiced in a variety of embodiments and that the foregoing description and examples below are for purposes of illustration and not limitation of the claims that follow.

EXAMPLES

Materials and methods of preparing the exemplified compounds of the invention are described below.

GNTbm-01, GNTbm-02, GNTbm-03, GNTbm-04, GNTbm-05, GNTbm-06, GNTbm-08, GNTbm-11, GNTbm-12, GNTbm-19, GNTbm-25, GNTbm-33, GNTbm-37, GNTbm-38, GNTbm-39, Entinostat-API (Active Pharmaceutical Ingredient), and Chidamide-API were provided by GNTbm [GNT Biotech & Medicals Co. Ltd (Taiwan)]. Celecoxib capsule product (Celebrex®, 200 mg) was purchased from (Pfizer, Taiwan). Regorafenib (HY-1031, 30 mg/kg, po daily, MedChemExpress USA). The following antibodies and reagents were used for animal experiments: mouse anti-PD-1 (CD279) monoclonal antibody (RMP1-14; Bio X Cell), and rat anti-IgG2a isotype monoclonal antibody (2A3; Bio X Cell). Electrospray Ionization Mass was recorded on a Bruker microTOF and Electrospray mass spectra (ESMS) were recorded as m/z values using Waters mass spectrometer. All commercial chemicals and solvents were reagent grade and used without further purification unless otherwise stated. All reactions were monitored for completion by thin layer chromatography using Merck 60 F254 silica gel glass backed plates (20×20 cm). Visualization of the resulting chromatograms was detected visually under UV irradiation (254 nm). $^1$H NMR and $^{13}$C NMR were recorded on a Bruker AVANCE 400 MHz PLUS and Bruker AVANCE III HD 600 MHz Spectrometer and instrument and the chemical shifts were recorded in parts per million (ppm, δ). Multiplicities are recorded as s (singlet), brs (broad singlet), d (doublet), t (triplet), q (quartet), dd (doublet of doublets), td (triplet of doublets), and m (multiplet). Coupling constants (J) are expressed in hertz. Purity of the final compound was determined with Waters ACQUITY Arc system using $C_{18}$ column (Waters XSelect HSS T3 5 μm, 4.6 mm×250 mm) operating at 40° C. Elution was carried out using water containing 0.1% trifluoroacetic acid as mobile phase A and methanol as mobile phase B. Elution condition: at 0 min, phase A 90%+phase B 10%; at 6 min, phase A 70%+phase B 30%; at 12 min, phase A 50%+phase B 50%; at 18 min, phase A 10%+phase B 90%; at 23 min, phase A 90%+phase B 10%. The flowrate of the mobile phase was 1 mL/min, the injection volume of the sample was 10 μL, and the run time was 30 minutes. Peaks were detected at 254 nm. Purity of final compound was found to be >90%.

PREPARATION EXAMPLES

Example 1 GNTbm-01

The synthetic route is shown below:

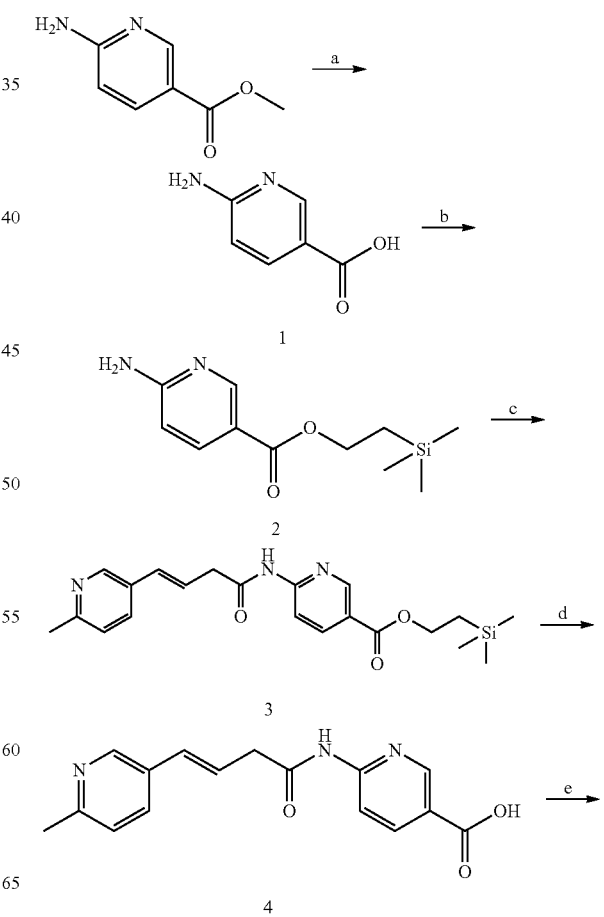

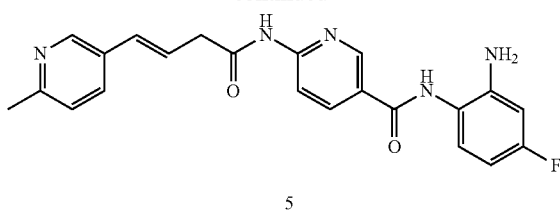

5

6-aminopyridine-3-carboxylic acid (1)

To the solution of methyl 6-aminopyridine-3-carboxylate (1.2 g) was added LiOH (3.309 g) in MeOH, and the mixture was stirred at 40~65° C. for 4~8 hr. After cool to RT, adjusted to acidic condition with 10% HCl (aq), filter by suction, and the product was dried on an oven for approximately 24 hours to yield the solid product compound 1.

2-(trimethylsilyl)ethyl 6-aminopyridine-3-carboxylate (2)

To the solution of compound 1 (1.5 g) and triphenylphosphine (2.848 g) in THF was added 2-(trimethylsilyl)ethanol (1.84 mL mmol) and Diisopropyl azodicarboxylate (DIAD, 2.56 mL) at −5~10° C. And the mixture was stirred at room temperature for approximately 8 hr. The mixture was concentrated, and purified by silica gel column chromatography to give compound 2.

2-(trimethylsilyl)ethyl 6-((E)-4-(6-methylpyridin-3-yl)but-3-enamido)pyridine-3-carboxylate (3)

To the solution of DCC (86.9 mg) in DCM was added compound 2 (50 mg) and (E)-4-(6-methylpyridin-3-yl)but-3-enoic acid (67.2 mg) in DCM at ice bath. And the mixture was stirred at room temperature for approximately 8 hr. The product was extracted using ethyl acetate and the organic layer was washed with water. The combined organic layers were dried over MgSO₄, concentrated, and purified by silica gel column chromatography to give compound 3.

6-((E)-4-(6-methylpyridin-3-yl)but-3-enamido)pyridine-3-carboxylic acid (4)

To the solution of compound 3 (50 mg) in THF (11 mL) was added 12 N HCl (11 mL), and the mixture was stirred at room temperature for 4~10 hr. The mixture was concentrated, and purified by silica gel column chromatography to give compound 4.

6-((E)-4-(6-methylpyridin-3-yl)but-3-enamido)-N-(2-amino-4-fluorophenyl)pyridine-3-carboxamide (5)

To the solution of 4-fluorobenzene-1,2-diamine (72.9 mg), EDC (89.7 mg), HOBt (46.8 mg) in DMF was stirred at −10~10° C. for 20~60 min. Compound 4 (85.9 mg) in DMF and Et₃N (161 μL) was added, and the mixture was stirred at room temperature for approximately 72 hr. The mixture was diluted with water and extracted with EtOAc. The combined organic layers were dried over MgSO₄, concentrated, and purified by silica gel column chromatography to produce compound 5. $^1$H NMR (400 MHz, acetone-$d_6$): δ2.46(3H, s), 3.52(2H, d), 4.95(2H, br), 6.39(1H, td), 6.59(3H, m), 7.21(1H, t), 7.77(1H, dd), 8.38(3H, m), 9.08 (1H, s), 9.75(1H, s). $^{13}$C NMR (100 MHz, DMSO-$d_6$): δ23.77, 40.47, 101.16, 101.41, 101.80, 102.03, 123.05, 124.73, 125.54, 128.76, 128.86, 129.21, 129.56, 132.84, 136.68, 138.02, 145.71, 147.16, 148.12, 156.82, 163.76, 170.27; ESI-MS m/z: 428.1496[M+Na⁺].

Example 2 GNTbm-02

The synthetic route is shown below:

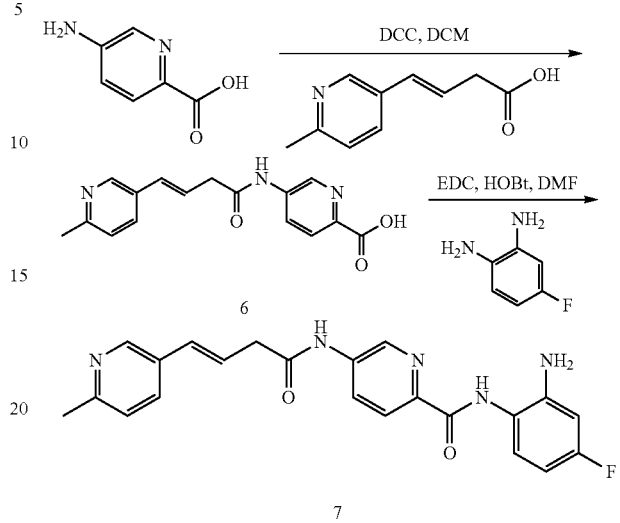

5-((E)-4-(6-methylpyridin-3-yl)but-3-enamido)pyridine-2-carboxylic acid (6)

The solution of (E)-4-(6-methylpyridin-3-yl)but-3-enoic acid (769 mg) and DCC (895 mg) in DCM was stirred at −10~10° C. for 20~60 min. 6-aminopyridine-3-carboxylic acid (500 mg) in DCM was added, and the mixture was stirred at room temperature for approximately 48 hr. The mixture was filtered for the collection of the solid powder. The solid powder was dissolved in MeOH, filtered and concentrated by rotavapor to give crude compound 6.

5-((E)-4-(6-methylpyridin-3-yl)but-3-enamido)-N-(2-amino-4-fluorophenyl)pyridine-2-carboxamide (7)

The solution of 4-fluorobenzene-1,2-diamine (42.4 mg) and EDC (52.2 mg, HOBt (26 mg) in DMF was stirred at −10~10° C. for 20~60 min. 5-((E)-4-(6-methylpyridin-3-yl) but-3-enamido)pyridine-2-carboxylic acid (compound 6) (50 mg) in DMF was added, and the mixture was stirred at room temperature for approximately 16 hr. The mixture was diluted with water and extracted with EtOAc. The combined organic layers were dried over MgSO₄, concentrated, and purified by silica gel column chromatography to give compound 7. $^1$H NMR (400 MHz, acetone-$d_6$): δ2.46(3H, s), 3.45(2H, d), 4.90(1H, br), 6.45(1H, m), 6.55(2H, m), 6.66 (1H, dd), 7.19(1H, d), 7.53(1H, dd), 7.76(1H, dd), 8.15(1H, d), 8.31(1H, dd), 8.47(1H, d), 8.91(1H, s), 9.66(1H, s), 9.72(1H, s). $^{13}$C NMR (100 MHz, MeOD-d): δ41.93, 104.06, 104.32, 105.16, 105.39, 124.08, 125.12, 125.94, 128.14, 128.41, 128.65, 130.93, 132.17, 135.42, 139.91, 141.19, 146.07, 147.83, 158.38, 165.26, 168.08, 172.56. ESI-MS m/z: 428.1479[M+Na⁺].

Example 3 GNTbm-03

The synthetic route is shown below:

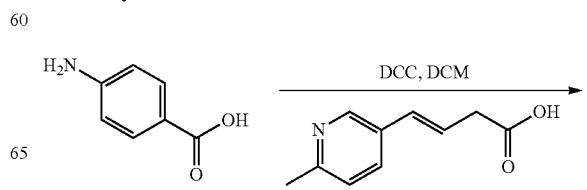

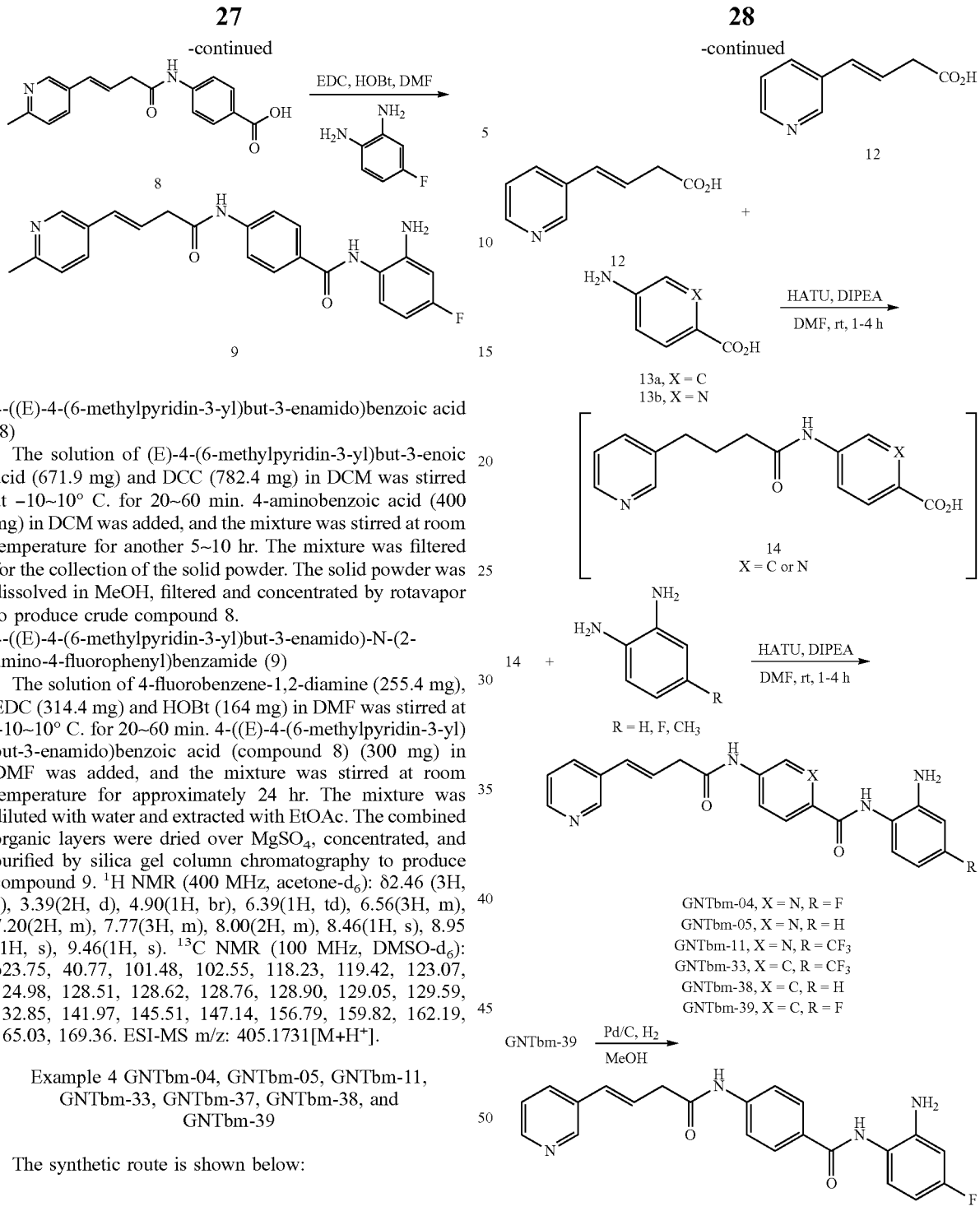

4-((E)-4-(6-methylpyridin-3-yl)but-3-enamido)benzoic acid (8)

The solution of (E)-4-(6-methylpyridin-3-yl)but-3-enoic acid (671.9 mg) and DCC (782.4 mg) in DCM was stirred at −10~10° C. for 20~60 min. 4-aminobenzoic acid (400 mg) in DCM was added, and the mixture was stirred at room temperature for another 5~10 hr. The mixture was filtered for the collection of the solid powder. The solid powder was dissolved in MeOH, filtered and concentrated by rotavapor to produce crude compound 8.

4-((E)-4-(6-methylpyridin-3-yl)but-3-enamido)-N-(2-amino-4-fluorophenyl)benzamide (9)

The solution of 4-fluorobenzene-1,2-diamine (255.4 mg), EDC (314.4 mg) and HOBt (164 mg) in DMF was stirred at −10~10° C. for 20~60 min. 4-((E)-4-(6-methylpyridin-3-yl)but-3-enamido)benzoic acid (compound 8) (300 mg) in DMF was added, and the mixture was stirred at room temperature for approximately 24 hr. The mixture was diluted with water and extracted with EtOAc. The combined organic layers were dried over MgSO₄, concentrated, and purified by silica gel column chromatography to produce compound 9. $^1$H NMR (400 MHz, acetone-$d_6$): δ2.46 (3H, s), 3.39(2H, d), 4.90(1H, br), 6.39(1H, td), 6.56(3H, m), 7.20(2H, m), 7.77(3H, m), 8.00(2H, m), 8.46(1H, s), 8.95 (1H, s), 9.46(1H, s). $^{13}$C NMR (100 MHz, DMSO-$d_6$): δ23.75, 40.77, 101.48, 102.55, 118.23, 119.42, 123.07, 124.98, 128.51, 128.62, 128.76, 128.90, 129.05, 129.59, 132.85, 141.97, 145.51, 147.14, 156.79, 159.82, 162.19, 165.03, 169.36. ESI-MS m/z: 405.1731[M+H$^+$].

Example 4 GNTbm-04, GNTbm-05, GNTbm-11, GNTbm-33, GNTbm-37, GNTbm-38, and GNTbm-39

The synthetic route is shown below:

Ethyl (E)-4-(pyridin-3-yl)but-3-enoate (11). To a solution of nicotinaldehyde 10 (10 g, 93 mmol), PPh3 (36.7 g, 140 mmol), ethyl acrylate (15.3 mL, 140 mmol) in n-hexanol (50 mL) was stirred at 120~160° C. for 12~18 h. The mixture was diluted with EA, washed with water, brine, and dried over Na₂SO₄. The mixture was filtered and concentrated to dryness. The crude product was purified by column chromatography to give compound 11 (6 g, 34%) as a yellow liquid. $^1$H NMR (600 MHz, CDCl3) δ 8.58 (d, J=1.8 Hz, 1H), 8.46 (dd, J=4.8, 1.5 Hz, 1H), 7.70 (dt, J=7.9, 1.8 Hz, 1H), 7.24 (dd, J=7.9, 4.9 Hz, 1H), 6.48 (d, J=16.0 Hz, 1H), 6.38 (dt, J=15.9, 7.0 Hz, 1H), 4.18 (q, J=7.1 Hz, 2H), 3.27 (dd, J=7.0, 1.3 Hz, 2H), 1.29 (t, J=7.1 Hz, 3H).

(E)-4-(Pyridin-3-yl)but-3-enoic acid (12) To a solution of compound 11 (6 g, 31 mmol) in THF (100 mL) was added LiOH (2.25 g in 50 mL of H$_2$O, 94 mmol) and stirred at RT (room temperature) for 1~4 h. The mixture was concentrated to remove THF. The aqueous solution was acidified with 1N HCl$_{(aq.)}$. The mixture was concentrated to dryness and the crude product was purified by column chromatography to give compound 12 (3.7 g, 72%) as a white solid. $_1$H NMR (600 MHz, DMSO-d6) δ 8.58 (d, J=2.0 Hz, 1H), 8.42 (dd, J=4.7, 1.5 Hz, 1H), 7.87 (dt, J=8.0, 1.9 Hz, 1H), 7.34 (dd, J=8.0, 4.7 Hz, 1H), 6.52 (d, J=16.0 Hz, 1H), 6.45 (dt, J=16.0, 6.5 Hz, 1H), 3.21 (d, J=6.5 Hz, 2H).

Procedure for the synthesis of GNTbm-04, GNTbm-05, GNTbm-11, GNTbm-33, GNTbm-38, and GNTbm-39. To a solution of compound 12 (1 eq), compound 13 (1.1 eq), and HATU (1.1 eq) in DMF was added DIPEA (1~2.5 eq). The mixture was stirred at RT for 1~4 h (monitored by LCMS). Aniline (1.1 eq), HATU (1.1 eq), and DIPEA (1~2.5 eq) were added to the reaction mixture. The mixture was stirred at RT for another 1~4 h (monitored by LCMS). The mixture was diluted with EA, washed with water, brine, and dried over Na2SO4. The mixture was filtered and concentrated to dryness. The crude product was purified by column chromatography to give the desired product.

GNTbm-04, Yield: 45 mg, 40%. $^1$H NMR (600 MHz, DMSO-d6) δ 10.60 (s, 1H), 9.86 (s, 1H), 8.92 (d, J=1.8 Hz, 1H), 8.63 (d, J=1.8 Hz, 1H), 8.44 (d, J=4.8 Hz, 1H), 8.25 (dd, J=8.7, 2.1 Hz, 1H), 8.09 (d, J=9 Hz, 1H), 7.91 (d, J=7.8 Hz, 1H), 7.38-7.32 (m, 2H), 6.62-6.55 (m, 3H), 6.39(td, J=8.7, 2.4 Hz, 1H), 5.20 (s, 2H), 3.42 (d, J=6 Hz, 2H). $^{13}$C NMR (100 MHz, DMSO-d$_6$): δ 40.48, 101.95, 102.12, 102.41, 102.56, 119.74, 122.81, 123.69, 125.78, 126.52, 126.73, 126.79, 129.29, 132.28, 132.57, 138.25, 138.95, 144.37, 144.41, 147.80, 148.40, 159.74, 161.33, 162.27, 169.76. LCMS (ESI) m/z 392.4 [M+H]$^+$. HPLC purity: 96.12%.

GNTbm-05, Yield: 88 mg, 53%. $^1$H NMR (600 MHz, DMSO-d6) δ 10.60 (s, 1H), 9.94 (s, 1H), 8.92 (d, J=1.6 Hz, 1H), 8.63 (d, J=1.5 Hz, 1H), 8.44 (d, J=4.7 Hz, 1H), 8.26 (dd, J=8.5, 2.0 Hz, 1H), 8.11 (d, J=8.6 Hz, 1H), 7.91 (d, J=8.0 Hz, 1H), 7.50 (d, J=7.9 Hz, 1H), 7.36 (dd, J=7.9, 4.8 Hz, 1H), 6.94 (t, J=7.6 Hz, 1H), 6.82 (d, J=7.9 Hz, 1H), 6.65 (t, J=7.9 Hz, 1H), 6.61-6.57 (m, 2H), 4.88 (s, 2H), 3.42 (d, J=6.0 Hz, 2H). $^{13}$C NMR (100 MHz, DMSO-d$_6$): δ 40.49, 116.75, 117.01, 122.76, 123.68, 124.16, 124.29, 125.67, 125.78, 126.58, 129.29, 132.28, 132.56, 138.26, 138.97, 141.56, 144.44, 147.80, 148.39, 161.86, 169.76. LCMS (ESI) m/z 374.3 [M+H]$^+$. HPLC purity: 99.32%.

GNTbm-11, Yield: 48 mg, 22%. $^1$H NMR (600 MHz, DMSO-d6) δ 10.62 (s, 1H), 10.01 (s, 1H), 8.94 (d, J=1.9 Hz, 1H), 8.63 (d, J=1.6 Hz, 1H), 8.44 (d, J=4.6 Hz, 1H), 8.26 (dd, J=8.6, 2.3 Hz, 1H), 8.11 (d, J=8.6 Hz, 1H), 7.91 (d, J=8.0 Hz, 1H), 7.77 (s, 1H), 7.36 (dd, J=7.9, 4.7 Hz, 1H), 7.27 (d, J=8.5 Hz, 1H), 6.91 (d, J=8.4 Hz, 1H), 6.62-6.55 (m, 2H), 5.63 (s, 2H), 3.42 (d, J=6.0 Hz, 2H). $^{13}$C NMR (100 MHz, DMSO-d$_6$): δ 40.49, 115.71, 121.95, 122.90, 122.94, 123.68, 125.76, 126.55, 129.30, 132.28, 132.57, 138.42, 138.97, 144.13, 145.75, 147.80, 162.50, 169.79. LCMS (ESI) m/z 442.4 [M+H]$^+$. HPLC purity: 93.63%.

GNTbm-33 Yield: 63 mg, 16%. $^1$H NMR (600 MHz, DMSO-d6) δ 10.32 (s, 1H), 9.60, (s, 1H), 8.63 (d, J=1.9 Hz, 1H), 8.44 (d, J=4.7, 1.5 Hz, 1H), 7.97 (d, J=8.7 Hz, 2H), 7.91 (dt, J=8.0, 1.8 Hz, 1H), 7.74 (d, J=8.7 Hz, 2H), 7.51 (d, J=1.2 Hz, 1H), 7.36 (dd, J=7.9, 4.8 Hz, 1H), 7.27 (dd, J=8.5, 1.7 Hz, 1H), 6.88 (d, J=8.4 Hz, 1H), 6.62-6.55 (m, 2H), 5.65 (s, 2H), 3.38 (d, J=5.5 Hz, 2H). $^{13}$C NMR (100 MHz, DMSO-d$_6$): δ 40.70, 115.22, 115.42, 115.63, 118.21, 122.44, 123.33, 123.69, 123.79, 124.10, 125.89, 126.19, 128.71, 128.82, 129.06, 132.34, 132.54, 142.05, 146.76, 147.78, 148.35, 165.15, 169.21. LCMS (ESI) m/z 441.4 [M+H]$^+$. HPLC purity: 96.40%.

GNTbm-33, Yield: 108 mg, 47%. $^1$H NMR (600 MHz, DMSO-d6) δ 10.30 (s, 1H), 9.56 (s, 1H), 8.63 (d, J=1.9 Hz, 1H), 8.44 (dd, J=4.7, 1.4 Hz, 1H), 7.96 (d, J=8.6 Hz, 2H), 7.91 (dt, J=8.0, 1.9 Hz, 1H), 7.73 (d, J=8.7 Hz, 2H), 7.36 (dd, J=7.9, 4.7 Hz, 1H), 7.16 (d, J=7.5 Hz, 1H), 6.96 (dt, J=7.9, 1.4 Hz, 1H), 6.78 (dd, J=8.0, 1.2 Hz, 1H), 6.62-6.57 (m, 3H), 4.87 (s, 2H), 3.37 (d, J=5.5 Hz, 2H). $^{13}$C NMR (100 MHz, DMSO-d$_6$): δ 40.69, 116.10, 116.24, 118.23, 118.34, 123.46, 123.68, 126.20, 126.32, 126.60, 128.66, 129.0, 129.04, 132.33, 132.53, 141.87, 143.08, 147.78, 148.34, 164.67, 169.17. LCMS (ESI) m/z 373.4 [M+H]$^+$. HPLC purity: 94.41%.

GNTbm-39, Yield: 60 mg, 25%. $^1$H NMR (600 MHz, DMSO-d6) δ 10.30 (s, 1H), 9.49 (s, 1H), 8.62 (d, J=2.0 Hz, 1H), 8.44 (dd, J=4.7, 1.6 Hz, 1H), 7.95 (d, J=8.6 Hz, 2H), 7.90 (dt, J=8.0, 1.9 Hz, 1H), 7.72 (d, J=8.7 Hz, 2H), 7.36 (dd, J=7.9, 4.8 Hz, 1H), 7.11 (dd, J=8.4, 6.6 Hz, 1H), 6.62-6.57 (m, 2H), 6.54 (dd, J=11.2, 2.9 Hz, 1H), 6.35 (td, J=8.5, 2.8 Hz, 1H), 5.20 (s, 2H), 3.37 (d, J=5.5 Hz, 2H). $^{13}$C NMR (100 MHz, DMSO-d$_6$): δ 40.69, 101.35, 101.52, 101.92, 102.07, 118.20, 118.32, 119.40, 123.68, 126.20, 128.42, 128.49, 128.68, 128.89, 129.05, 132.33, 132.53, 141.89, 145.38, 145.45, 147.78, 148.34, 160.14, 161.73, 164.95, 169.17. LCMS (ESI) m/z 391.4 [M+H]$^+$. HPLC purity: 94.66%.

Synthesis of GNTbm-37

To a solution of GNTbm-39 (0.11 g, 0.3 mmol), in MeOH (2 mL) was added Pd/C (22 mg) and stirred at RT for 8~16 h. The mixture was filtered through a Celite pad and the filtrate was concentrated to dryness to give GNTbm-37 (95 mg, 86%) as a white solid.

GNTbm-37, Yield: 110 mg, 49%. $_1$H NMR (600 MHz, DMSO-d6) δ 10.20 (s, 1H), 9.52 (s, 1H), 8.45 (s, 1H), 8.41 (d, J=4.0 Hz, 1H), 7.93 (d, J=8.2 Hz, 2H), 7.70 (d, J=8.1 Hz, 2H), 7.66 (d, J=7.6 Hz, 1H), 7.32 (dd, J=7.3, 4.9 Hz, 1H), 7.10 (t, J=7.1 Hz, 1H), 6.54 (dd, J=11.1, 2.0 Hz, 1H), 6.35 (t, J=7.2 Hz, 1H), 5.21 (s, 2H), 2.66 (t, J=7.4 Hz, 2H), 2.38 (t, J=7.2 Hz, 2H), 1.93 (m, J=7.4 Hz, 2H). $^{13}$C NMR (100 MHz, DMSO-d$_6$): δ 26.20, 31.56, 35.63, 99.13, 101.36, 101.52, 101.91, 102.06, 118.07, 119.44, 123.45, 128.44, 128.64, 135.84, 136.95, 142.06, 145.39, 145.47, 147.22, 149.63, 160.13, 161.71, 164.98, 171.20. LCMS (ESI) m/z 393.4 [M+H]$^+$. HPLC purity: 95.87%.

GNTbm-06 and GNTbm-12

The synthetic route is shown below:

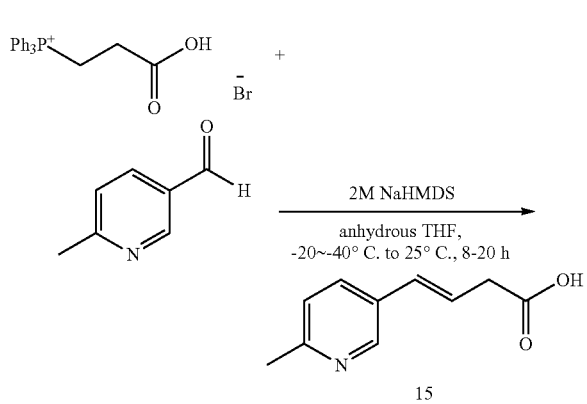

15

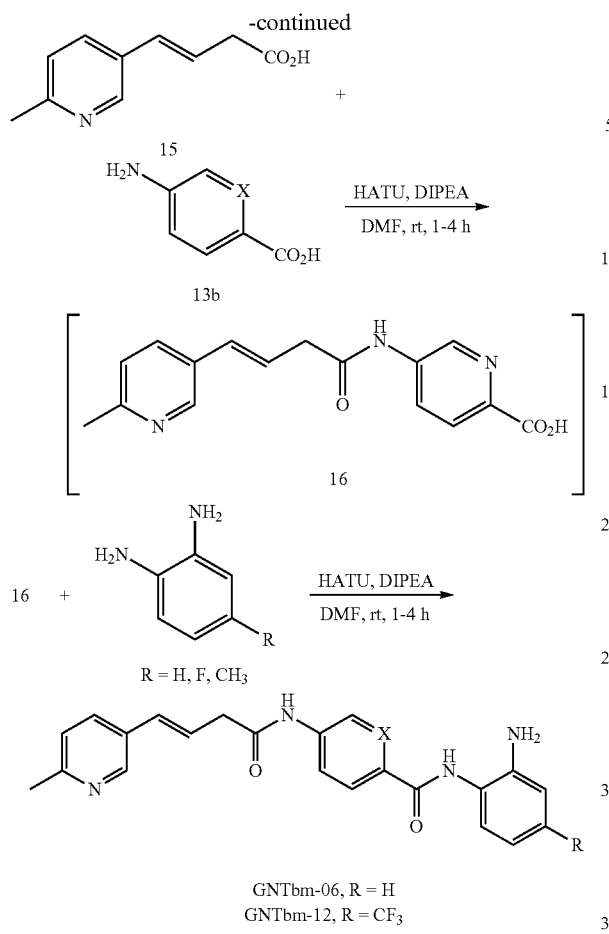

GNTbm-06, R = H
GNTbm-12, R = CF₃

(E)-4-(6-methyl-3-pyridyl)but-3-enoic acid(15), To a dried round-bottomed flask with 2-carboxyethyl(triphenyl) phosphonium bromide (37.7 g, 90.8 mmol) anhydrous THF (200 ml) was added and the solution was cooled to −20~40° C. To the white suspension was added 2.00M NaHMDS in THF (82.6 ml) dropwise. The resulting orange solution was stirred for 1-5 h at −20~40° C. 6-methylpyridine-3-carbaldehyde (10.0 g, 82.6 mmol) was added, and the resulting mixture was stirred at room temperature for 8-20 h. The reaction mixture was quenched with water (10 mL) and concentrated to dryness. The mixture was added water (300 mL) and washed with EA (200 mL) and DCM (200 mL). The organic layer was removed and the aqueous layer was acidified by 6N HCl(aq.), and washed with EA (200 mL) and DCM (200 mL). The organic layer was removed and the aqueous layer was adjusted pH by 4N NaOH(aq.) and concentrated to dryness. The residue was purified by column chromatography to give (E)-4-(6-methyl-3-pyridyl)but-3-enoic acid (5.10 g, 35%) as a white solid.

Procedure for the synthesis of GNTbm-06, and GNTbm-12. To a solution of compound 15 (1 eq), compound 13b (1.1 eq), and HATU (1.1 eq) in DMF was added DIPEA (1~2.5 eq). The mixture was stirred at RT for 1~4 h (monitored by LCMS). Aniline (1.1 eq), HATU (1.1 eq), and DIPEA (1~2.5 eq) were added to the reaction mixture. The mixture was stirred at RT for another 1~4 h (monitored by LCMS). The mixture was diluted with EA, washed with water, brine, and dried over Na2SO4. The mixture was filtered and concentrated to dryness. The crude product was purified by column chromatography to give the desired product.

GNTbm-06, Yield: 95 mg, 43%. $^1$H NMR (600 MHz, DMSO-d6) δ 10.59 (s, 1H), 9.94 (s, 1H), 8.91 (s, 1H), 8.47 (s, 1H), 8.26 (dd, J=8.7, 2.0 Hz, 1H), 8.11 (d, J=8.6 Hz, 1H), 7.80 (d, J=8.1 Hz, 1H), 7.50 (d, J=7.9 Hz, 1H), 7.22 (d, J=8.0 Hz, 1H), 6.94 (t, J=7.6 Hz, 1H), 6.82 (d, J=7.9 Hz, 1H), 6.65 (t, J=7.6 Hz, 1H), 6.57 (d, J=16.1 Hz, 1H), 6.50 (dt, J=15.5, 7.0 Hz, 1H), 4.88 (s, 2H), 3.40 (d, J=6.7 Hz, 2H), 2.45 (s, 3H). $^{13}$C NMR (100 MHz, DMSO-d$_6$): δ 23.71, 40.49, 116.75, 117.01, 122.75, 122.98, 124.16, 124.29, 124.48, 125.66, 126.56, 129.25, 129.47, 132.80, 138.28, 138.96, 139.05, 141.55, 144.43, 147.12, 156.80, 161.86, 169.87. LCMS (ESI) m/z 388.4 [M+H]$^+$. HPLC purity: 94.56%.

GNTbm-12, Yield: 45 mg, 14%. $^1$H NMR (600 MHz, DMSO-d6) δ 10.61 (s, 1H), 10.01 (s, 1H), 8.94 (d, J=2.2 Hz, 1H), 8.48 (d, J=1.7 Hz, 1H), 8.26 (dd, J=8.6, 2.3 Hz, 1H), 8.11 (d, J=8.6 Hz, 1H), 7.80 (dd, J=8.1, 2.0 Hz, 1H), 7.77 (s, 1H), 7.27 (d, J=8.4 Hz, 1H), 7.22 (d, J=8.1 Hz, 1H), 6.91 (d, J=8.4 Hz, 1H), 6.57 (d, J=16.1 Hz, 1H), 6.50 (dt, J=15.8, 6.9 Hz, 1H), 5.63 (s, 2H), 3.40 (d, J=6.8 Hz, 2H), 2.45 (s, 3H). $^{13}$C NMR (100 MHz, DMSO-d$_6$): δ 23.70, 40.49, 115.71, 121.92, 122.90, 122.94, 122.98, 124.46, 126.53, 129.26, 129.47, 132.80, 138.43, 138.96, 144.11, 145.74, 147.12, 156.81, 162.49, 169.89. LCMS (ESI) m/z 456.5 [M+H]$^+$. HPLC purity: 92.94%.

Example 6 GNTbm-08, GNTbm-19, and GNTbm-25

The synthetic route is shown below:

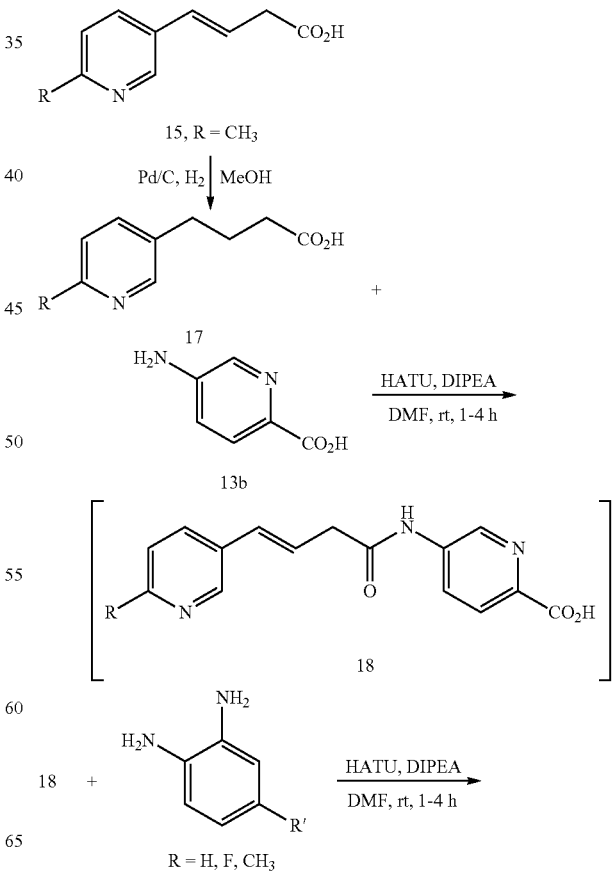

-continued

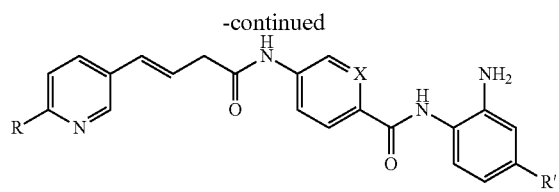

GNTbm-08, X = N, R = CH₃, R' = F
GNTbm-19, X = N, R = CH₃, R' = H
GNTbm-25, X = N, R = CH₃, R' = CF₃

4-(6-Methylpyridin-3-yl)butanoic acid (17) To a solution of 15 (1 g, 5.6 mmol), in MeOH (10 mL) was added Pd/C (200 mg) and stirred at RT for 1~8 h. The mixture was filtered through a Celite pad and the filtrate was concentrated to dryness to give compound 17 (1 g, 99%) as a white solid. $^1$H NMR (600 MHz, DMSO-d6) δ 12.07 (s, 1H), 8.26 (d, J=2.0 Hz, 1H), 7.49 (dd, J=7.9, 2.3 Hz, 1H), 7.16 (d, J=7.9 Hz, 1H), 2.55 (t, J=7.7 Hz, 1H), 2.41 (s, 1H), 2.20 (t, J=7.4 Hz, 1H), 1.77 (quint, J=7.5 Hz, 1H).

Procedure for the synthesis of GNTbm-08, GNTbm-19, and GNTbm-25. To a solution of compound 17 (1 eq), compound 13b (1.1 eq), and HATU (1.1 eq) in DMF was added DIPEA (1~2.5 eq). The mixture was stirred at RT for 1~4 h (monitored by LCMS). Aniline (1.1 eq), HATU (1.1 eq), and DIPEA (1~2.5 eq) were added to the reaction mixture. The mixture was stirred at RT for another 1~4 h (monitored by LCMS). The mixture was diluted with EA, washed with water, brine, and dried over Na₂SO₄. The mixture was filtered and concentrated to dryness. The crude product was purified by column chromatography to give the design product.

GNTbm-8, Yield: 35 mg, 25%. $^1$H NMR (600 MHz, DMSO-d6) δ 10.41 (s, 1H), 9.85 (s, 1H), 8.86 (d, J=2.3 Hz, 1H), 8.31 (d, J=1.9 Hz, 1H), 8.23 (dd, J=8.6, 2.4 Hz, 1H), 8.07 (d, J=8.5 Hz, 1H), 7.53 (dd, J=7.9, 2.1 Hz, 1H), 7.34 (dd, J=8.6, 6.4 Hz, 1H), 7.17 (d, J=7.9 Hz, 1H), 6.58 (dd, J=11.1, 2.9 Hz, 1H), 6.39 (td, J=12.8, 2.8 Hz, 1H), 5.19 (s, 2H), 2.62 (t, J=7.5 Hz, 2H), 2.42 (s, 3H), 2.40 (t, J=7.5 Hz, 2H), 1.92 (quint, J=7.5 Hz, 2H). $^{13}$C NMR (100 MHz, DMSO-d₆): δ 23.54, 26.90, 31.10, 35.47, 101.97, 102.14, 102.42, 102.57, 119.78, 122.68, 126.31, 126.67, 126.74, 133.58, 136.13, 138.53, 138.83, 144.16, 144.33, 148.78, 155.29, 159.72, 161.31, 162.29, 171.76. LCMS (ESI) m/z 408.5 [M+H]⁺. HPLC purity: 93.92%.

GNTbm-19, Yield: 43 mg, 20%. $^1$H NMR (600 MHz, DMSO-d6) δ 10.42 (s, 1H), 9.92 (s, 1H), 8.86 (s, 1H), 8.31 (s, 1H), 8.25 (d, J=8.5 Hz, 1H), 8.09 (d, J=8.5 Hz, 1H), 7.53 (d, J=7.9 Hz, 1H), 7.50 (d, J=7.8 Hz, 1H), 7.17 (d, J=7.9 Hz, 1H), 6.94 (t, J=7.6 Hz, 1H), 6.82 (d, J=7.9 Hz, 1H), 6.65 (t, J=7.6 Hz, 1H), 4.88 (s, 2H), 2.62 (t, J=7.4 Hz, 2H), 2.42 (s, 3H), 2.40 (t, J=7.4 Hz, 2H), 1.92 (quint, J=7.4 Hz, 2H). $^{13}$C NMR (100 MHz, DMSO-d₆): δ 23.53, 26.09, 31.10, 35.47, 116.76, 117.02, 122.68, 124.20, 124.23, 125.63, 126.36, 133.25, 136.14, 138.36, 136.85, 141.51, 144.20, 148.77, 155.28, 161.87, 171.77. LCMS (ESI) m/z 390.4 [M+H]⁺. HPLC purity: 99.12%.

GNTbm-25, Yield: 30 mg, 12%. $^1$H NMR (600 MHz, DMSO-d6) δ 10.43 (s, 1H), 10.00 (s, 1H), 8.88 (d, J=1.7 Hz, 1H), 8.31 (s, 1H), 8.24 (dd, J=8.7, 1.8 Hz, 1H), 8.09 (d, J=8.5 Hz, 1H), 7.77 (s, 1H), 7.53 (dd, J=8.1, 1.8 Hz, 1H), 7.26 (d, J=8.3 Hz, 1H), 7.17 (d, J=7.9 Hz, 1H), 6.91 (d, J=8.4 Hz, 1H), 5.62 (s, 2H), 2.62 (t, J=7.5 Hz, 2H), 2.42 (s, 3H), 2.40 (t, J=7.1 Hz, 2H), 1.92 (quint, J=7.4 Hz, 2H). $^{13}$C NMR (100 MHz, DMSO-d₆): δ 23.54, 26.09, 31.11, 35.48, 115.73, 116.07, 116.28, 131.89, 122.69, 122.89, 122.94, 124.06, 125.85, 126.34, 133.58, 136.14, 138.52, 138.86, 143.88, 145.71, 148.78, 155.30, 162.52, 171.80. LCMS (ESI) m/z 458.5 [M+H]⁺. HPLC purity: 92.03%.

Example 7 Determination of Saturation Solubility of Chidamide, GNTbm-02, GNTbm-03, GNTbm-04, and GNTbm-06

Samples of 5 mg of compounds were added to 5 ml volumetric flasks containing ddH₂O and shaken at 100 rpm in an incubator at 25° C. for 90 minutes. The resulting suspension was filtered through a 0.22 μm filter. The concentrations of compounds were determined spectrophotometrically at 256 nm. The saturation solubility of each sample was determined in triplicates and the mean value and standard deviation were reported.

Example 8 In Vitro Cytotoxicity Assay

Six different cell lines were used, including human breast cancer cell line MDA-MB-231 (6×10³), MDA-MB-453 (2.4×10⁴), SK-BR-3 (6×10³), human breast epithelial cell line M10 (6×10³), human gastric carcinoma NCI-N87 (2.4×10⁴), and human colorectal adenocarcinoma SW48 (2.4×10⁴), and seeded in a 96 well plate. Cell lines were obtained from Bioresource Collection and Research Center, BCRC, Taiwan. All cell lines were treated with the compounds including GNTbm compound series, Chidamide (as positive control) and Entinostat (as positive control), with doses ranging from 50 μM to 0.39 μM, and then incubated at 37° C. under 5% CO₂ for 72 h. After 72 h, MTT assay (Cayman™) was used to determine the cellular viability. MDA-MB-231, MDA-MB-453, SK-BR-3 cell lines were maintained in DMEM/F12 supplemented with 10% FBS, 0.2% antibiotic (MycoZap™, Pulse-CL). M10 cell line was maintained in MEM Alpha (gibco™) supplemented with 10% FBS, 0.2% antibiotic (MycoZap™, Pulse-CL). NCI-N87 cell line was maintained in RPMI 1640 (CORNING™) supplemented with 10% FBS, 0.2% antibiotic (MycoZap™, Pulse-CL). SK-BR-3 cell line was maintained in DMEM (CORNING™) supplemented with 10% FBS, 0.2% antibiotic (MycoZap™, Pluse-CL).

Example 9 Measurement of IC₅₀ on HDACs 1, 2, and 3 Enzymatic Inhibitions was Determined HDACs assay was performed according to standard Protocols (Fluorgenic HDACs 1, 2, and 3 assay kit, BPS Bioscience™). All of the compounds, with Chidamide and Entinostat as positive control, at doses ranging from 20 μM to 1.28 nM, were mixed with kit buffer and incubated at 37° C. for 1 hour. After 1 h, assay developer was added to the samples and the absorbance was read at fluorogenic wavelength. The relative inhibition to HDACs 1, 2, and 3 activities in each sample was determined.

Example 10 Enzyme Inhibition Kinetic of HDAC3 by GNTbm-02 was Determined

HDAC3 enzymatic kinetic assay was performed according to standard Protocols (Fluorgenic HDAC3 assay kit, BPS Bioscience™). Series of GNTbm-01, GNTbm-02, and GNTbm-03 compounds, Chidamide and Entinostat at dose of 2 μM were mixed with kit buffer and incubated at 37° C. for 20 min, 40 min and 60 min. After incubation, assay developer was added to the samples and the absorbance was read at fluorogenic wavelength. The relative inhibition to HDAC3 activity in each sample was determined.

Example 11 Comparison of $IC_{50}$ Between GNTbm-02 and Entinostat (MS-275) on HDACs 1-11 Enzymatic Inhibition was Determined The finished assay report is from BPS Bioscience Inc. (6042 Cornerstone Court West, Ste. B, San Diego, CA 92121, USA). The purpose of the study is to determine the effects of two compounds of GNTbm-02 and positive control Entinostat (MS-275) on the activities of recombinant HDAC1, HDAC2, HDAC3, HDAC4, HDAC5, HDAC6, HDAC7, HDAC8, HDAC9, and HDAC11 using an in vitro enzymatic assay. HDAC assay was performed according to standard Protocols (Fluorgenic HDACs 1-11 assay kit, BPS Bioscience™). GNTbm-02 and Entinostat (positive control) at doses ranging from 10 µM to 0.51 nM were mixed with kit buffer and incubated at 37° C. for 0.5 hours. After 0.5 h, assay developer was added to the samples and the absorbance was read at fluorogenic wavelength. The relative inhibition to HDACs 1, 2, 3, 4, 5, 6, 7, 8, 9, and 11 activities was determined in each sample. More details are described below. All of the compounds were dissolved in DMSO. The serial dilution of the compounds was first performed in 100% DMSO with the highest concentration at 1 mM. Each intermediate compound dilution (in 100% DMSO) would then get directly diluted 10× fold into assay buffer for an intermediate dilution of 10% DMSO in HDAC assay buffer and 5 µl of the dilution was added to a 50 µl reaction so that the final concentration of DMSO is 1% in all of the reactions. The enzymatic reactions for the HDAC enzymes were conducted in duplicate at 37° C. for 30 minutes in a 50 µl mixture containing HDAC assay buffer, 5 µg BSA, an HDAC substrate, a HDAC enzyme and a test compound. After enzymatic reactions, 50 µl of 2× HDAC Developer was added to each well for the HDAC enzymes and the plate was incubated at room temperature for an additional 15 minutes. Fluorescence intensity was measured at an excitation of 360 nm and an emission of 460 nm using a Tecan Infinite M1000 microplate reader. HDAC activity assays were performed in duplicate at each concentration. The fluorescent intensity data were analyzed using the computer software, Graphpad Prism. In the absence of the compound, the fluorescent intensity (Ft) in each data set was defined as 100% activity. In the absence of HDAC, the fluorescent intensity (Fb) in each data set was defined as 0% activity. The percent activity in the presence of each compound was calculated according to the following equation: % activity= (F−Fb)/(Ft−Fb), where F=the fluorescent intensity in the presence of the compound. The values of % activity versus a series of compound concentrations were then plotted using non-linear regression analysis of Sigmoidal dose-response curve generated with the equation Y=B+(T−B)/1+10 ((LogEC50−X)×Hill Slope), where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

Example 12 Cell Apoptosis and Cell Cycle Arrest were Analyzed by Flow Cytometry

A PI/RNase staining assay (BD Bioscience™) was performed to reveal the presence of cell cycle arrest and apoptotic cells after treatment with GNTbm compounds, Chidamide and Entinostat. Human breast cancer cell line MDA-MB-231($1.5×10^5$) and human breast epithelial cell line M10 ($1.5×10^5$) were treated with GNTbm compounds, Chidamide and Entinostat (1.625 to 25 µM), respectively, for 72 h or treated with indicated doses from 3 h to 72 h. Human colorectal adenocarcinoma SW48 cells ($5×10^5$) were treated with GNTbm compounds series, Chidamide and Entinostat (as indicated doses) for 72 h or treated at concentration of an indicated dose from 3 h to 72 h. After treatment cells were harvested, fixed with 80% ethanol for 24 h, washed with 1×PBS and stained with PI/RNase for 15 min at room temperature. The cells were then analyzed using Flow Cytometer within 1 h.

Example 13 Western Blot Assay

Human breast cancer MDA-MB-231 cells and human colorectal adenocarcinoma SW48 cells were analyzed. MDA-MB-231 and SW48 were obtained from Bioresource Collection and Research Center (BCRC, Taiwan). MDA-MB-231 and SW48 were grown at 37° C. under humidified air supplemented without $CO_2$ in Leibovitz's L-15 (cat. #11415114, Thermo Fisher Scientific) containing 10% heat inactivated fetal calf serum (Thermo Scientific), 1× concentration of MycoZap antibiotics (cat. #VZA-2011, Lonza). Cells were treated with GNTbm compounds series, Chidamide or Entinostat for different time periods or at varied doses. Cells were treated with indicated doses for 24 h or cells were treated with indicated doses for different time periods. Cell pellets were dissolved with RIPA buffer (cat. #20-188, Merck) with protease and phosphatase inhibitors (cat. #K272, BioVision) and clarified by centrifugation. Equal amounts of total protein were resolved by SDS-PAGE and transferred to polyvinylidene fluoride membranes (cat. #1620177, BIO-RAD). Blots were incubated with primary antibodies against β-actin (cat. #sc-47778, Santa Cruz Biotechnology), Histone 3ac (cat. #61637, Active Motif), and HRP secondary antibodies anti-rabbit (ab6721, Abcam) and anti-mouse (sc-2005, Santa Cruz). Blots were developed using the ECL Western Blotting Substrate (cat. #sc-2048, Santa Cruz Biotechnology). Image blots were analyzed with the iBright FL1000 (Thermo Fisher Scientific) imaging systems.

Example 14 Anti-cancer Activity in Animal Models

Animal study was approved and overseen by the Taipei Medical University Institutional Animal Care and Use Committee (TMU IACUC, NO: LAC-2019-0286, LAC-2020-0306). Six- to eight-week-old male BALB/c mice (National Laboratory Animal Center, Taiwan) were used in each treatment group for all animal experiments. Tumors were established by s.c. injection of $1×10^6$ or $5×10^6$ CT26 cells [(CRL-2638; murine colorectal adenocarcinoma). CT26 cell line was purchased from ATCC. CT26 tumor cells were grown in McCoy's 5A supplemented with 10% (vol/vol) FBS at 37° C., 5% $CO_2$. CT26 cells were mixed with Matrigel (cat. #354248, Corning®) and inoculated into the left flank of mice, and tumor growth was determined by measuring two perpendicular diameters. Tumors were allowed to grow for 8-11 days (tumor size about 150-250 $mm^3$) before randomization and treatment. Animals were euthanized when tumors reached more than 3000 $mm^3$ in diameter. CT26-bearing mice were given 2.5 mg/kg of anti-IgG (cat. #BE0089, Lot #716719J3, Bio X Cell) and anti-PD-1 (cat. #BE0146, Lot #735019J3, Bio X Cell) antibody by i.p. administration on days 8, 11, 14, 17, 20 and 23 post tumor implantation, and all antibodies were diluted to appropriate concentrations in 100 μL of sterile PBS (pH 7.4) (Invitrogen Life Technologies). Regorafenib (HY-1031, 30 mg/kg, po daily, MedChemExpress USA), Celecoxib (50 mg/kg, po daily capsule/Celebrex®), Chidamide-K30 (50 mg/kg, po daily, produced from GNTbm, Taipei, Taiwan) and GNTbm-02/k30, GNTbm-03/k30, GNTbm-04/k30, GNTbm-05/k30, GNTbm-06/k30, GNTbm-11/k30, GNTbm-38/k30, GNTbm-39/k30 compounds (50, 25 or 12.5 mg/kg, dissolved in water to create stock solutions, po daily) were orally administered to treat tumor bearing mice at various doses daily from day 8 to day 23 for 16 days. The anti-cancer activity was measured from the start of the treatment until the tumor volume reached 3,000 mm$^3$. Tumor volume was calculated as length×width$^2$×0.5.

Example 15 Survival Rate in Animal Models

The administration of antibody or drugs was performed for 16 days from day 8 to day 23. The tumor continued to grow in the tumor-bearing mice. The tumor volume of the mice was measured once every three or four days (twice/week). The tumor-bearing mice were regarded as dead when the tumor volume reached 3,000 mm$^3$. All treatment groups were recorded and analyzed.

Example 16 Tumor Rechallenge Study in Tumor-bearing Mice Animal Model

All mice with PR/CR response after treatment went rechallenged with CT26 cells on the contralateral side (please see Table 6). The rechallenge with CT26 was performed on day 33, which was 7 days (day 33) after first tumor assessment (day 26), with injection of 5×10$^6$ CT26 cells to the right flank of each mouse. After rechallenge with CT26 cells, the tumor was allowed to grow for another 7 days (day 40) to determine the baseline as 1 fold. After a further 10 days (day 50), the tumor growth was evaluated for the rechallenge. If both of the following criteria are met, the response will be considered as relapse: first, the tumor size over 2 folds when compared to that of baseline; second, the tumor volume at day 50 was over 300 mm$^3$. Relapse happens when immune memory activity is not sufficiently activated. If the tumor growth is inhibited, it means the immune memory is activated.

Example 17 Flow Cytometry

The following antibodies and reagents were used for flow cytometry: CD8a PerCP-Cy5.5 (53-6.7; BioLegend), CD4 PE (GK 1.5; BioLegend), CD25 PerCP-Cy5.5 (PC61; BioLegend), Foxp3 PE (MF14; BioLegend), CD3 APC (17A2; BioLegend), CD11b APC (M1/70; BioLegend), Ly-6C PerCP-Cy5.5 (HK 1.4; BioLegend), Ly-6G PE (1A8; BioLegend), MHC-11-PE (BM8; BioLegend), CD45 FITC (30-F11; BioLegend). Flow cytometry was performed on a FACS Caliber flow cytometer (BD Biosciences) and the data were analyzed with FACS Diva software (BD Biosciences). To assess the level of circulating cell population, blood samples were collected from the mice on days 8, 12, 16 after initiation of the anti-PD-1 antibody (2.5 mg/kg) treatments with or without GNTbm-02 (12.5-50 mg/kg) or Chidamide (50 mg/kg, as positive control) plus Celecoxib (50 mg/kg). One hundred and fifty microliters of blood were collected in a K2EDTA BD Microtainer (BD Biosciences) from either the right or left facial vein. RBCs from anticoagulated blood samples were immediately lysed using 2 mL of 1× RBC lysis buffer (Qiagen, Valencia, CA) for 10 min, and the samples were washed twice in ice-cold PBS (BD Biosciences). The samples were stained with the appropriate antibodies. For analysis, we used previously established phenotypic criteria of these cells as CD45$^+$CD11b$^+$Ly6G$^+$Ly6C$^-$ (PMN-MDSC), CD45$^+$CD11b$^+$Ly6G$^-$Ly6C$^+$ cells (M-MDSC), CD45$^+$CD3$^+$CD25$^+$Foxp3$^+$ cells (Treg), CD45$^+$CD11b$^+$MHC-11$^+$Ly6C$^+$ cells (TAM), and CD45$^+$CD3$^+$CD4$^+$/CD45$^+$CD3$^+$CD8$^+$ cells (CD4$^+$ or CD8$^+$ T cell). Total mononuclear cells were used as a common denominator. To assess the level of tumor-infiltrating lymphocytes in tumor, the intratumoral CD8$^+$, CD4+, regulatory T-cell (Treg), PMN-MDSC, M-MDSC, and TAM cells were first purified from tumor samples excised from mice 12 days after initiation of the anti-PD-1 antibody treatments with or without GNTbm-02 or Chidamide plus celecoxib. Briefly, primary tumor tissues were harvested, weighed, and minced to fine fragments. Collagenase IV (Sigma-Aldrich) at 1 mg/mL in HBSS (Invitrogen Life Technologies) was added to each sample at a ratio of 1 mL per 200 mg of tumor tissue. Samples were incubated on an end-over-end shaker for 150 min at 37° C. The resulting tissue homogenates were 0.4-μm filtered and washed three times in PBS (BD Biosciences), separated via Percoll gradient to isolate mononuclear cells, and 1×10$^6$ cells per sample were used for antibody labeling. CD8$^+$ T-cell level was assessed using previously established phenotypic criteria of CD45$^+$CD3$^+$CD8$^+$. Treg cell level was assessed using previously established phenotypic criteria of D45$^+$CD3$^+$CD25$^+$Foxp3$^+$. PMN-MDSC/M-MDSC cell level was assessed using previously established phenotypic criteria of CD45$^+$CD11b$^+$Ly6G$^+$Ly6C$^-$/CD45$^+$CD11b$^+$Ly6G$^-$Ly6C$^+$. TAM cell level was assessed using previously established phenotypic criteria of CD45$^+$CD11b$^+$MHC-11$^+$Ly6C$^+$, and total mononuclear cells were used as a common denominator.

Example 18 Anti-Cancer Activity in Nude Mice Model

Animal study was approved and overseen by the Taipei Medical University Institutional Animal Care and Use Committee (TMU IACUC, NO: LAC-2019-0086). Six- to eight-week-old male BALB/C nude mice (National Laboratory Animal Center, Taiwan) were used in each treatment group for all animal experiments. Tumors were established by s.c. injection of 5×10$^6$ CT26 cells with matrigel (cat. #354248, Corning®) into the left flank of mice, and growth determined by measuring two perpendicular diameters. Tumors were allowed to grow for 8 days (tumor size about 100~150 mm$^3$) before randomization and treatment. Animals were euthanized when tumor volume reached 3000 mm$^3$. CT26-bearing mice were given 2.5 mg/kg of anti-IgG (cat. #BE0089, Lot #716719J3, Bio X Cell) and anti-PD-1 (cat. #BE0146, Lot #735019J3, Bio X Cell) antibody by i.p. administration on days 8, 11, 14, 17, 20 and 23 post-implantation, and all antibodies were diluted to appropriate concentrations in 100 μL of sterile PBS (pH 7.4) (Invitrogen Life Technologies). GNTbm Compounds and celecoxib (capsule/Celebrex®, 200 mg) were administered orally on day 8 post-implantation. GNTbm compounds (dissolved in DMSO to create stock solutions) were diluted or suspended by water and orally administered to treat tumor-bearing mice at various doses daily from days 8 to 23. Celecoxib from capsule was orally administered to treat tumor-bearing mice at 50 mg/kg from days 8 to 23. The anti-cancer activity was

Results

A Series of Synthetic Picolinamide and Benzamide Derivatives of Potent and Novel Class I HDAC Inhibitors (Called GNTbm Compounds Series)

GNTbm has developed a series of novel class I HDAC inhibitors possessing potent epigenetic immunomodulatory properties, which could inhibit the enzyme activities of HDACs 1, 2, and 3. Our research found that class I HDAC inhibitors possessing potent regulatory capability in the tumor microenvironment (TME) greatly boosted the immune response against tumor growth. Therefore, to design and synthesize such novel class I HDAC inhibitors was an intriguing task for the enhancement of therapeutic effect in immunotherapy. Benzamide-based class I HDAC inhibitors had been studied in the field of controlling the TME, such as Entinostat (MS-275), Tucidinostat (Chidamide/HBI-8000), and Mocetinostat, etc. In this present study, we designed and synthesized a series of potent and novel class I HDAC inhibitors based on the structure of picolinamide. GNTbm-01 [6-((E)-4-(6-methylpyridin-3-yl)but-3-enamido)-N-(2-amino-4-fluorophenyl)pyridine-3-carboxamide] was the first synthetic novel compound based on the core structure of carboxamide as shown in FIG. 1 and Table 1. Compound GNTbm-01 was assayed for the enzymatic inhibition of HDACs 1, 2, and 3 as shown in Table 4. The results demonstrated that GNTbm-01 compound was a weaker class I HDAC inhibitor when compared with Entinostat or Chidamide. We optimized the structure and changed the position of an N atom that created a novel compound GNTbm-02 [5-((E)-4-(6-methylpyridin-3-yl)but-3-enamido)-N-(2-amino-4-fluorophenyl)picolinamide] as shown in FIG. 1 and Table 1. GNTbm-02 compound possesses the same molecular formula ($C_{22}H_{20}FN_5O_2$) as GNTbm-01 compound but only with a change in the position of an N atom in the core of picolinamide. As shown in Table 4, GNTbm-02 compound was very potent in the inhibition of enzymatic activity of HDACs 1, 2, and 3 when compared with Entinostat or Chidamide. The result also demonstrated that GNTbm-02 was more potent in the inhibition of HDACs 1, 2, and 3 enzyme activities than GNTbm-01. Next, we designed the benzamide-based compound GNTbm-03 with the removal of an N atom (that is, replaced with a C atom) and tested the difference on the inhibition of enzyme activities of HDACs 1, 2, and 3, in comparison with GNTbm-02. The synthetic benzamide-based class I HDAC inhibitor GNTbm-03 [[4-((E)-4-(6-methylpyridin-3-yl)but-3-enamido)-N-(2-amino-4-fluorophenyl)benzamide]] is shown in FIG. 1 and Table 1. As shown in Table 4, GNTbm-03 was shown to inhibit the enzyme activities of HDACs 1, 2, and 3. The results demonstrated that GNTbm-03 was potent to inhibit class I HDACs 1, 2, and 3 enzyme activities when compared with Entinostat or Chidamide. It is also shown that GNTbm-03 possessed similar inhibition of enzymatic activity of HDACs 1, 2, and 3 when compared with GNTbm-02. Taken together, picolinamide-based derivative GNTbm-02 was the first in its chemical class as a class I HDAC inhibitor. We were very interested in designing picolinamide-based and benzamide-based derivatives of potent and novel class I HDAC inhibitors. The novel series of GNTbm compounds were synthesized and assayed, such as GNTbm-04, GNTbm-05, GNTbm-06, GNTbm-08, GNTbm-11, GNTbm-12, GNTbm-19, GNTbm-25, GNTbm-33, GNTbm-37, GNTbm-38, and GNTbm-39.

To Analyze the Saturation Solubility of GNTbm-02, GNTbm-03, GNTbm-04, and GNTbm-06

The solubility was a very important decisive parameter for oral bioavailability. An analysis of the saturation solubility of GNTbm-02, GNTbm-03, GNTbm-04, and GNTbm-06 is shown in Table 2. The results showed that Chidamide possessed decreased saturation solubility when compared with GNTbm-02 and GNTbm-04. The saturation solubility of GNTbm-02 and GNTbm-04 was 33.6 and 7.2 µg/mL, respectively. These results suggested that GNTbm-02 and GNTbm-04 may possess better oral bioavailability compared to Chidamide.

In Vitro Cytotoxicity Assay of GNTbm Compounds Series

We evaluated the cytotoxicity effect of GNTbm compounds series in several cancer cell lines including three human breast cancer cell lines (SK-BR-3, MDA-MB-453, and MDA-MB-231), human colorectal adenocarcinoma SW48, human gastric carcinoma NCI-N87, and human breast epithelial cell line M10 (normal cell line). The results have demonstrated that Chidamide or Entinostat as a positive control markedly induced cytotoxicity effect especially in SK-BR-3 and MDA-MB-453 cells. Totally, six cell lines were sensitive to the treatment as shown in Table 3, 8, and 9. The compound GNTbm-01 partially induced cytotoxicity effect when compared with Entinostat. As shown in Table 3, the result demonstrated that GNTbm-02 was very potent in inducing cytotoxicity effect, especially in SK-BR-3, MDA-MB-453, and SW48 cells in comparison with GNTbm-01. This result demonstrated that the structure containing picolinamide core in GNTbm-02 was very important. The replacement of the picolinamide core structure with benzamide would hinder the cytotoxicity effect. As shown in Table 3, compound GNTbm-03 was weaker in inducing the cytotoxicity effect than GNTbm-02 in SK-BR-3, MDA-MB-231, and SW48 cells. This result suggested that GNTbm-02 with picolinamide core structure was superior in inducing cytotoxicity than GNTbm-03 with a benzamide core structure. Taken together, these results suggested that GNTbm-02 is a potent and novel class I HDAC inhibitor and possesses a potent capacity to induce cytotoxicity in several human cancer cells. Furthermore, we were interested in evaluating cytotoxicity effect of several novel synthetic picolinamide-based and benzamide-based derivatives. As shown in Table 8, the cytotoxicity effect of the picolinamide-based compounds were analyzed. GNTbm-04, GNTbm-05, GNTbm-06, and GNTbm-11 were more potent in inducing cytotoxicity effect in six cell lines than Chidamide or Entinostat. In the benzamide-based compounds, GNTbm-33, GNTbm-38, and GNTbm-39 were more potent in inducing the cytotoxicity effect than Chidamide or Entinostat. These data demonstrated that these novel picolinamide-based and benzamide-based derivatives were potent in inducing cytotoxicity effect than the well-known class I HDAC inhibitor Chidamide or Entinostat.

Picoliamide-based GNTbm Compounds Series for Inhibition of HDACs 1, 2, and 3

Figures 16A, 16B:
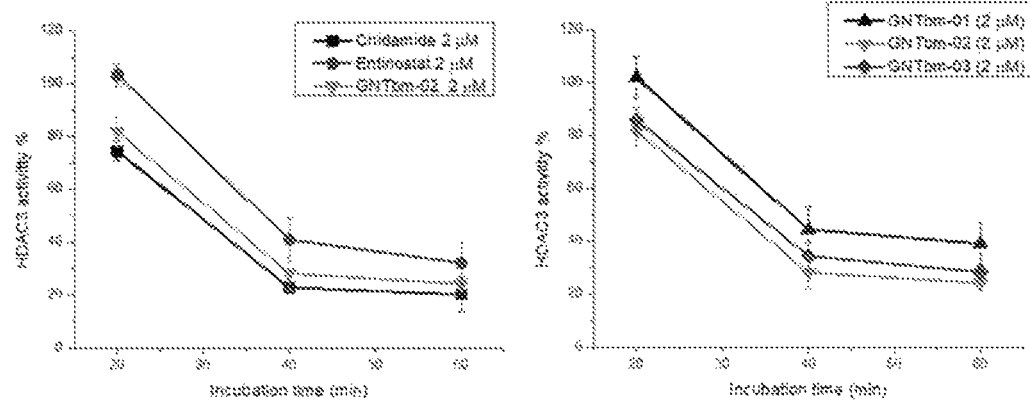
FIGS. 16A-16B show the effect of GNTbm-02 inhibiting the enzyme activity of HDAC3.

It was shown that GNTbm compounds series inhibited the enzyme activities of HDACs 1, 2, and 3 enzyme activities. As shown in Table 4 and 10, Entinostat as a positive control was a potent class I HDAC inhibitor selectively inhibiting HDACs 1, 2, and 3 enzyme activities. Chidamide (Tucidinostat) is another potent HDAC inhibitor approved for relapsed or refractory peripheral T cell lymphoma (PTCL) and advanced $ER^+/Her-2^-$ breast cancer by NMPA in China. Chidamide is a subtype-selective inhibitor for inhibition of enzymatic activity of HDACs 1, 2, 3, and 10. Both Entinostat and Chidamide showed potent inhibition of enzymatic activity of HDACs 1, 2, and 3 in Table 4. Next, GNTbm-01 was evaluated and demonstrated to possess mild potency for the inhibition of enzymatic activity of HDACs 1, 2, and 3 in comparison with Entinostat as shown in Table 4. Dramatically, GNTbm-02 possessed very potent activities to inhibit HDACs 1, 2, and 3 enzyme activities in the nanomolar level. The comparison of GNTbm-02 with Entinostat or Chidamide in the inhibition of enzyme activities of HDACs 1, 2, and 3 showed a similar inhibitory effect. These results suggested that GNTbm-02 is a potent and selective class I HDAC inhibitor. As shown in Table 4, GNTbm-03 was a potent HDAC inhibitor with an inhibitory effect similar to GNTbm-02. Next, the inhibition of HDAC 3 enzymatic kinetics was investigated. As shown in FIG. 16a, Chidamide and GNTbm-02 showed stronger inhibition of HDAC 3 enzyme activities than Entinostat. As shown in FIG. 16b, GNTbm-02 and GNTbm-03 showed stronger inhibition of HDAC 3 enzyme activities than GNTbm-01. Taken together, all these results suggested that GNTbm-02 containing picolinamide core structure may possess a more potent capacity to inhibit HDACs 1, 2, and 3 enzyme activities. Furthermore, we were interested in evaluating all the novel synthetic picolinamide-based GNTbm compounds as shown in Table 10. GNTbm-04, GNTbm-05, GNTbm-06, GNTbm-08, and GNTbm-11 were more potent in inhibiting HDAC 3 enzyme activities than Chidamide or Entinostat. GNTbm-05 and GNTbm-06 were more potent in inhibiting HDAC 1 enzyme activities than Chidamide or Entinostat. However, we also evaluated the novel synthetic benzamide-based GNTbm compound as shown in Table 11. GNTbm-38 and GNTbm-39 seem weaker with respect to inhibiting the activities of HDACs 1, 2, and 3 than Chidamide or Entinostat.

GNTbm-02 is a Picoliamide-based Subtype-selective Class I HDAC Inhibitor

To further confirm the subtype-selective inhibition of HDACs 1-11 enzyme activities, GNTbm-02 was tested by BPS Bioscience Inc. (6042 Cornerstone Court West, Ste. B, San Diego, CA 92121, USA). As shown in Table 5, the inhibition of HDACs 1-11 (except HDAC 10) enzyme activities was analyzed with Entinostat (MS-275) as a positive control. This result demonstrated that GNTbm-02 was more potent in inhibiting HDACs 1, 2, and 3 than Entinostat in the same conditions. GNTbm-02 inhibited class I HDAC1, HDAC2, and HDAC3 with $IC_{50}$ of 0.39, 0.91, and 0.73 μM, respectively. However, Entinostat inhibits class I HDAC1, HDAC2, and HDAC3 with $IC_{50}$ of 0.95, 2.3, and 4.6 μM, respectively. Other HDACs including 4, 5, 6, 7, 8, 9, and 11 were not inhibited by GNTbm-02 or Entinostat at a concentration up to 10 μM. These results suggested that GNTbm-02 is a potent and subtype-selective class I HDAC inhibitor. GNTbm-02 is a picolinamide-based class I HDAC inhibitor. However, Entinostat is a benzamide-based class I HDAC inhibitor. GNTbm-02 is more potent in inhibiting HDACS 1, 2, and 3 enzyme activities than Entinostat.

GNTbm Compounds Series Significantly Impact Human Cancer Cell Proliferation and Morphology.

Figure 3A:
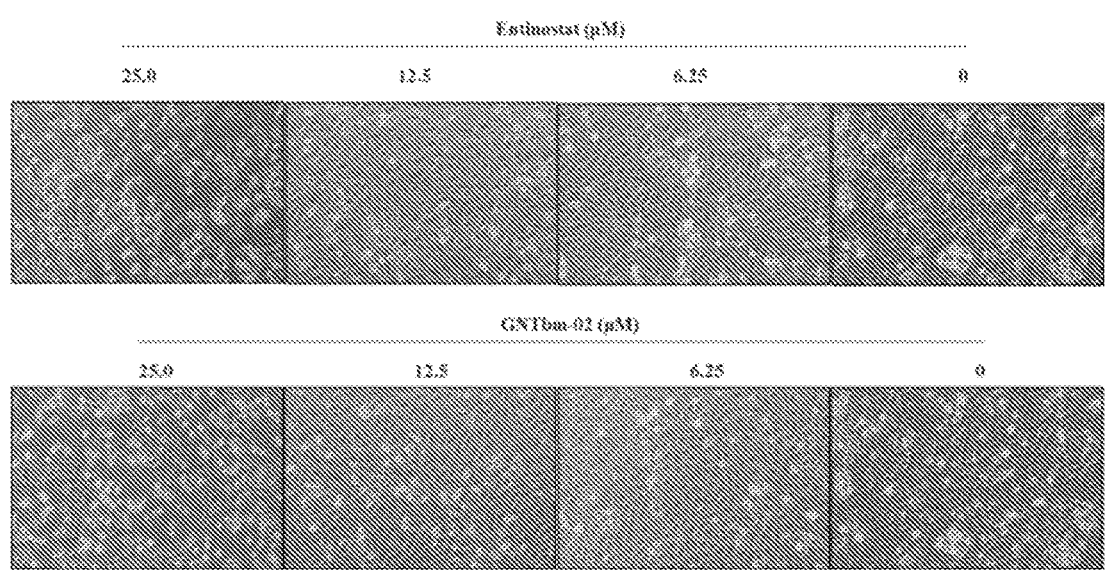
FIGS. 3A-3C show cell morphology observed by phase-contrast light microscopy after treatment: The change of cell morphology was observed by phase-contrast light microscopy.
Figure 3B:
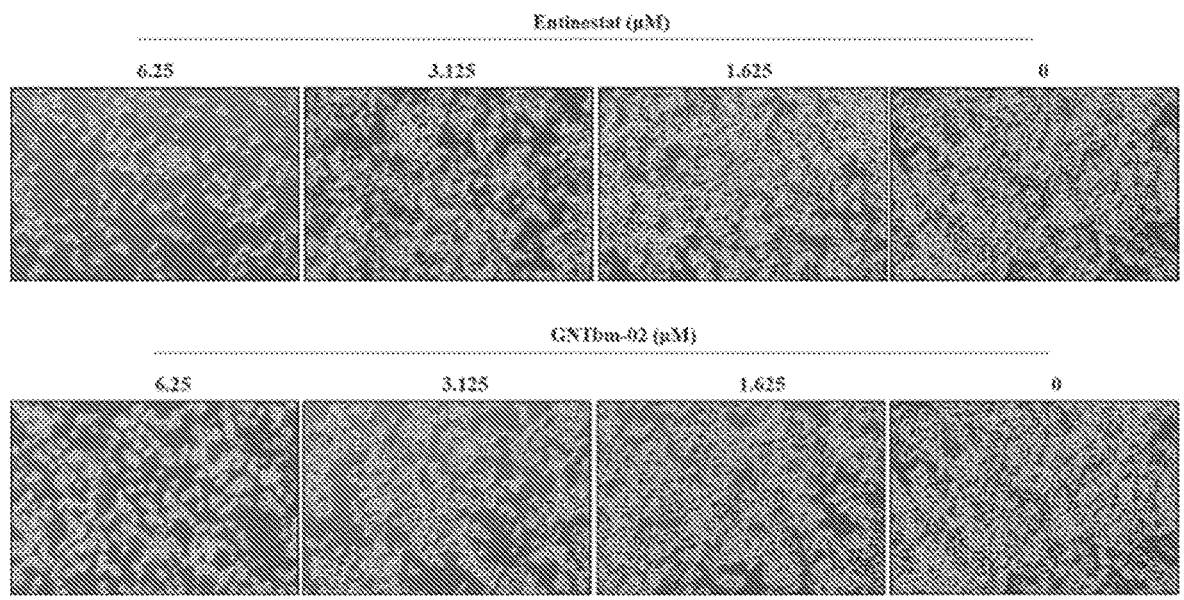
Figure 3C:
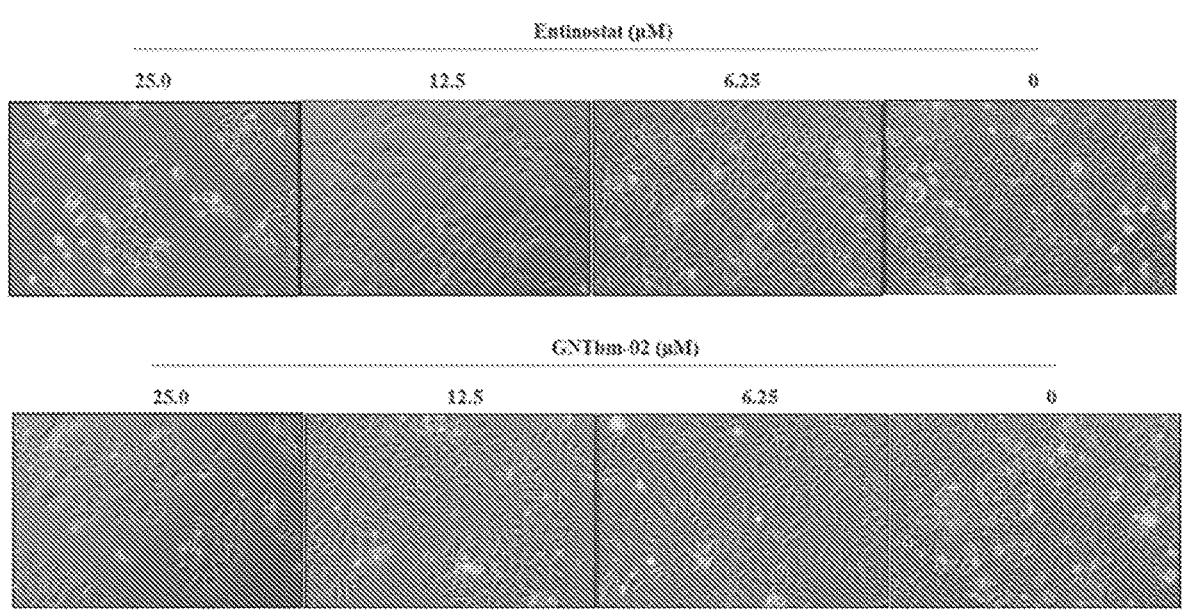

The inhibitory effect of GNTbm-02 to human cancer cell proliferation is shown in FIG. 3. GNTbm-02 and Entinostat at various concentrations were used to treat MDA-MB-231 cells for 72 h. As shown in FIG. 3a, the potency of inhibitory effect was similar for GNTbm-02 and Entinostat, at a concentration of 12.5 μM significantly inhibiting cell proliferation. As shown in FIG. 3b, the potency of the inhibitory effect was more obvious for SW48 cells when treated with GNTbm-02 or Entinostat at a concentration of 3.125 μM for 72 h. Next, M10 cells were treated with GNTbm-02 or Entinostat at a concentration of 12.5 μM, which significantly inhibited cell proliferation as shown in FIG. 3c. Taken together, these results suggested that GNTbm-02 possessed potent capacity to inhibit cell proliferation.

Figure 4A:
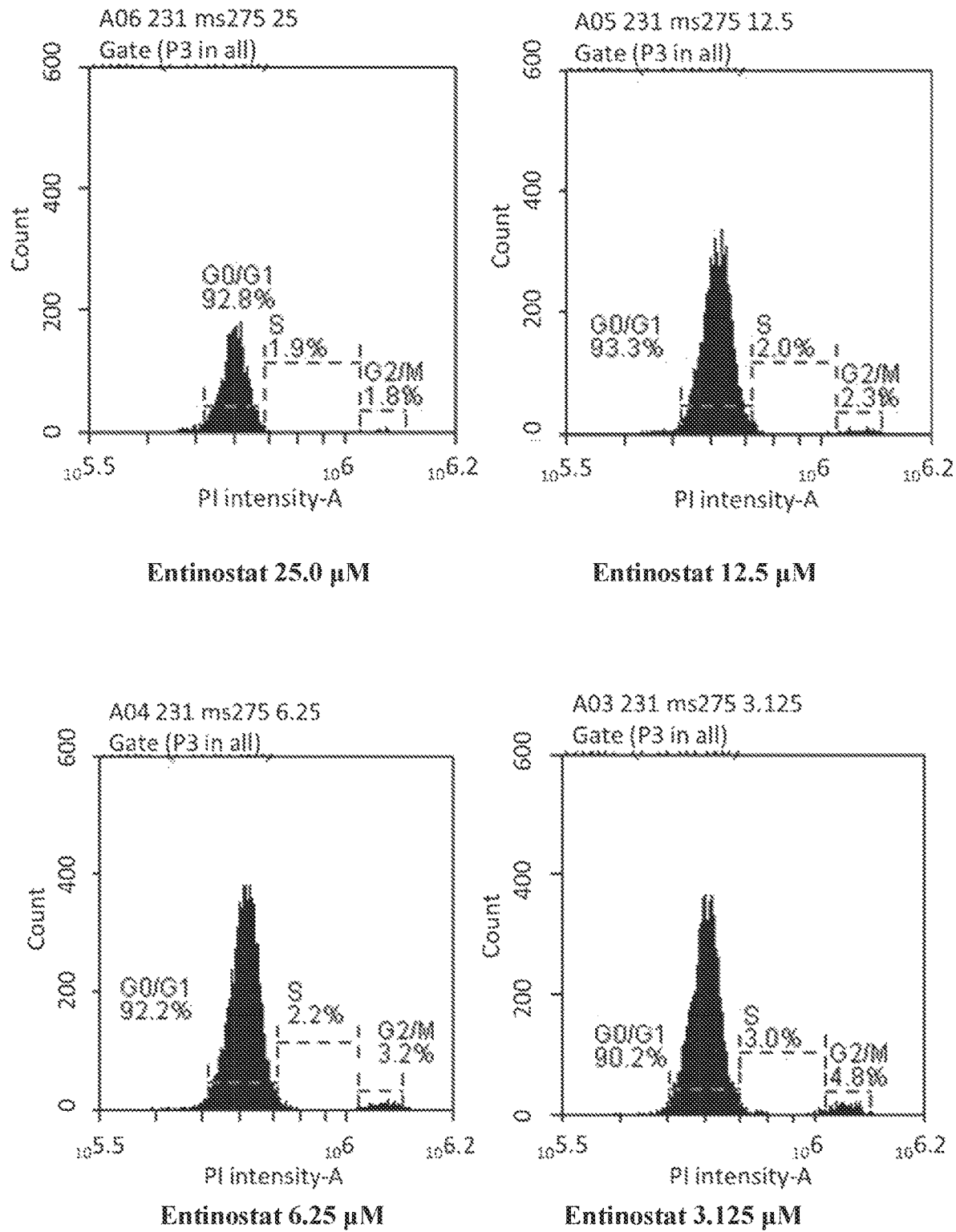
FIGS. 4A-4D show results from the assessment of GNTbm-02 induced cell cycle arrest in G0/G1 phase in MDA-MB-231 cells: assessment was performed after treatment with GNTbm-02 and Entinostat in MDA-MB-231 cells in a dose-dependent and time-dependent manner. The cells were stained with PI, and by using flow cytometer, the percentages of cells in different cell cycle phases were analyzed.
Figure 4A:
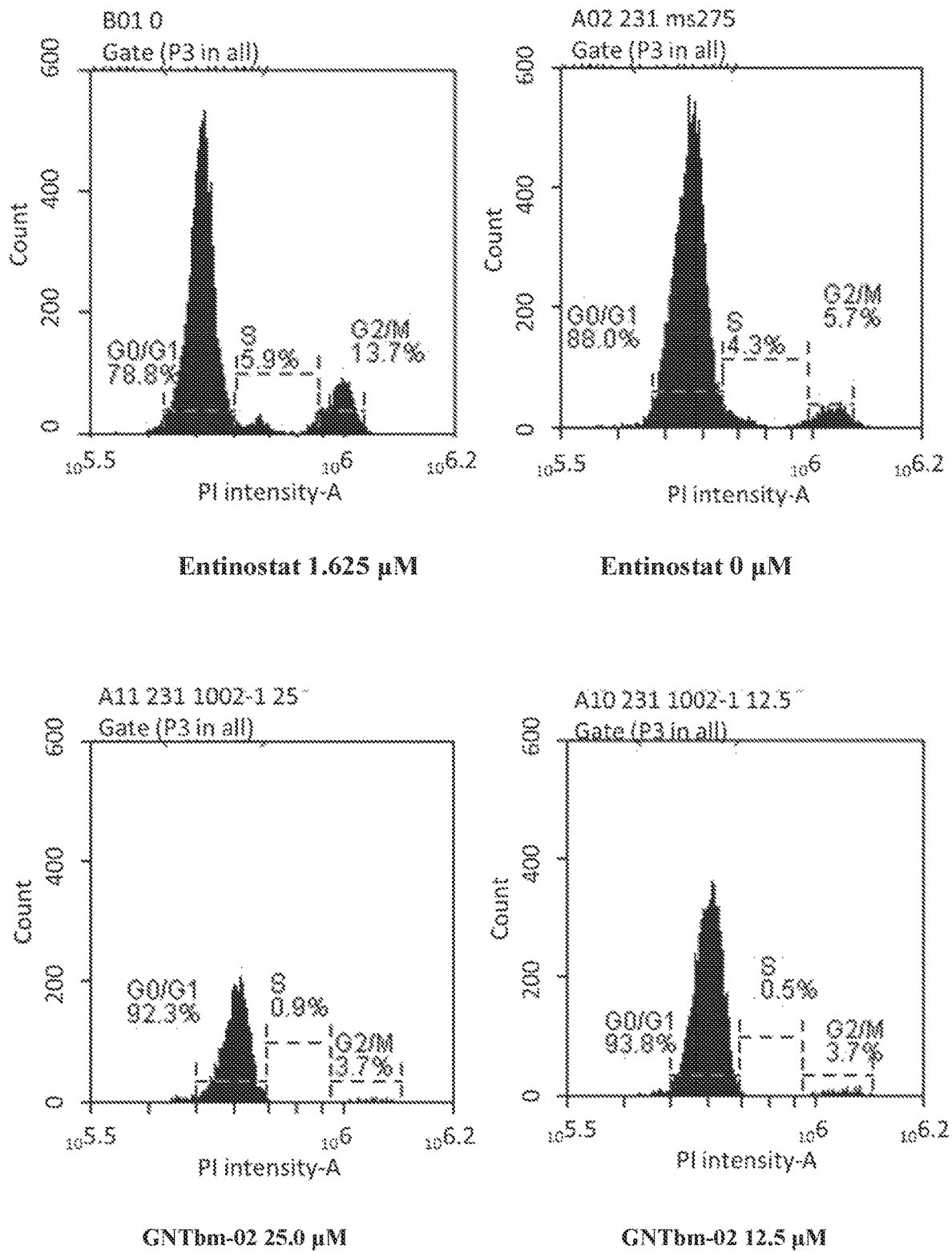
Figure 4A:
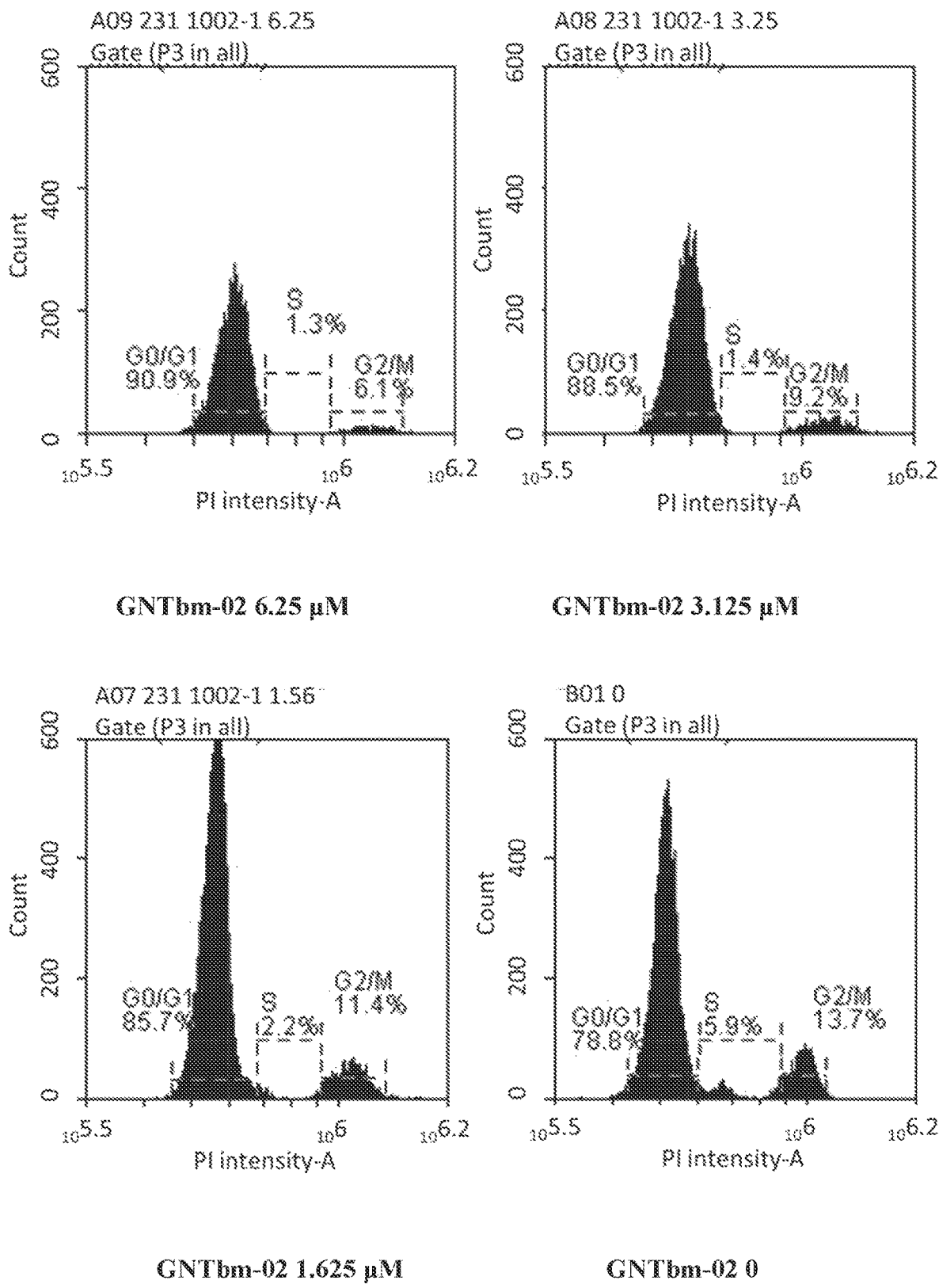
Figure 4B:
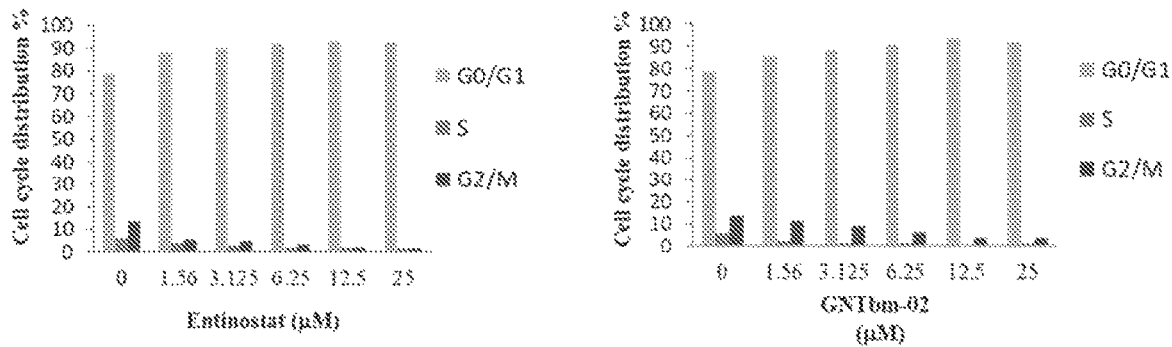
Figure 4D:
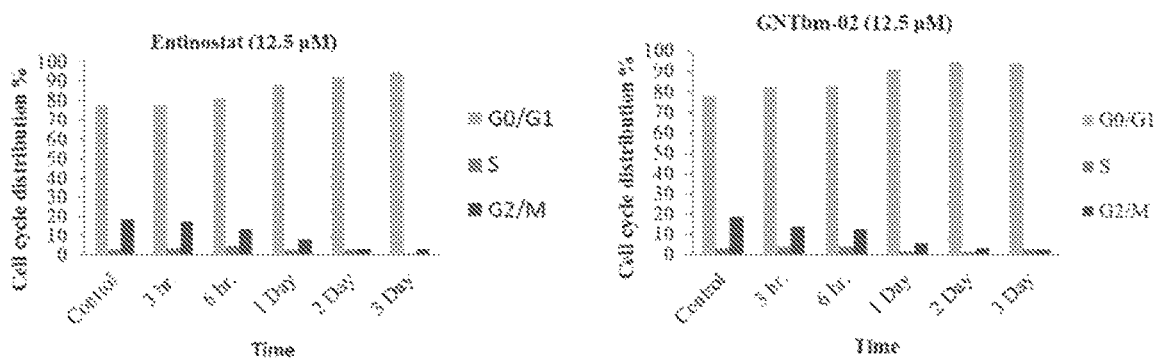
Figure 5B:
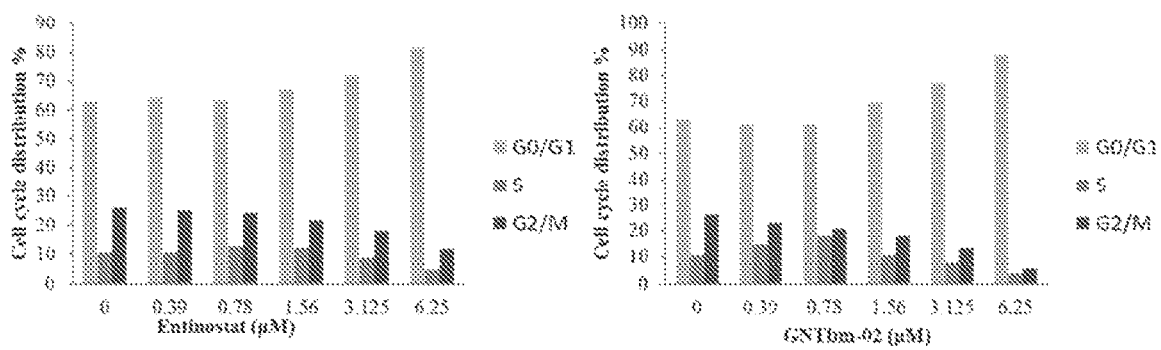
FIGS. 5A-5D show results from the assessment of GNTbm-02 induced cell cycle arrest in G0/G1 phase in SW48 cells: assessment was performed after treatment with GNTbm-02 and Entinostat in SW48 cells in a dose-dependent and time-dependent manner. The cells were stained with PI, and by using flow cytometer, the percentages of cells in different cell cycle phases were analyzed.
Figure 5D:
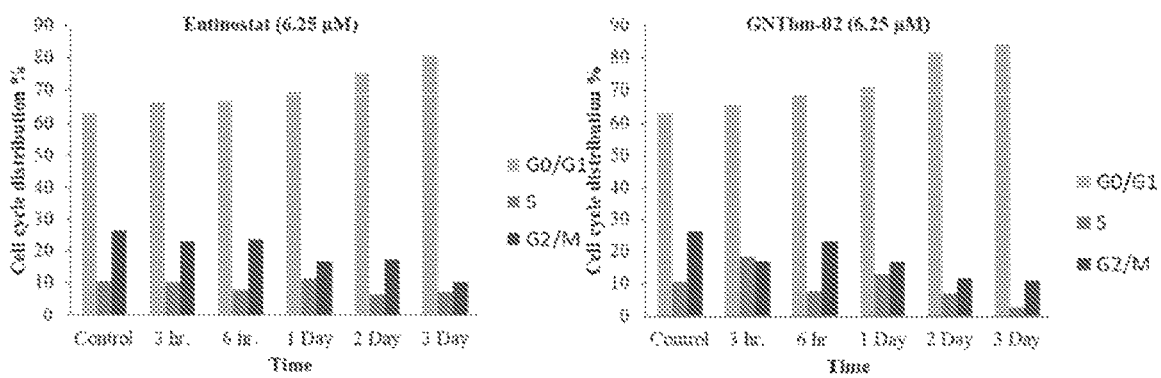
Figure 4C:
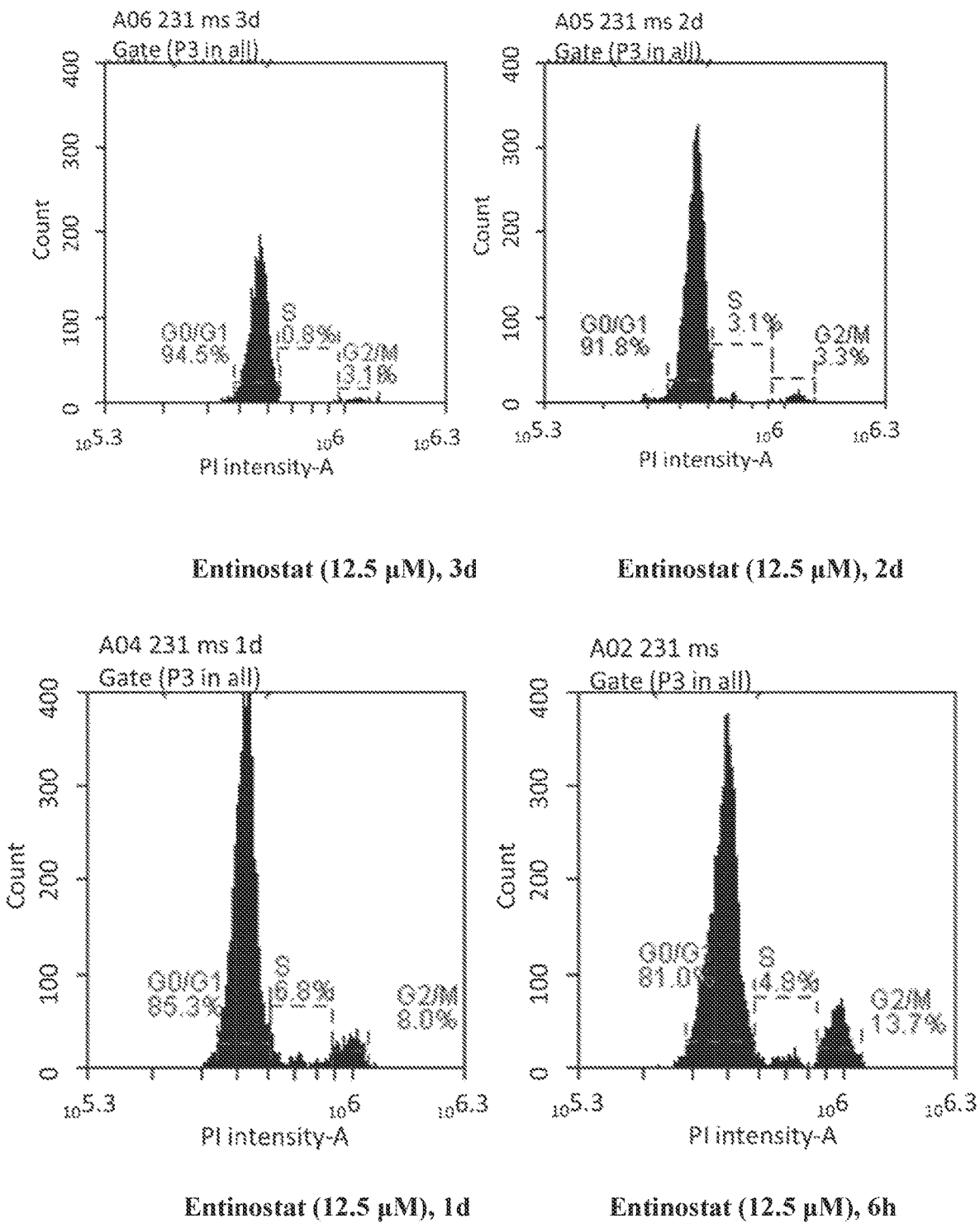
Figure 4C:
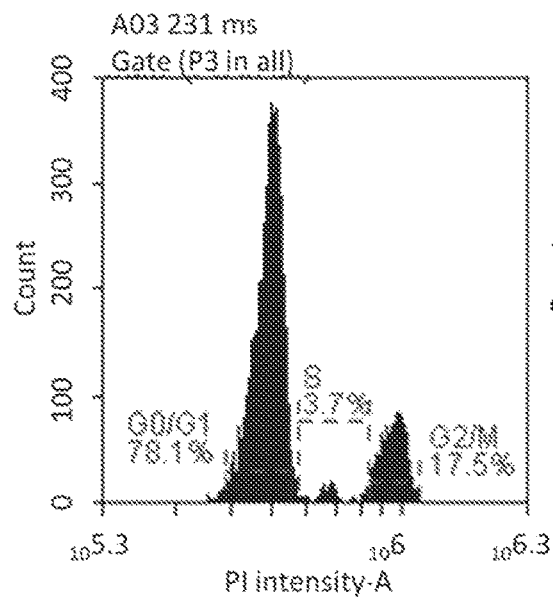
Figure 4C:
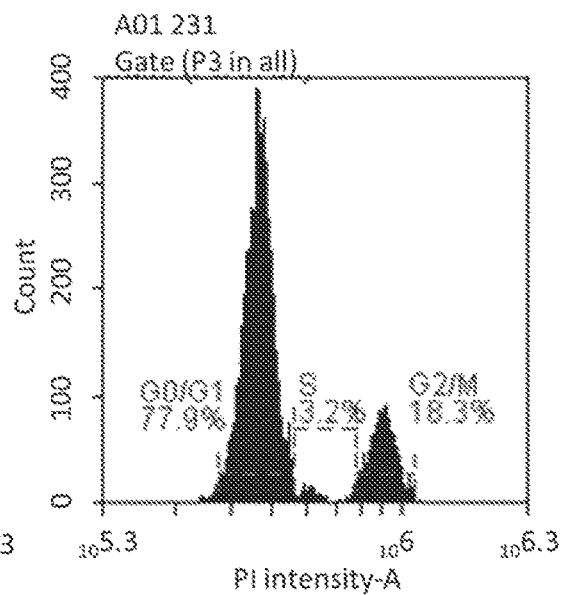
Figure 4C:
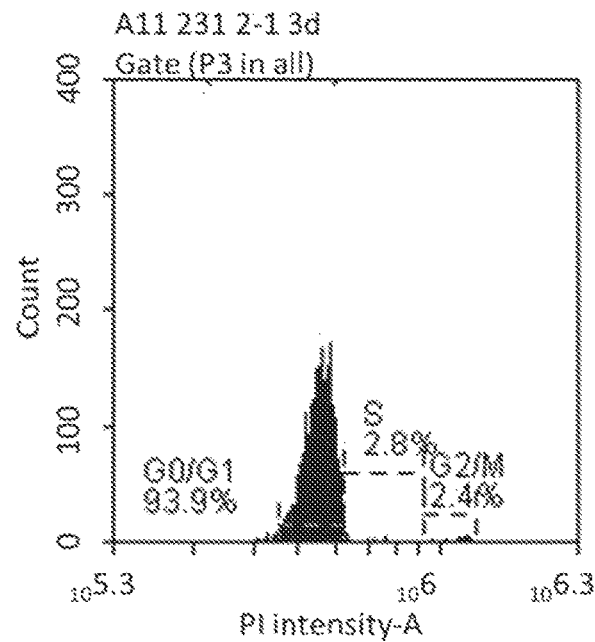
Figure 4C:
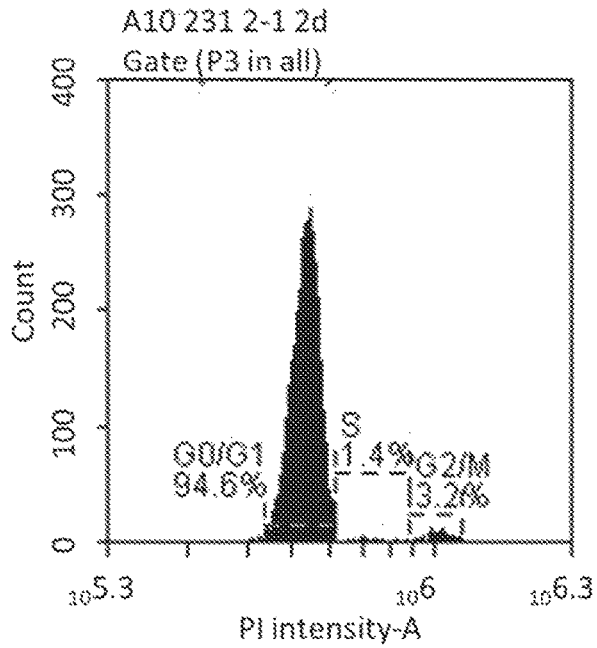
Figure 4C:
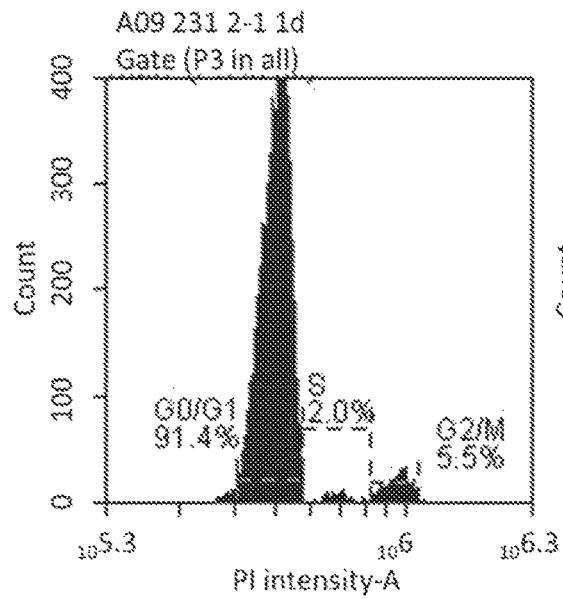
Figure 4C:
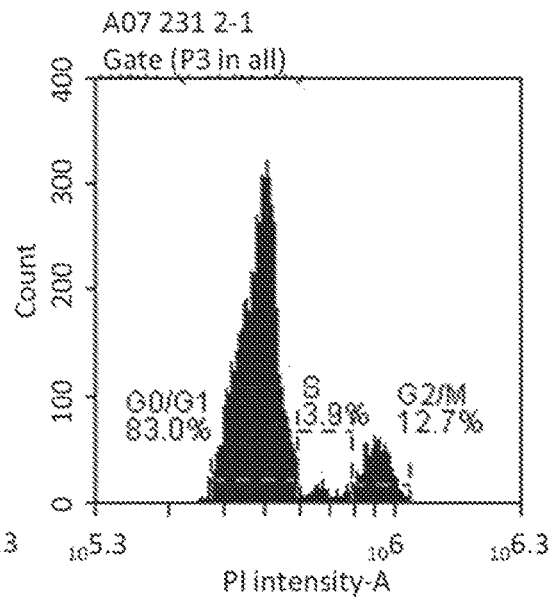
Figure 4C:
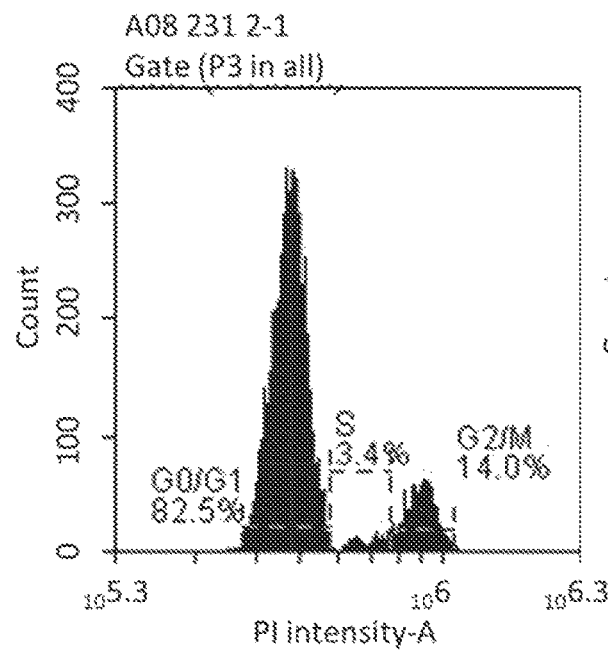
Figure 4C:
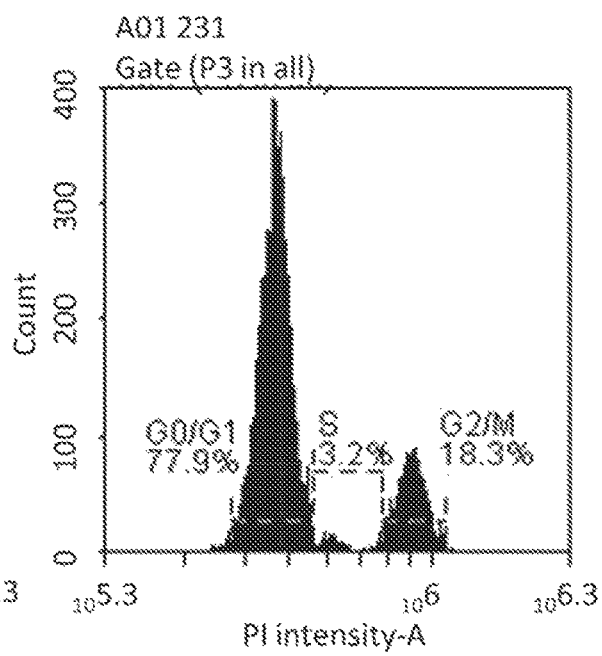
Figure 5A:
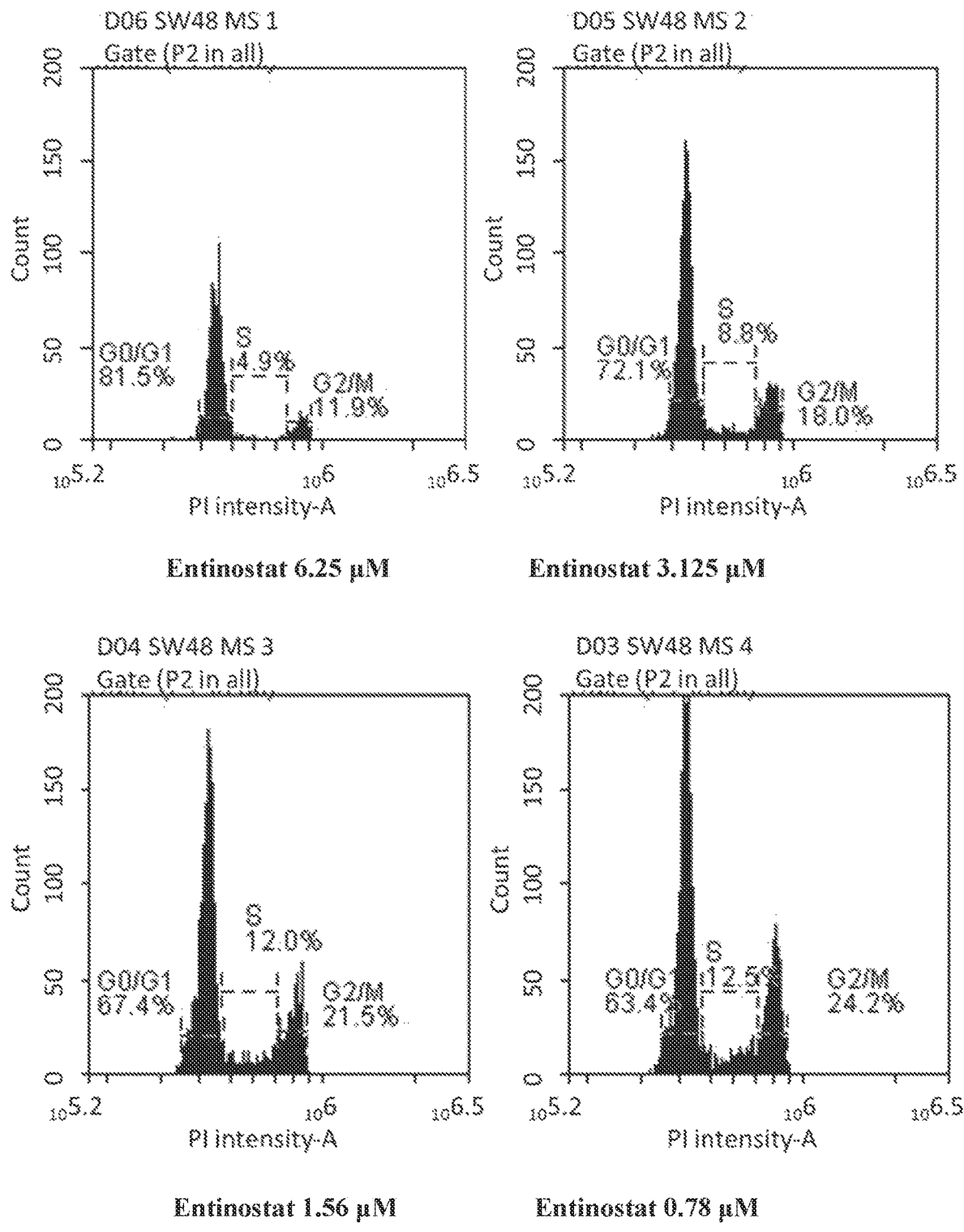
Figure 5A:
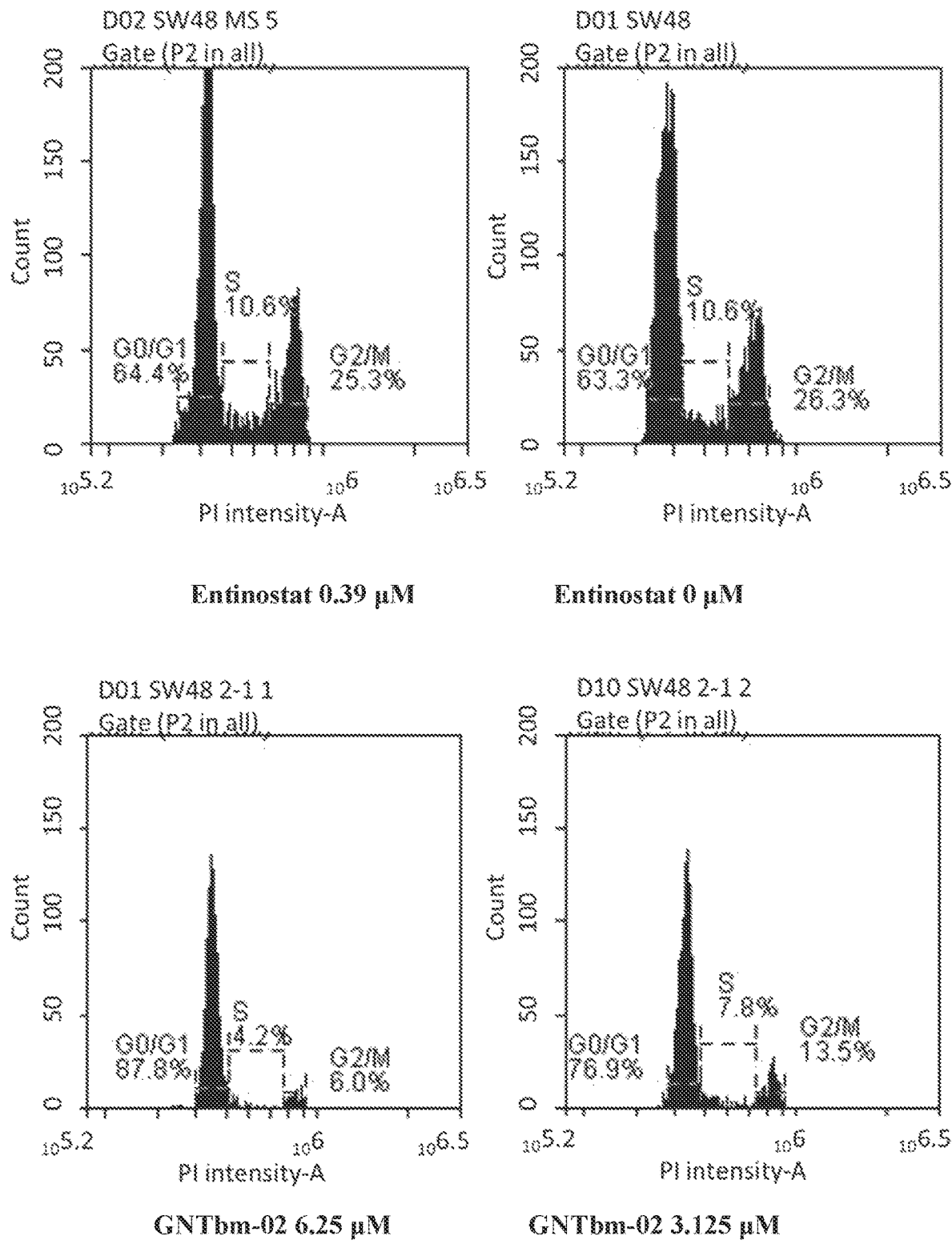
Figure 5A:
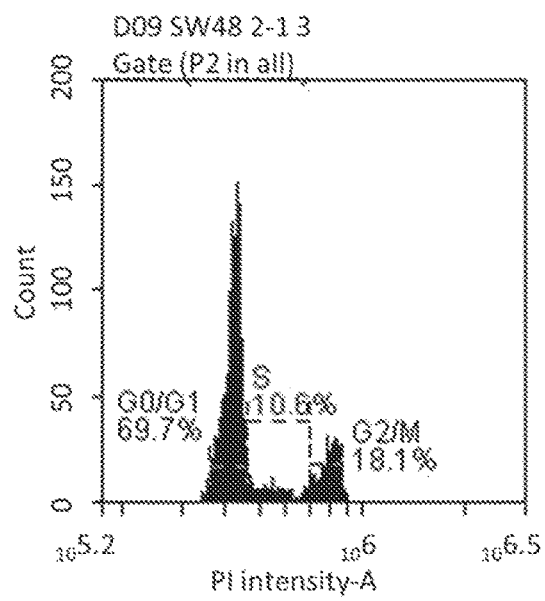
Figure 5A:
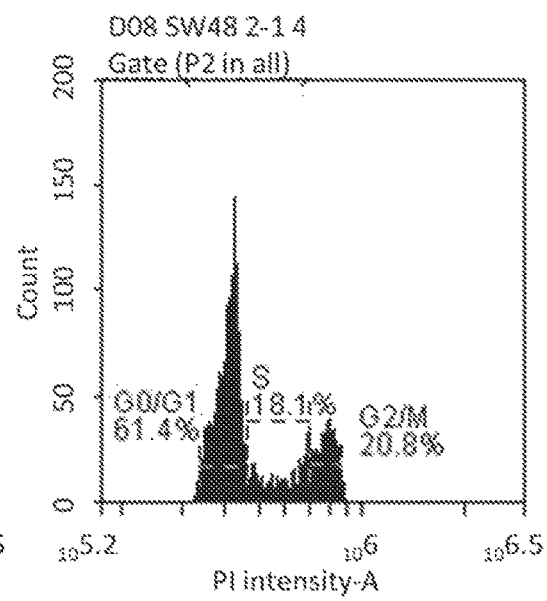
Figure 5A:
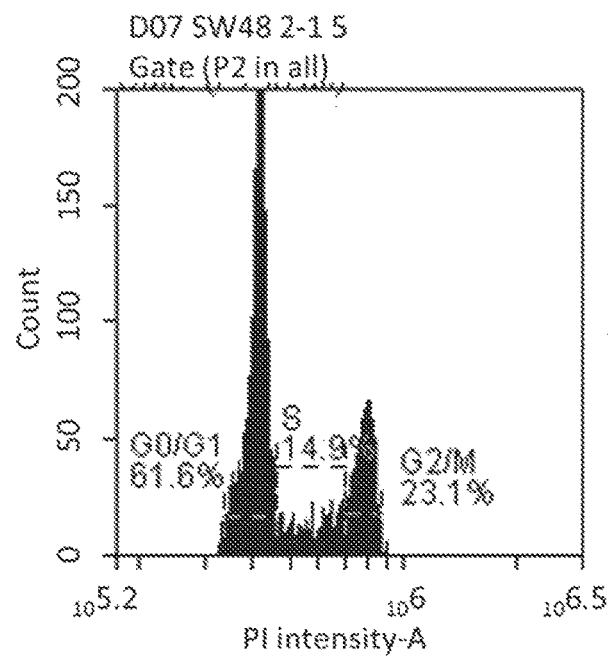
Figure 5A:
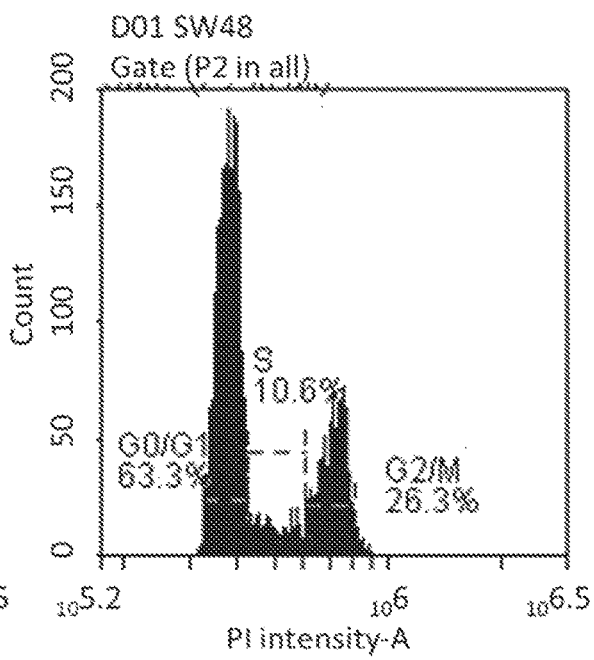
Figure 5C:
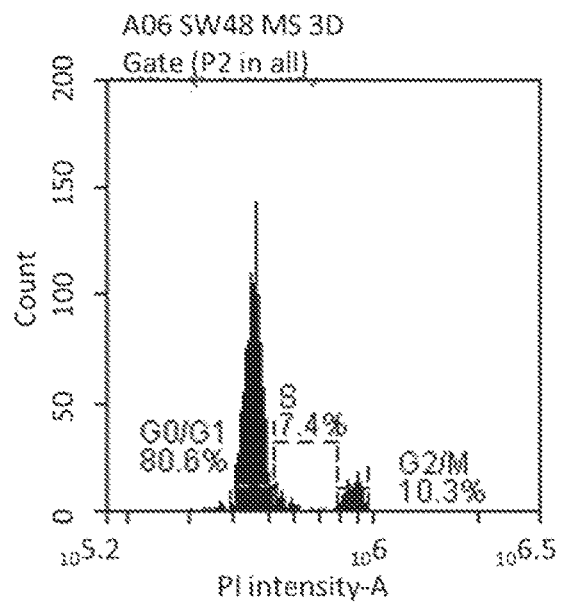
Figure 5C:
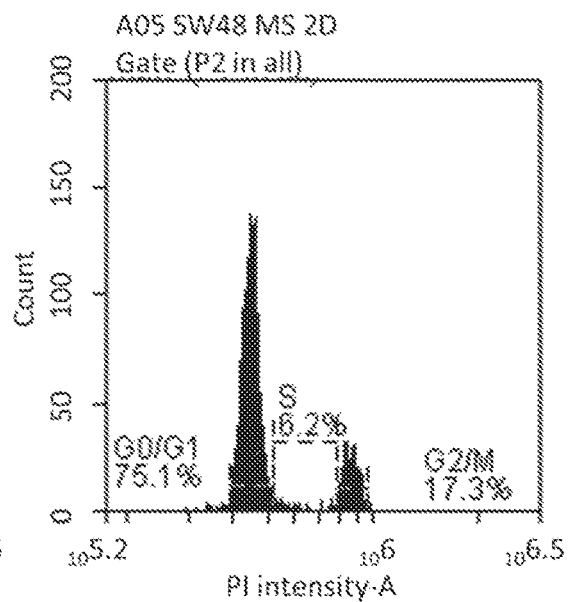
Figure 5C:
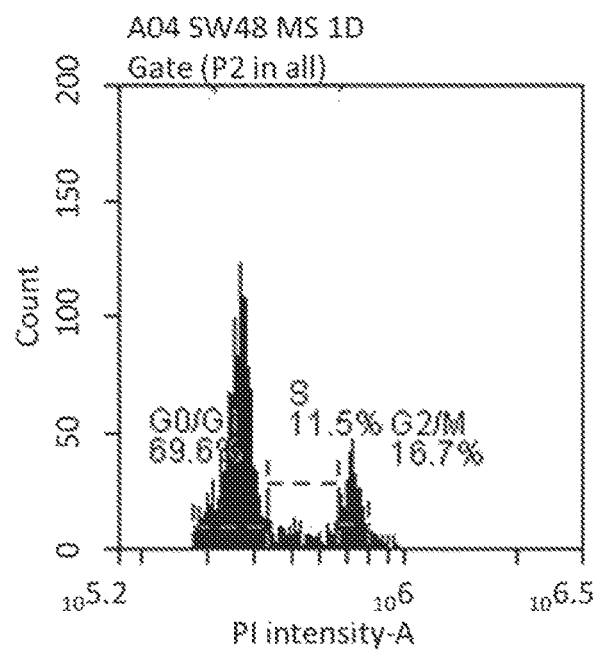
Figure 5C:
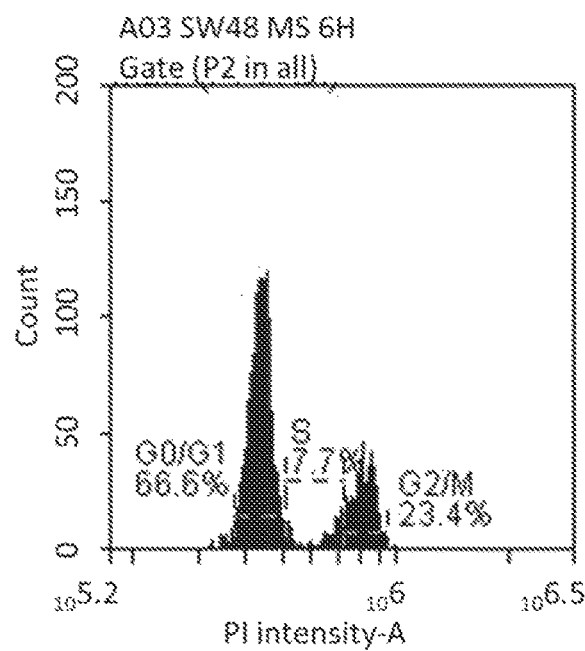
Figure 5C:
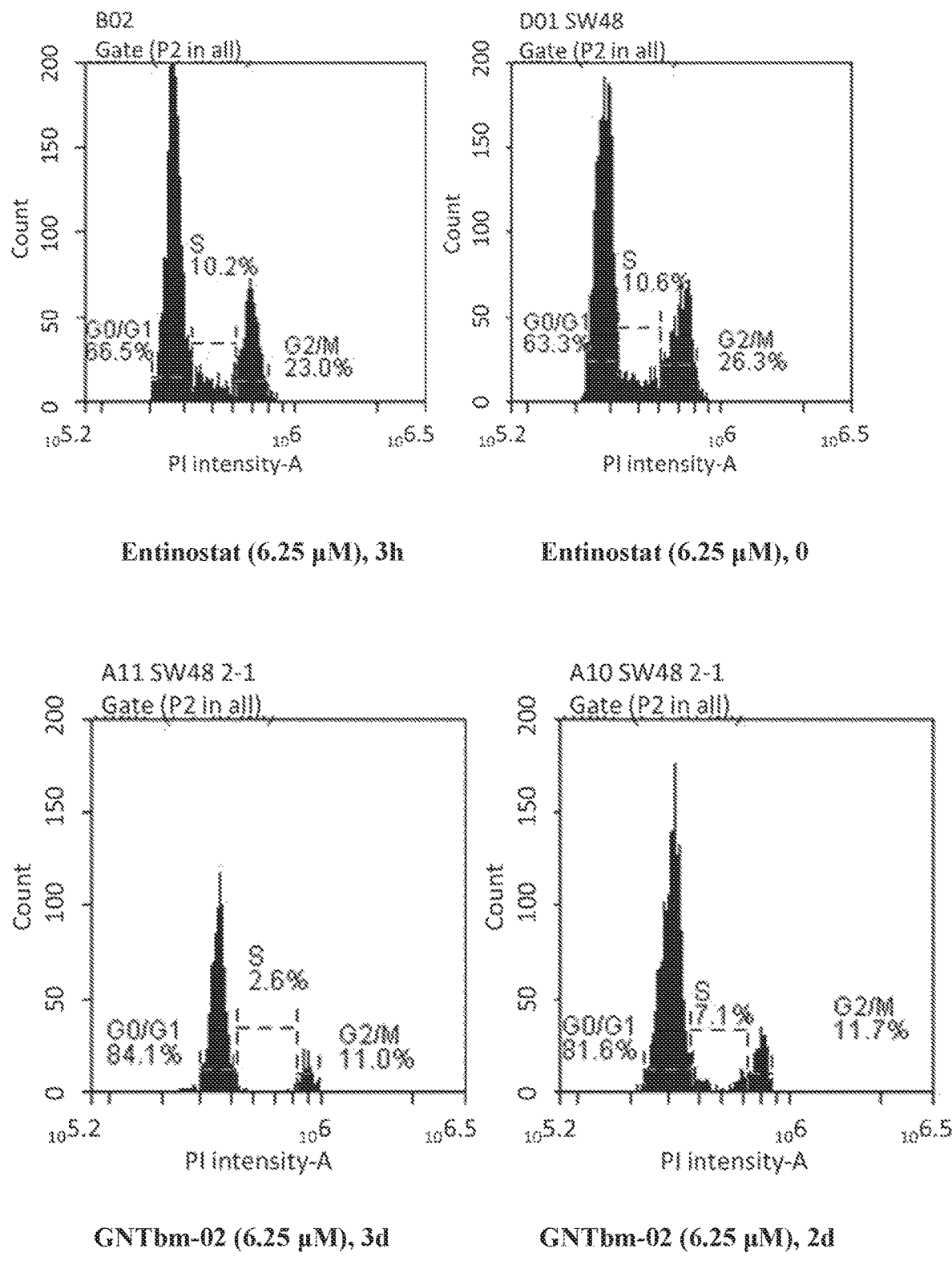
Figure 5C:
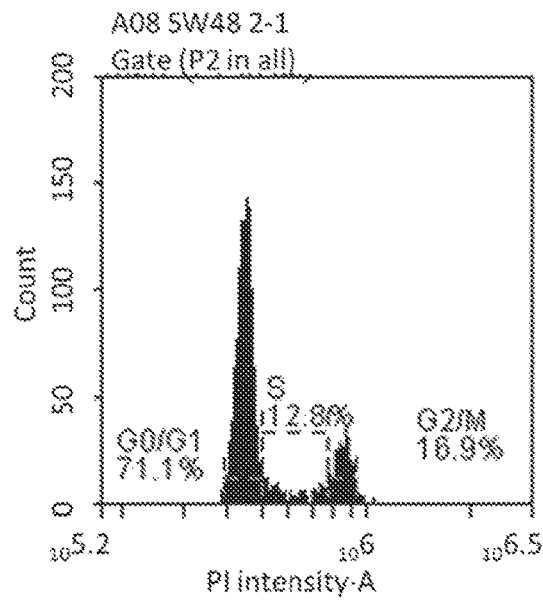
Figure 5C:
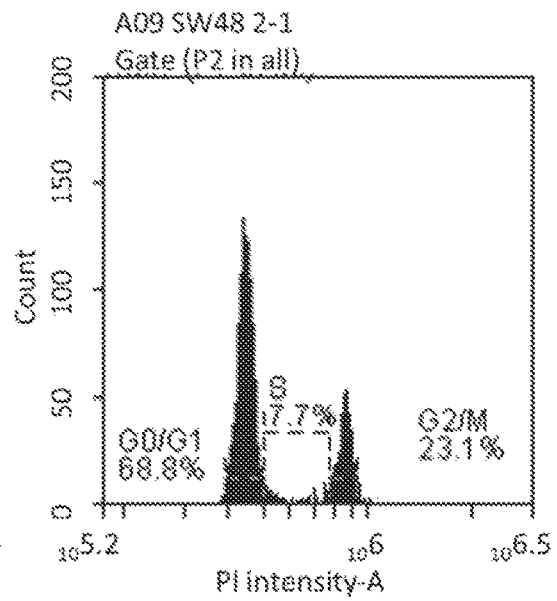
Figure 5C:
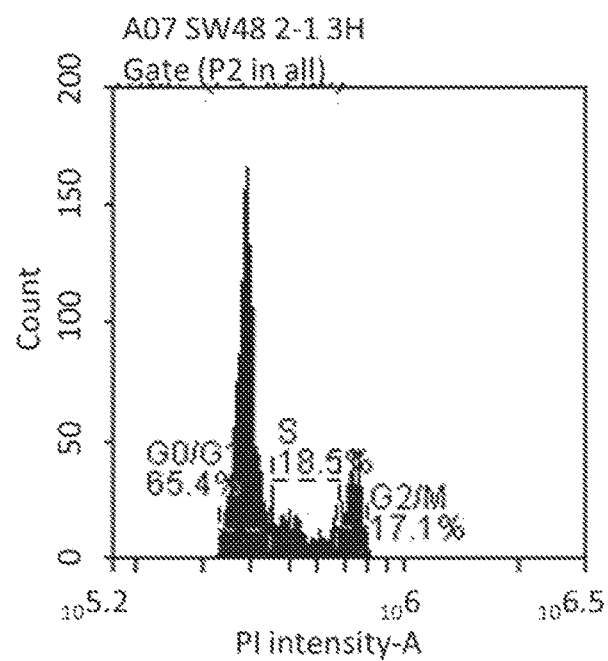
Figure 5C:
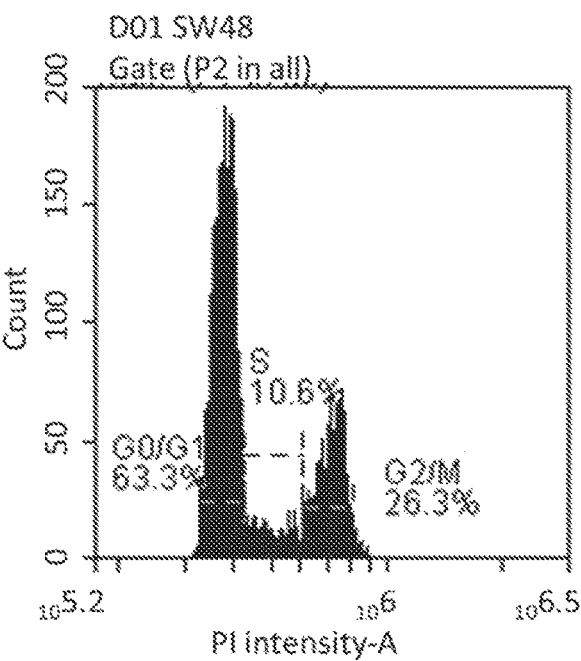

GNTbm Compounds Series Induced Cell Cycle Arrest in G0/G1 or G2/M Phase in Human Cancer MDA-MB-231 and SW48 Cells To investigate the mechanism of inhibition of cell proliferation, flow cytometry was used to analyze the cell cycle arrest. As shown in FIG. 4a, GNTbm-02 and Entinostat at various concentrations from 1.625 to 25 μM were used to treat MDA-MB-231 cells for 72 h. The results demonstrated that GNTbm-02 and Entinostat possessed a similar mechanism, which significantly induced cell cycle arrest in G0/G1 phase at concentration of 3.125 μM as shown in FIGS. 4a and b. As shown in FIGS. 4c and d, cell cycle was arrested in G0/G1 phase by treatment with GNTbm-02 and Entinostat at a concentration of 12.5 μM in a time-dependent manner. The result indicated that treatment with GNTbm-02 or Entinostat for 1 day significantly induced cell cycle arrest in G0/G1 phase. In SW48 cells, a similar mechanism was also shown. As shown in FIGS. 5a and b, GNTbm-02 and Entinostat at various concentrations from 0.39 to 6.25 μM were used to treat SW48 cells for 72 h. The results demonstrated that GNTbm-02 and Entinostat significantly induced cell cycle arrest in G0/G1 phase at a concentration of 3.125 μM as shown in FIGS. 5a and b. The result showed that GNTbm-02 (76.9%) seem to be more potent in inducing cell cycle arrest in G0/G1 phase than Entinostat (72.1%) at the same concentration of 3.125 μM. As shown in FIGS. 5c and d, the cell cycle was arrested in G0/G1 phase by treatment with GNTbm-02 and Entinostat at a concentration of 6.25 μM in a time-dependent manner. The results indicated that the treatment with GNTbm-02 or Entinostat for 2 days significantly induced cell cycle arrest in G0/G1 phase. Taken together, all these data indicated that GNTbm-02 and Entinostat possessed a similar mechanism to inhibit human cancer cell proliferation through induced cell cycle arrest in G0/G1 phase. Furthermore, we were interested in evaluating several potent picolinamide-based and benzamide-based novel synthetic derivatives such as GNTbm-04, GNTbm-05, GNTbm-38, and GNTbm-39. As shown in Table 12, GNTbm-04 significant induced cell cycle arrest in G0/G1 phase in SW48 cells. This was similar to Chidamide induced cell cycle arrest in the G0/G1 phase. However, similar chemical structures of GNTbm-05, GNTbm-38, and GNTbm-39 significantly induced cell cycle arrest in the G2/M phase in SW48 cells. Therefore, the chemical structures of these potent compounds were very similar, but the cell cycle arrest mechanisms were very different.

GNTbm-02 Induced Cell Cycle Arrest in G2/M Phase in M10 Cells

Figure 6A:
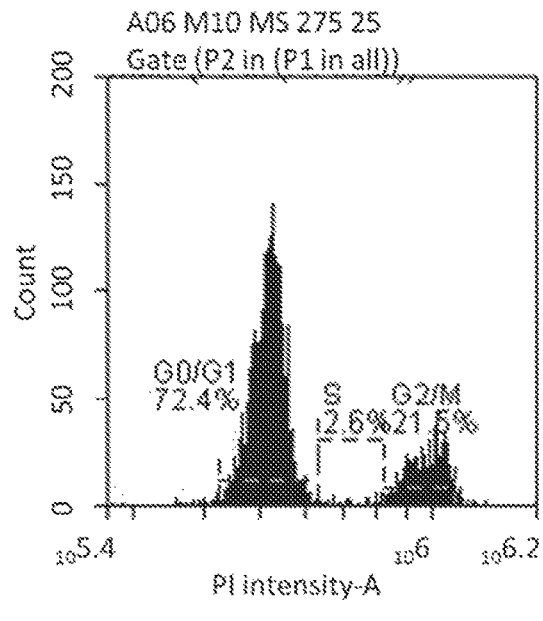
FIGS. 6A-6D show results from the assessment of GNTbm-02 induced cell cycle arrest in G2/M phase in M10 cells: assessment was performed after treatment with GNTbm-02 and Entinostat in M10 cells in a dose-dependent and time-dependent manner. The cells were stained with PI, and by using flow cytometer, the percentages of cells in different cell cycle phases were analyzed.
Figure 6A:
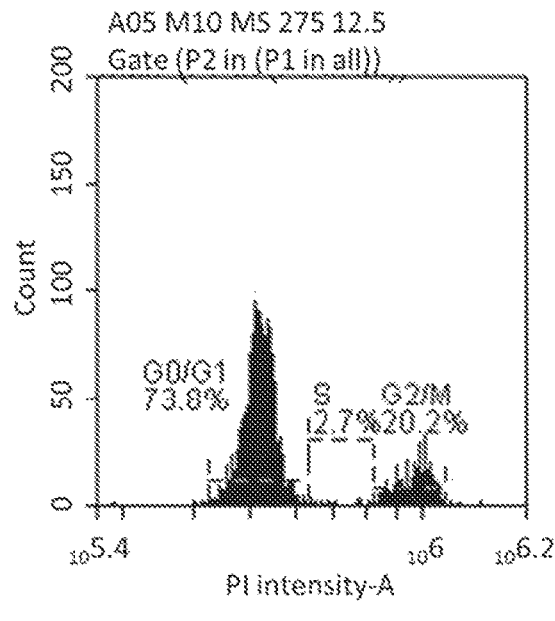
Figure 6A:
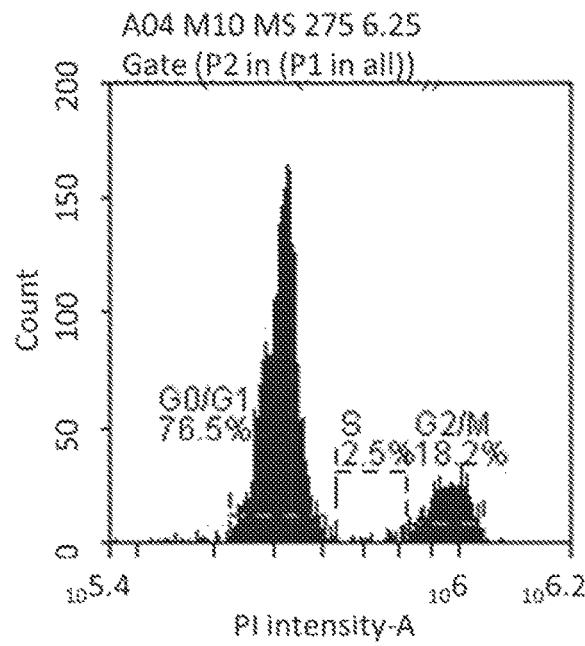
Figure 6A:
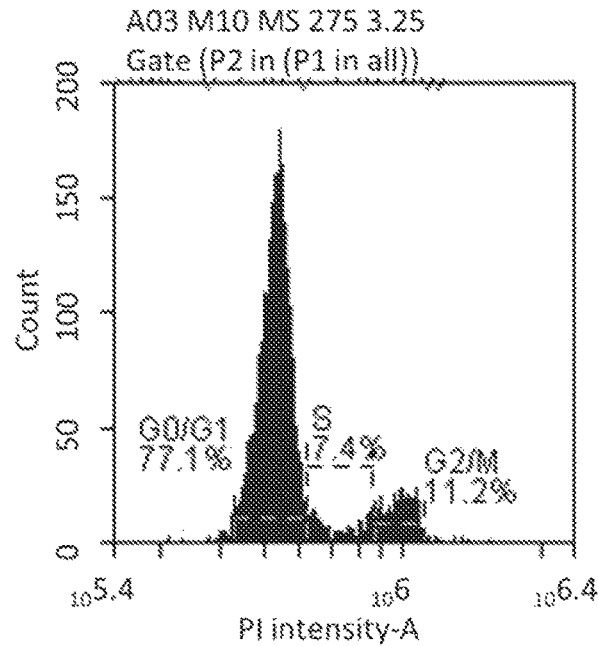
Figure 6A:
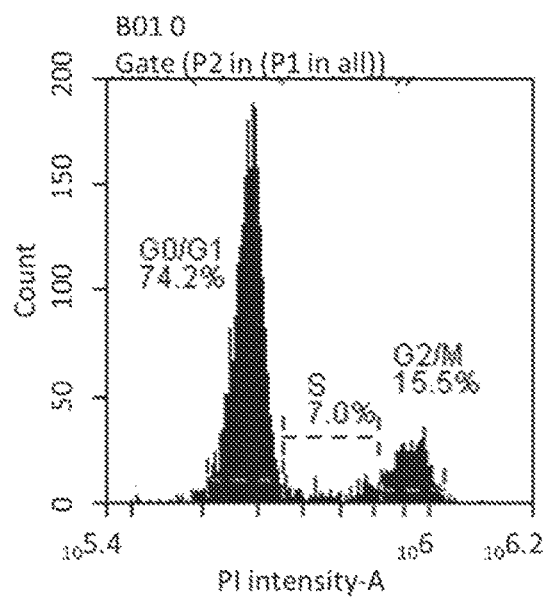
Figure 6A:
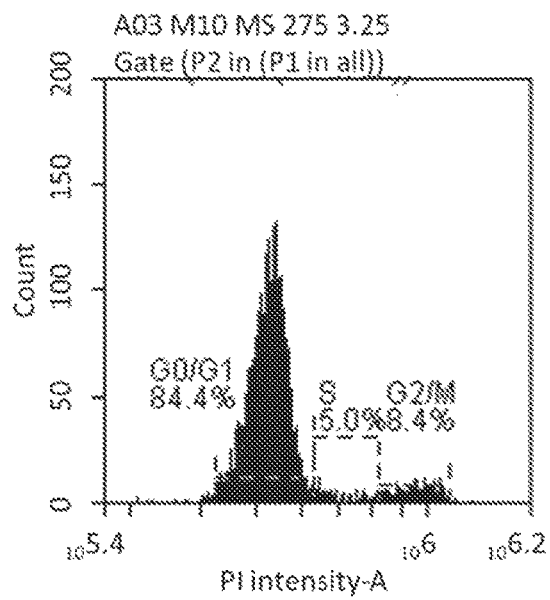
Figure 6A:
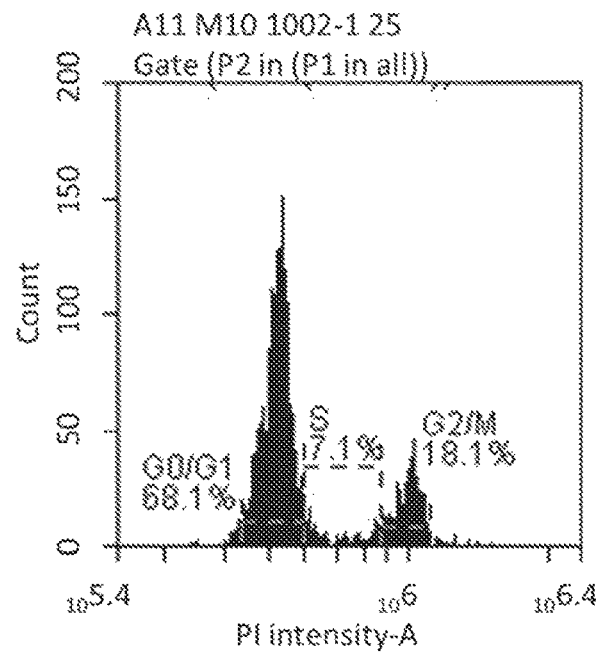
Figure 6A:
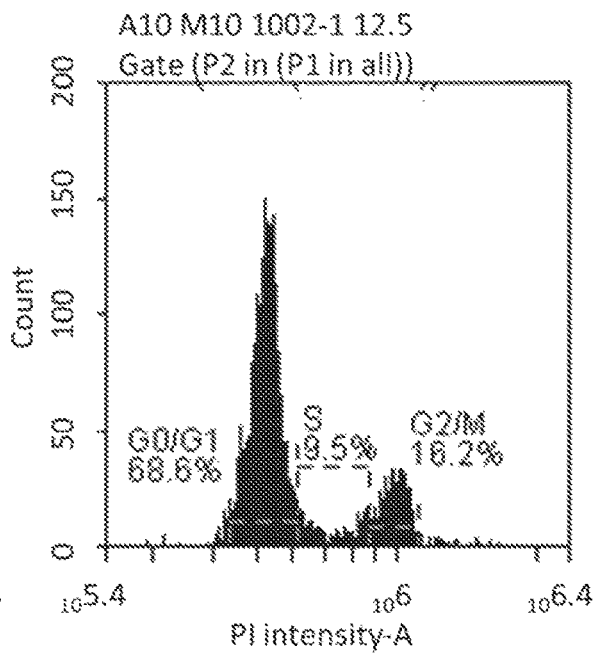
Figure 6A:
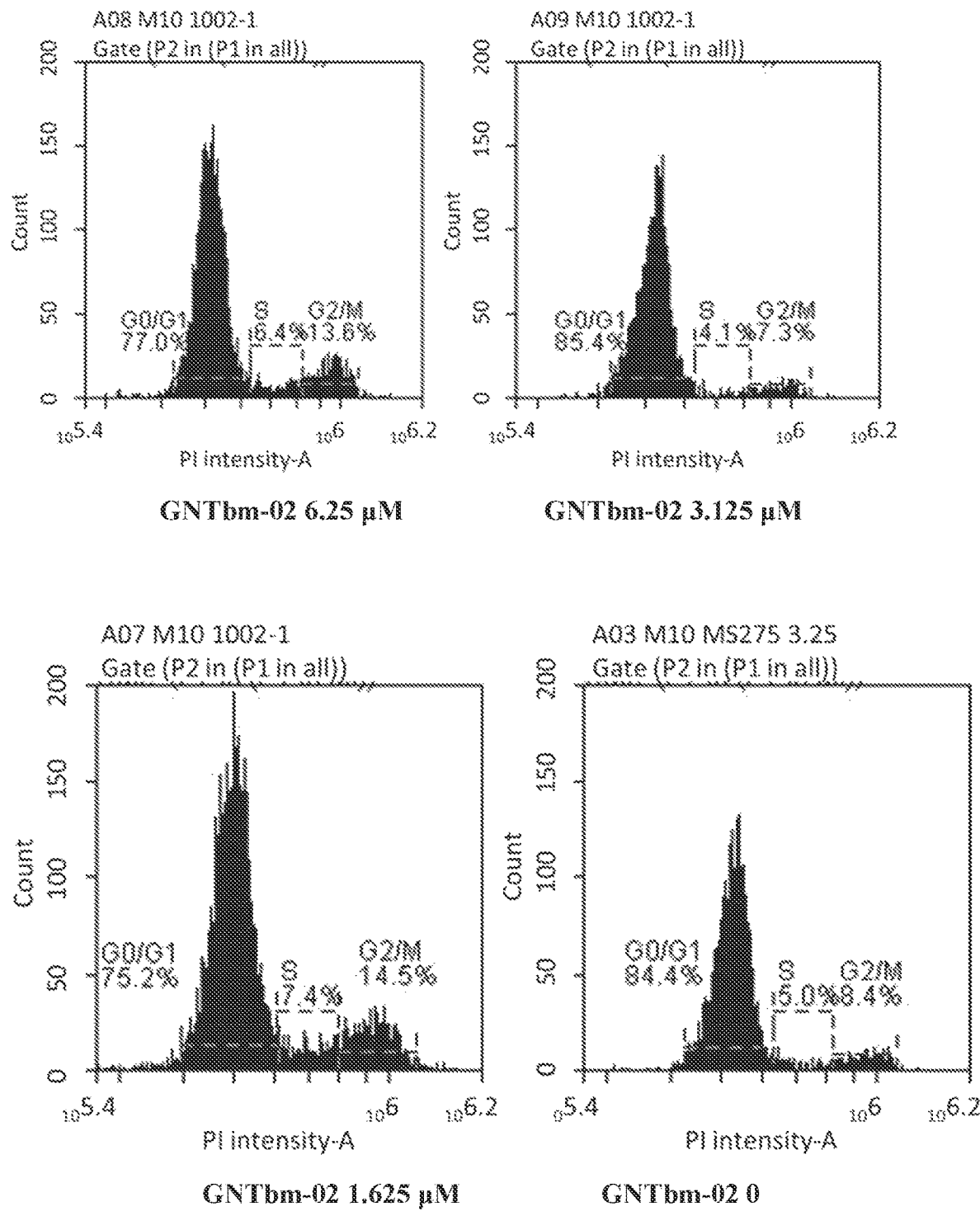
Figure 6B:
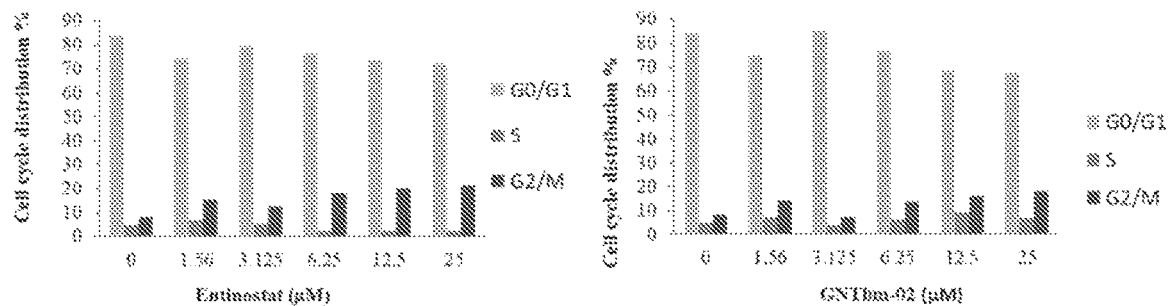
Figure 6D:
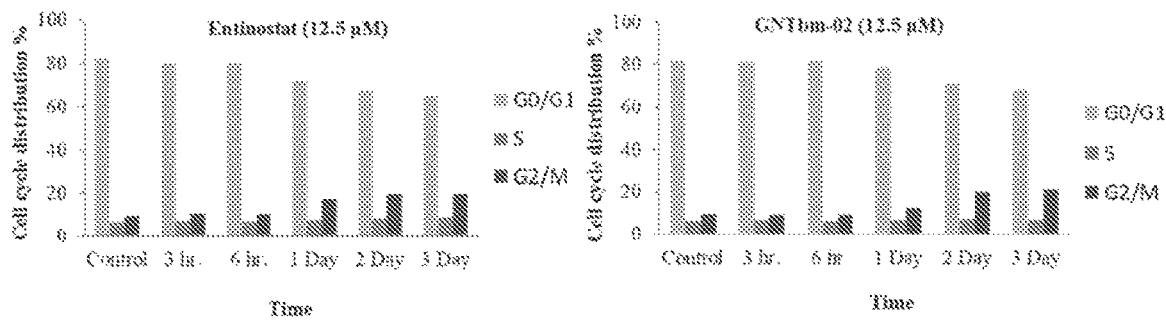
Figure 7B:
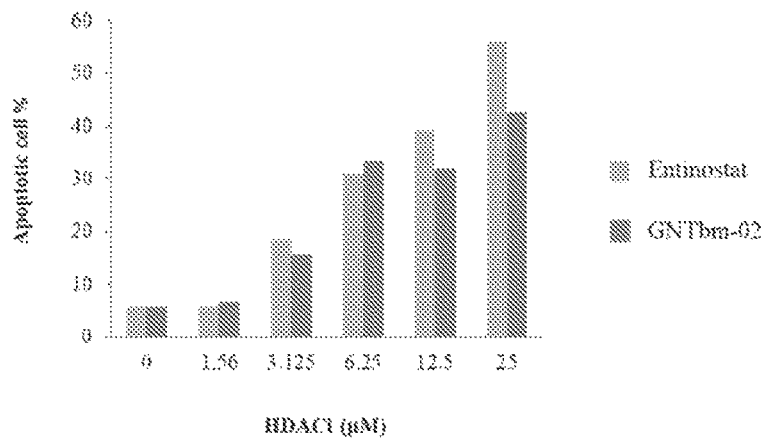
FIGS. 7A-7D show results from the assessment of GNTbm-02 induced cell apoptosis in MDA-MB-231 cells: assessment was performed after treatment with GNTbm-02 and Entinostat in MDA-MB-231 cells in a dose-dependent and time-dependent manner. The cells were stained with PI, and by using flow cytometer, the percentage of cells in sub-G1 phase was analyzed.
Figure 7D:
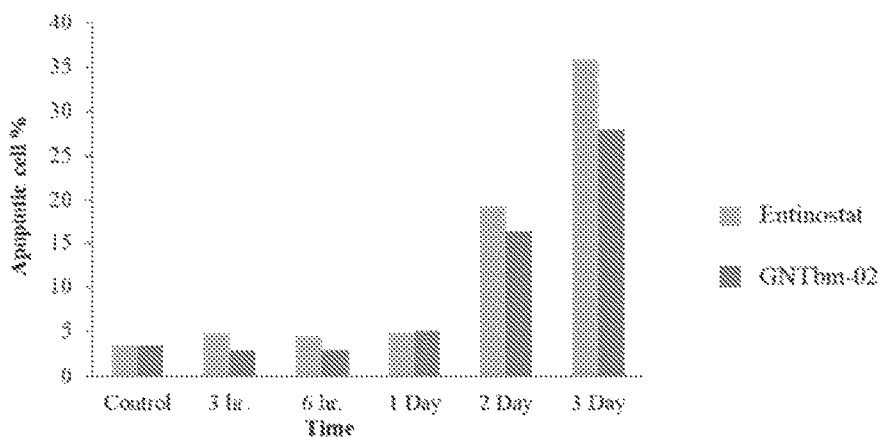
Figure 6C:
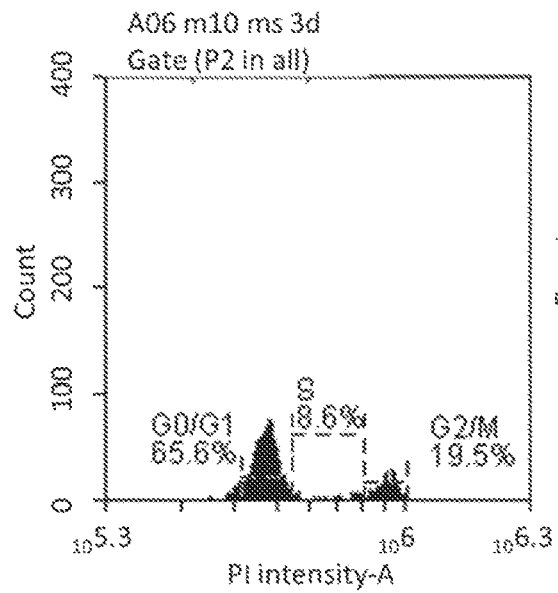
Figure 6C:
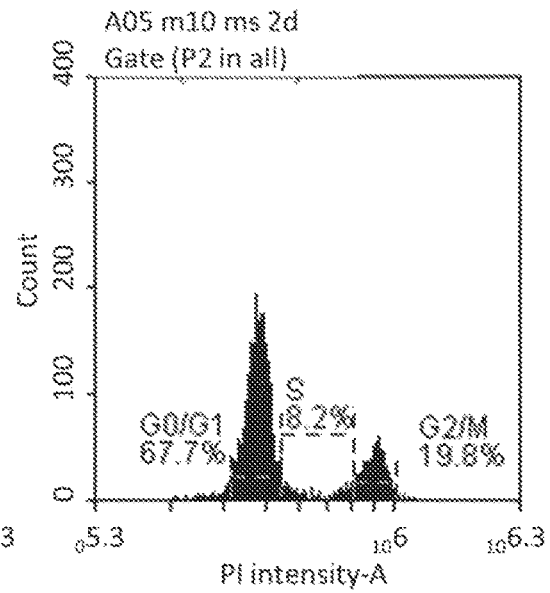
Figure 6C:
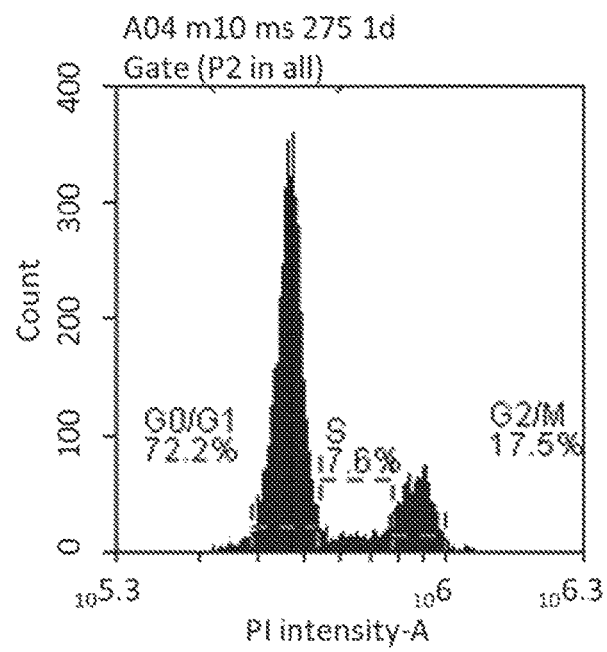
Figure 6C:
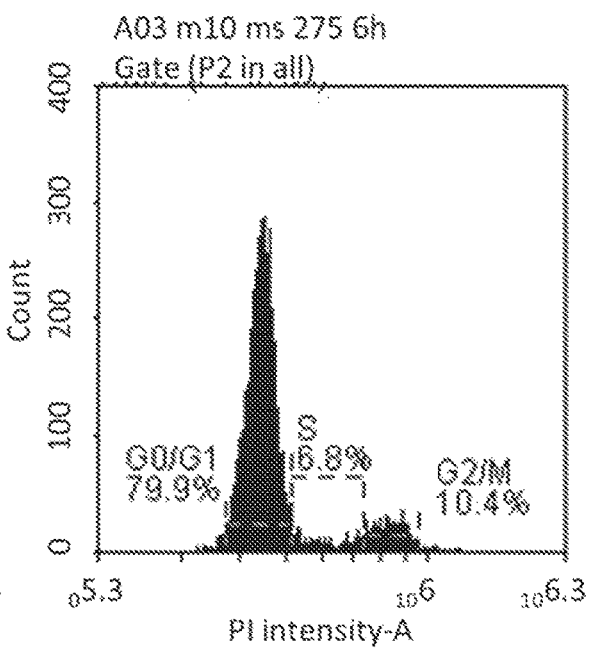
Figure 6C:
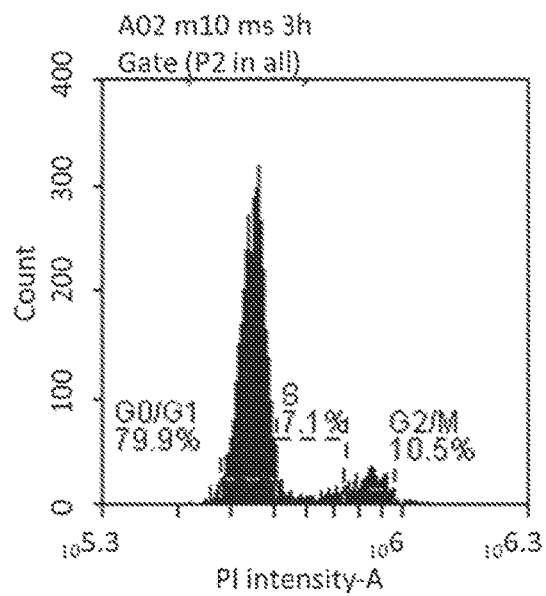
Figure 6C:
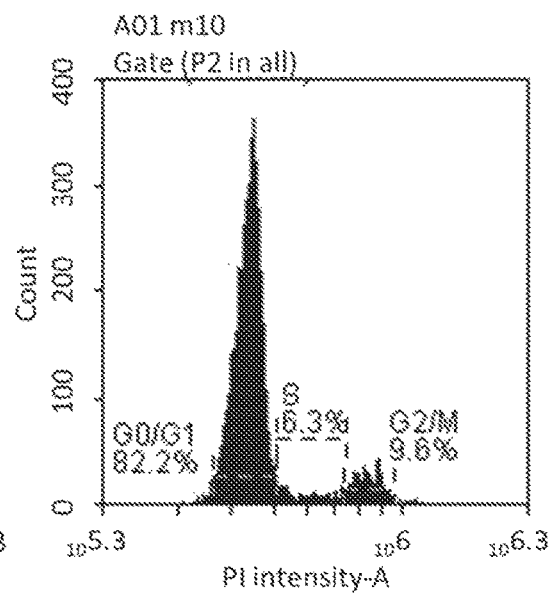
Figure 6C:
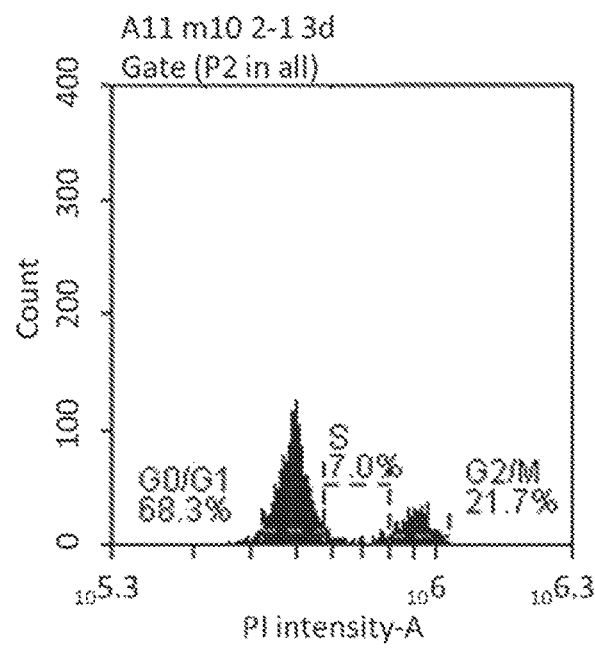
Figure 6C:
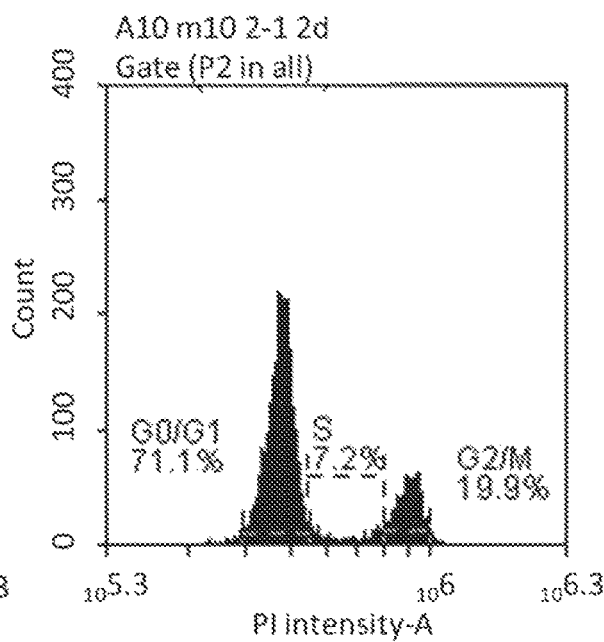
Figure 6C:
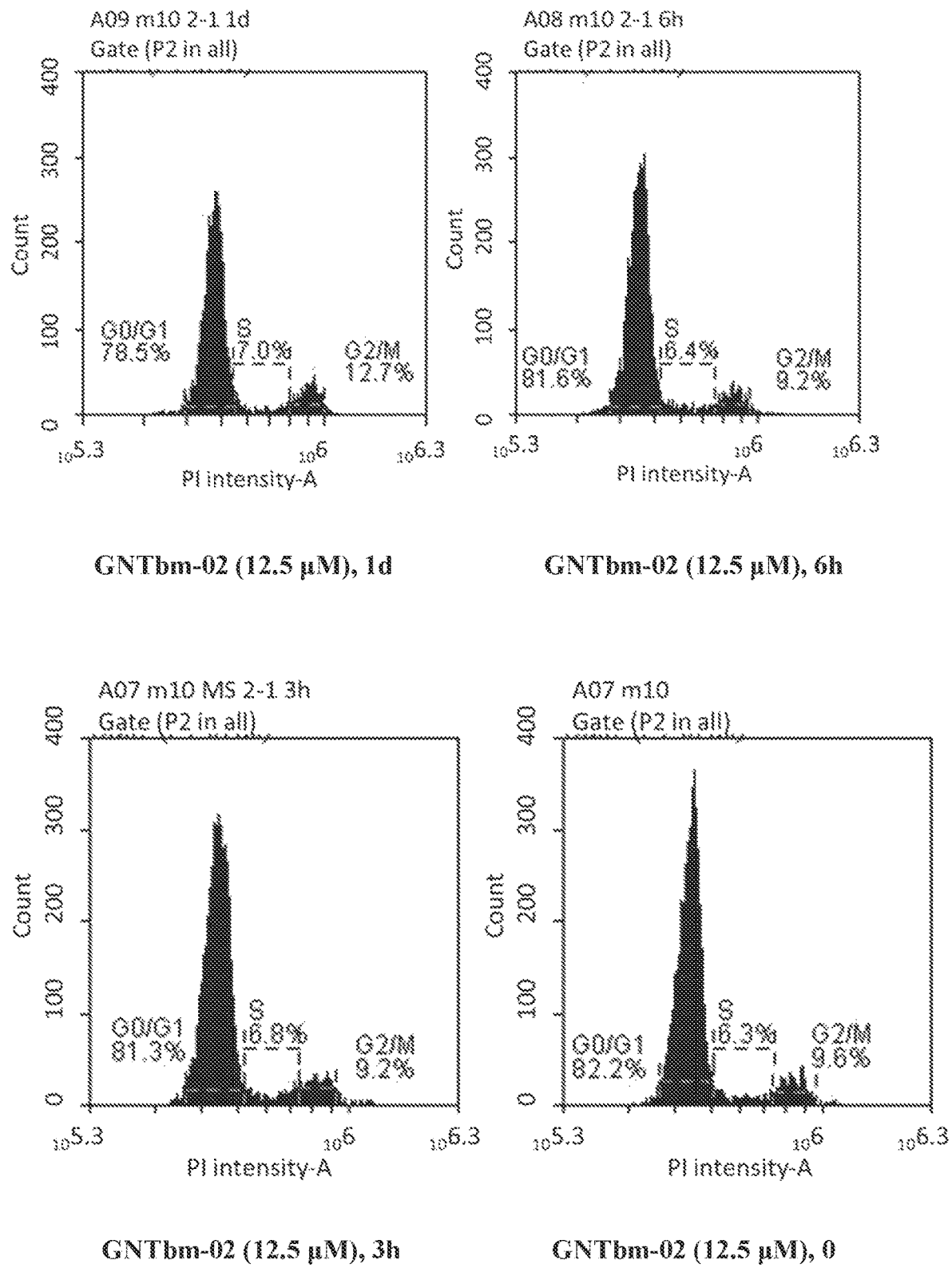

Human breast epithelial cell line M10 was treated with different doses from 1.625 to 25.0 μM of GNTbm-02 or Entinostat for 72 has shown in FIGS. 6a and b. The results demonstrated that GNTbm-02 and Entinostat at a concentration of 12.5 μM significantly induced cell cycle arrest of M10 cells in the G2/M phase. Entinostat (20.2%) was more potent than GNTbm-02 (16.2%) in induction of cell cycle arrest in the G2/M phase as shown in FIGS. 6a and b. As shown in FIGS. 6c and d, cell cycle was arrested in the G2/M phase by treatment with GNTbm-02 and Entinostat at a concentration of 12.5 μM in a time-dependent manner. The results indicated that the treatment with GNTbm-02 and Entinostat for 2 days significantly induced cell cycle arrest in the G2/M phase in M10 cells. These results suggested that GNTbm-02 and Entinostat treatment for human cancer cells significantly inhibited cancer cell proliferation through induced cell cycle arrest in the G0/G1 phase; however, GNTbm-02 and Entinostat treatment for human normal cells significantly inhibited cell proliferation through induced cell cycle arrest in the G2/M phase.

GNTbm Compounds Series Induced Apoptosis in Several Cell Lines

Figure 7A:
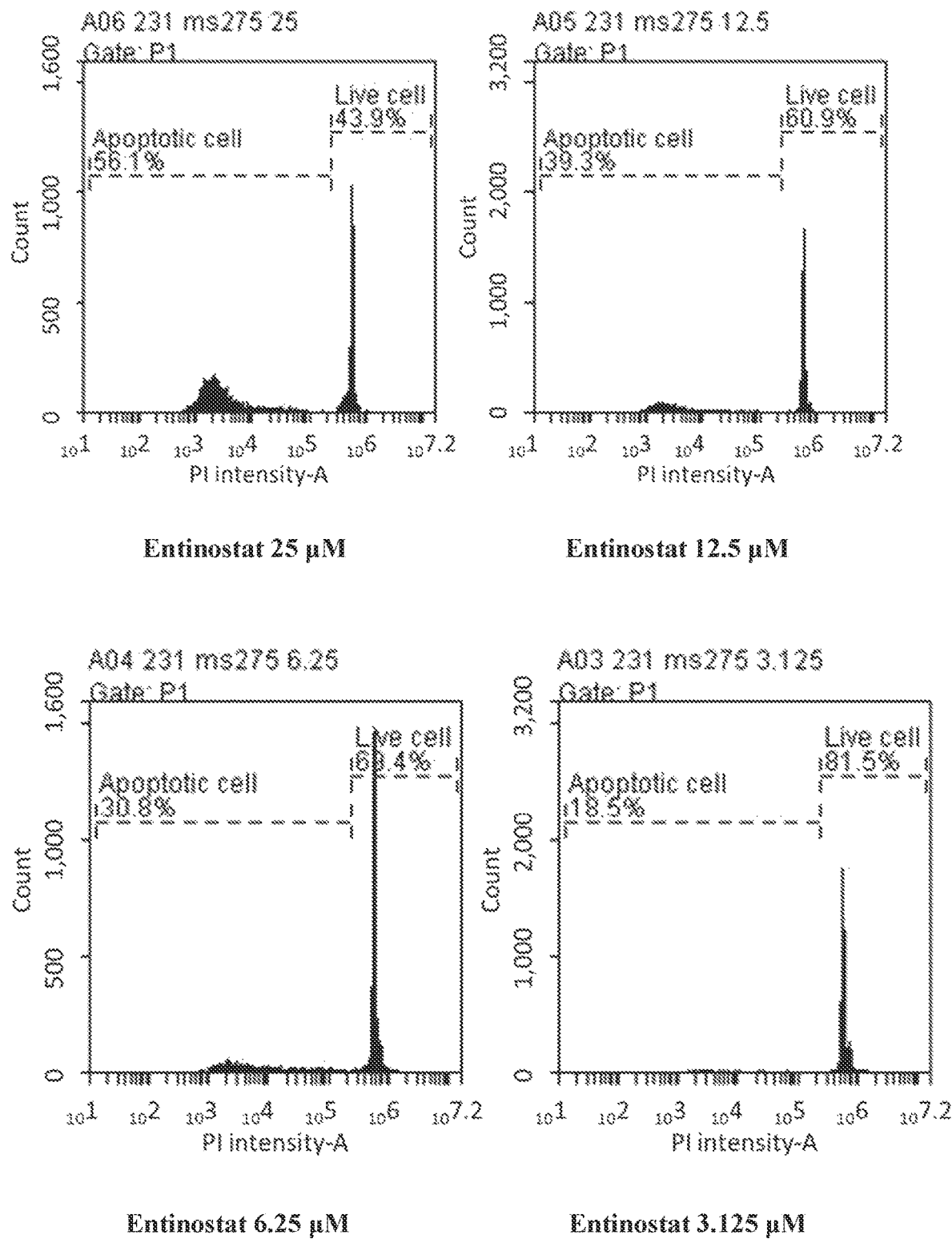
Figure 7A:
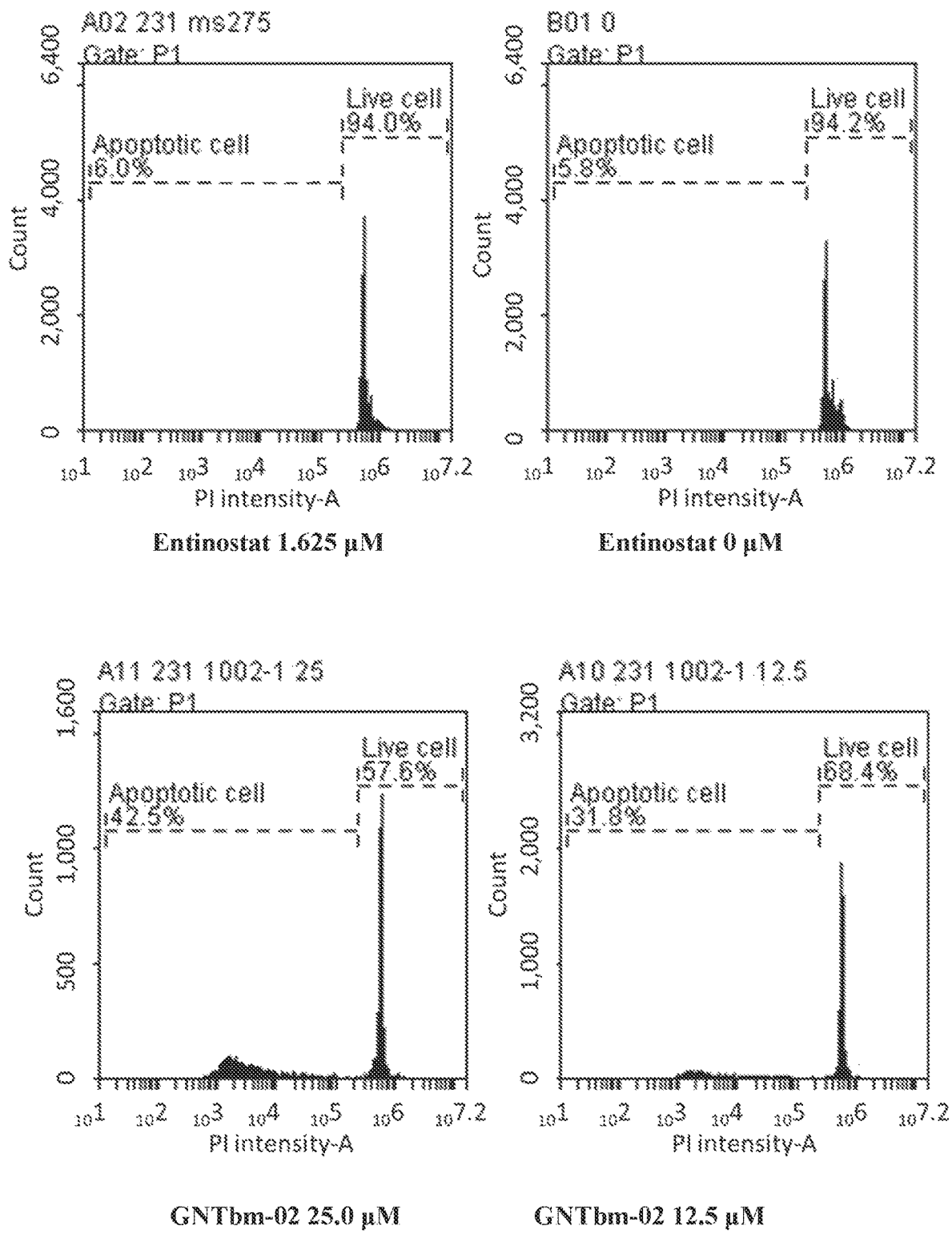
Figure 7A:
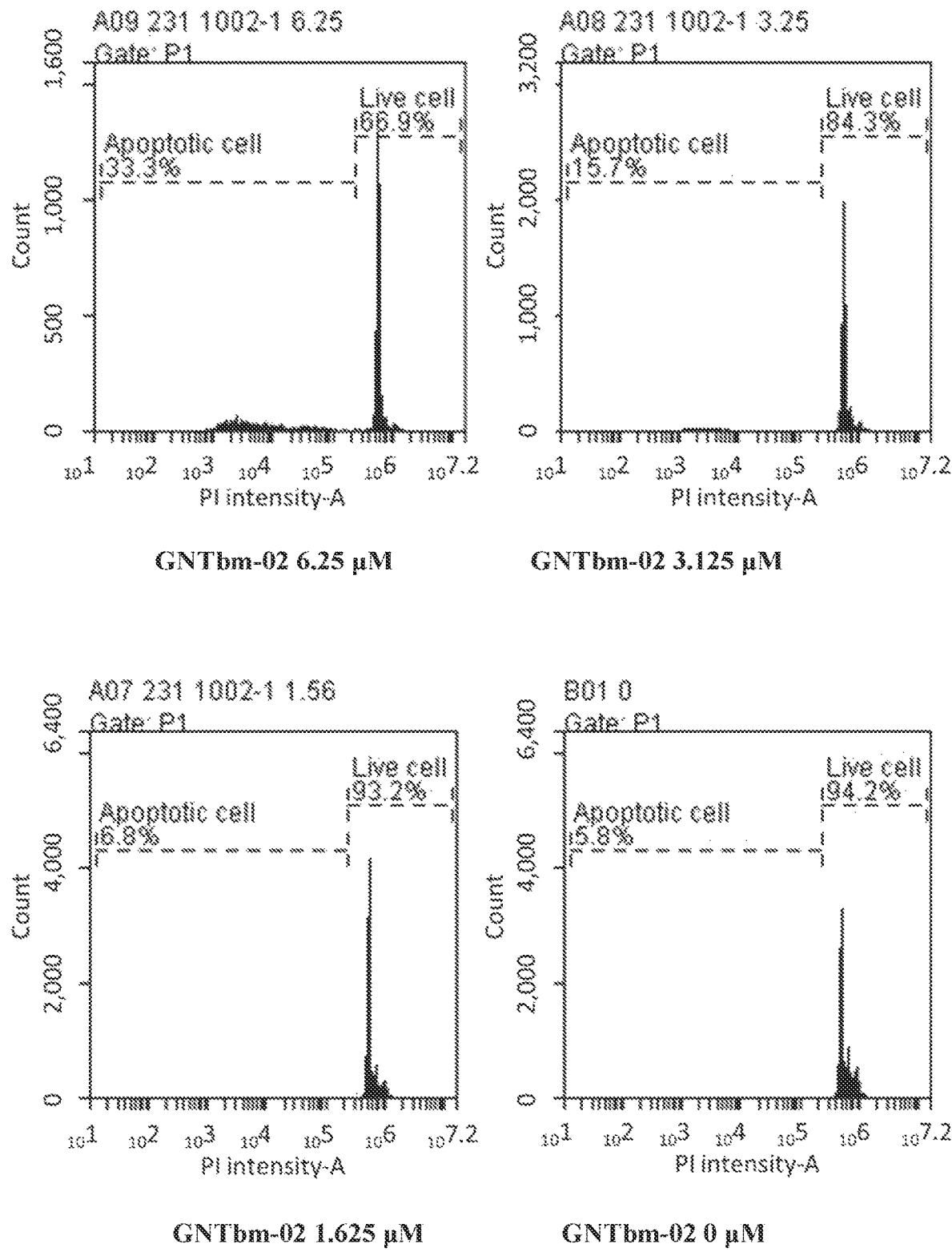
Figure 7C:
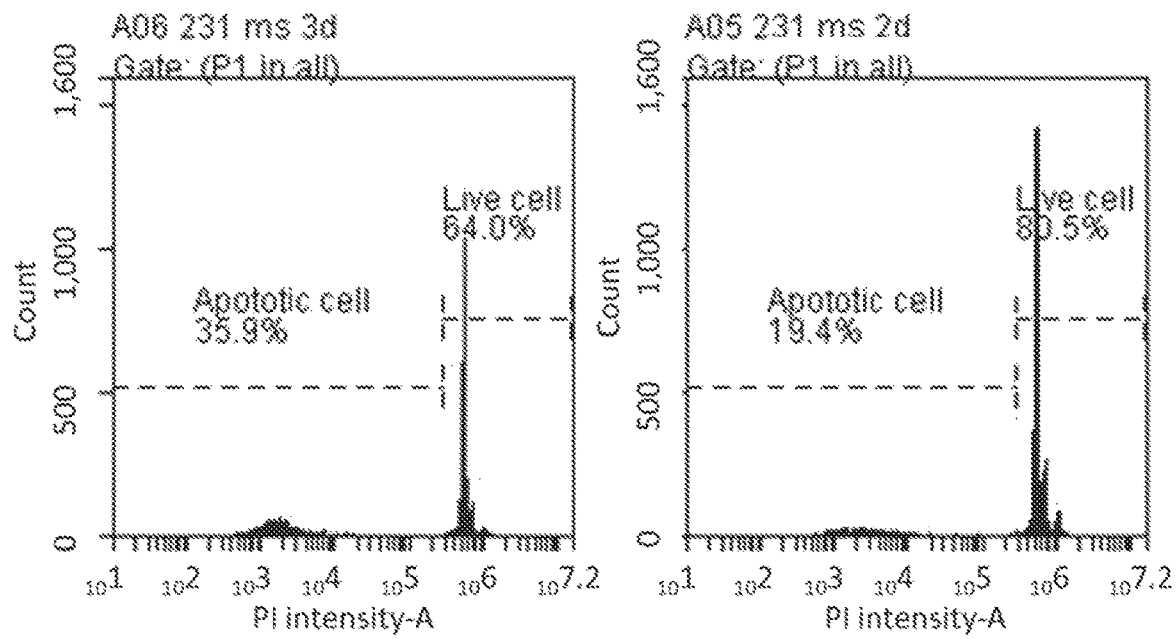
Figure 7C:
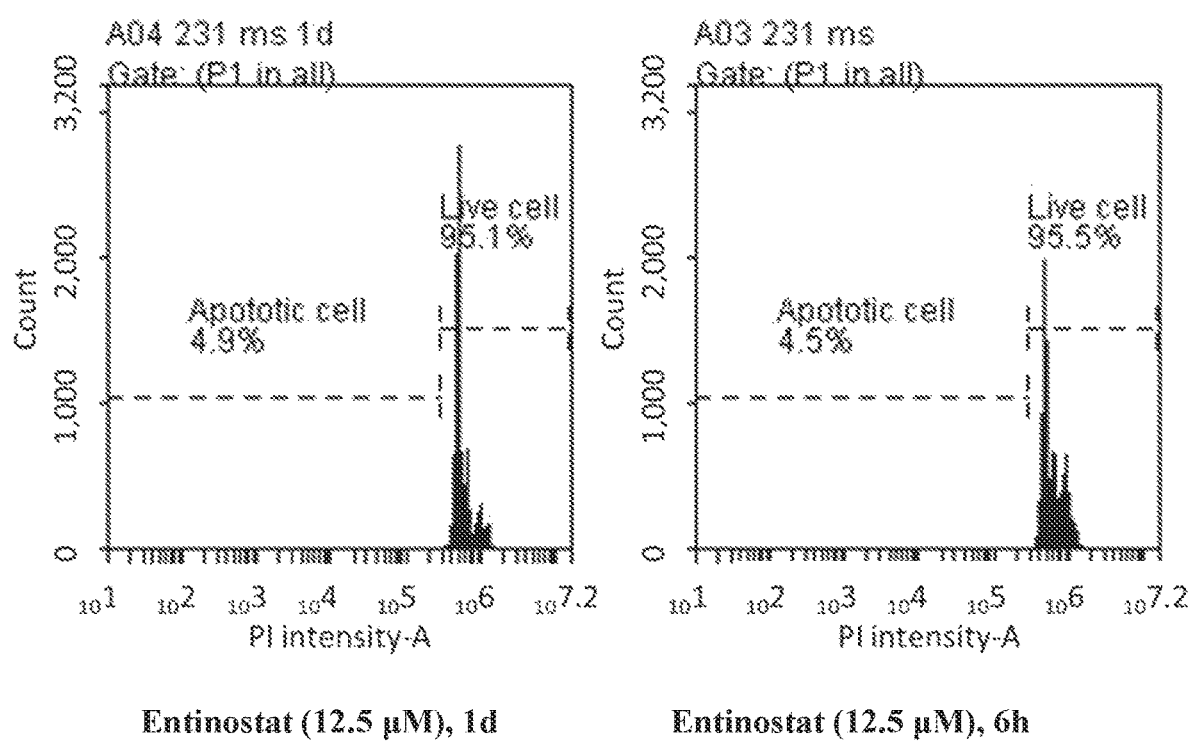
Figure 7C:
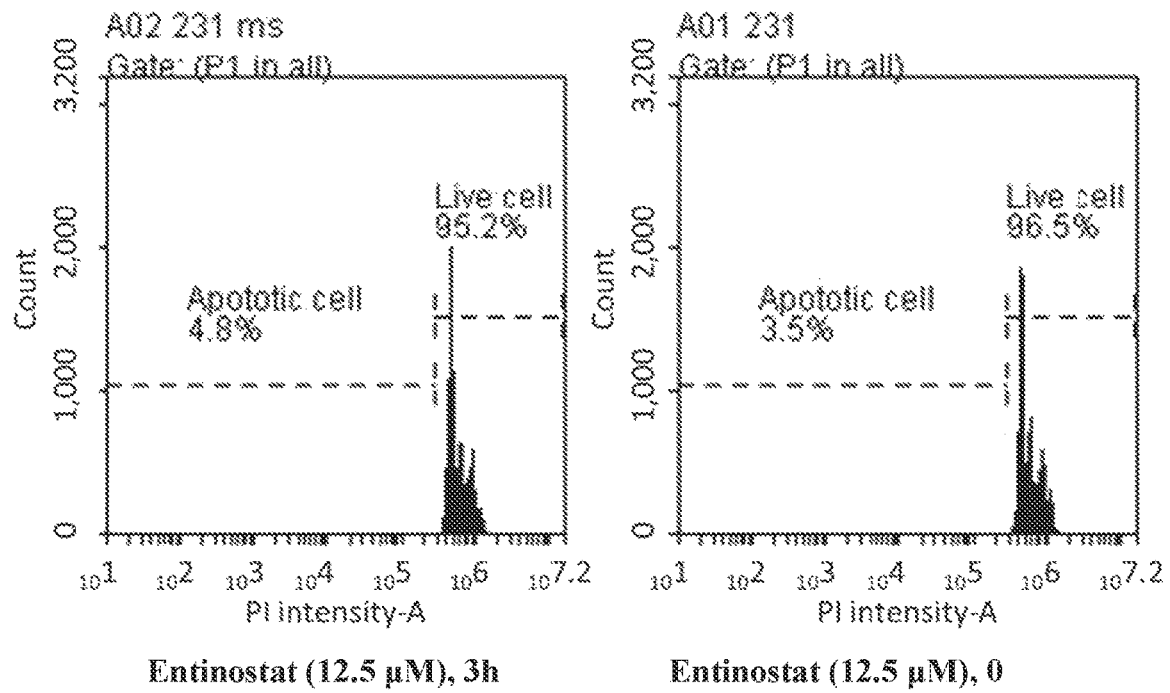
Figure 7C:
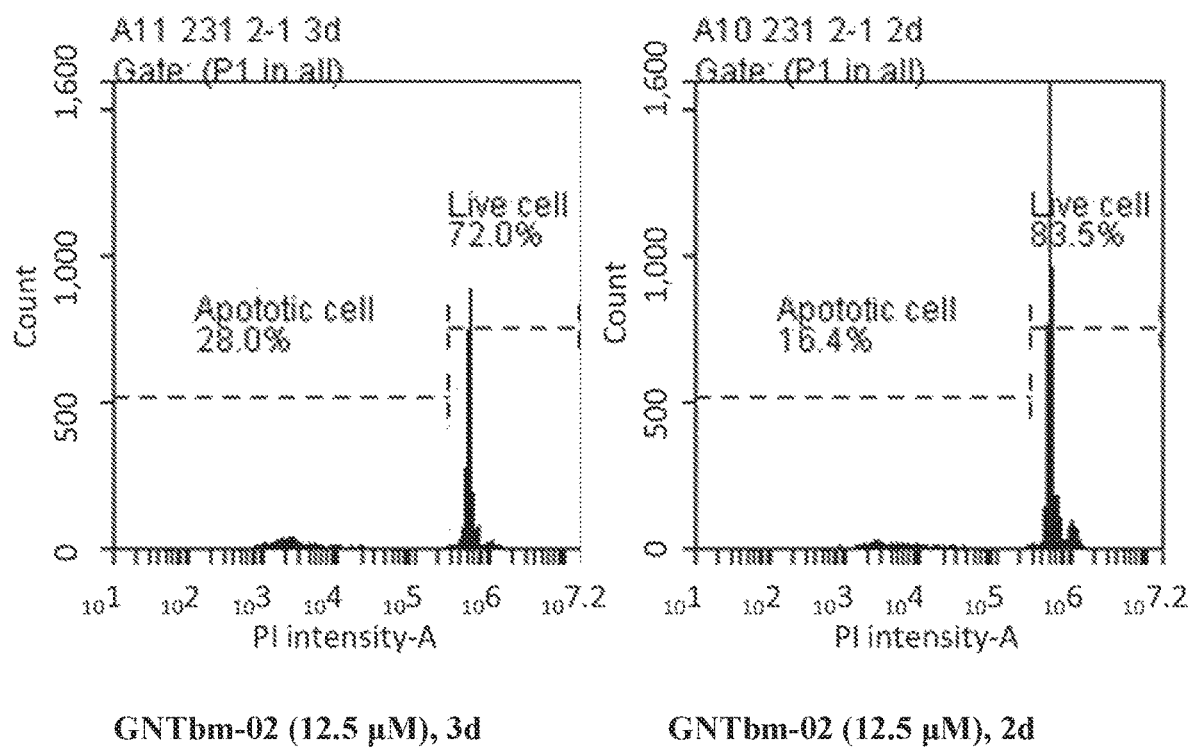
Figure 7C:
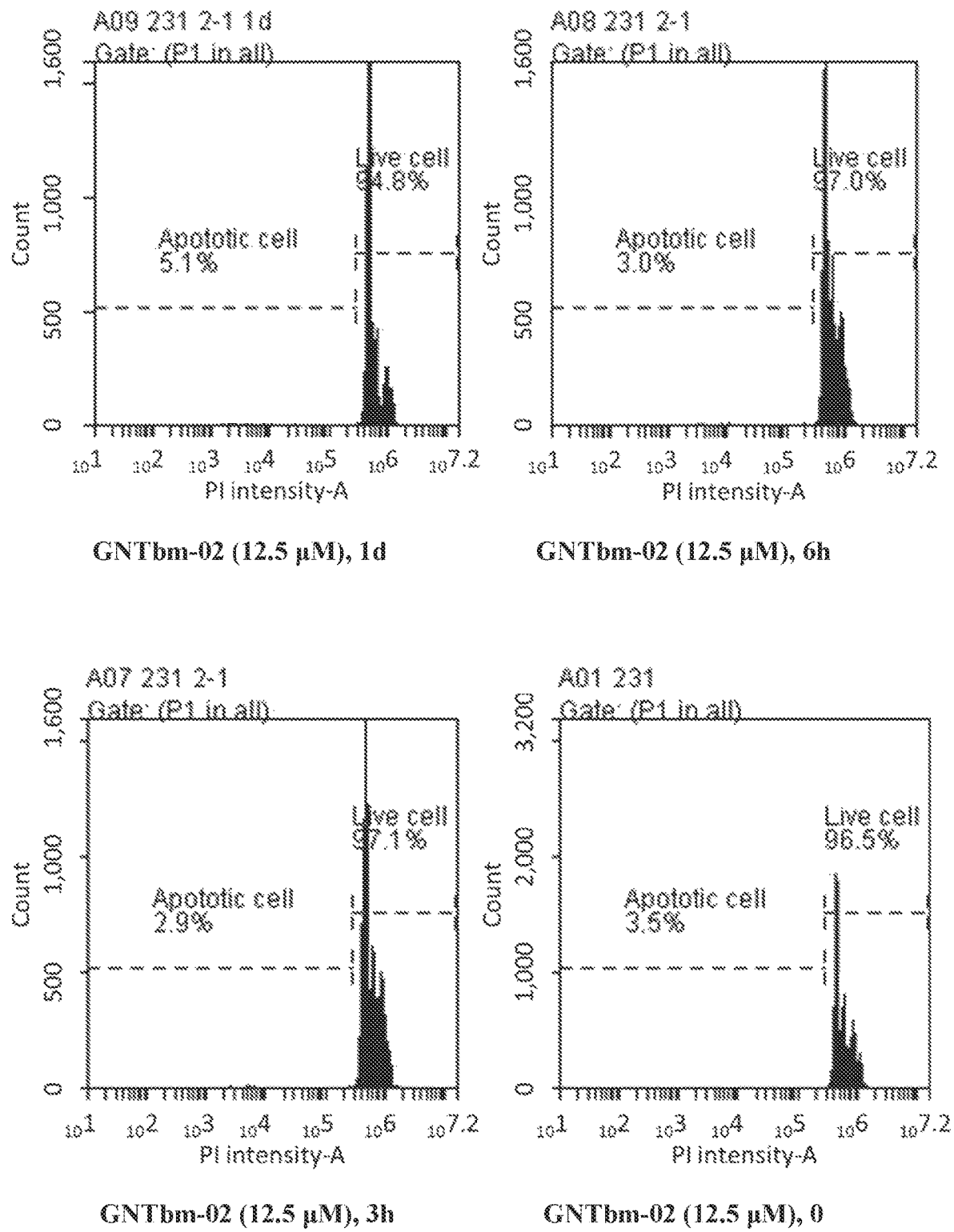
Figure 8A:
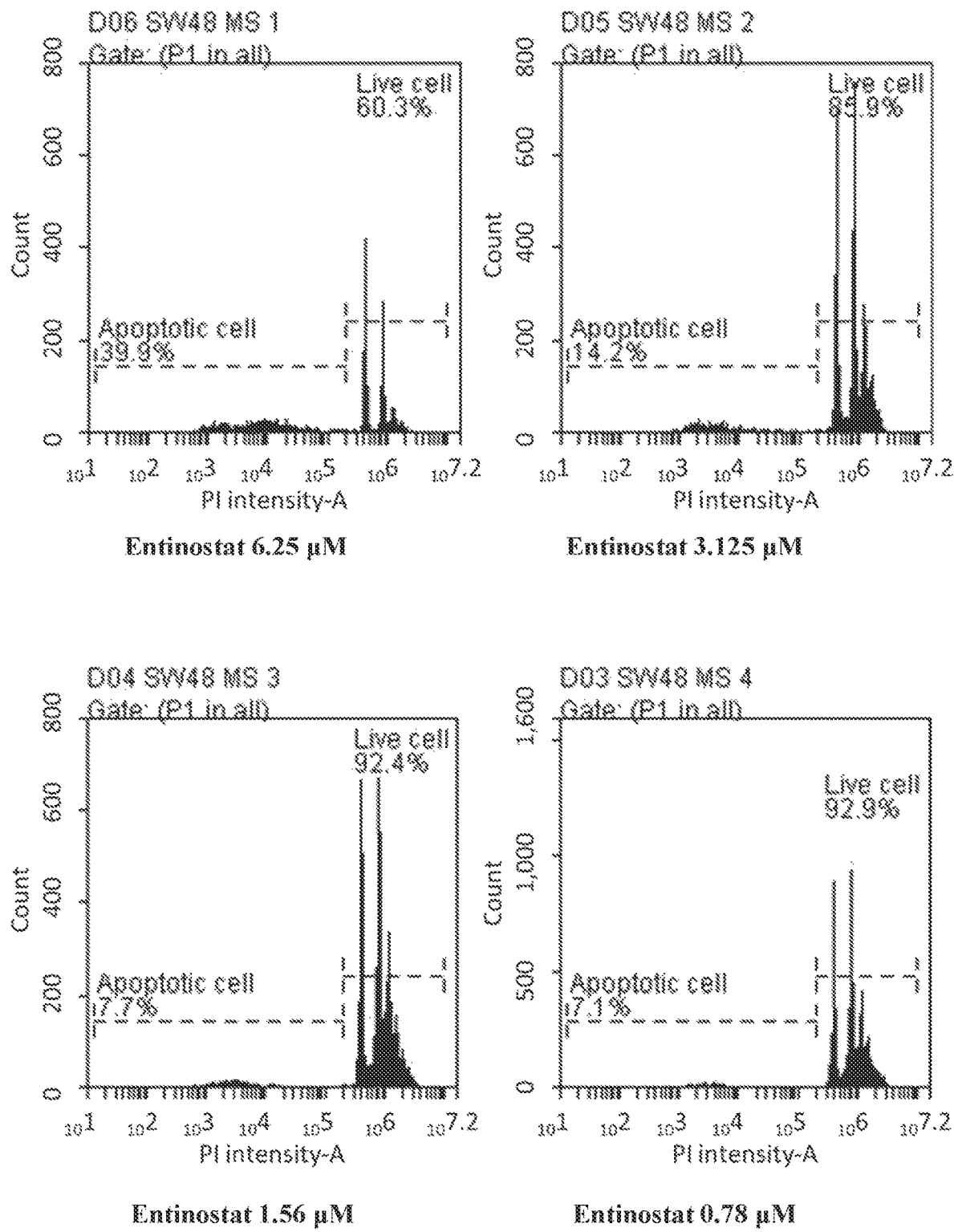
FIGS. 8A-8D show results from the assessment of GNTbm-02 induced cell apoptosis in SW48 cells: assessment was performed after treatment with GNTbm-02 and Entinostat in SW48 cells in a dose-dependent and time-dependent manner. The cells were stained with PI, and by using flow cytometer, the percentage of cells in sub-G1 phase was analyzed.
Figure 8A:
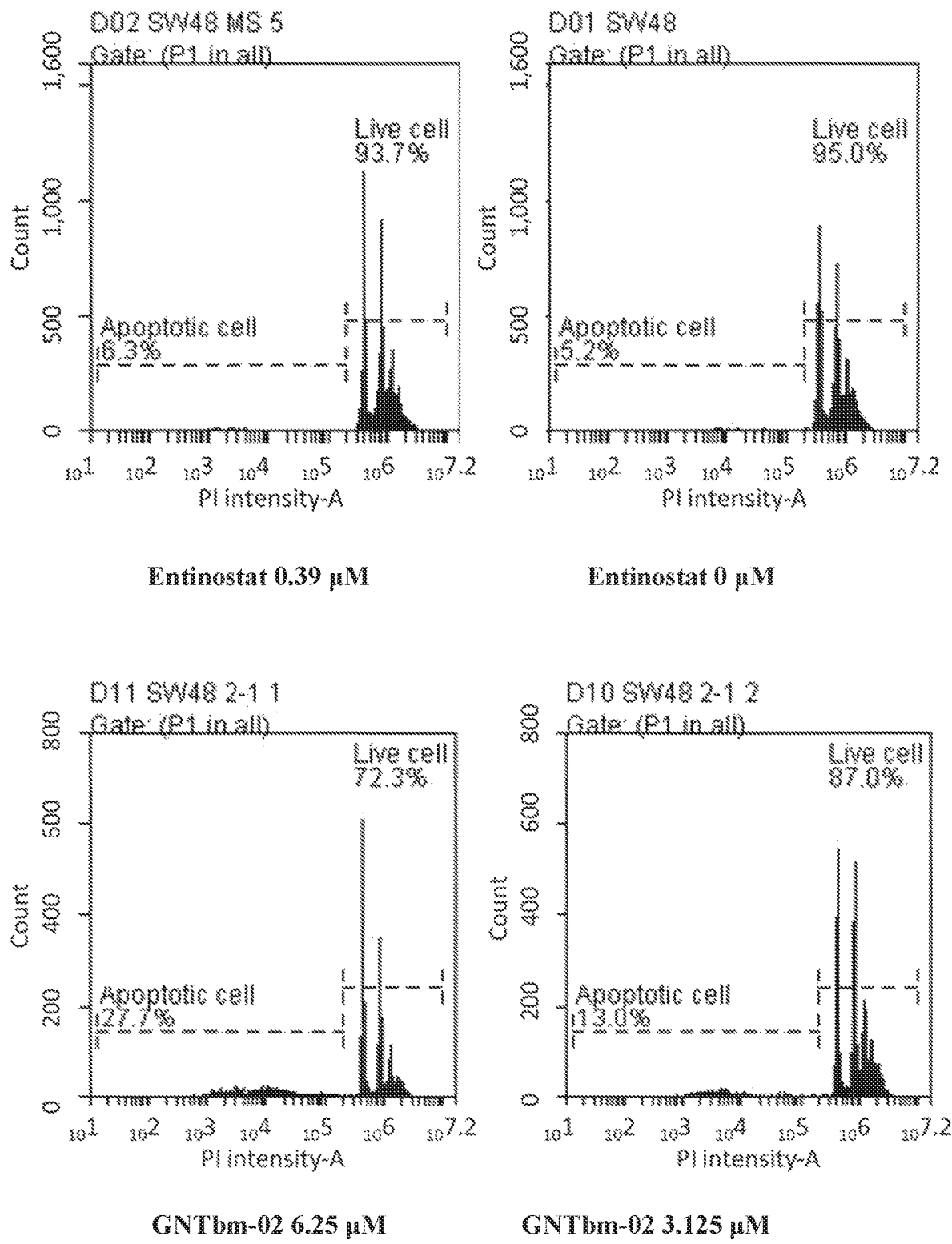
Figure 8A:
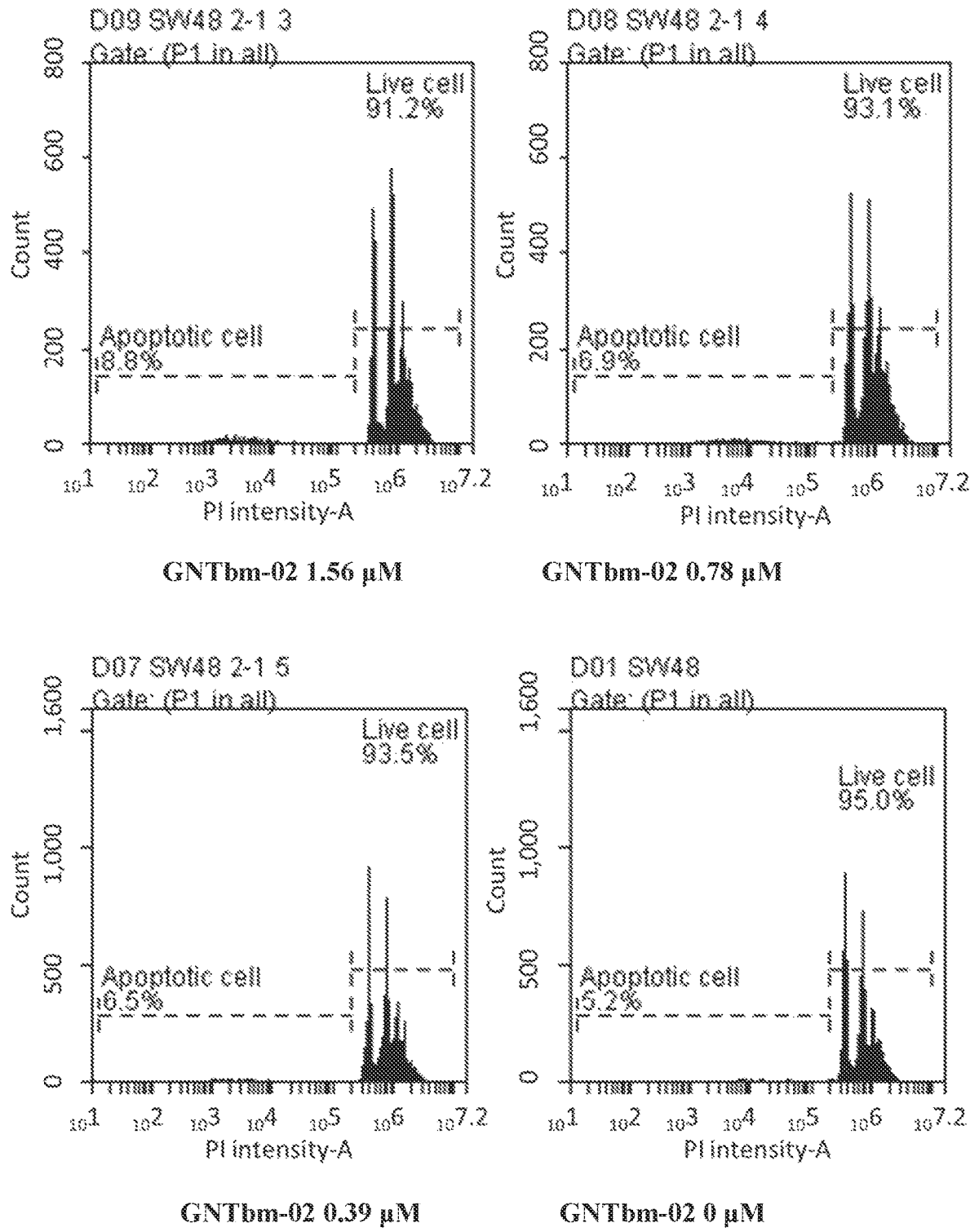
Figure 8B:
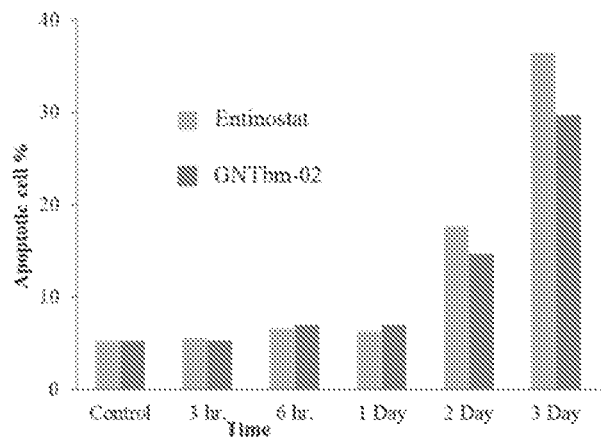
Figure 8D:
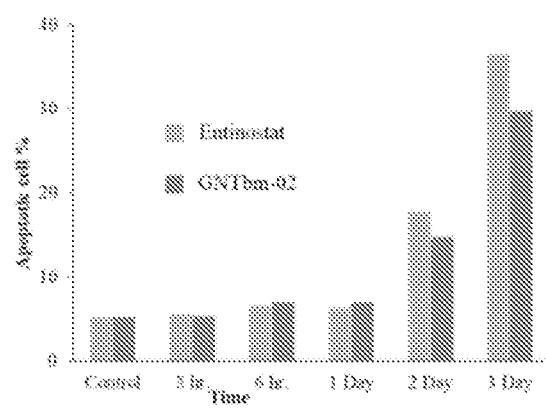
Figure 9B:
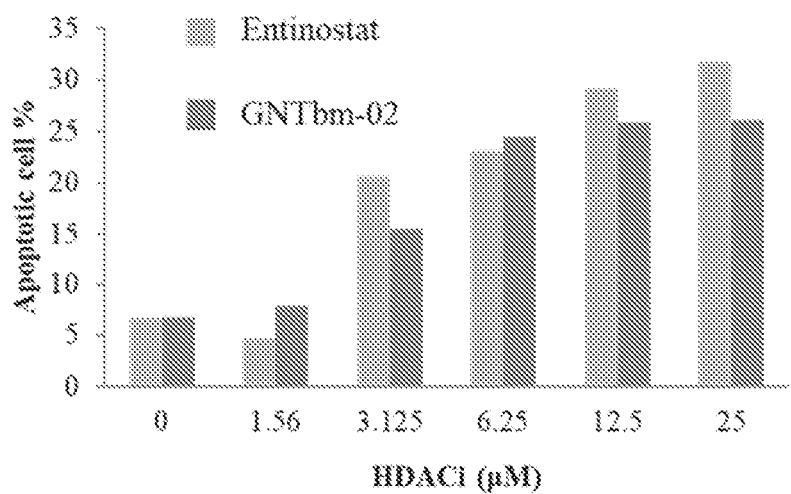
FIGS. 9A-9D show results from the assessment of GNTbm-02 induced cell apoptosis in M10 cells: assessment was performed after treatment with GNTbm-02 and Entinostat in M10 cells in a dose-dependent and time-dependent manner. The cells were stained with PI, and by using flow cytometer, the percentage of cells in sub-G1 phase was analyzed.
Figure 9D:
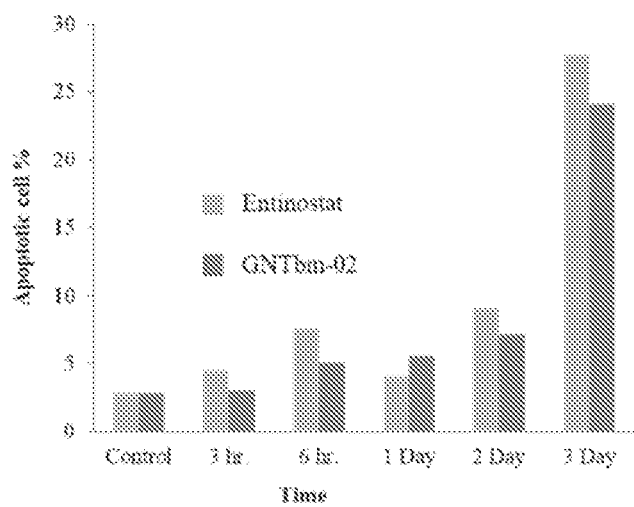
Figure 8C:
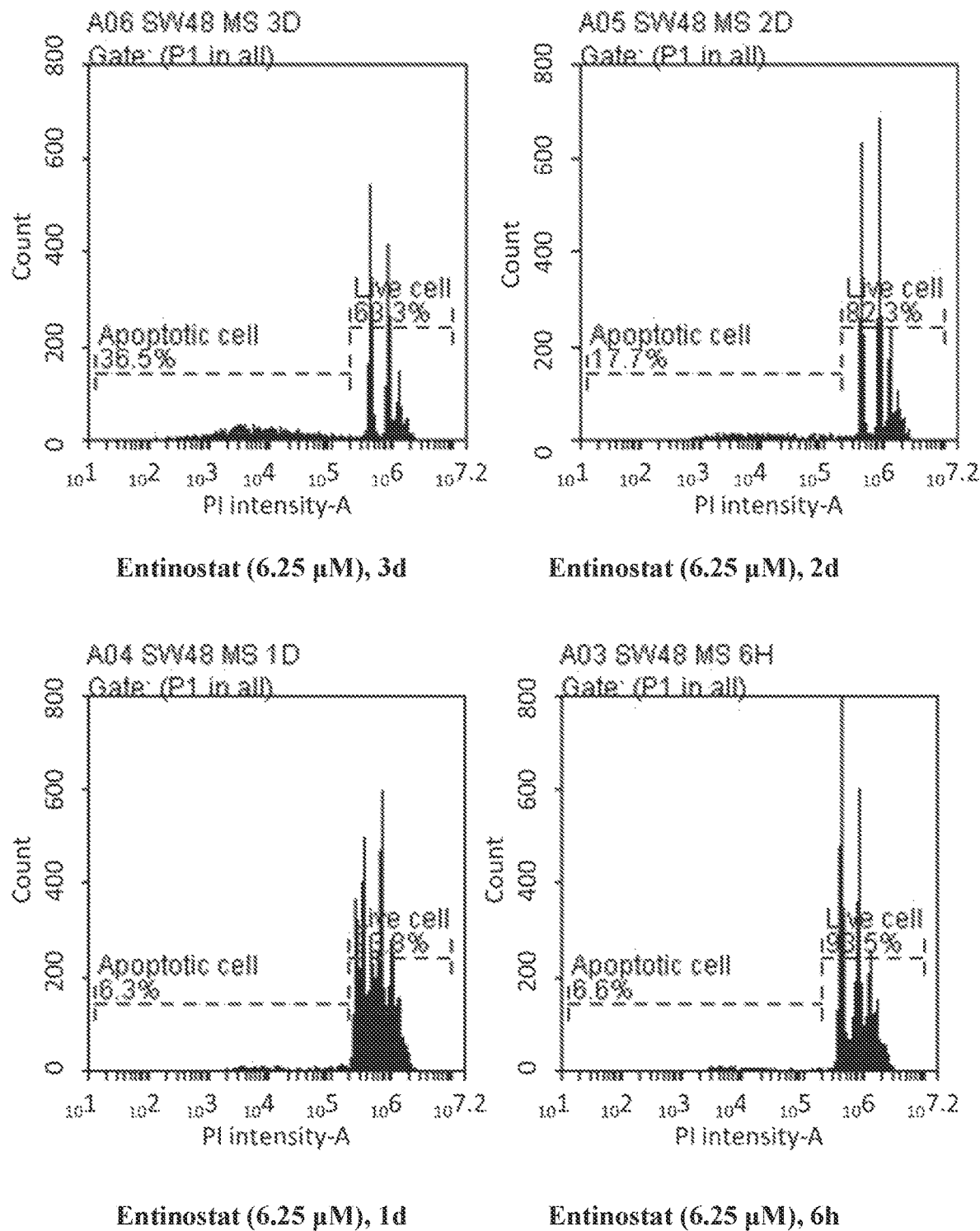
Figure 8C:
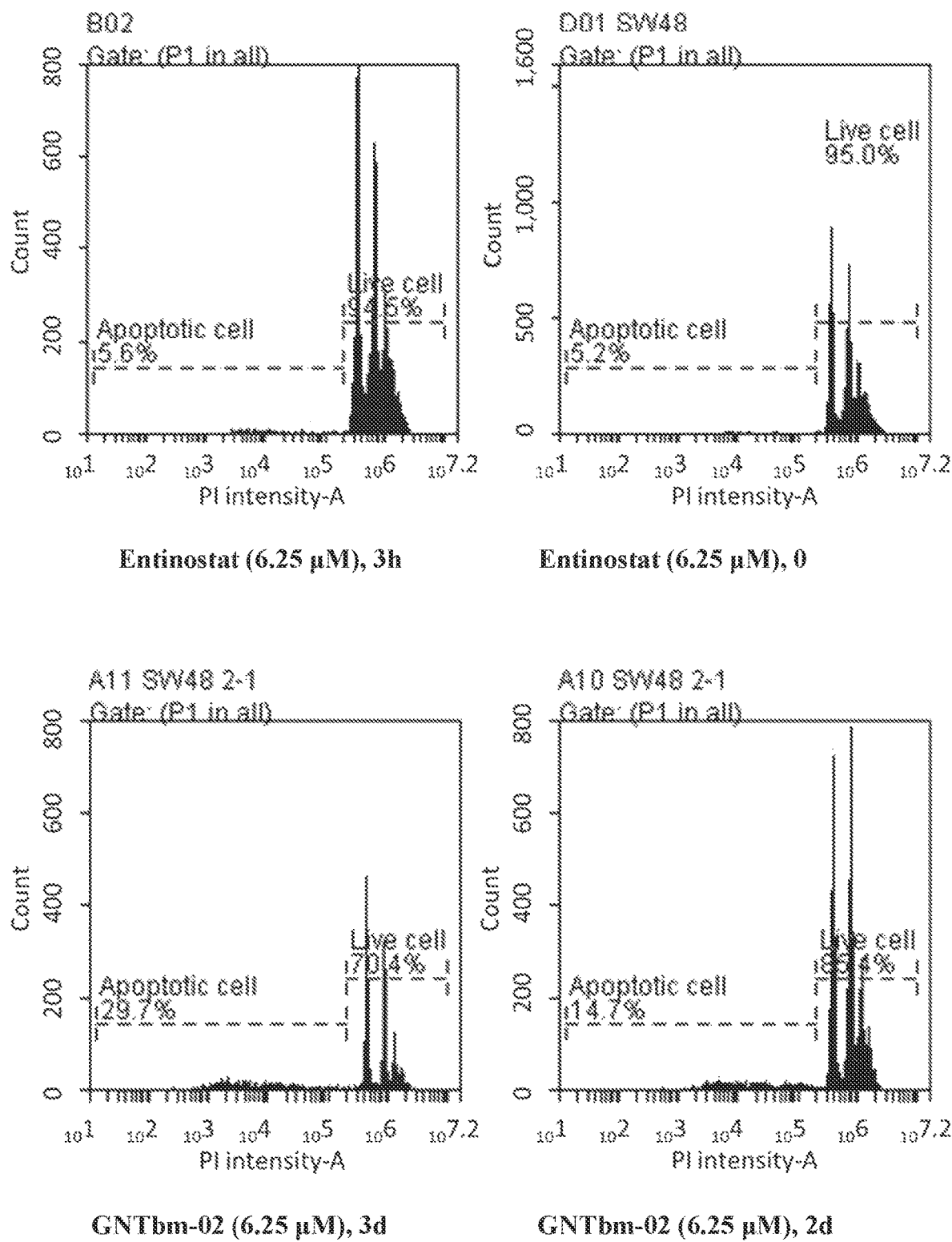
Figure 8C:
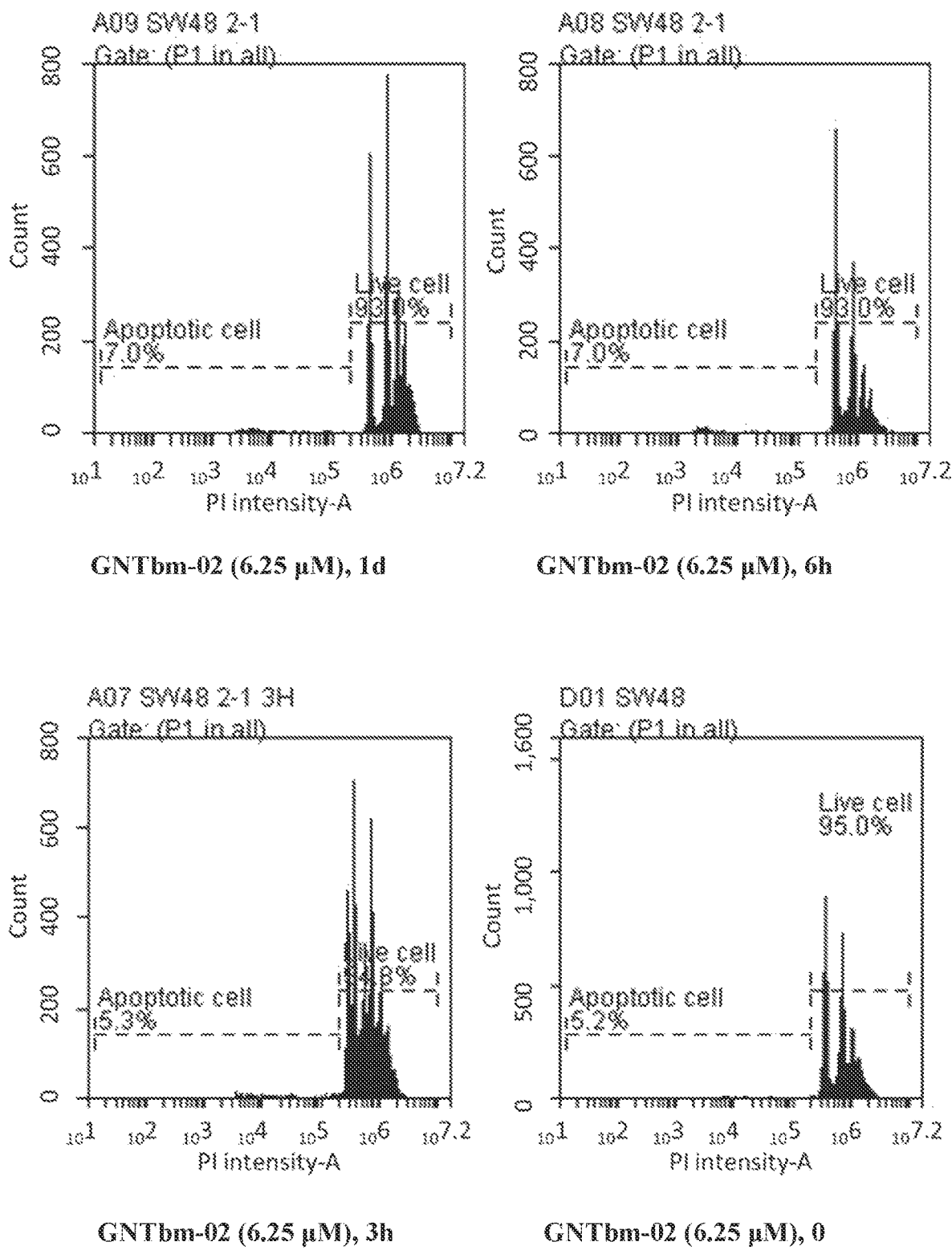
Figure 9A:
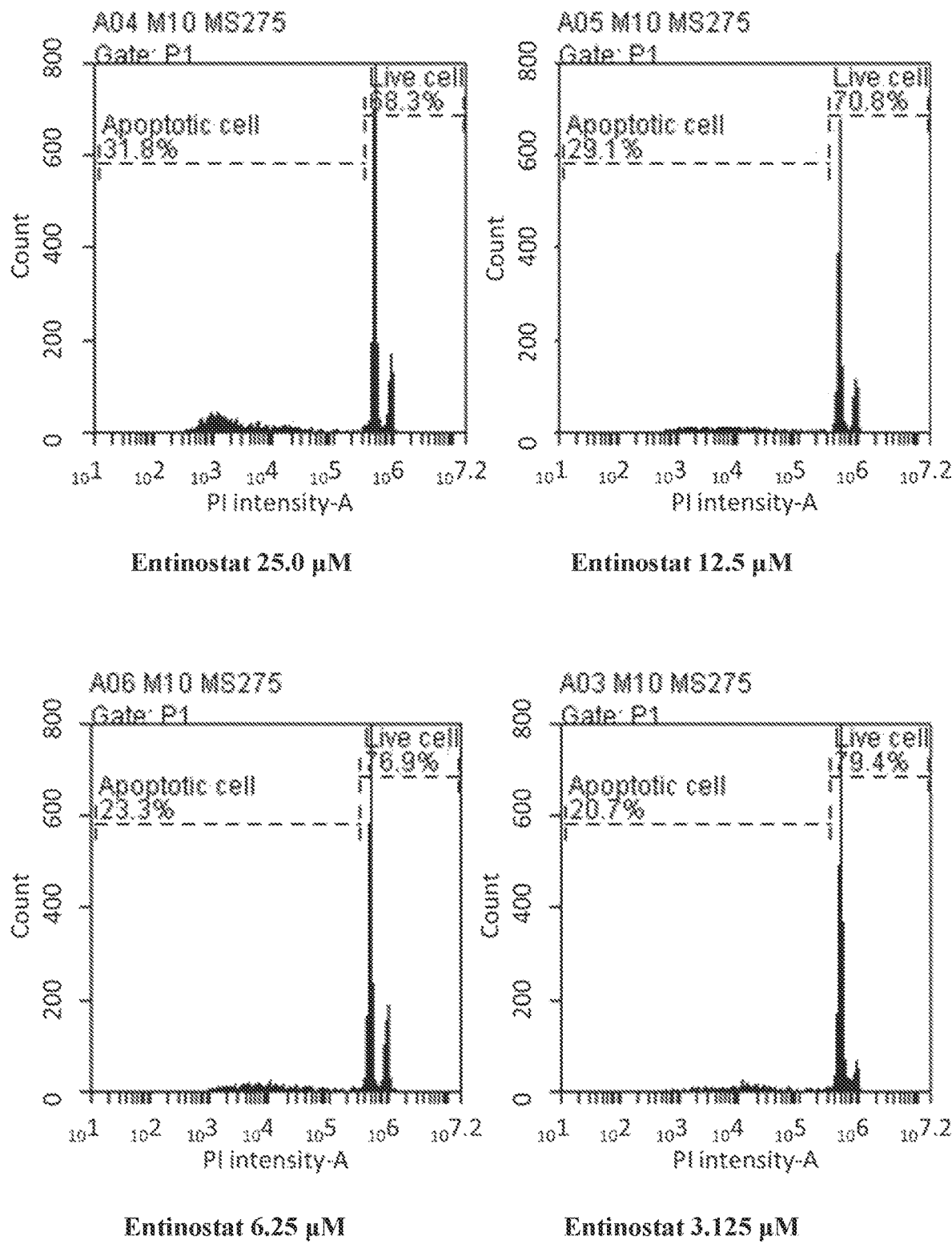
Figure 9A:
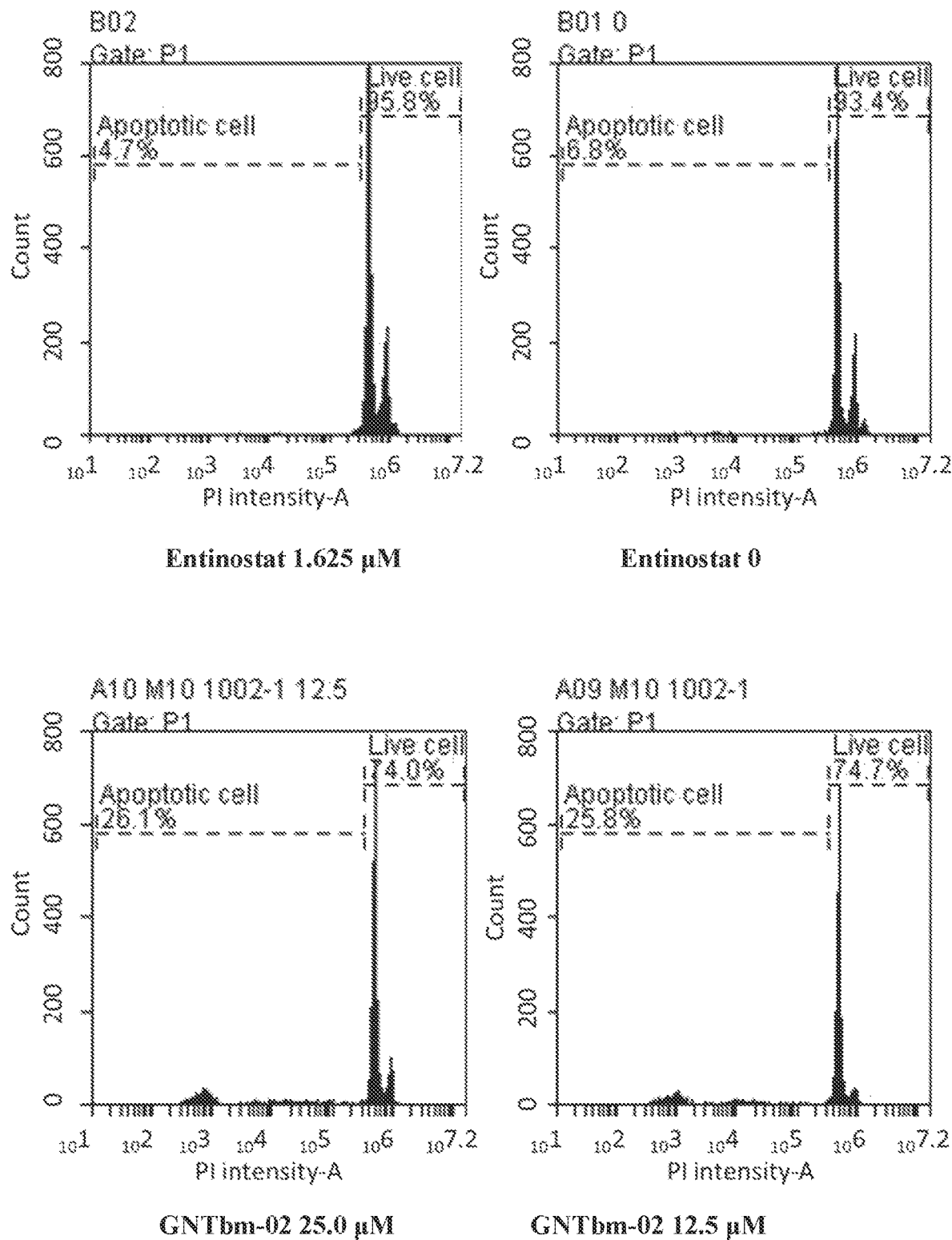
Figure 9A:
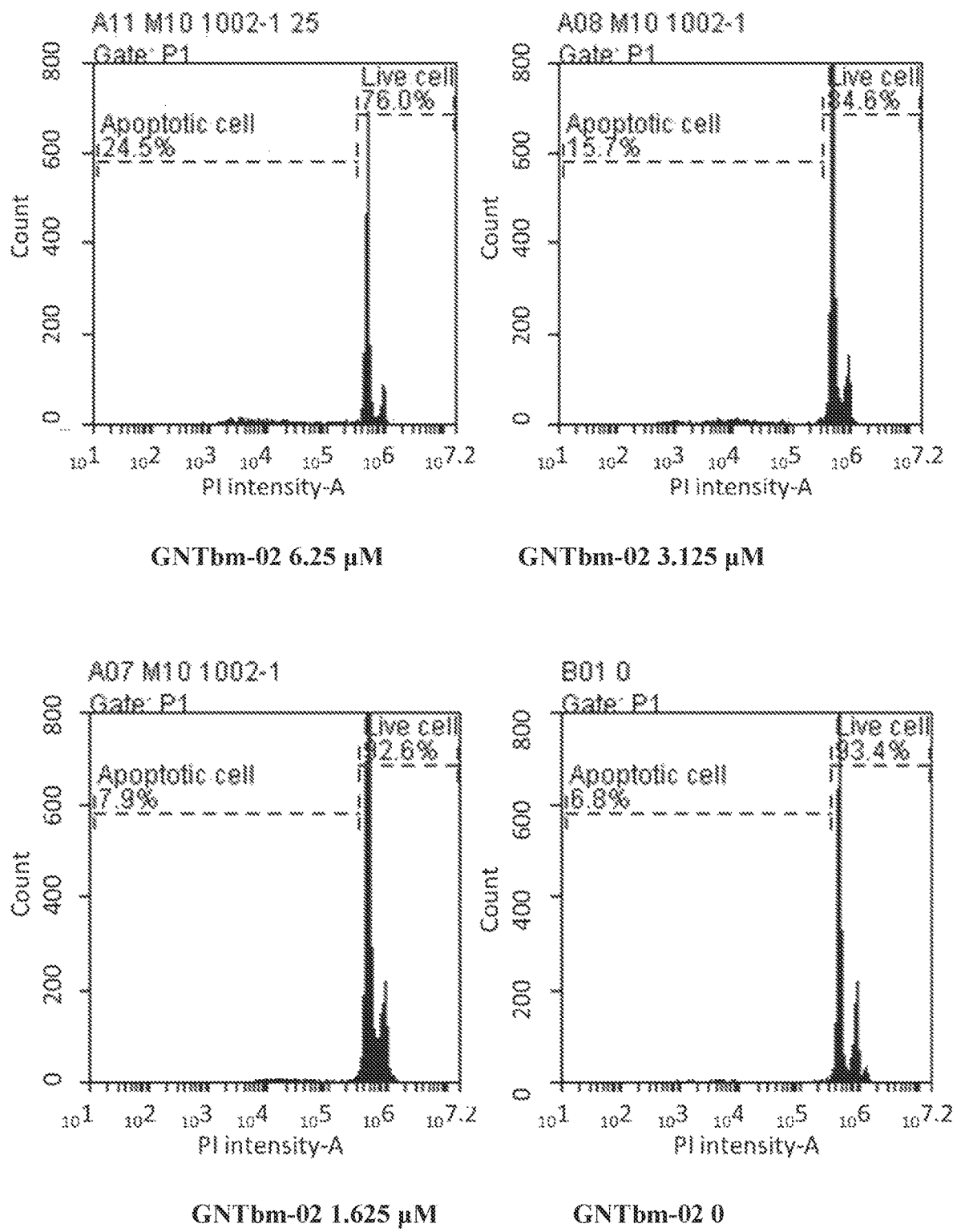
Figure 9C:
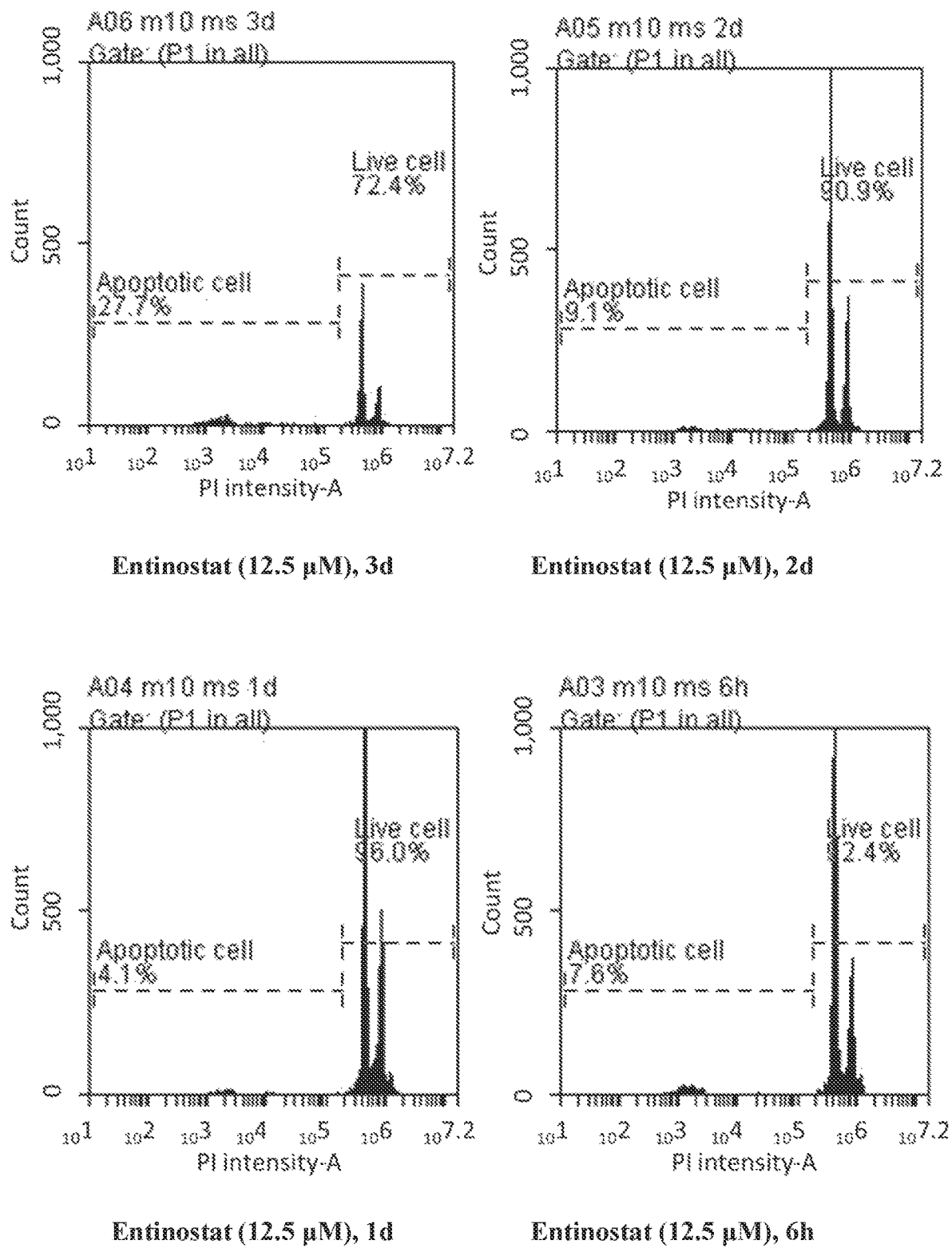
Figure 9C:
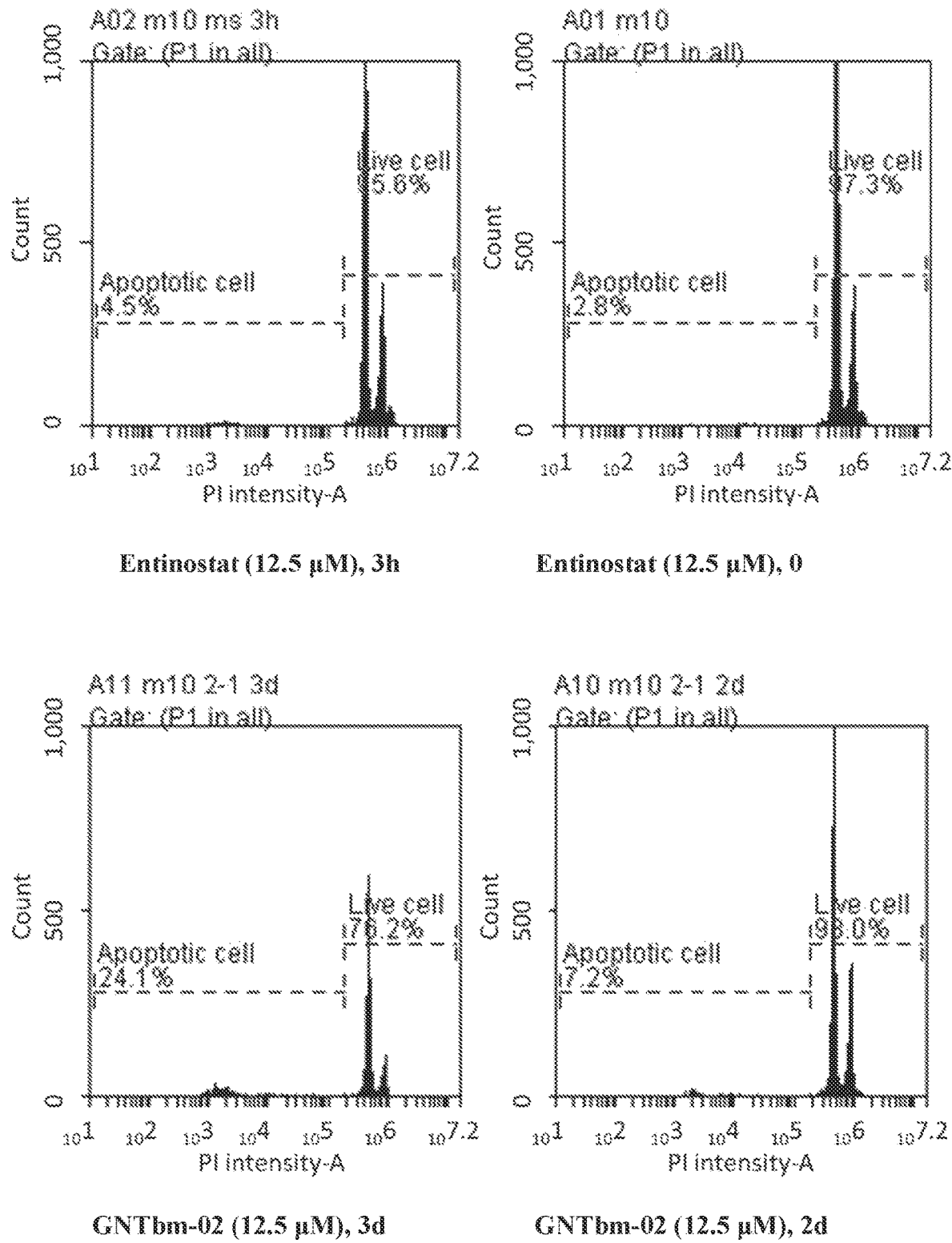
Figure 9C:
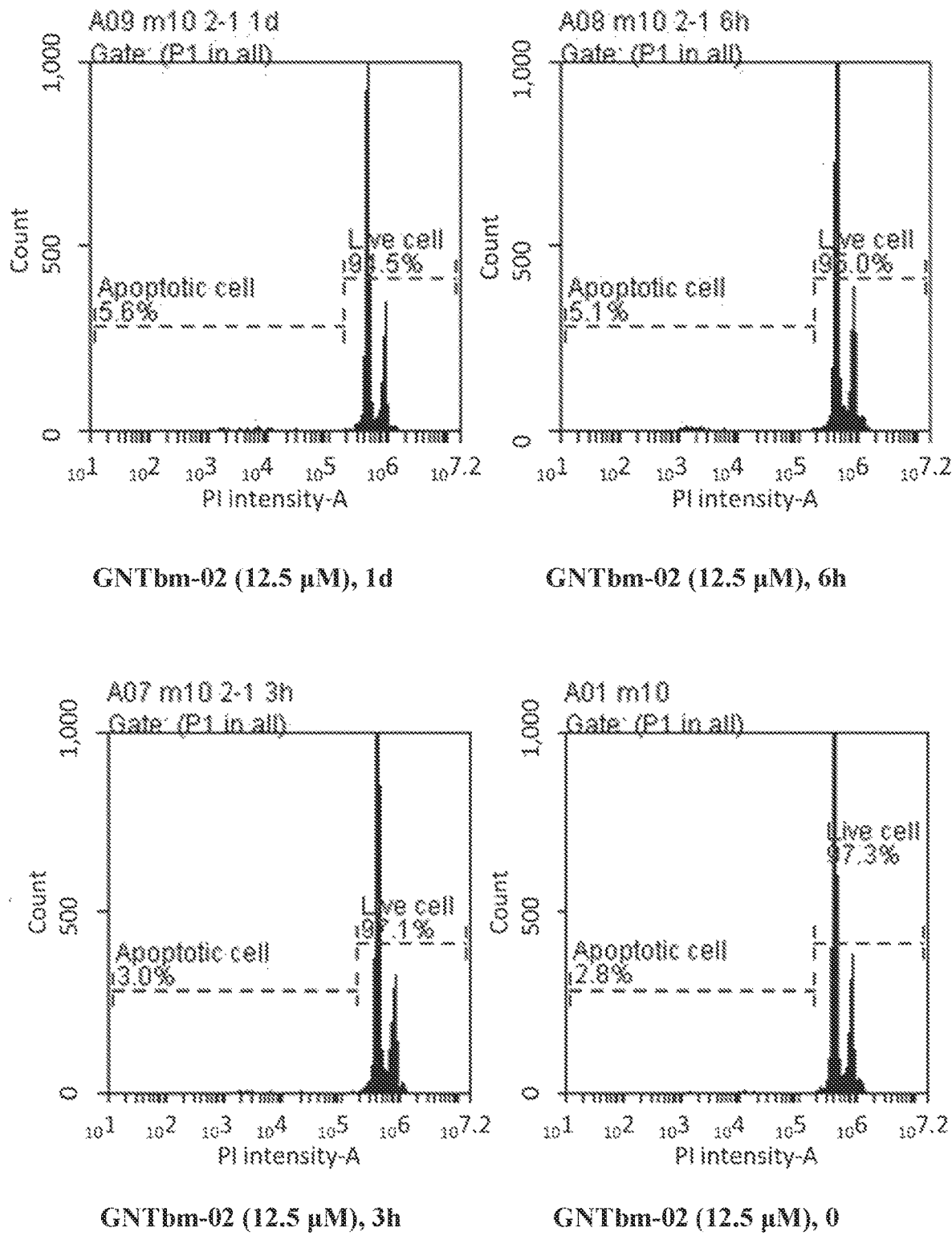

To investigate if GNTbm-02 induced apoptosis in cancer cells, the results after treatment with GNTbm-02 and Entinostat (as positive control) for MDA-MB-231 cells at various concentrations from 1.625 to 25.0 μM for 72 h are shown in FIGS. 7a and b. The results demonstrated that GNTbm-02 and Entinostat at a concentration of 6.25 μM significantly induced apoptosis (increased the percentage of sub-G1 phase) as shown in FIGS. 7a and b. As shown in FIGS. 7c and d, cell apoptosis was induced by treatment with GNTbm-02 and Entinostat for MDA-MB-231 cells in a time-dependent manner. The results indicated that GNTbm-02 and Entinostat at concentration of 12.5 μM for 72 h (3 days) significantly induced apoptosis in MDA-MB-231 cells. Entionstat was very potent in inducing apoptosis in a dose-dependent or time-dependent manner when compared with GNTbm-02 as shown in FIG. 7. Next, cell apoptosis was also evaluated in SW48 cells. As shown in FIGS. 8a and b, GNTbm-02 and Entinostat induced apoptosis in a dose-dependent manner. The results indicated that treatment with GNTbm-02 and Entinostat at various concentrations from 0.39 to 6.25 μM for 72 h induced cell apoptosis in SW48 cells. GNTbm-02 and Entinostat significantly induced apoptosis at a concentration of 6.25 μM for 72 h as shown in FIGS. 8a and b. As shown in FIGS. 8c and d, it was demonstrated that treatment with Entinostat and GNTbm-02 induced apoptosis at a fixed concentration of 6.25 μM in a time-dependent manner. GNTbm-02 and Entinostat at concentration of 6.25 μM for 72 h (3 days) significantly induced apoptosis in SW48 cells. Entinostat was very potent in inducing apoptosis in SW48 cells in a dose-dependent or time-dependent manner in comparison with GNTbm-02 as shown in FIG. 8. Finally, the induction of cell apoptosis by GNTbm-02 and Entinostat in normal cell line M10 was also investigated. As shown in FIGS. 9a and b, treatment with GNTbm-02 and Entinostat at various concentrations from 1.625 to 25.0 μM for 72 h induced cell apoptosis. GNTbm-02 and Entinostat at a concentration of 12.5 μM for 72 h significantly induced apoptosis in M10 cells. As shown in FIGS. 9c and d, GNTbm-02 and Entinostat treatment induced apoptosis at a concentration of 12.5 μM in a time-dependent manner. The results indicated that GNTbm-02 and Entinostat treatment at a fixed concentration of 12.5 μM in M10 cells for 72 h (3 days) significantly induced apoptosis as shown in FIGS. 9c and d. Entinostat showed very potent induced apoptosis in M10 cells in a dose-dependent or time-dependent manner in comparison with GNTbm-02 as shown in FIG. 9. But, M10 cells seems to be more resistant to induced apoptosis when treated with GNTbm-02 and Entinostat at a concentration of 25.0 μM for 72 h, in comparison with the result of MDA-MB-231 cells as shown in FIG. 7. Next, we were interested in investigating the activity of induction of apoptosis by GNTbm-04, GNTbm-05, GNTbm-38, and GNTbm-39 in SW48 cells. Apoptosis induced by these compounds was evaluated in SW48 cells treated with indicated doses for 72 h. As shown in Table 13, GNTbm-04, GNTbm-05, GNTbm-38, and GNTbm-39 were potent in inducing apoptosis in SW48 cells.

Figure 11A:
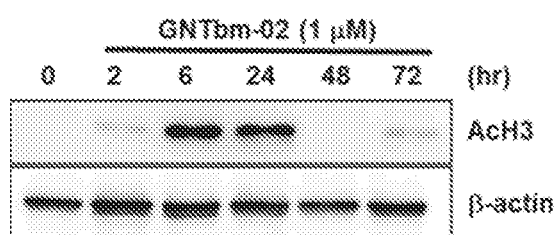
FIGS. 11A-11D illustrate the time course of induction of histone H3 acetylation by GNTbm-02 Class I HDAC inhibitor: MDA-MB-231 or SW48 cells were treated with GNTbm-02 at a concentration of 1 μM for 2, 6, 24, 48, 72 hours.
Figure 11B:
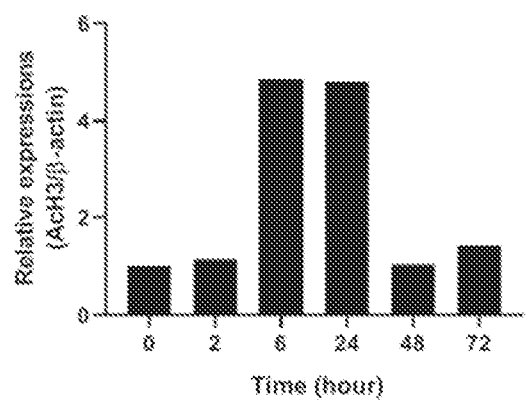
Figure 11C:
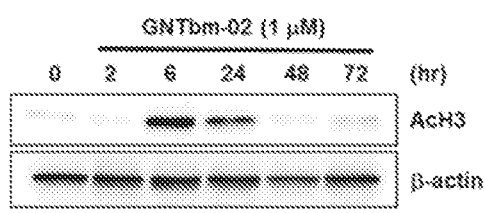
Figure 11D:
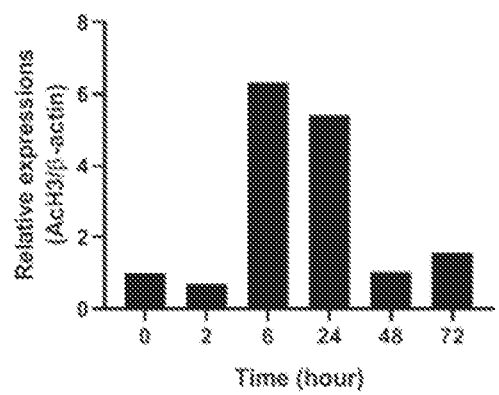
Figure 12:
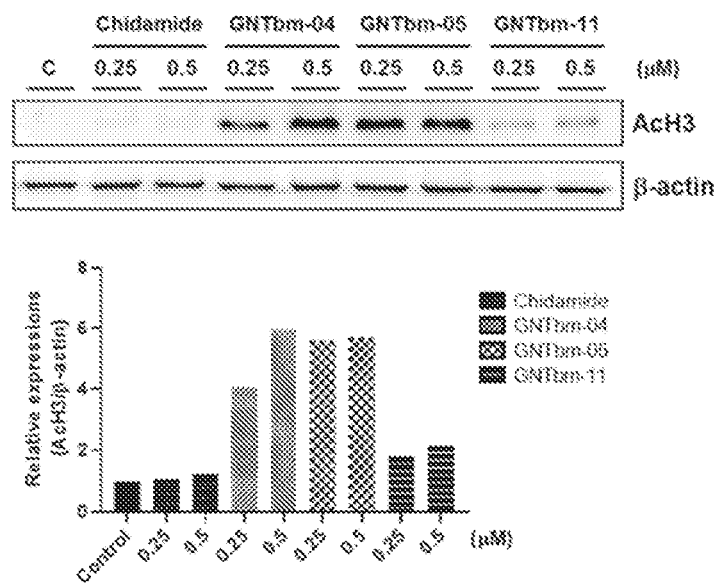
FIGS. 12A-12C show the results of Western Blot analysis of the acetylation level of histone H3 in cells treated with GNTbm-04, GNTbm-05, GNTbm-06, GNTbm-11, GNTbm-38, GNTbm-39 and Chidamide (as positive control): representative immunoblot analysis of acetyl histone H3, β-actin in SW48 cells. Cells were treated with the indicated concentrations of compound for 24 hours. Control cells were incubated with a vehicle.
Figure 12B:
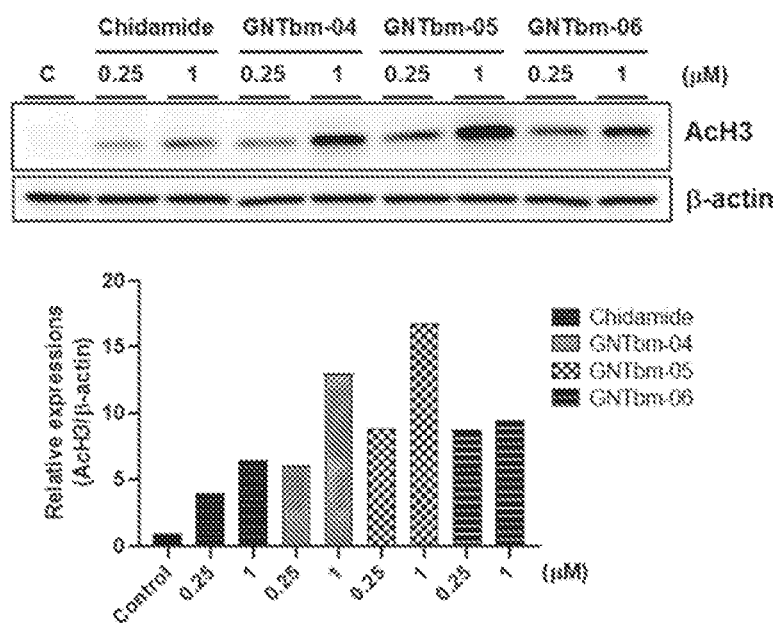
Figure 12C:
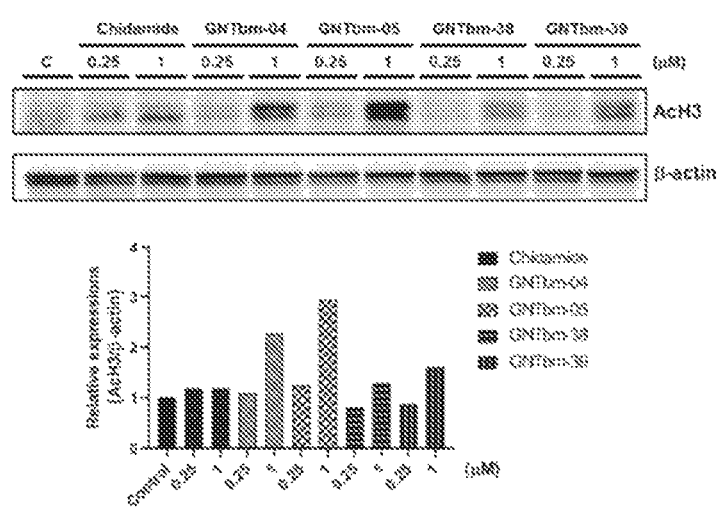

GNTbm Compounds Series Induced Histone H3 Acetylation in Several Human Cancer Cell Lines GNTbm-02 and Entinostat were proven to be potent class I HDAC inhibitors. The induced histone H3 acetylation by GNTbm-02 and Entinostat in a dose-dependent or time-dependent manner in MDA-MB-231 and SW48 cells was investigated. As shown in FIGS. 10a and b, treatment with GNTbm-02 and Entinostat for MDA-MB-231 cells at various concentrations from 0.1 to 10.0 μM for 24 h induced histone H3 acetylation. The results indicated that GNTbm-02 and Entinostat at a concentration of 1.0 μM significantly increased the level of histone H3 acetylation. As shown in FIGS. 10c and d, SW48 cells were more sensitive in inducing histone H3 acetylation by treatment with GNTbm-02 and Entinostat at various concentrations from 0.1 to 10.0 μM for 24 h. As shown in FIGS. 11a and b, treatment with GNTbm-02 at a concentration of 1.0 μM for 2, 6, 24, 48, and 72 h induced histone H3 acetylation in MDA-MB-231 cells in a time-dependent manner. The results indicated that GNTbm-02 potently induced histone H3 acetylation in MDA-MB-231 cell after 6 h treatment. Similar results were also demonstrated in SW48 cells as shown in FIGS. 11c and d. Treatment with GNTbm-02 at a concentration of 1.0 μM in SW48 cells for 2, 6, 24, 48, and 72 h showed histone H3 acetylation in a time-dependent manner. GNTbm-02 potently induced histone H3 acetylation level in SW48 cells after 6 h treatment. Taken together, all these data suggested that GNTbm-02 was a potent class I HDAC inhibitor and induced histone H3 acetylation in several human cancer cell lines. Furthermore, we were interested in analyzing whether the novel compounds possessed more powerful activity to increase the histone 3 acetylation expression in SW48 cells as shown in FIG. 12. Cells were treated with the same doses of GNTbm-04, GNTbm-05, GNTbm-11, and Chidamide as a positive control for 24 h in SW48 cells as shown in FIG. 12a. GNTbm-05 and GNTbm-04 at dose of 0.25 μM were very potent in inducing the histone 3 acetylation than the positive control of Chidamide in SW48 cells. Similar results also demonstrated that GNTbm-04, GNTbm-05, and GNTbm-06 at dose of 0.25 μM were very potent in inducing the histone 3 acetylation in SW48 cells as shown in FIG. 12b. Furthermore, the four potent compounds (GNTbm-04, GNTbm-05, GNTbm-38, GNTbm-39) inducing the histone 3 acetylation were evaluated as shown in FIG. 12c. The results demonstrated that GNTbm-05, GNTbm-04, GNTbm-38, and GNTbm-39 were more potent in inducing the histone 3 acetylation expression in SW48 cells than Chidamide.

Figure 13A:
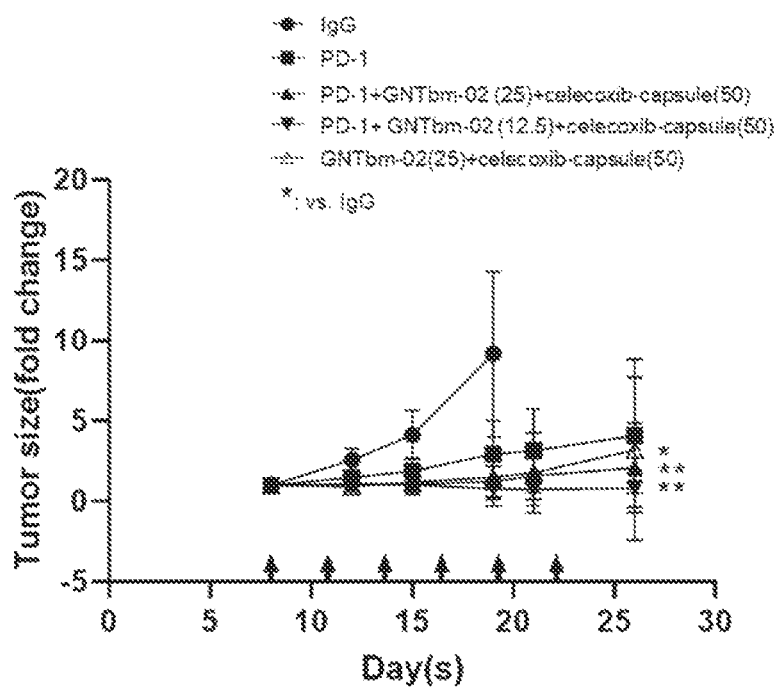
FIGS. 13A-13E show results from the assessment of a therapeutic response of GNTbm-02 plus Celecoxib at various doses combined with anti-PD-1 antibody in CT26 tumor-bearing mice: BALB/c mice bearing a CT26 tumor were treated with various therapeutic modalities as indicated. IgG, anti-IgG control (2.5 mg/kg); PD-1, anti-PD-1 monoclonal antibody (2.5 mg/kg); Celecoxib (50 mg/kg); GNTbm-02 (12.5, 25 mg/kg). Total tumor volumes (FIG. 13A) & (FIG. 13B), individual tumor volumes (FIG. 13C), mice body weight (FIG. 13D), and survival rate (FIG. 13E) were recorded. CT26 tumor bearing mice were treated as indicated and euthanized when tumor volume reached 3000 mm³ after tumor implantation. Data are given as the mean±SEM; *P<0.05, P<0.01, *P<0.001, one-way ANOVA with Tukey's test. Gehan-Breslow-Wilcoxon test (FIG. 13E). *, compared to IgG control. #, compared to PD-1 group.
Figure 13B:
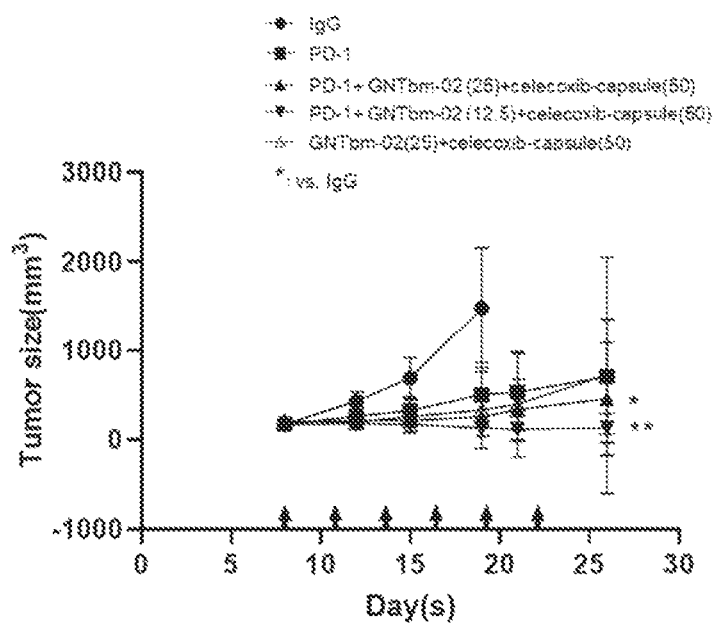
Figure 13C:
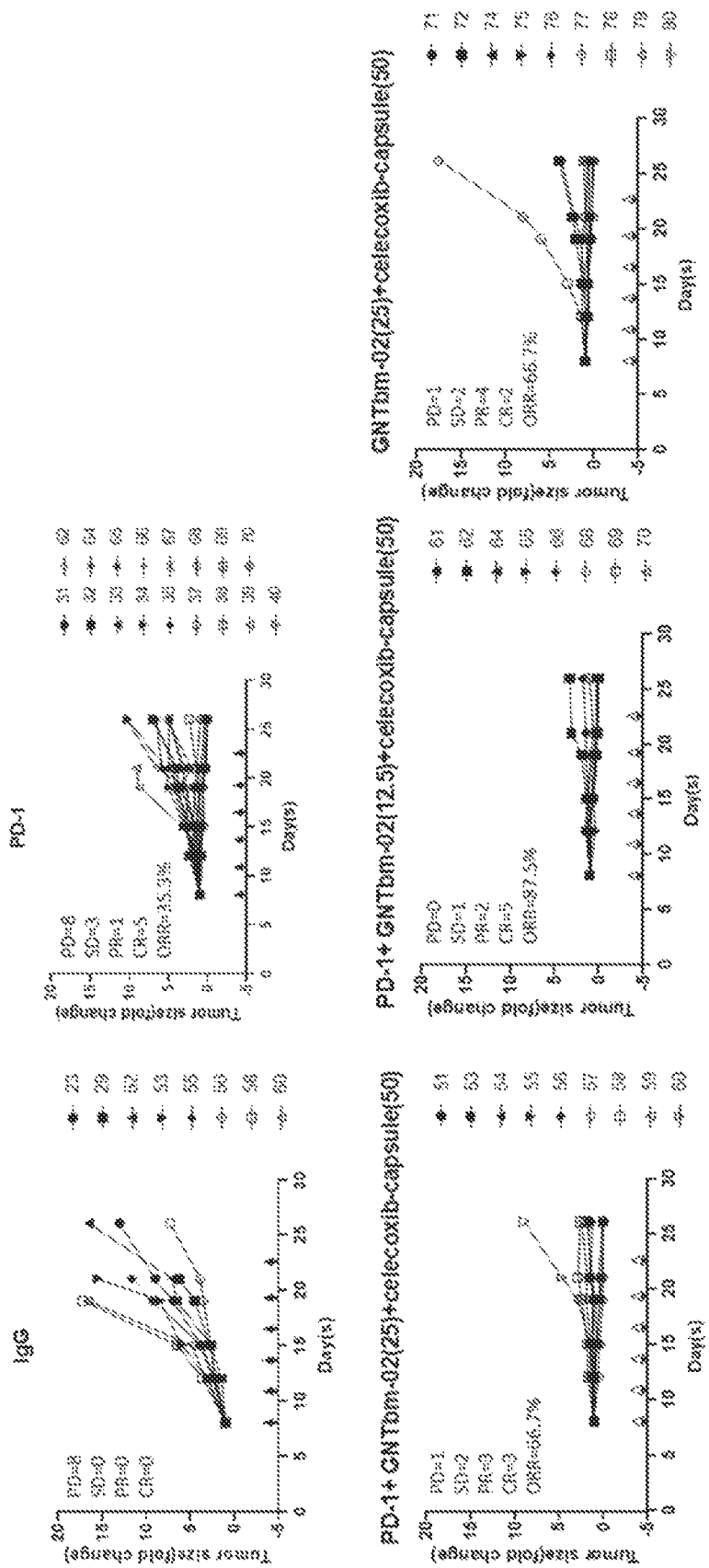
Figure 13D:
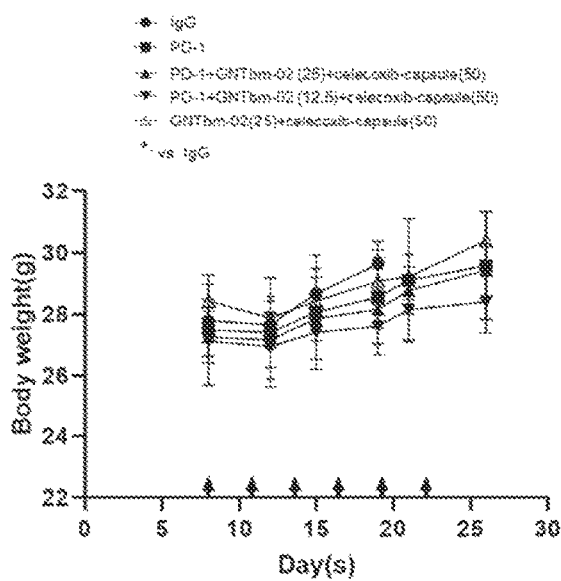
Figure 13E:
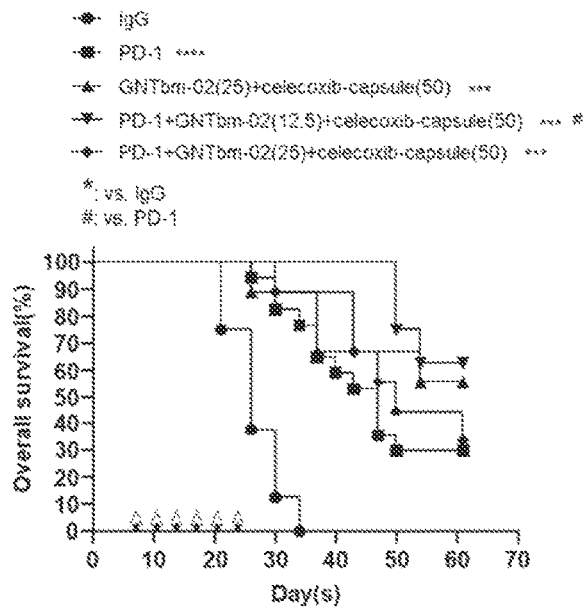

GNTbm Compounds Series Possessed Epigenetic Immunomodulatory Properties in the CT26-Bearing Mice Model To investigate whether GNTbm-02 possessed epigenetic immunomodulatory properties, in vivo animal model of BALB/c CT26 colon tumor-bearing mice were used for evaluation. The BALB/c mice bearing murine CT26 colon tumors were treated with various therapeutic modalities as indicated. IgG, anti-IgG control (vehicle, 2.5 mg/kg); PD-1, anti-PD-1 monoclonal antibody (2.5 mg/kg); GNTbm-02 12.5 and 25.0 mg/kg; Celecoxib-capsule 50 mg/kg (Celebrex®). The tumor size in the CT26 tumor-bearing mice grew to about 150-200 mm$^3$ at day 8. Total tumor volumes and fold change of tumor size are shown in FIGS. 13a and b. The results indicated that the regimen of anti-PD-1 antibody (2.5 mg/kg) plus GNTbm-02 (12.5 mg/kg) combined with celecoxib (50 mg/kg) possessed more significant inhibition effect on tumor growth than the regimen of anti-PD-1 antibody (2.5 mg/kg) plus GNTbm-02 (25.0 mg/kg) combined with Celecoxib (50 mg/kg) or regimen of GNTbm-02 25 mg/kg plus Celecoxib 50 mg/kg in the absence of anti-PD-1 antibody. So, the inhibition effect of tumor growth was anti-PD-1 antibody plus GNTbm-02 (12.5 mg/kg) combined with Celecoxib regimen>anti-PD-1 antibody plus GNTbm-02 (25.0 mg/kg) combined with Celecoxib regimen>GNTbm-02 (25.0 mg/kg) combined with Celecoxib regimen>anti-PD-1 antibody>anti-IgG regimen. However, the result also indicated that GNTbm-02 combined with Celecoxib possessed a potent inhibition effect to suppress tumor growth. Previously, our research demonstrated that HDAC inhibitor combined with COX-2 inhibitor significantly regulated the TME and therefore improved the inhibition effect of tumor growth and the immune response rate. These results demonstrated that GNTbm-02 was a potent and novel epigenetic immunomodulator. The individual tumor volumes were analyzed as shown in FIG. 13c. In this study, we defined Complete Response (CR, ≤0.5 time tumor growth in the tumor bearing mice at three days after the end of treatment); Partial Response (PR, tumor size >0.5 time tumor growth, but ≤2 times tumor growth in the tumor bearing mice at three days after the end of treatment); Stable Disease (SD, between two and five times tumor growth in the tumor bearing mice at three days after the end of treatment); Progressive Disease (PD, equal to or greater than five times tumor growth in the tumor bearing mice at three days after the end of treatment) for the evaluation of treatment efficacy. The results indicated that anti-PD-1 antibody (2.5 mg/kg) group achieved 5 CR, 1 PR, 3 SD and 8 PD, with the ORR (objective response rate) 35.3%; anti-PD-1 antibody (2.5 mg/kg) plus GNTbm-02 (25 mg/kg) combined with Celecoxib (50 mg/kg) group achieved 3 CR, 3 PR, 2 SD and 1 PD, with the ORR 66.7%; anti-PD-1 antibody (2.5 mg/kg) plus GNTbm-02 (12.5 mg/kg) combined with Celecoxib (50 mg/kg) group achieved 5 CR, 2PR, 1 SD and 0 PD, with the ORR 87.5%; GNTbm-02 (25 mg/kg) combined with Celecoxib (50 mg/kg) group achieved 2 CR, 4 PR, 2 SD and 1 PD, with the ORR 66.7%. These results suggested that GNTbm-02 at dose of 12.5 mg/kg was the optimal dose and that GNTbm-02 possessed potent immunomodulatory activity. The body weight of CT26 tumor-bearing mice as shown in FIG. 13d indicated that these regimens had no obvious toxicity to cause body weight loss. Finally, the survival rate was analyzed as shown in FIG. 13e. CT26 tumor-bearing mice were euthanized when tumor volume reached 3000 mm³ after tumor implantation. The results indicated that anti-PD-1 antibody group achieved survival rate 30%; anti-PD-1 antibody (2.5 mg/kg) plus GNTbm-02 (25 mg/kg) combined with Celecoxib (50 mg/kg) group achieved survival rate 33%; GNTbm-02 (25 mg/kg) combined with Celecoxib (50 mg/kg) group achieved survival rate 56%; anti-PD-1 antibody (2.5 mg/kg) plus GNTbm-02 (12.5 mg/kg) combined with Celecoxib (50 mg/kg) group achieved survival rate 63%. Taken together, these data suggested that GNTbm-02 plus Celecoxib or GNTbm-02 plus Celecoxib combined with anti-PD-1 antibody significantly improved ORR and survival rate in comparison with anti-PD-1 antibody alone. Our data also demonstrated that GNTbm-02 at dose of 12.5 mg/kg showed better efficacy than 25.0 mg/kg in the combination regimen of anti-PD-1 antibody plus GNTbm-02 combined with Celecoxib. Next, we were interested in evaluating the regulation of tumor microenvironment activities using novel synthetic compounds such as GNTbm-02, GNTbm-03, GNTbm-04, GNTbm-06 and Chidamide as a positive control. Solid dispersion of Chidamide prepared by coating on PVP-K30 was used to improve the water solubility of Chidamide-API, which ultimately will improve the PK (pharmacokinetics) profile. Therefore, we used the common preparation technique in the art to produce the solid dispersions of test compounds such as GNTbm-02, GNTbm-03, GNTbm-04, GNTbm-06, and Chidamide as a positive control. All test compounds were coated on PVP-K30 to prepare the solid dispersions named GNTbm-02/k30, GNTbm-03/k30, GNTbm-04/k30, GNTbm-06/k30, and Chidamide/k30. A previous study had proven that Chidamide/k-30 combined with Regorafenib possessed very potent anti-cancer activity through an immunomodulatory mechanism in CT-26 tumor-bearing mice. The anti-cancer activity of GNTbm-02/k-30 combined with Regorafenib was further studied to confirm its potency in CT26 tumor-bearing mice. We defined more strict criteria of CR (≤0.5 time tumor growth in the tumor bearing mice at three days after the end of treatment); PR (tumor size >0.5 time tumor growth, but ≤1 times tumor growth in the tumor bearing mice at three days after the end of treatment); SD (between one and five times tumor growth in the tumor bearing mice at three days after the end of treatment); PD (equal to or greater than five times tumor growth in the tumor bearing mice at three days after the end of treatment) for the evaluation of treatment efficacy. As shown from FIG. 14(f) to FIG. 14(i), the GNTbm-02/k-30 combined with Regorafenib vs. Chidamide/k-30 combined with Regorafenib was evaluated. The results demonstrated that GNTbm-02/k-30 (50 mg/kg) combined with Regorafenib (30 mg/kg) possessed potent inhibition of tumor growth, but weaker than that of Chidamide/k-30 combined with Regorafenib (ORR: 10% vs. 30%). However, GNTbm-03/k-30 as shown in FIG. 14(i) to FIG. 14(m) demonstrated that GNTbm-03/k-30 combined with Regorafenib possessed similar anti-cancer activity in comparison with Chidamide/k-30 combined with Regorafenib (ORR: 40% vs. 30%). GNTbm-04/k-30 combined with Regorafenib was more potent in inhibiting tumor growth than Chidamide/k-30 combined with Regorafenib as shown from FIG. 14(n) to FIG. 14(q) (ORR: 50% vs. 30%). GNTbm-06/k-30 combined with Regorafenib possessed similar anti-cancer activity in comparison with Chidamide/k-30 combined with Regorafenib as shown from FIG. 14(r) to FIG. 14(u) (ORR: 50% vs. 30%). After 16 days of treatment, we continued to monitor the tumor size up to day 60. When tumor growth reappeared and tumor size reached at least 5 fold in mice with CR or PR response after first tumor assessment, it was defined as relapse/recurrence. As shown in Table 14, Chidamide/k-30 combined with Regorafenib showed 0% tumor recurrence, GNTbm-02/k-30 combined with Regorafenib showed 100% tumor recurrence, GNTbm-03/k-30 combined with Regorafenib showed 25% tumor recurrence, GNTbm-04/k-30 combined with Regorafenib showed 20% tumor recurrence, GNTbm-06/k-30 combined with Regorafenib showed 0% tumor recurrence. With the exception of GNTbm-02/k-30 combined with Regorafenib group, which only had 1 mouse with PR in the study, the result suggested that GNTbm compounds combined with Regorafenib may possess more potent activity in activating the immune system to avoid a relapse. Furthermore, we also investigate epigenetic immunomodulatory properties in series of GNTbm compounds including GNTbm-05/k-30, GNTbm-11/k-30, GNTbm-38/k-30 and GNTbm-39/k-30. As shown in Table 14, efficacy comparison of GNTbm-05/k-30, GNTbm-11/k-30, GNTbm-38/k-30, GNTbm-39/k-30 and Chidamide/k-30 combined with Regorafenib was evaluated. The results demonstrated that Chidamide/k30 (50 mg/kg) combined with Regorafenib (30 mg/kg) group achieved 2 CR, 4 PR, 4 SD and 0 PD, with the ORR 60%; GNTbm-05/k30 (50 mg/kg) combined with Regorafenib (30 mg/kg) group achieved 3 CR, 0 PR, 4 SD and 3 PD, with the ORR 30%; GNTbm-11/k30 (50 mg/kg) combined with Regorafenib (30 mg/kg) group achieved 1 CR, 1 PR, 4 SD and 4 PD, with the ORR 20%; GNTbm-38/k30 (50 mg/kg) combined with Regorafenib (30 mg/kg) group achieved 8 CR, 0 PR, 2 SD and 0 PD, with the ORR 80%; GNTbm-39/k30 (50 mg/kg) combined with Regorafenib (30 mg/kg) group achieved 2 CR, 1 PR, 5 SD and 2 PD, with the ORR 30%. Taken together, these in vivo animal data demonstrated that when comparing all of the GNTbm compounds with positive control Chidamide, in combination with Regorafenib, GNTbm-38/k-30 showed a superior epigenetic immunomodulatory activity achieving an ORR of 80%, and without combination with Regorafenib, GNTbm-38/k-30 alone achieving an ORR of 56%.

To Confirm the Epigenetic Immunomodulatory Properties of GNTbm Compounds Series

Figure 14A:
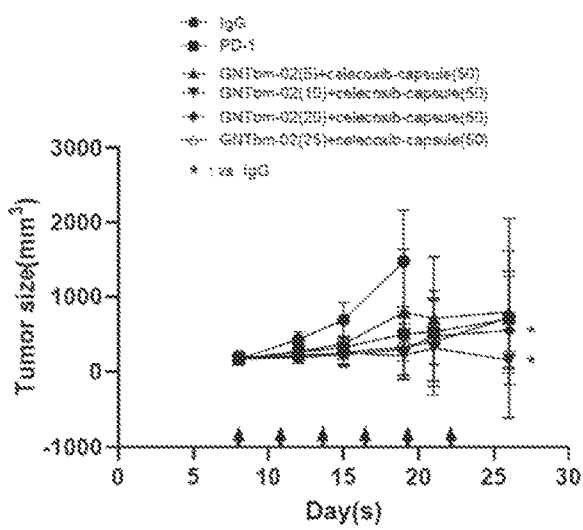
FIGS. 14A-14U show the assessment of the combination therapy response of GNTbm compounds series in CT26 tumor-bearing mice. BALB/c mice bearing a CT26 tumor were treated with various therapeutic modalities as indicated. IgG, anti-IgG control (2.5 mg/kg); PD-1, anti-PD-1 monoclonal antibody (2.5 mg/kg); Chidamide (50 mg/kg); Celecoxib (50 mg/kg); GNTbm-02 (5, 10, 20, 25, 50 mg/kg); GNTbm-03 (50 mg/kg); GNTbm-04 (50 mg/kg); GNTbm-06 (50 mg/kg); Regorafenib (30 mg/kg). Total tumor volumes (FIG. 14A), (FIG. 14B), (FIG. 14F), (FIG. 14J), (FIG. 14N), (FIG. 14R), individual tumor volumes (FIG. 14C), (FIG. 14G), (FIG. 14K), (FIG. 14O), (FIG. 14S), mice body weight (FIG. 14D), (FIG. 14H), (FIG. 14L), (FIG. 14P), (FIG. 14T), and survival rate (FIG. 14E), (FIG. 14I), (FIG. 14M), (FIG. 14Q), (FIG. 14U) were recorded. CT26 tumor bearing mice were treated as indicated and euthanized when tumor volume reached 3000 mm³ after tumor implantation. Data are given as the mean±SEM; one-way ANOVA with Tukey's test (*P<0.05, P<0.01, *P<0.001 vs. anti-IgG control). Gehan-Breslow-Wilcoxon test (e).
Figure 14B:
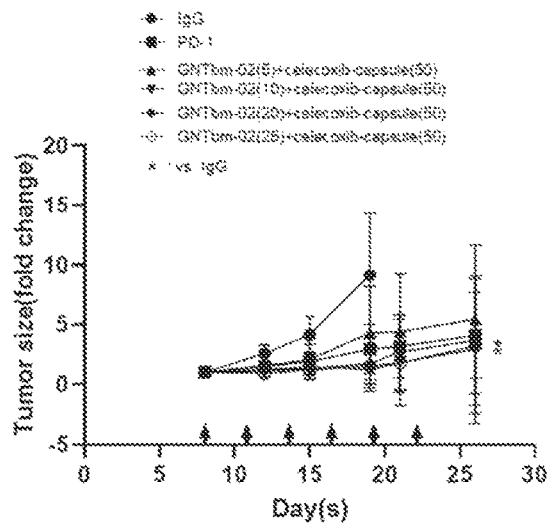
Figure 14C:
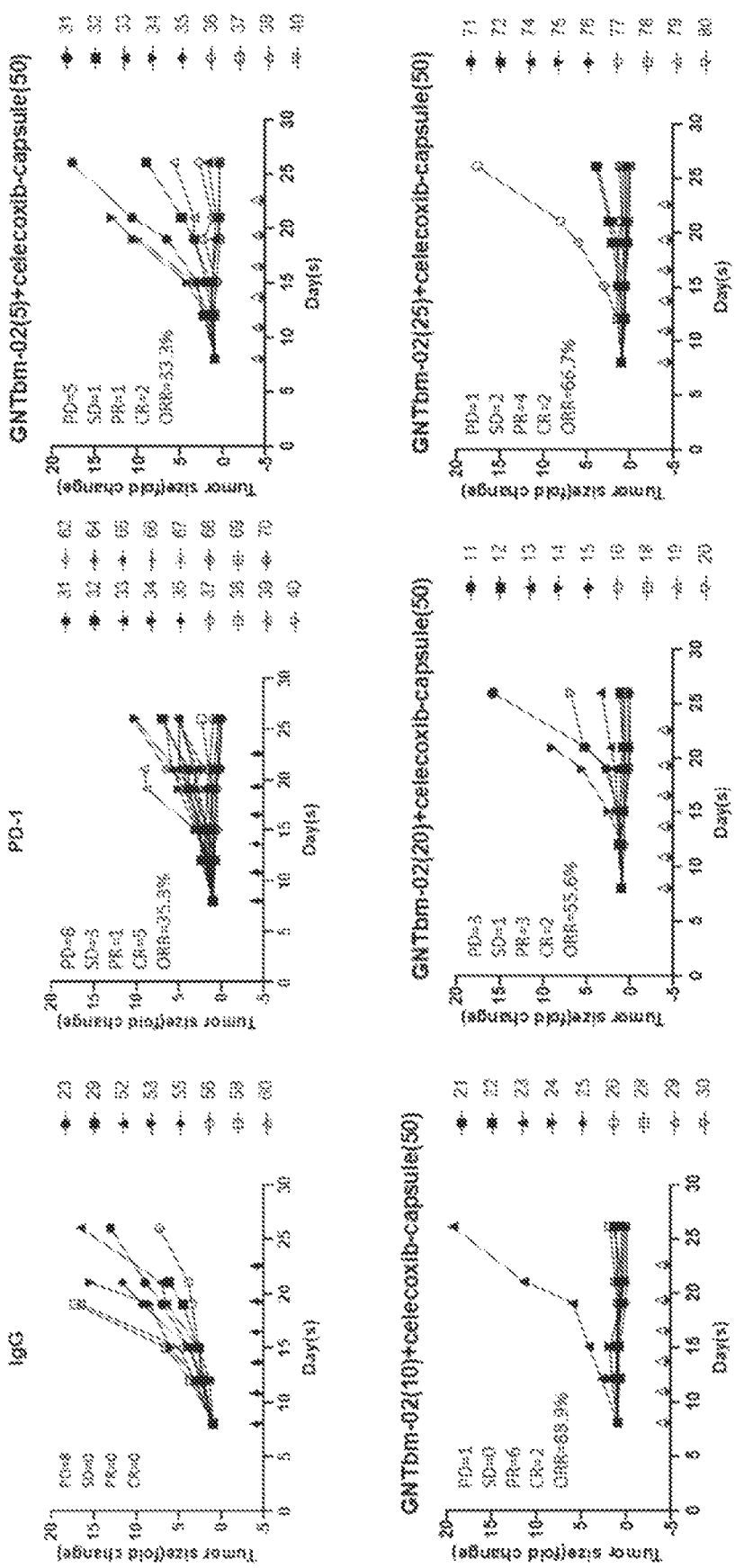
Figure 14G:
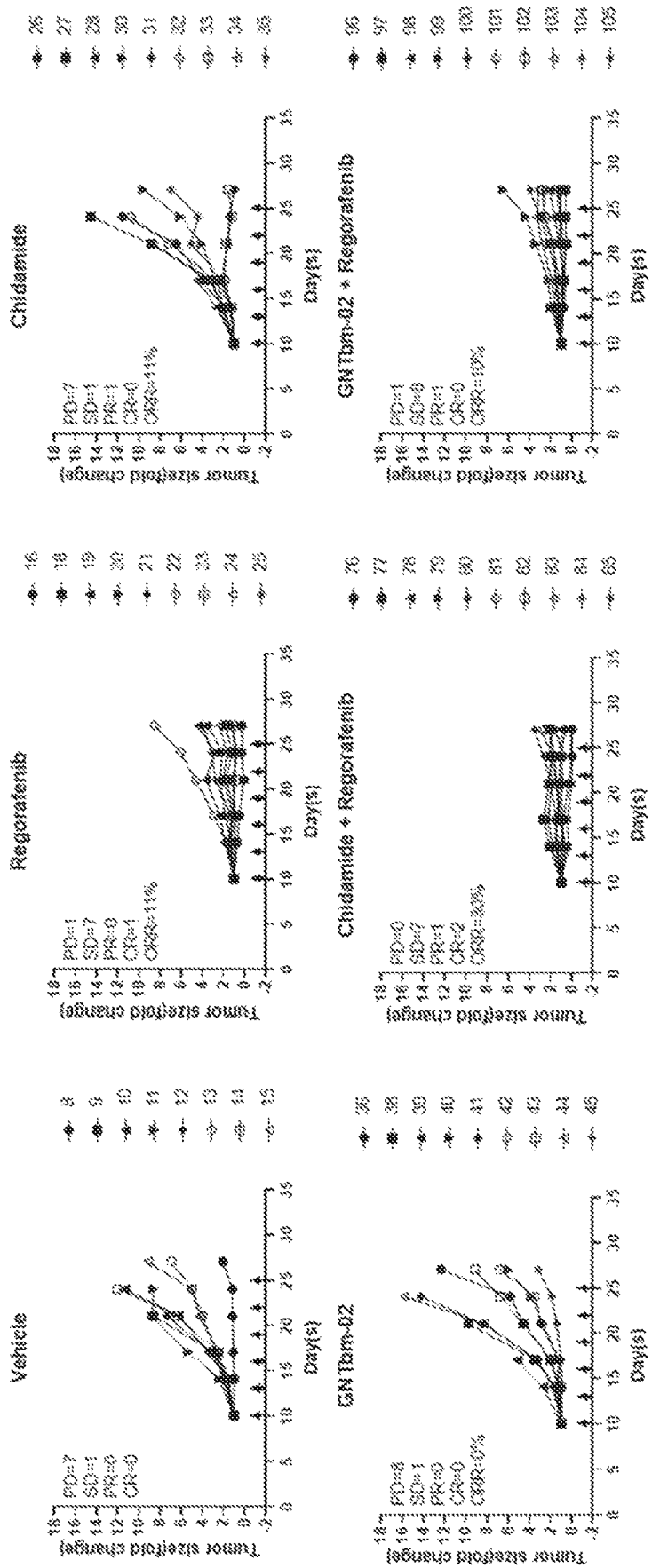
Figure 14H:
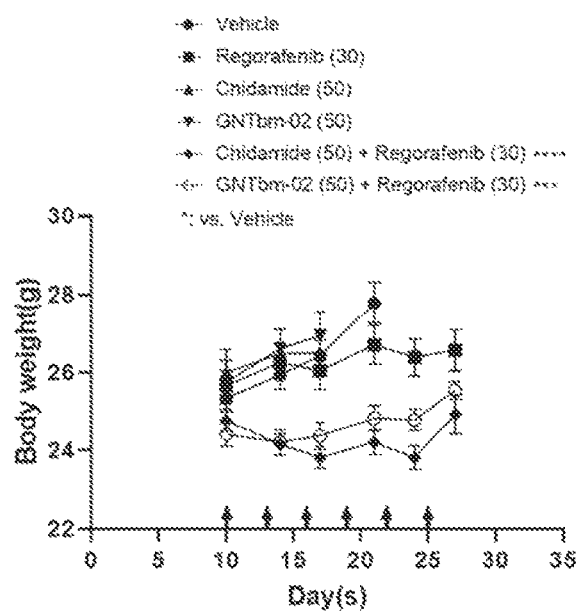
Figure 14I:
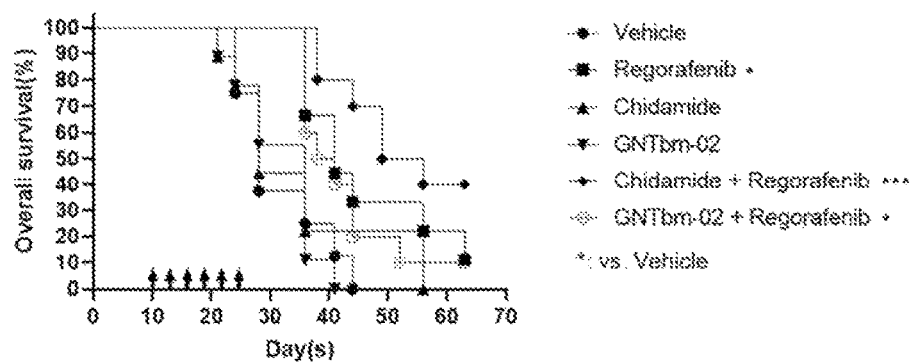
Figure 14J:
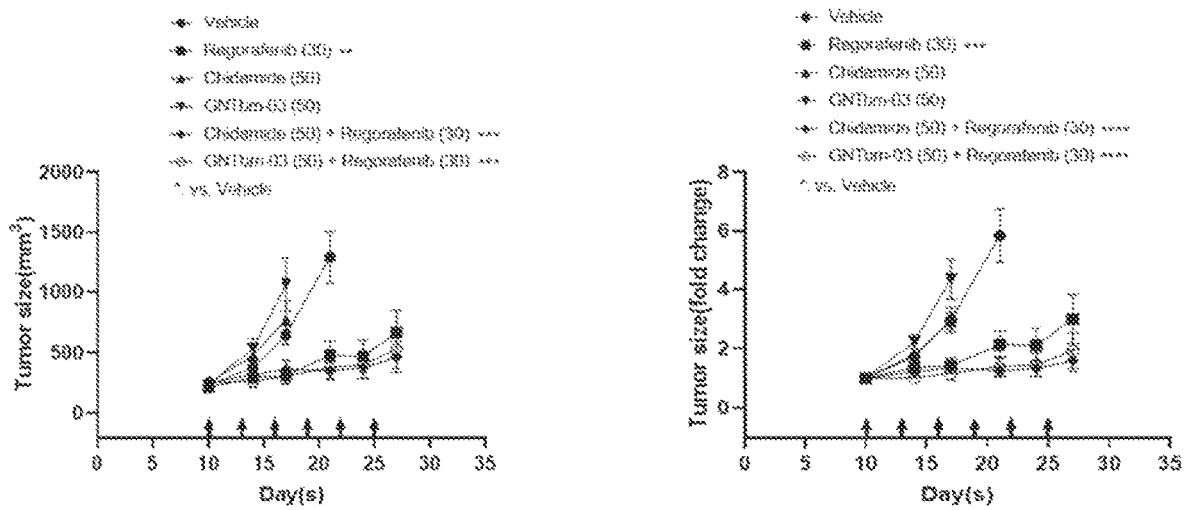
Figure 14K:
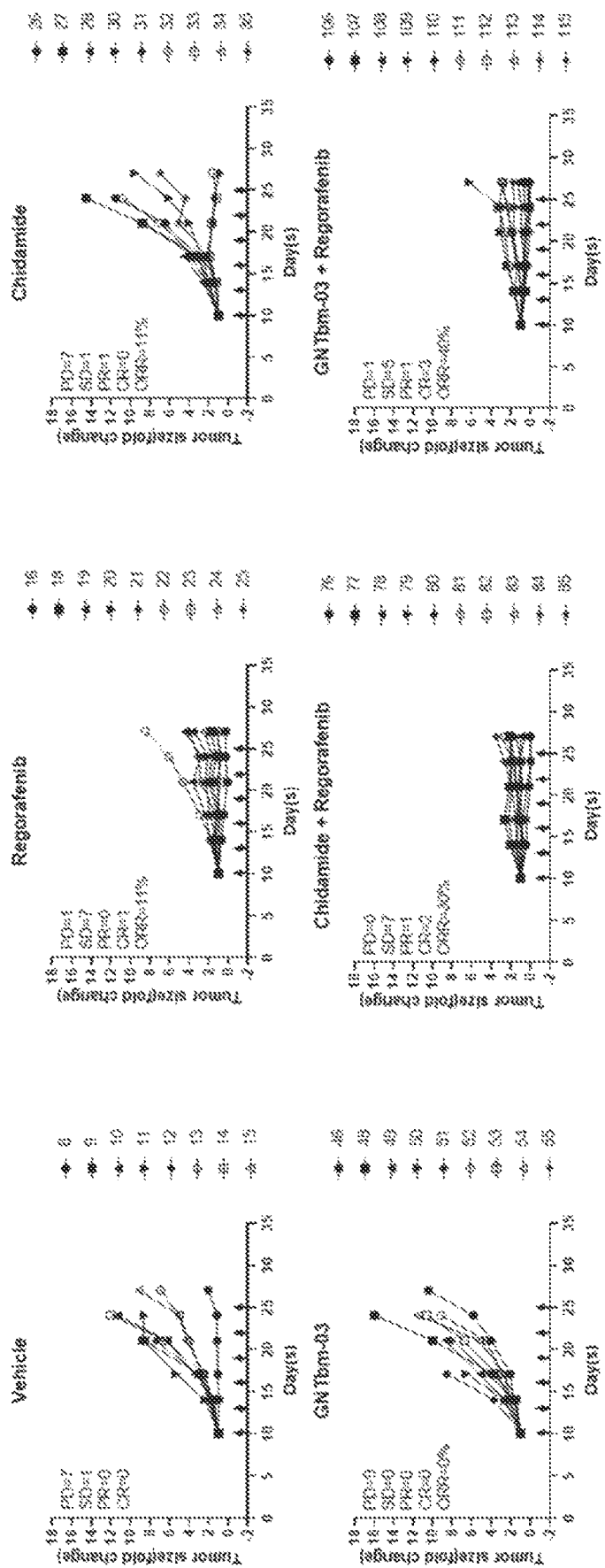
Figure 14L:
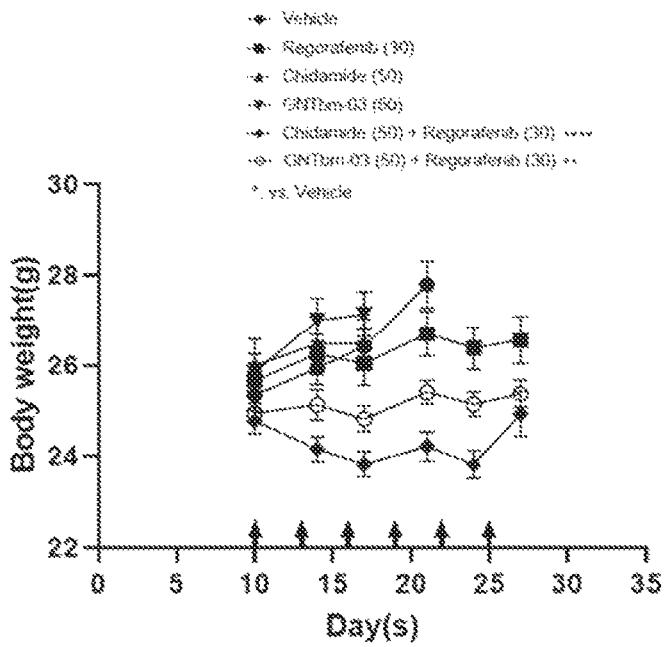
Figure 14M:
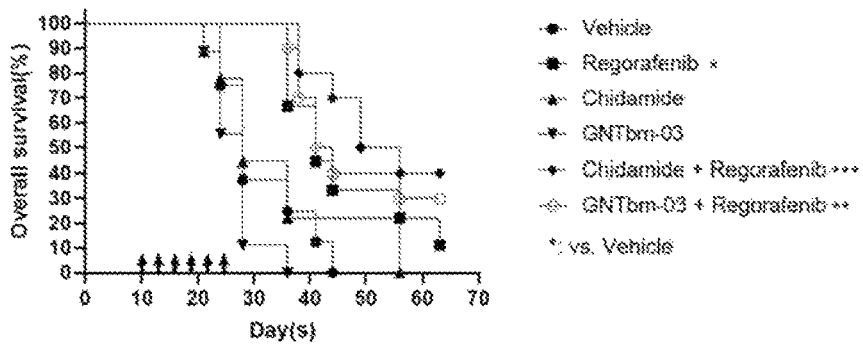
Figure 14N:
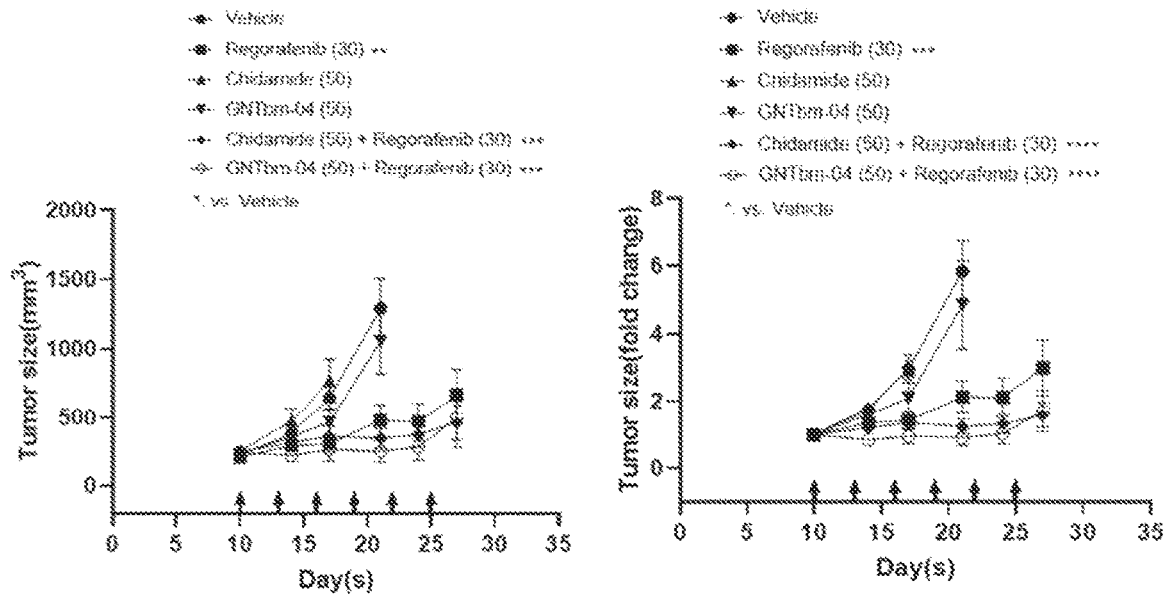
Figure 14O:
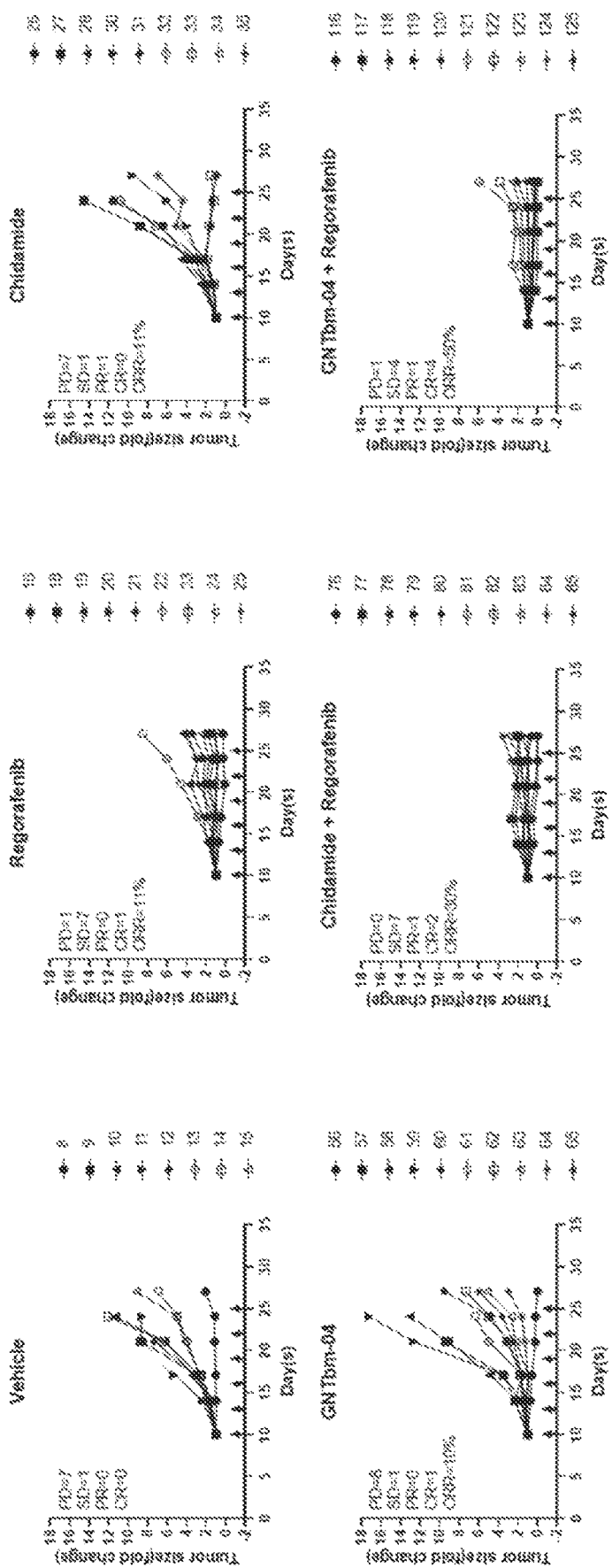
Figure 14P:
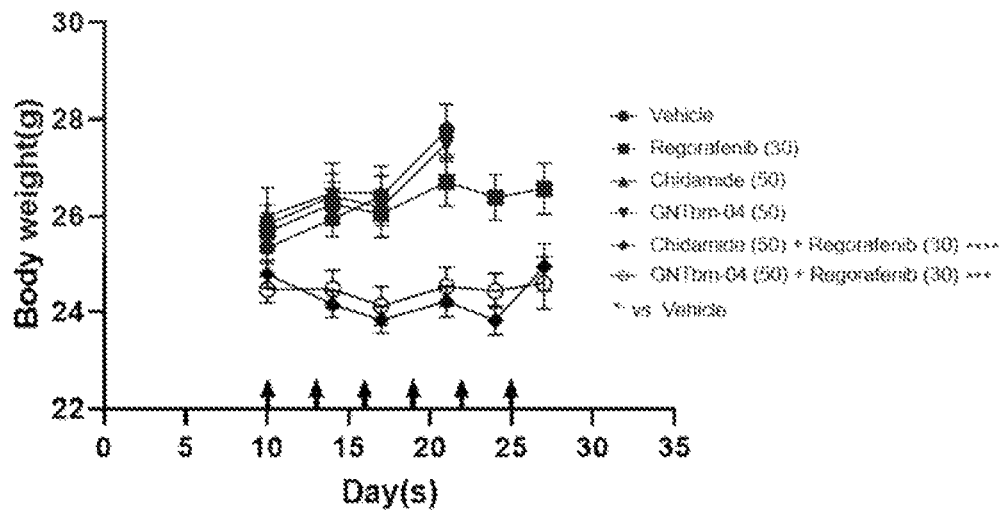
Figure 14Q:
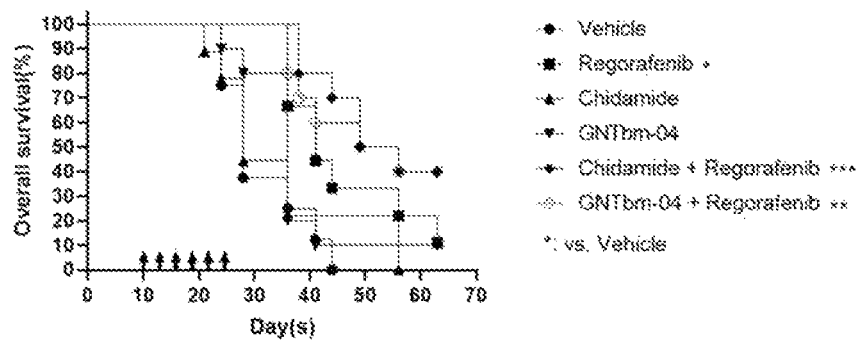
Figure 14R:
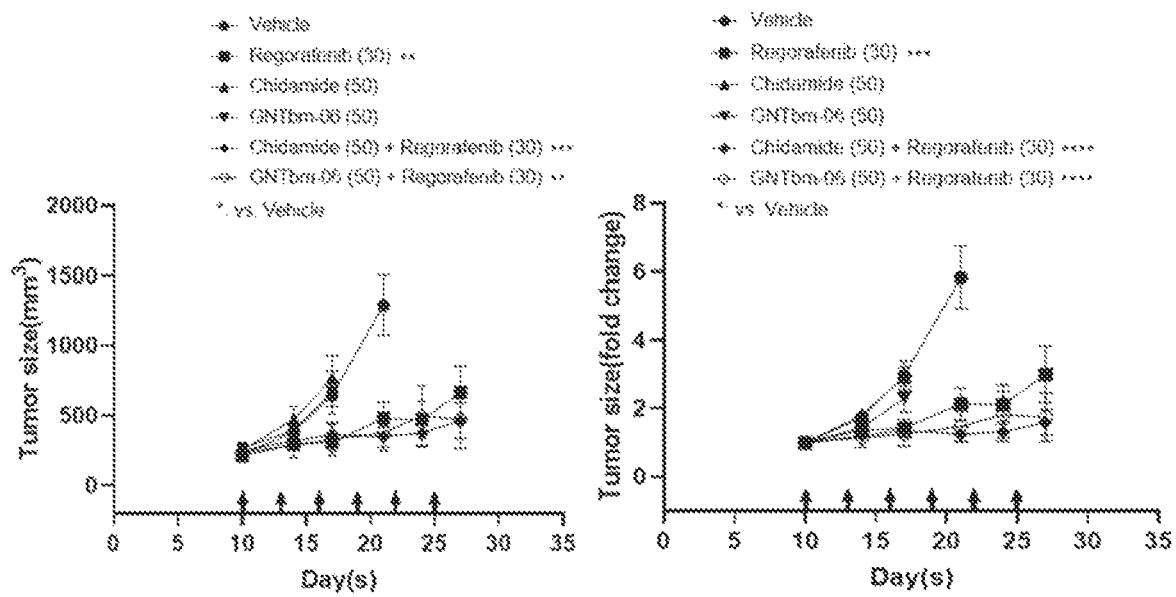
Figure 14S:
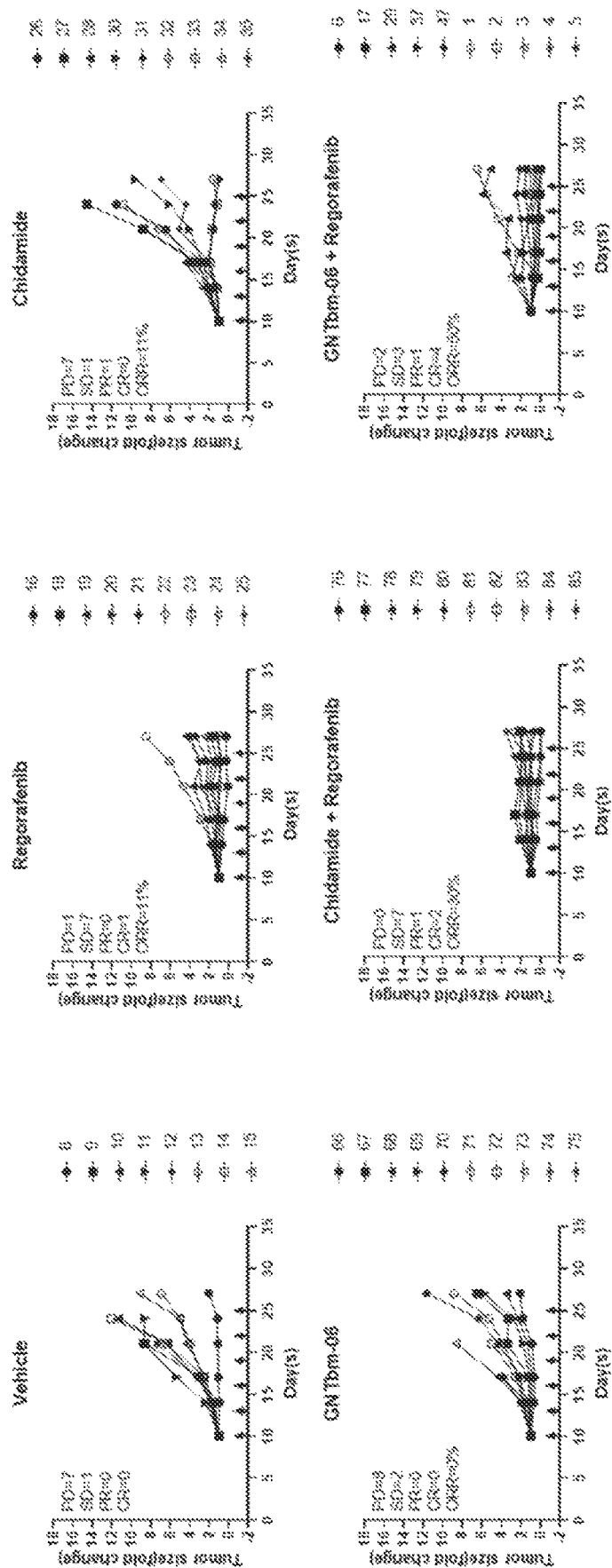
Figure 14T:
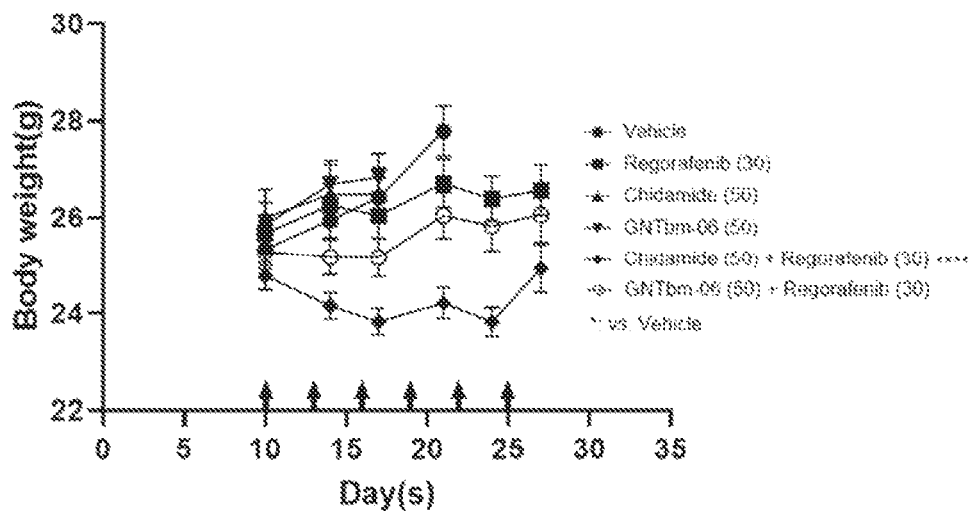
Figure 14U:
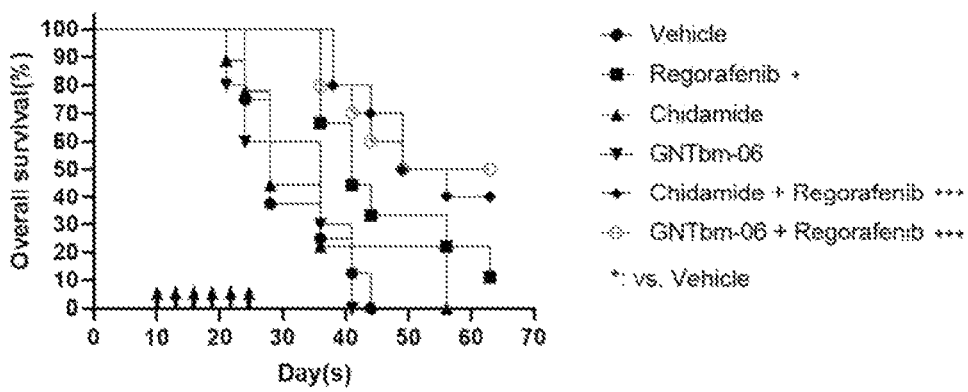

The optimal dose of GNTbm-02 in combination with Celecoxib (a selective COX-2 inhibitor) was analyzed and confirmed. IgG, anti-IgG control (vehicle, 2.5 mg/kg); PD-1, anti-PD-1 monoclonal antibody (2.5 mg/kg); GNTbm-02, 5, 10, 20, and 25.0 mg/kg; Celecoxib-capsule 50 mg/kg (Celebrex®). The tumor size in the CT26 tumor-bearing mice grew to about 150-200 mm$^3$ at day 8. Total tumor volumes and fold change of tumor size as shown in FIGS. 14a and b indicated that GNTbm-02 (10 mg/kg) combined with Celecoxib (50 mg/kg) group was more powerful in the inhibition of tumor growth than GNTbm-02 (20 mg/kg) combined with Celecoxib (50 mg/kg) group or GNTbm-02 (5 mg/kg) combined with Celecoxib (50 mg/kg) group. This result also suggested that GNTbm-02 combined with Celecoxib in an optimal ratio was essential to control the TME and improved the inhibition effect of tumor growth in CT26 bearing mice model. The individual tumor volumes and ORR as shown in FIG. 14c indicated that anti-PD-1 antibody (2.5 mg/kg) group achieved 5 CR, 1 PR, 3 SD and 8 PD, with the ORR (objective response rate) 35.3%; GNTbm-02 (5 mg/kg) combined with Celecoxib (50 mg/kg) group achieved 2 CR and 1 PR, 1 SD and 5 PD, with the ORR 33.3%; GNTbm-02 (10 mg/kg) combined with Celecoxib (50 mg/kg) group achieved 2 CR, 6 PR, 0 SD and 1 PD, with the ORR 88.9%; GNTbm-02 (20 mg/kg) combined with Celecoxib (50 mg/kg) group achieved 2 CR, 3 PR, 1 SD and 3 PD, with the ORR 55.6%; GNTbm-02 (25 mg/kg) combined with Celecoxib (50 mg/kg) group achieved 2 CR, 4 PR, 2 SD and 1PD, with the ORR 66.7%. These data suggested that GNTbm-02 (10 mg/kg) combined with Celecoxib (50 mg/kg) group achieved the best ORR, resulting from the optimal ratio for the control of TME. This result was also observed in FIG. 13, in which anti-PD-1 antibody (2.5 mg/kg) plus GNTbm-02 (12.5 mg/kg) combined with Celecoxib (50 mg/kg) regimen achieved better ORR. From these data it was suggested that GNTbm-02 10 mg/kg combined with Celecoxib 50 mg/kg possessed potent activities on the regulation of TME and therefore improved the immune response rate. The body weight of CT26 tumor-bearing mice as shown in FIG. 14d indicated that these regimens possessed no marked toxicity to cause the loss of body weight. Finally, the survival rate was analyzed as shown in FIG. 14e. CT26 tumor-bearing mice were euthanized when tumor volume reached 3000 mm$^3$ after tumor implantation. The results indicated that anti-PD-1 antibody group achieved survival rate 30%; GNTbm-02 (5 mg/kg) combined with Celecoxib (50 mg/kg) group achieved survival rate 22%; GNTbm-02 (10 mg/kg) combined with Celecoxib (50 mg/kg) group achieved survival rate 44%; GNTbm-02 (20 mg/kg) combined with Celecoxib (50 mg/kg) group achieved survival rate 33%; GNTbm-02 (25 mg/kg) combined with Celecoxib (50 mg/kg) group achieved survival rate 56%. Taken together, these data suggested that GNTbm-02 plus Celecoxib significantly improved ORR and survival rate in comparison with anti-PD-1 antibody alone. Our data also demonstrated that GNTbm-02 at dose of 10 mg/kg was better than the other doses when GNTbm-02 was combined with Celecoxib.

GNTbm-02 Plus Celecoxib with or without Anti-PD-1 or GNTbm Compounds Series Combined with Regorafenib Markedly Induced the Immune Memory The immune memory induced after treatment with different regimens as shown in FIGS. 13 and 14 was investigated for the status as shown in Table 6 and 7. The mice were treated with different regimens for 16 days, and then the first tumor assessment was performed (day 26). The mice with CR or PR went into wash-out stage of 7 days (until day 33) without any further treatment. Then rechallenge was performed with the same kind of cancer cells (CT26; 5×10$^6$) inoculated on the opposite flank for about another 7 days (day 40), and then the tumor volume would be determined as baseline (1 fold). The rechallenge tumor was allowed to grow for 10 days (day 50), and then the tumor size was measured to evaluate the immune memory as positive or negative. If the evaluation was negative, it had to meet both of the two conditions: the tumor volume was over 300 mm$^3$ and the tumor size was over 2 fold when compared to baseline. If the immune memory induced after prior treatment was active and specific for the recognition of the cancer cells with the same antigen, the growth of tumors inoculated during the rechallenge would be inhibited, and therefore the immune memory was defined as positive. If the immune memory was not induced or not fully activated, then the growth of tumors inoculated during the rechallenge would not be inhibited. By this evaluation process, GNTbm-02 plus Celecoxib combined with or without anti-PD-1 antibody regimens were investigated to answer whether the regimens possessed the property of inducing immune memory. As shown in Table 6, the anti-PD-1 antibody group had only 2 mice achieving CR, which after rechallenge showed 0% tumor progression. The result demonstrated that these CR mice achieved 100% active immune memory. The regimen of GNTbm-02 (25 mg/kg) plus Celecoxib (50 mg/kg) combined with anti-PD-1 antibody (2.5 mg/kg) group achieved 4 mice of CR/PR, which after rechallenge also showed 0% tumor progression. It also demonstrated 100% with active immune memory. The regimen of GNTbm-02 (12.5 mg/kg) plus Celecoxib (50 mg/kg) combined with anti-PD-1 antibody (2.5 mg/kg) group achieved 7 mice of CR/PR, which after rechallenge showed 29% with tumor progression. It demonstrated 71% with active immune memory. The regimen of GNTbm-02 (25 mg/kg) combined with Celecoxib (50 mg/kg) group achieved 6 mice of CR/PR, which after rechallenge showed 17% with tumor progression. It also demonstrated 83% with active immune memory. However, as shown in Table 7, the regimen of GNTbm-02 (10 mg/kg) combined with Celecoxib (50 mg/kg) group achieved 7 mice of CR/PR, which after rechallenge showed 14% with tumor progression. It demonstrated 86% with active immune memory. The mice with CR possessed stronger immune memory activity than the mice with PR from these data. Taken together, GNTbm-02 plus Celecoxib combined with or without ICI induced potent immune memory activity. Same phenomena were also reflected in other GNTbm compounds combined with Regorafenib. As shown in Table 14, GNTbm-02/k-30 (50 mg/kg) combined with Regorafenib (30 mg/kg) group achieved 1 mice of CR/PR, which after rechallenge also showed 0% tumor progression; GNTbm-03/k-30 (50 mg/kg) combined with Regorafenib (30 mg/kg) group achieved 4 mice of CR/PR, which after rechallenge also showed 0% tumor progression; GNTbm-04/k-30 (50 mg/kg) combined with Regorafenib (30 mg/kg) group achieved 5 mice of CR/PR, which after rechallenge also showed 0% tumor progression; GNTbm-06/k-30 (50 mg/kg) combined with Regorafenib (30 mg/kg) group achieved 5 mice of CR/PR, which after rechallenge also showed 0% tumor progression. These results indicated that GNTbm compounds combined with Regorafenib were significant in inducing the immune memory.

Figure 15A:
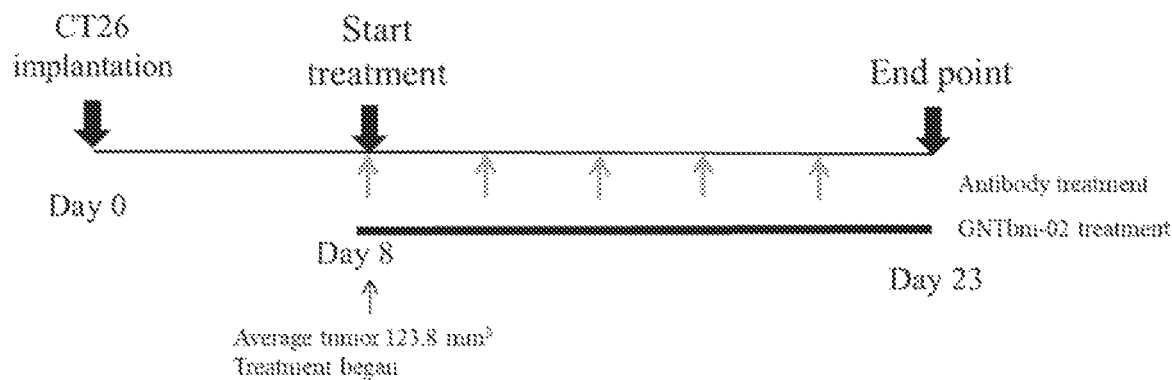
FIGS. 15A-15E show treatment results from BALB/c nude mice bearing a CT26 tumor treated with various therapeutic modalities: anti-IgG control (2.5 mg/kg); anti-PD-1 monoclonal antibody (2.5 mg/kg); Celecoxib (50 mg/kg); GNTbm-02 (10 mg/kg).
Figure 15B:
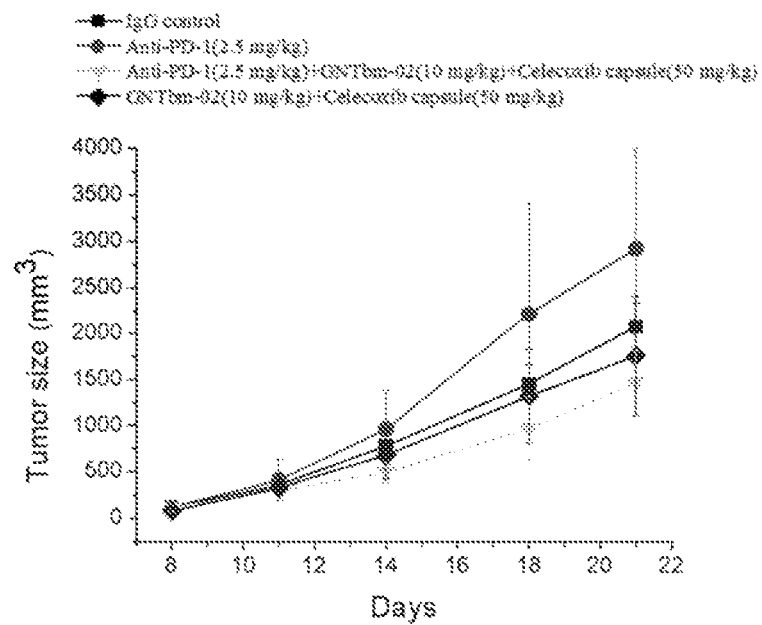
Figure 15C:
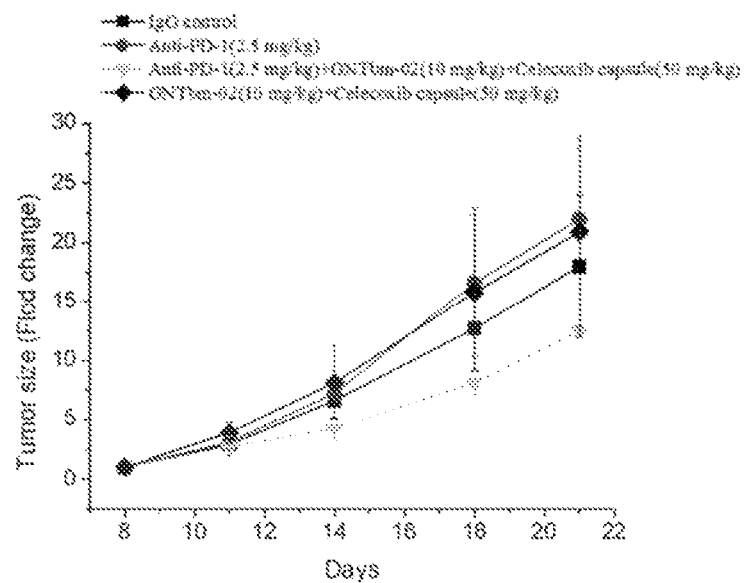
Figure 15D:
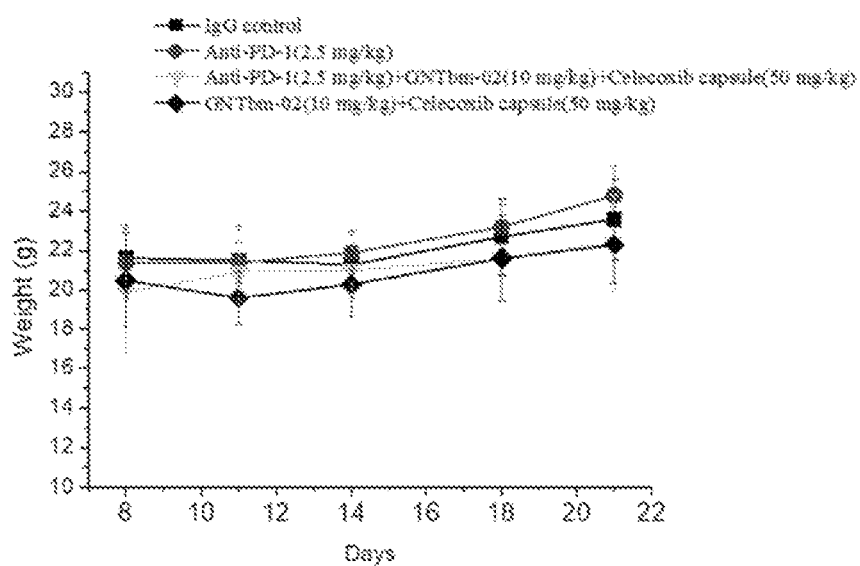
Figure 15E:
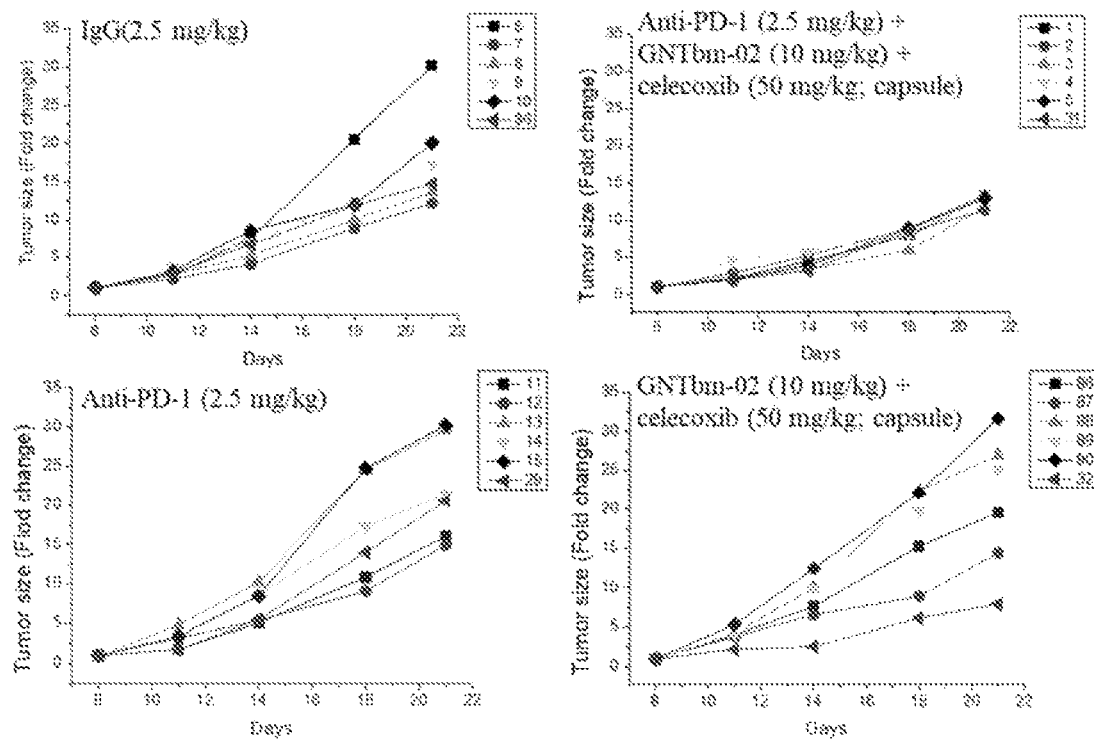

The Anti-Tumor Activity after Treatment with GNTbm-02 Plus Celecoxib was Through the Immunomodulatory Effect, Resulting in Activation of CTL The mice treated as shown in FIGS. 13 and 14 were normal mice with complete immune systems. The regimen of GNTbm-02 plus Celecoxib combined with or without anti-PD-1 antibody significantly achieved a high overall response rate (ORR) in the wild type normal mice. Next, treatment with the regimen of GNTbm-02 plus Celecoxib combined with or without anti-PD-1 antibody in the BALB/C nude mice model (with deficient T-cell function) was investigated. As shown in FIG. 15a, the nude mice were inoculated with CT26 cells by s.c. injection. After 8 days, when the average of tumor volume about 123.8 mm$^3$, then the mice were randomized into four groups and treated with anti-IgG antibody, anti-PD-1 antibody, GNTbm-02 plus Celecoxib combined with anti-PD-1 antibody, and GNTbm-02 plus celecoxib for 15 days. As shown in FIGS. 15b and c, all these treatment groups did not significantly inhibit tumor growth in nude mice with deficient T-cell function. These results showed that GNTbm-02 plus Celecoxib possessed potent activity in inhibiting tumor growth by regulation of activation of CTL (cytotoxic T lymphocytes) in TME. As shown in FIG. 15d, all treatment groups did not show significant loss of body weight. As shown in FIG. 15e, all mice of treatment groups were shown to have low anti-cancer activities in the nude mice, and none of them achieved ORR. These results demonstrated that to achieve a significant inhibition of tumor growth by combination regimen of GNTbm-02 plus Celecoxib combined with or without anti-PD-1 antibody, an immune system with functional T cells is essential (FIGS. 13, 14, and 15). This also demonstrated that GNTbm-02 plus Celecoxib inhibited tumor growth by regulating activation of T cells (CTL) in TME for the killing of cancer cells. This anti-cancer activity was through an immunomodulatory effect rather than a cytotoxicity effect. Taken together, we confirmed that GNTbm-02 possessed potent epigenetic immunomodulatory activity, and when combined with Celecoxib, was more potent in regulating TME in comparison with GNTbm-02 alone.

Figure 17A:
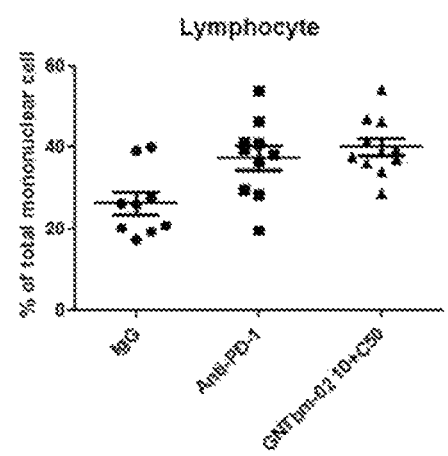
Figure 17B:
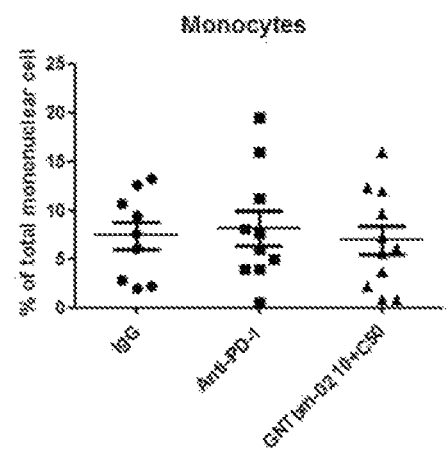
Figure 17C:
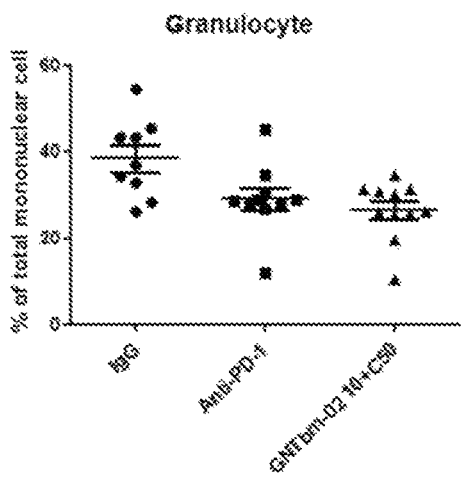
Figure 17D:
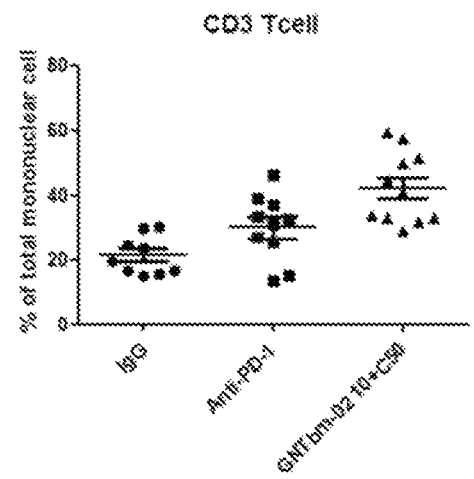
Figure 17E:
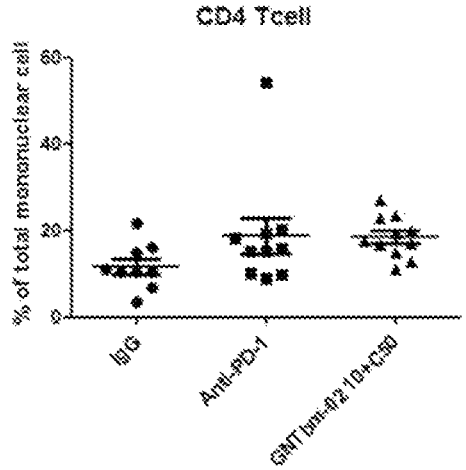
Figure 17F:
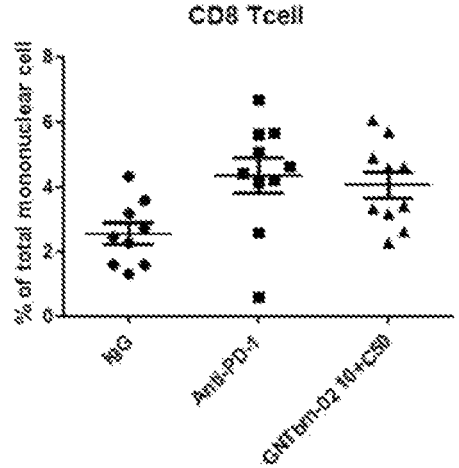

Anti-Tumor Activity of GNTbm-02 Plus Celecoxib is Associated with Decrease of Immunosuppressive Cells HDACi treatment has been shown to alter the TME by reducing Treg cell activity and enhancing CD8 T cell infiltration. To determine whether the inhibition of tumor growth resulting from the treatment with GNTbm-02 plus Celecoxib was associated with an enhanced immune response, we examined the circulating white blood cell populations. On the last day of treatment (i.e. on day 16 of the treatment period), blood samples were collected from CT26 tumor-bearing mice and studied by FACS analysis. We observed a significant increase of lymphocyte cells and decrease of granulocyte in the circulating blood after treatment with GNTbm-02 plus Celecoxib (FIGS. 17a and c). However, there is no significant difference in circulating monocyte cells (FIG. 17b). We also observed a significant increase of CD3$^+$ T cells in the circulating blood after treatment with GNTbm-02 plus Celecoxib (FIG. 17d). The moderate increase of CD8$^+$ T cells was observed after treatment with anti-PD-1 or GNTbm-02 plus Celecoxib (FIG. 17f). However, there is no significant difference in circulating CD4$^+$ T cells and Tregs (FIGS. 17e and g). In addition to FoxP3$^+$ Tregs, there are other immunosuppressive myeloid cells recruited to the TME including tumor associated macrophages (TAMs) and myeloid derived suppressor cells (MDSCs). Upon migration of immature myeloid cells to the tumor, these cells are often primed to become TAMs in response to chemokine and cytokine released from the cancer cells. MDSCs develop from immature myeloid cells and contribute to the immune suppression in TME by inhibiting anti-cancer T cell activity. MDSCs are present in two phenotypically defined sub-populations: granulocytic Ly6G$^+$Ly6C$^-$ (PMN-MDSCs) and monocytic Ly6C$^+$Ly6G$^-$ MDSCs (M-MDSCs). Treatment with GNTbm-02 plus Celecoxib caused a slight decrease in phenotypically defined CD11b$^+$Ly6G$^+$ Ly6C$^+$ and M-MDSC in circulation, while treatment with anti-PD-1 alone led to a reduction in the CD11b$^+$ populations (FIGS. 17h, i and j). There was no decrease of PMN-MDSC after treatment with GNTbm-02 plus Celecoxib (FIG. 17k).

In summary, as immunotherapy is an important promising field for anti-cancer therapy, especially for the treatment of advanced cancers, the claimed invention was assessed for the potential applications in immunotherapy. In combination with Celecoxib, GNTbm-02 was found to possess more powerful immunomodulation activity for inhibition of tumor growth in tumor microenvironment (TME) when compared with GNTbm-02. Furthermore, when GNTbm-02 plus Celecoxib was used in combination with immune checkpoint inhibitors, such as anti-PD-1/anti-PD-L1/anti-CTLA-4 antibodies, it was shown to have more powerful anti-cancer activity, significantly boosting the response rate via the synergistic effect attributed to the blocking of inhibitory signals to CTL (cytotoxic T lymphocyte) by anti-PD-1/anti-PD-L1/anti-CTLA-4 antibodies and the immunomodulation activities of GNTbm-02 plus Celecoxib in TME. Based on the studies, GNTbm-02 is a novel epigenetic immunomodulatory with a great potential for cancer treatment. Furthermore, we were interested in the immunomodulation activities of GNTbm compounds series. Our data demonstrated that GNTbm-02, GNTbm-03, GNTbm-04, GNTbm-06 and GNTbm-38 were very potent in possessing epigenetic immunomodulation activities to control TME when combined with Celecoxib or Regorafenib. These results suggested that GNTbm compounds series were novel and powerful epigenetic immunomodulators.

Tables mentioned above are provided below:

TABLE 1

$^1$H-NMR and $^{13}$C-NMR Spectroscopic Study (400 MHz, $d_6$-Acetone) for Compounds GNTbm-01, GNTbm-02 and GNTbm-03.

| GNTbm-01 | | | GNTbm-02 | | | GNTbm-03 | | |
|---|---|---|---|---|---|---|---|---|
| position | | $\delta_H$ (J in Hz) | position | | $\delta_H$ (J in Hz) | position | | $\delta_H$ (J in Hz) |
| 30 | CH3 | 2.46, s | 30 | CH3 | 2.46, s | 30 | CH3 | 2.46, s |
| 20 | CH2 | 3.52, d | 20 | CH2 | 3.45, d | 20 | CH2 | 3.39, d |
| 16 | NH2 | 4.95, br | 16 | NH2 | 4.90, br | 16 | NH2 | 4.90, br |
| 12 | CH | 6.39, td | 12 | CH | 6.45, m | 12 | CH | 6.39, td |
| 11, 22, 23 | CH | 6.59, m | 22, 23 | CH | 6.55, m | 11, 22, 23 | CH | 6.56, m |
| 14, 28 | CH | 7.21, t | 11 | CH | 6.66, dd | 14, 28 | CH | 7.20, m |
| 5 | CH | 7.77, dd | 28 | CH | 7.19, d | 3, 5, 29 | CH | 7.77, m |
| 2, 6, 29 | CH | 8.38, m | 14 | CH | 7.53, dd | 2, 6 | CH | 8.00, m |
| 25 | CH | 8.92, s | 29 | CH | 7.76, dd | 25 | CH | 8.46, s |
| 18 | NH | 9.08, s | 5 | CH | 8.15, d | 18 | NH | 8.95, s |
| 8 | NH | 9.75, s | 6 | CH | 8.31, dd | 8 | NH | 9.46, s |
| | | | 25 | CH | 8.47, d | | | |
| | | | 3 | CH | 8.91, s | | | |
| | | | 18 | NH | 9.66, s | | | |
| | | | 8 | NH | 9.72, s | | | |

TABLE 2

Analysis of the Saturation Solubility of GNTbm-02, GNTbm-03, GNTbm-04, and GNTbm-06

| Compounds | Saturation Solubility (μg/mL) |
|---|---|
| Chidamide | BDL |
| GNTbm-02 | 33.6 ± 6.4 |
| GNTbm-03 | BDL |
| GNTbm-04 | 7.2 ± 2.9 |
| GNTbm-06 | BDL |

*BDL: Below detection limit

TABLE 3

The $IC_{50}$ Values of Entinostat, GNTbm-01, GNTbm-02 and GNTbm-03 Against Different Cancer and Normal Cell Lines.

| Cell Lines | SK-BR-3 | M10 | MDA-MB-453 | MDA-MB-231 | SW48 |
|---|---|---|---|---|---|
| Entinostat (positive control) $IC_{50}$ ± SD (μM) | 1.94 ± 0.1 | 4.34 ± 0.01 | 1.82 ± 0.024 | 13.16 ± 1.34 | 5.21 ± 0.37 |
| Chidamide (positive control) $IC_{50}$ ± SD (μM) | 3.24 ± 0.98 | 2.72 ± 2.6 | 1.77 ± 0.02 | 25.6 ± 3.05 | 2.66 ± 0.08 |
| GNTbm-01 $IC_{50}$ ± SD (μM) | 28.5 ± 1.85 | 24.8 ± 1.15 | 20.9 ± 4.44 | 49.8 ± 4.9 | >50 |
| GNTbm-02 $IC_{50}$ ± SD (μM) | 2 ± 0.015 | 4.31 ± 0.16 | 1.69 ± 0.008 | 13.5 ± 1.78 | 2.51 ± 0.11 |
| GNTbm-03 $IC_{50}$ ± SD (μM) | 4.07 ± 0.68 | 6.1 ± 0.134 | 1.81 ± 0.008 | 26.7 ± 5.8 | 5.26 ± 0.9 |

$IC_{50}$, half maximal cytotoxic concentrations.

SD, standard deviation

±, are the estimated $IC_{50}$ interval

TABLE 4

The Inhibition Effect of Chidamide, Entinostat, GNTbm-01, GNTbm-02 and GNTbm-03 to Individual HDAC1-3 Isoforms.

| Compounds | HDAC 1 IC$_{50}$, μM | HDAC 2 IC$_{50}$, μM | HDAC 3 IC$_{50}$, μM |
|---|---|---|---|
| Chidamide | 0.4 ± 0.011 | 0.263 ± 0.009 | 0.69 ± 0.02 |
| Entinostat (positive control) | 0.25 ± 0.05 | 0.21 ± 0.06 | 0.98 ± 0.19 |
| GNTbm-01 | 6.77 ± 0.76 | 2.68 ± 0.2 | 2.75 ± 0.13 |
| GNTbm-02 | 0.52 ± 0.02 | 0.55 ± 0.06 | 0.67 ± 0.005 |
| GNTbm-03 | 0.56 ± 0.04 | 0.51 ± 0.05 | 0.67 ± 0.06 |

TABLE 5

The Inhibition Effect of Entinostat and GNTbm-02 to Individual HDAC1-11 Isoforms (Not Including HDAC10)

| | IC$_{50}$ (μM) | |
|---|---|---|
| Enzymes | GNTbm-02 | MS-275 (Entinostat, positive control) |
| HDAC1 | 0.39 | 0.95 |
| HDAC2 | 0.91 | ~2.3 |
| HDAC3/NCOR2 | 0.73 | ~4.6 |
| HDAC4 | >10 μM No Inhibition at 10 μM | >10 μM No Inhibition at 10 μM |
| HDAC5 | >10 μM No Inhibition at 10 μM | >10 μM No Inhibition at 10 μM |
| HDAC6 | >10 μM No Inhibition at 10 μM | >10 μM No Inhibition at 10 μM |
| HDAC7 | >10 μM No Inhibition at 10 μM | >10 μM No Inhibition at 10 μM |
| HDAC8 | >10 μM No Inhibition at 10 μM | >10 μM 17% Inhibition at 10 μM |
| HDAC9 | >10 μM No Inhibition at 10 μM | >10 μM No Inhibition at 10 μM |
| HDAC11 | >10 μM No Inhibition at 10 μM | >10 μM No Inhibition at 10 μM |

TABLE 6

Treatment with GNTbm-02 plus Celecoxib with Anti-PD-1 Antibody Markedly Induced the Immune Memory

| Status | Groups PD-1 | Day 40 mm$^3$ | Fold change | Day 43 mm$^3$ | Fold change | Day 47 mm$^3$ | Fold change | Day 50 mm$^3$ | Fold change | Score | Tumor progression(%) |
|---|---|---|---|---|---|---|---|---|---|---|---|
| CR | 31 | 52.06 | 1 | 48.33 | 0.93 | 0.00 | 0.00 | 0.00 | 0.00 | − | 0% (0/2) |
| CR | 37 | 119.26 | 1 | 85.33 | 0.72 | 47.90 | 0.40 | 0.00 | 0.00 | − | |
| PD-1 + GNTbm-02(25) + celecoxib-capsule(50) | | | | | | | | | | | |
| CR | 54 | 52.69 | 1 | 64.24 | 1.22 | 20.58 | 0.39 | 0.00 | 0.00 | − | 0% (0/4) |
| CR | 55 | 73.18 | 1 | 98.12 | 1.34 | 17.77 | 0.24 | 0.00 | 0.00 | − | |
| PR | 56 | 133.08 | 1 | 64.50 | 0.48 | 23.45 | 0.18 | 0.00 | 0.00 | − | |
| CR | 57 | 62.94 | 1 | 57.47 | 0.91 | 26.07 | 0.41 | 0.00 | 0.00 | − | |
| PD-1 + GNTbm-02(12.5) + celecoxib-capsule(50) | | | | | | | | | | | |
| CR | 61 | 42.53 | 1 | 42.92 | 1.01 | 40.68 | 0.96 | 0.00 | 0.00 | − | 29% (2/7) |
| CR | 64 | 85.73 | 1 | 47.85 | 0.56 | 41.30 | 0.48 | 0.00 | 0.00 | − | |
| CR | 65 | 109.45 | 1 | 54.55 | 0.50 | 43.41 | 0.40 | 0.00 | 0.00 | − | |
| PR | 66 | 61.73 | 1 | 135.01 | 2.19 | 118.42 | 1.92 | 492.51 | 7.98 | + | |
| PR | 68 | 101.19 | 1 | 96.71 | 0.96 | 110.46 | 1.09 | 291.76 | 2.88 | + | |
| CR | 69 | 60.28 | 1 | 22.84 | 0.38 | 22.48 | 0.37 | 58.56 | 0.97 | − | |
| CR | 70 | 79.08 | 1 | 57.91 | 0.73 | 0.00 | 0.00 | 0.00 | 0.00 | − | |
| GNTbm-02(25) + celecoxib-capsule(50) | | | | | | | | | | | |
| PR | 74 | 69.04 | 1 | 34.31 | 0.50 | 29.31 | 0.42 | 0.00 | 0.00 | − | 17% (1/6) |
| CR | 75 | 92.10 | 1 | 62.55 | 0.68 | 63.40 | 0.69 | 43.36 | 0.47 | − | |
| PR | 76 | 69.64 | 1 | 38.35 | 0.55 | 25.11 | 0.36 | 0.00 | 0.00 | − | |
| PR | 78 | 143.14 | 1 | 172.17 | 1.20 | 225.62 | 1.58 | 483.98 | 3.38 | + | |
| CR | 79 | 112.36 | 1 | 57.07 | 0.51 | 86.40 | 0.77 | 0.00 | 0.00 | − | |
| PR | 80 | 105.83 | 1 | 30.91 | 0.29 | 14.91 | 0.14 | 0.00 | 0.00 | − | |

+: tumor size was larger than 300 mm$^3$ and ≥2-fold (normalized to tumor size measured 7 days after tumor rechallenge)

TABLE 7

Treatment with GNTbm-02 Combined with Celecoxib Markedly Induced the Immune Memory.

| Status | Groups | Day 40 mm³ GNTbm-02(10) + celecoxib-capsule(50) | Fold change | Day 50 mm³ | Fold change | Score | Tumor progression(%) |
|---|---|---|---|---|---|---|---|
| PR | 21 | 84.12 | 1 | 32.26 | 0.38 | − | 14% (1/7) |
| PR | 22 | 97.9 | 1 | 46.85 | 0.48 | − | |
| PR | 24 | 131.26 | 1 | 87.34 | 0.67 | − | |
| CR | 25 | 85.02 | 1 | 36.85 | 0.43 | − | |
| PR | 26 | 82.04 | 1 | 0 | 0 | − | |
| PR | 28 | 116.9 | 1 | 343.76 | 2.94 | + | |
| CR | 29 | 140.75 | 1 | 22.92 | 0.16 | − | |

+: tumor size was larger than 300 mm³ and ≥2-fold (normalized to tumor size measured 7 days after tumor rechallenge)

TABLE 8

The $IC_{50}$ Values of Picolinamide-based HDAC Inhibitors Against Different Cancer Cell Lines.

| Compounds | Cell Lines | | | | | |
|---|---|---|---|---|---|---|
| $IC_{50}$ (µM) | NCI-N87 | M10 | MDA-MB-453 | MDA-MB-231 | SW48 | SK-BR-3 |
| Chidamide (Positive Control) | 3.09 ± 0.2 | 4.94 ± 0.87 | 1.36 ± 0.12 | 17.4 ± 1.98 | 5.43 ± 1.057 | 3.24 ± 0.98 |
| Entinostat (Positive Control) | — | 4.34 ± 0.01 | 1.82 ± 0.02 | 13.16 ± 1.34 | 5.21 ± 0.37 | 1.94 ± 0.1 |
| GNTbm-01 | — | 24.8 ± 1.15 | 20.9 ± 4.44 | 49.8 ± 4.9 | >50 | 28.5 ± 1.85 |
| GNTbm-02 | 4.01 ± 0.49 | 4.31 ± 0.16 | 1.69 ± 0.01 | 13.5 ± 1.78 | 2.51 ± 0.11 | 2 ± 0.02 |
| GNTbm-04 | 0.34 ± 0.04 | 1.81 ± 0.06 | 1.59 ± 0.003 | 1.64 ± 0.004 | 0.6 ± 0.09 | — |
| GNTbm-05 | 0.28 ± 0.01 | 0.43 ± 0.03 | 1.58 ± 0.003 | 1.66 ± 0.02 | 1.64 ± 0.02 | — |
| GNTbm-06 | 2.2 ± 0.03 | 1.95 ± 0.03 | 1.59 ± 0.01 | 3.87 ± 0.7 | 2.32 ± 0.08 | — |
| GNTbm-08 | 15.5 ± 1.7 | 20.8 ± 0.14 | 3.78 ± 0.5 | >50 | 18.44 ± 1.0 | — |
| GNTbm-11 | 1.87 ± 0.04 | 1.65 ± 0.2 | 2.28 ± 0.06 | 1.71 ± 0.04 | 2.6 ± 0.45 | — |
| GNTbm-12 | >50 | 38.48 ± 5.9 | 15.8 ± 3.9 | >50 | >50 | — |
| GNTbm-19 | 4.3 ± 1.4 | 2.89 ± 0.12 | 1.81 ± 0.02 | 5.69 ± 1.7 | 8.73 ± 0.24 | — |
| GNTbm-25 | >50 | >50 | 19.12 ± 2.07 | >50 | >50 | — |

$IC_{50}$, half maximal cytotoxic concentrations.
SD, standard deviation

TABLE 9

The $IC_{50}$ Values of Benzamide-based HDAC Inhibitors Against Different Cancer Cell Lines.

| Compounds | Cell Lines | | | | | |
|---|---|---|---|---|---|---|
| $IC_{50}$ (µM) | NCI-N87 | M10 | MDA-MB-453 | MDA-MB-231 | SW48 | SK-BR-3 |
| Chidamide (Positive Control) | 3.09 ± 0.2 | 4.94 ± 0.87 | 1.36 ± 0.12 | 17.4 ± 1.98 | 5.43 ± 1.06 | 3.24 ± 0.98 |
| Entinostat (Positive Control) | — | 4.34 ± 0.01 | 1.82 ± 0.024 | 13.16 ± 1.34 | 5.21 ± 0.37 | 1.94 ± 0.1 |
| GNTbm-03 | — | 6.1 ± 0.13 | 1.81 ± 0.01 | 26.7 ± 5.8 | 5.26 ± 0.9 | 4.07 ± 0.68 |
| GNTbm-33 | 1.75 ± 0.02 | 2.01 ± 0.09 | 1.94 ± 0.22 | 1.62 ± 0.02 | 1.79 ± 0.03 | — |
| GNTbm-37 | 10.65 ± 0.6 | 8.85 ± 0.59 | 4.89 ± 0.34 | 8.07 ± 0.54 | 21.3 ± 1.64 | — |
| GNTbm-38 | 0.42 ± 0.08 | 1.99 ± 0.06 | 1.67 ± 0.01 | 3.55 ± 0.45 | 1.64 ± 0.005 | — |
| GNTbm-39 | 0.64 ± 0.03 | 1.96 ± 0.02 | 1.84 ± 0.02 | 2.93 ± 0.45 | 1.73 ± 0.01 | — |

±, are the estimated $IC_{50}$ interval
$IC_{50}$, half maximal cytotoxic concentrations.
SD, standard deviation

TABLE 10

The Inhibition Effect of Picolinamide-based compounds to Individual HDAC1-3 Isoforms.

| Compounds IC$_{50}$ (μM) | HDAC 1 | HDAC 2 | HDAC 3 |
|---|---|---|---|
| Chidamide (Positive Control) | 0.14 ± 0.004 | 0.22 ± 0.04 | 0.62 ± 0.06 |
| Entinostat (Positive Control) | 0.25 ± 0.05 | 0.21 ± 0.06 | 0.98 ± 0.19 |
| GNTbm-01 | 6.77 ± 0.76 | 2.68 ± 0.2 | 2.75 ± 0.13 |
| GNTbm-02 | 0.52 ± 0.02 | 0.55 ± 0.06 | 0.67 ± 0.005 |
| GNTbm-04 | 0.38 ± 0.04 | 0.54 ± 0.007 | 0.20 ± 0.1 |
| GNTbm-05 | 0.14 ± 0.002 | 0.36 ± 0.02 | 0.001 ± 0.00004 |
| GNTbm-06 | 0.1 ± 0.02 | 0.39 ± 0.02 | 0.009 ± 0.01 |
| GNTbm-08 | 0.37 ± 0.31 | 1.54 ± 0.28 | 0.001 ± 0.00002 |
| GNTbm-11 | >20 | >20 | 0.001 |
| GNTbm-12 | >20 | >20 | >20 |
| GNTbm-19 | 0.48 ± 0.03 | 1.42 ± 0.19 | 2.98 ± 0.08 |
| GNTbm-25 | >20 | >20 | >20 |

TABLE 11

The Inhibition Effect of Benzamide-based compounds to Individual HDAC1-3 Isoforms.

| Compounds IC$_{50}$ (μM) | HDAC 1 | HDAC 2 | HDAC 3 |
|---|---|---|---|
| Chidamide (Positive Control) | 0.14 ± 0.004 | 0.22 ± 0.037 | 0.62 ± 0.056 |
| Entinostat (Positive Control) | 0.25 ± 0.05 | 0.21 ± 0.06 | 0.98 ± 0.19 |
| GNTbm-03 | 0.56 ± 0.04 | 0.51 ± 0.05 | 0.67 ± 0.06 |
| GNTbm-33 | >20 | >20 | >20 |
| GNTbm-37 | 9.04 ± 0.6 | 3.15 ± 0.31 | 1.74 ± 0.29 |
| GNTbm-38 | 0.69 ± 0.03 | 0.28 ± 0.01 | 1.2 ± 0.01 |
| GNTbm-39 | 3.7 ± 0.04 | 0.68 ± 0.03 | 0.89 ± 0.13 |

TABLE 12

GNTbm Compounds Series Induced Cell Cycle Arrest in G0/G1 or G2/M Phase in SW48 Cells.

| Compounds | Treatment Doses (μM) | G0/G1 | S | G2/M |
|---|---|---|---|---|
| Chidamide (Positive Control) | 0 | 64.7 | 17.9 | 17.4 |
| | 0.3125 | 65.7 | 17.6 | 16.7 |
| | 0.625 | 68.1 | 14.4 | 17.5 |
| | 1.25 | 70.6 | 14.1 | 15.3 |
| | 2.5 | 76.5 | 10.8 | 12.7 |
| | 5 | 79.9 | 8.5 | 11.6 |
| GNTbm-04 | 0 | 59.5 | 14.7 | 25.8 |
| | 0.125 | 56.9 | 17.9 | 25.2 |
| | 0.25 | 57.9 | 18.2 | 23.9 |
| | 0.5 | 63.2 | 17.5 | 19.3 |
| | 1 | 67.2 | 13.9 | 18.9 |
| | 2 | 70.5 | 10.8 | 18.7 |
| GNTbm-05 | 0 | 61.6 | 17.2 | 21.2 |
| | 0.125 | 61.5 | 19.8 | 18.7 |
| | 0.25 | 57.8 | 19.3 | 22.9 |
| | 0.5 | 59.2 | 18.6 | 22.2 |
| | 1 | 55.4 | 12.8 | 31.8 |
| | 2 | 53.6 | 11.8 | 34.6 |
| GNTbm-38 | 0 | 64.7 | 17.9 | 17.4 |
| | 0.125 | 63.3 | 19.3 | 17.4 |
| | 0.25 | 62.4 | 15.7 | 21.9 |
| | 0.5 | 61.8 | 10.4 | 27.8 |
| | 1 | 57.7 | 12.5 | 29.8 |
| | 2 | 53.9 | 13.6 | 32.5 |
| GNTbm-39 | 0 | 64.7 | 17.9 | 17.4 |
| | 0.125 | 57.2 | 20.5 | 22.3 |
| | 0.25 | 57.8 | 17.7 | 24.5 |
| | 0.5 | 58.8 | 16.5 | 24.7 |
| | 1 | 46.5 | 20.7 | 32.8 |
| | 2 | 42.3 | 18.8 | 38.9 |

TABLE 13

GNTbm Compounds Series Induced Cell Apoptosis in SW48 Cells.

| Compounds | Treatment Doses (μM) | Percentages of Cell Apoptosis (%) |
|---|---|---|
| Chidamide (Positive Control) | 0 | 3.2 |
| | 0.3125 | 9.0 |
| | 0.625 | 10.2 |
| | 1.25 | 15.1 |
| | 2.5 | 21.2 |
| | 5 | 35.4 |
| GNTbm-04 | 0 | 2.6 |
| | 0.125 | 2.9 |
| | 0.25 | 4.4 |
| | 0.5 | 10.8 |
| | 1 | 20.8 |
| | 2 | 32 |
| GNTbm-05 | 0 | 7.9 |
| | 0.125 | 9.0 |
| | 0.25 | 14.4 |
| | 0.5 | 17.9 |
| | 1 | 27.2 |
| | 2 | 42.4 |
| GNTbm-38 | 0 | 3.2 |
| | 0.125 | 8.5 |
| | 0.25 | 9.1 |
| | 0.5 | 18.3 |
| | 1 | 24.4 |
| | 2 | 37.3 |
| GNTbm-39 | 0 | 3.2 |
| | 0.125 | 9.5 |
| | 0.25 | 10.8 |
| | 0.5 | 17.8 |
| | 1 | 25.4 |
| | 2 | 37.8 |

TABLE 14

The Efficacy of GNTbm Compounds Series Combined with Tyrosine Kinase Inhibitor Regorafenib in CT26 Tumor-bearing Mice Model.

| Exp Regimens | Initial tumor volume (mm3) | ORR (%) | PD | SD | PR | CR | ORR (%)<sup>&</sup> | PD<sup>&</sup> | SD<sup>&</sup> | PR<sup>&</sup> | CR<sup>&</sup> | Survival rate (%) | Relapse* (recurrence) | Immunity<sup>#</sup> (rechallenge) |
|---|---|---|---|---|---|---|---|---|---|---|---|---|---|---|
| Exp 1 | | | | | | | | | | | | | | |
| vehicle | 245 | 0% | 7 | 1 | 0 | 0 | 0% | 8 | 0 | 0 | 0 | 0% | — | — |
| Regorafenib | | 11% | 1 | 7 | 0 | 1 | 22% | 5 | 2 | 0 | 2 | 11% | 0% (0/1) | 100% (1/1) |
| Chidamide/k-30 | | 11% | 7 | 1 | 1 | 0 | 0% | 7 | 2 | 0 | 0 | 0% | 100% (1/1) | — |
| Chidamide/k-30 combined with Regorafenib | | 30% | 0 | 7 | 1 | 2 | 40% | 2 | 4 | 0 | 4 | 40% | 0% (0/3) | 100% (3/3) |
| GNTbm-02/k-30 | | 0% | 8 | 1 | 0 | 0 | 0% | 9 | 0 | 0 | 0 | 0% | 0% (0/0) | — |
| GNTbm-02/k-30 combined with Regorafenib | | 10% | 1 | 8 | 1 | 0 | 10% | 6 | 3 | 1 | 0 | 10% | 100% (1/1) | 100% (1/1) |
| GNTbm-03/k-30 | | 0% | 9 | 0 | 0 | 0 | 0% | 9 | 0 | 0 | 0 | 0% | 0% (0/0) | — |
| GNTbm-03/k-30 combined with Regorafenib | | 40% | 1 | 5 | 1 | 3 | 30% | 5 | 2 | 0 | 3 | 30% | 25% (1/4) | 100% (3/3) |
| GNTbm-04/k-30 | | 10% | 8 | 1 | 0 | 1 | 10% | 9 | 0 | 0 | 1 | 10% | 0% (0/1) | 100% (1/1) |
| GNTbm-04/k-30 combined with Regorafenib | | 50% | 1 | 4 | 1 | 4 | 40% | 4 | 2 | 0 | 4 | 40% | 20% (1/5) | 100% (4/4) |
| GNTbm-06/k-30 | | 0% | 8 | 2 | 0 | 0 | 0% | 10 | 0 | 0 | 0 | 0% | 0% (0/0) | — |
| GNTbm-06/k-30 combined with Regorafenib | | 50% | 2 | 3 | 1 | 4 | 50% | 5 | 0 | 0 | 5 | 50% | 0% (0/5) | 100% (5/5) |
| Exp 2 | | | | | | | | | | | | | | |
| vehicle | 192 | 0% | 8 | 1 | 0 | 0 | 0% | 9 | 0 | 0 | 0 | — | — | — |
| Regorafenib | | 0% | 8 | 1 | 0 | 0 | 0% | 9 | 0 | 0 | 0 | — | — | — |
| Chidamide/k-30 | | 44% | 4 | 1 | 1 | 3 | 33% | 5 | 1 | 0 | 3 | — | — | — |
| Chidamide/k-30 combined with Regorafenib | | 60% | 0 | 4 | 4 | 2 | 60% | 1 | 3 | 0 | 6 | — | — | — |
| GNTbm-05/k-30 | | 0% | 8 | 1 | 0 | 0 | 0% | 8 | 1 | 0 | 0 | — | — | — |
| GNTbm-05/k-30 combined with Regorafenib | | 30% | 3 | 4 | 0 | 3 | 20% | 7 | 1 | 0 | 2 | — | — | — |
| GNTbm-11/k-30 | | 11% | 7 | 1 | 0 | 1 | 0% | 8 | 1 | 0 | 0 | — | — | — |
| GNTbm-11/k-30 combined with Regorafenib | | 20% | 4 | 4 | 1 | 1 | 20% | 7 | 1 | 1 | 1 | — | — | — |
| GNTbm-38/k-30 | | 56% | 3 | 1 | 0 | 5 | 56% | 4 | 0 | 0 | 5 | — | — | — |
| GNTbm-38/k-30 combined with Regorafenib | | 80% | 0 | 2 | 0 | 8 | 100% | 0 | 0 | 1 | 9 | — | — | — |
| GNTbm-39/k-30 | | 0% | 7 | 2 | 0 | 0 | 0% | 9 | 0 | 0 | 0 | — | — | — |
| GNTbm-39/k-30 combined with Regorafenib | | 30% | 2 | 5 | 1 | 2 | 30% | 4 | 3 | 1 | 2 | — | — | — |

*The relapse/recurrence was defined as when having tumor growth at least 5 fold in mice with CR or PR response after first tumor assessment.
<sup>#</sup>mice resistant to CT26 re-challenge.
<sup>&</sup>the second tumor assessment on day 40

A person of ordinary skill in the art of the subject invention should understand that variations and modifications may be made to the teaching and the disclosure of the subject invention without departing from the spirit and scope of the subject application. Based on the contents above, the subject application intends to cover any variations and modification thereof with the proviso that the variations or modifications fall within the scope as defined in the appended claims or their equivalents.

What is claimed is:

1. A method for epigenetic immunomodulation of tumor microenvironment (TME) and/or treatment of cancer in a subject in need thereof, the method comprising administrating an effective amount of a compound of formula (I) to the subject:

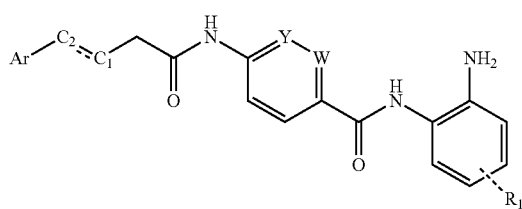

(I)

wherein W and Y are each independently selected from CH and N;

$R_1$ is each independently selected from hydrogen, halogen, $C_1$-$C_3$ alkyl and halogenated $C_1$-$C_3$ alkyl, and can be mono-, di-, tri- or tetra-substitution;

$C_1$ and $C_2$ are C atoms linked by a double bond;

Ar is selected from the group consisting of the following:

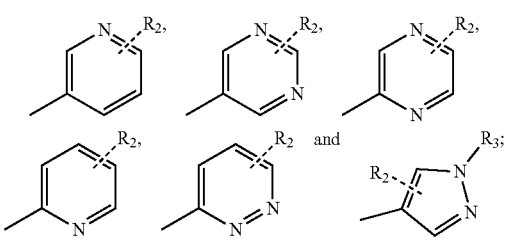

wherein Ar is linked to $C_2$ via the solid line;

$R_2$ has the same meaning as described for $R_1$; and $R_3$ is hydrogen or $C_1$-$C_3$ alkyl;

or a pharmaceutically acceptable salt, hydrate, stereoisomer or solvate thereof.

2. The method of claim 1, wherein the compound has the formula (Ia):

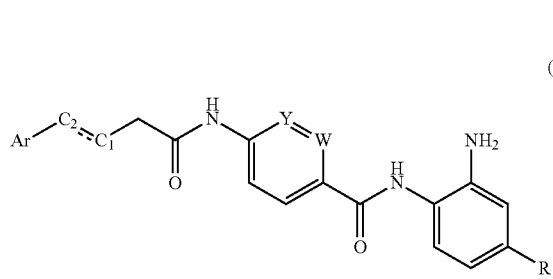

(Ia)

wherein W, Y, $R_1$, $C_1$, $C_2$ and Ar have the same meaning as described in formula (I), or a pharmaceutically acceptable salt, hydrate, stereoisomer or solvate thereof.

3. The method of claim 1, wherein in Formula (I) Ar is selected from the six-membered rings, and $R_2$ and the atom of Ar linked to $C_2$ are at para-positions.

4. The method of claim 1, wherein in Formula (I) W and Y are selected from the following combinations: (1) W is N and Y is CH, (2) W is CH and Y is N, and (3) W and Y are CH.

5. The method of claim 1, wherein in Formula (I) W is N and Y is CH.

6. The method of claim 1, wherein in Formula (I) $R_1$ is F or fluorinated $C_1$-$C_3$ alkyl.

7. The method of claim 1, wherein in Formula (I) $R_2$ is $C_1$-$C_3$ alkyl or fluorinated $C_1$-$C_3$ alkyl.

8. The method of claim 1, wherein the compound is selected from the group consisting of:

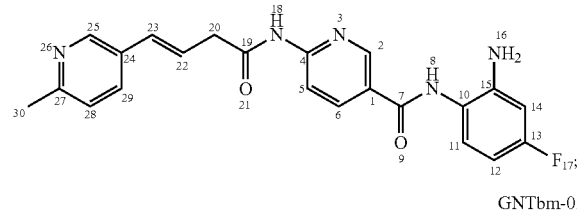

GNTbm-01

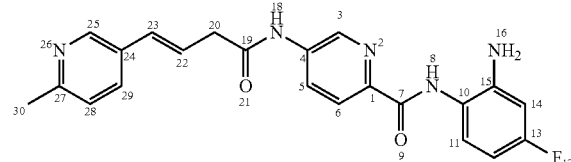

GNTbm-02

GNTbm-03

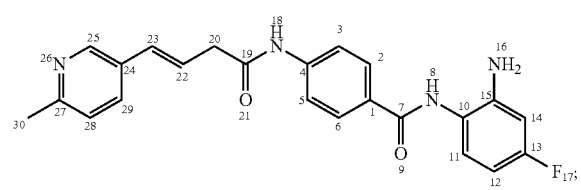

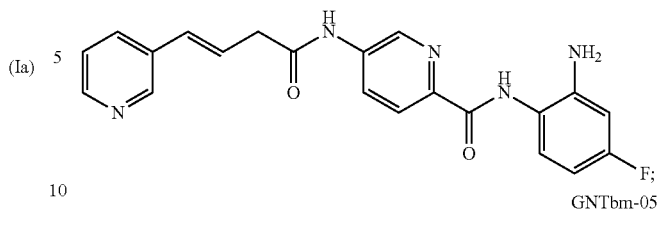

GNTbm-04

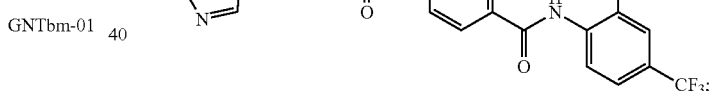

GNTbm-05

GNTbm-06

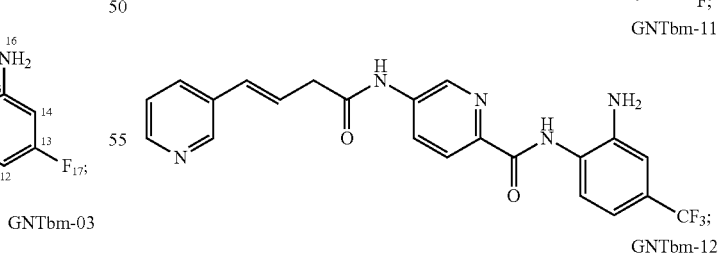

GNTbm-07;

GNTbm-09;

GNTbm-10;

GNTbm-11;

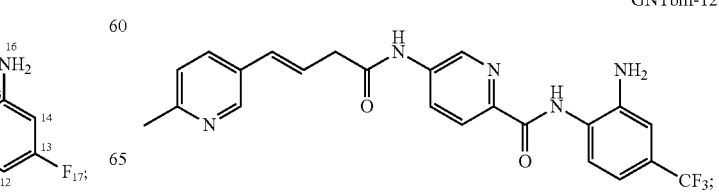

GNTbm-12;

GNTbm-13
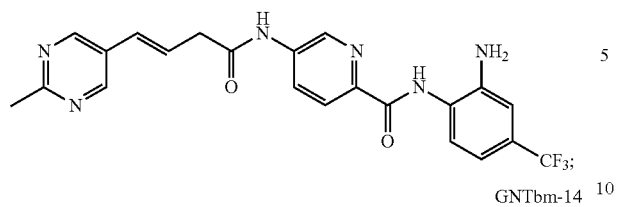
GNTbm-14
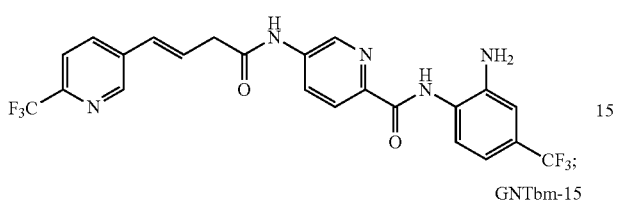
GNTbm-15
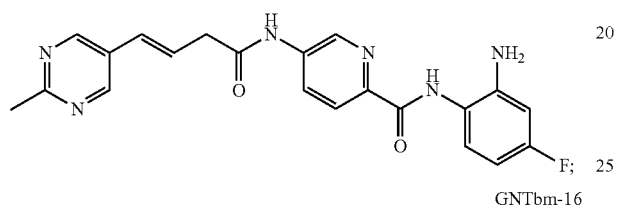
GNTbm-16
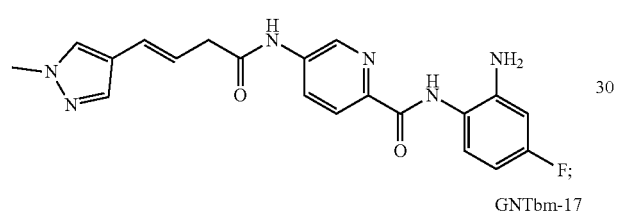
GNTbm-17
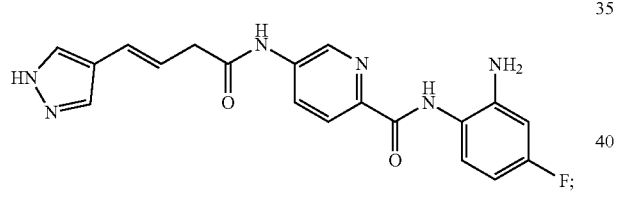
GNTbm-18
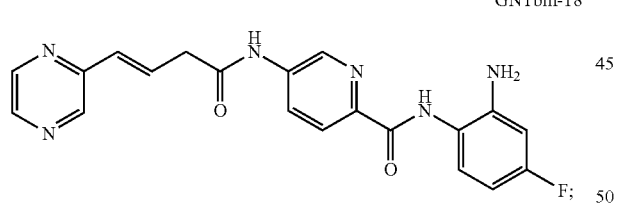
GNTbm-20
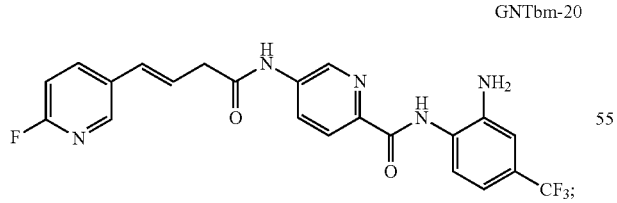
GNTbm-21
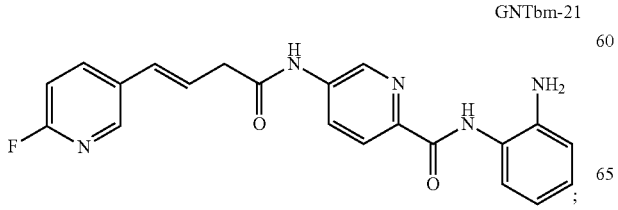
GNTbm-24
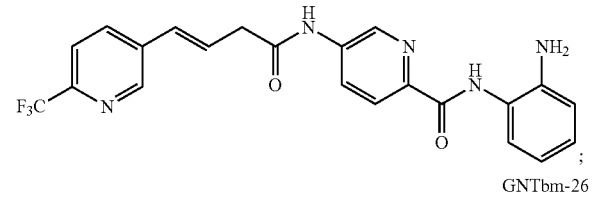
GNTbm-26
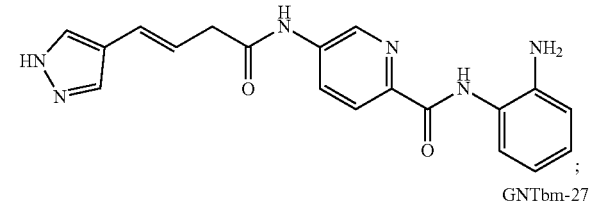
GNTbm-27
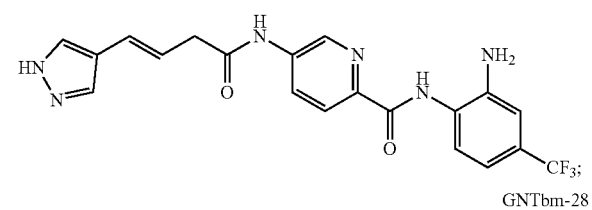
GNTbm-28
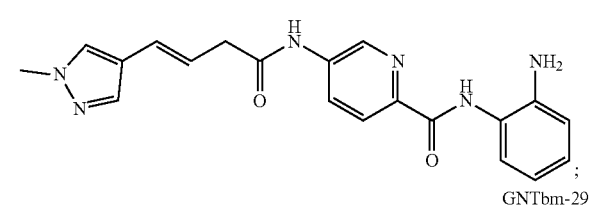
GNTbm-29
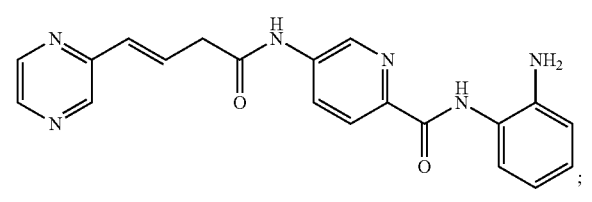
GNTbm-30
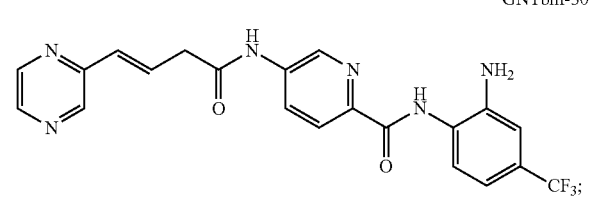
GNTbm-31
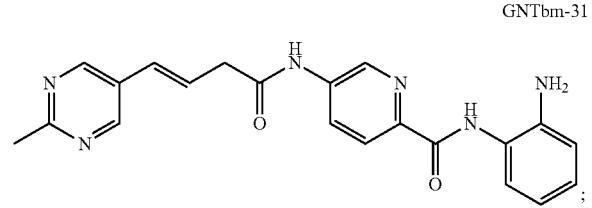
GNTbm-33
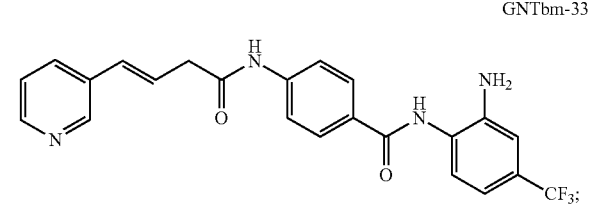

-continued

GNTbm-38

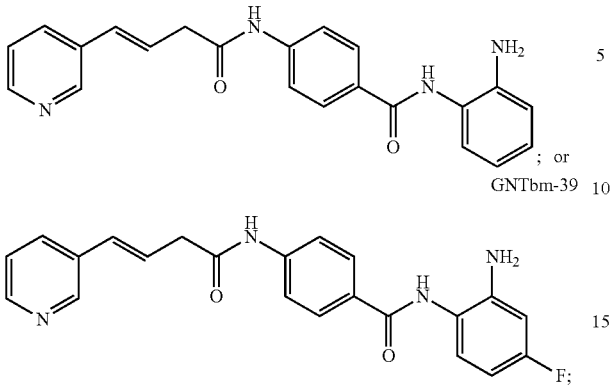

; or

GNTbm-39

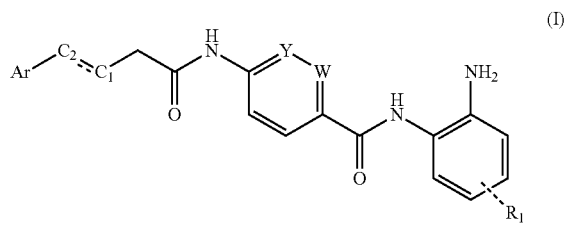

or a pharmaceutically acceptable salt, hydrate, stereoisomer or solvate thereof.

9. The method of claim 1, wherein one or more second agent can be further administered in combination with the compound of formula (I).

10. The method of claim 9, wherein the one or more second agent is an immune checkpoint inhibitor, an NSAID, a TKI or an anti-cancer agent or a combination thereof.

11. The method of claim 1, wherein the method is for inducing cell cycle arrest of tumor cells, for inducing apoptosis of tumor cells, for inducing histone H3 acetylation, for inducing immune memory, for activating CTL, for decreasing immunosuppressive cells.

12. A method for treating or preventing the disease associated with class I HDAC in a subject in need thereof comprising administrating an effective amount of a compound of formula (I) to the subject:

(I)

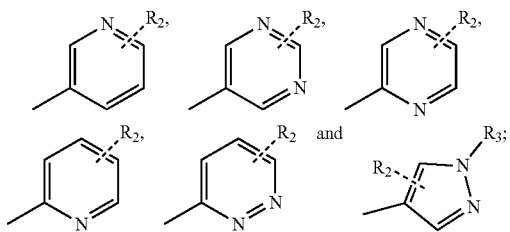

wherein W and Y are each independently selected from CH and N;
$R_1$ is each independently selected from hydrogen, halogen, $C_1$-$C_3$ alkyl and halogenated $C_1$-$C_3$ alkyl, and can be mono-, di-, tri- or tetra-substitution;
$C_1$ and $C_2$ are C atoms linked by a double bond;
Ar is selected from the group consisting of the following:

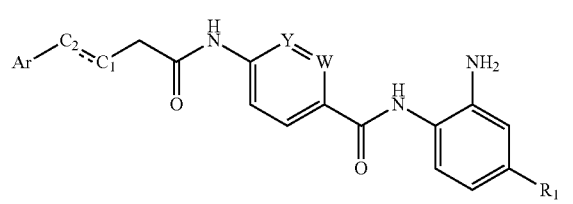

wherein Ar is linked to $C_2$ via the solid line;
$R_2$ has the same meaning as described for $R_1$; and
$R_3$ is hydrogen or $C_1$-$C_3$ alkyl;
or a pharmaceutically acceptable salt, hydrate, stereoisomer or solvate thereof.

13. The method of claim 12, wherein the compound has the formula (Ia):

(Ia)

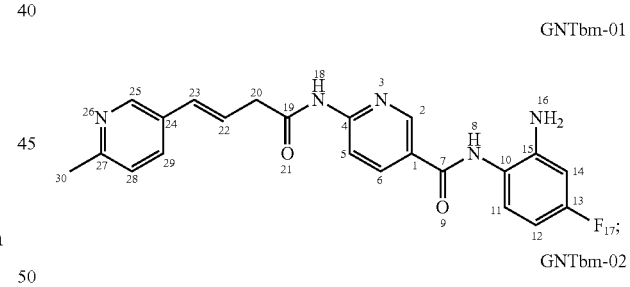

wherein W, Y, $R_1$, $C_1$, $C_2$ and Ar have the same meaning as described in formula (I), or a pharmaceutically acceptable salt, hydrate, stereoisomer or solvate thereof.

14. The method of claim 12, wherein in Formula (I) Ar is selected from the six-membered rings, and $R_2$ and the atom of Ar linked to $C_2$ are at para-positions.

15. The method of claim 12, wherein in Formula (I) W and Y are selected from the following combinations: (1) W is N and Y is CH, (2) W is CH and Y is N, and (3) W and Y are CH.

16. The method of claim 12, wherein in Formula (I) W is N and Y is CH.

17. The method of claim 12, wherein in Formula (I) $R_1$ is F or fluorinated $C_1$-$C_3$ alkyl.

18. The method of claim 12, wherein in Formula (I) $R_2$ is $C_1$-$C_3$ alkyl or fluorinated $C_1$-$C_3$ alkyl.

19. The method of claim 12, wherein the compound is selected from the group consisting of:

GNTbm-01

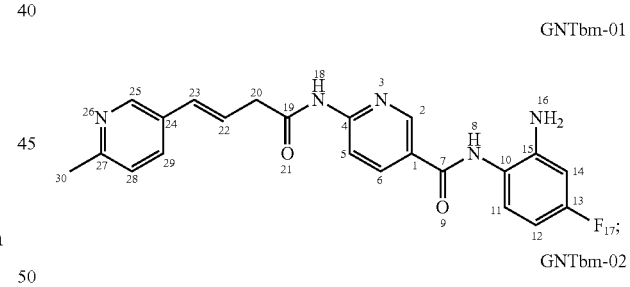

GNTbm-02

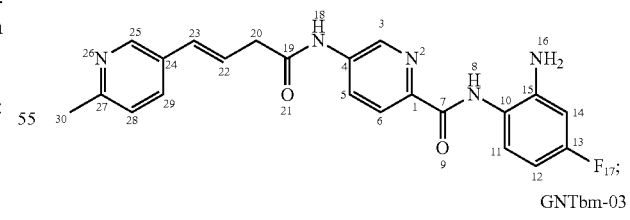

GNTbm-03

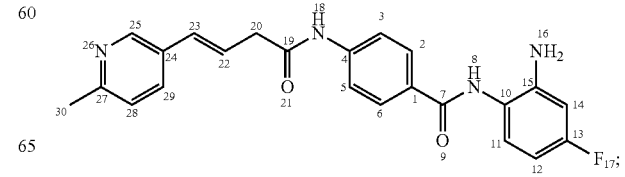

GNTbm-04
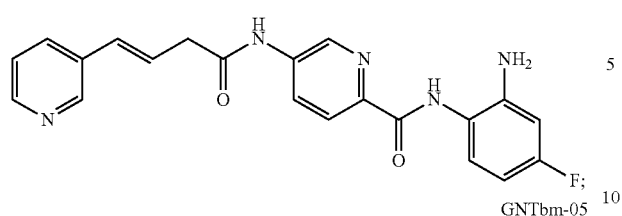
GNTbm-05
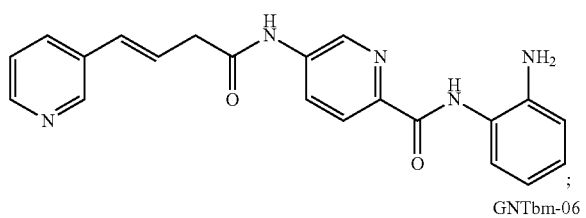
GNTbm-06
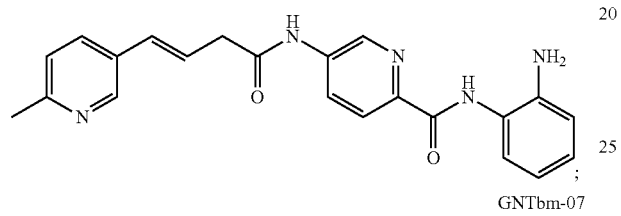
GNTbm-07
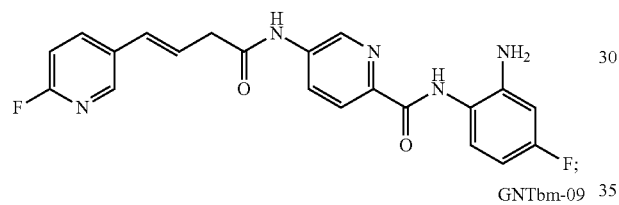
GNTbm-09
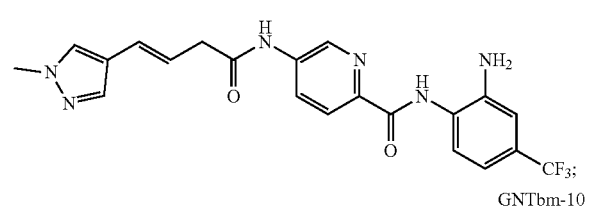
GNTbm-10
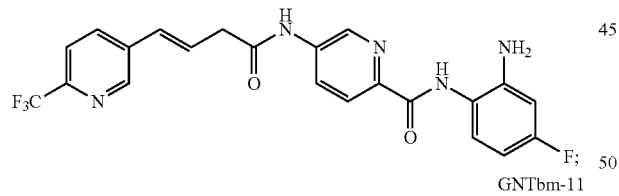
GNTbm-11
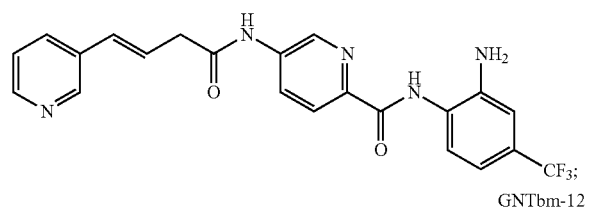
GNTbm-12
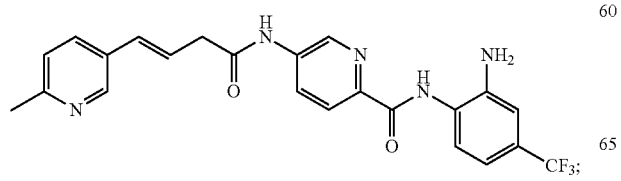
GNTbm-13
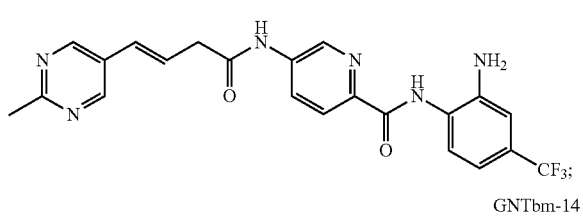
GNTbm-14
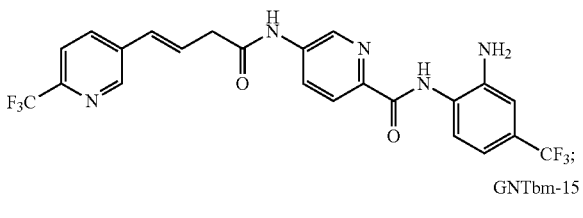
GNTbm-15
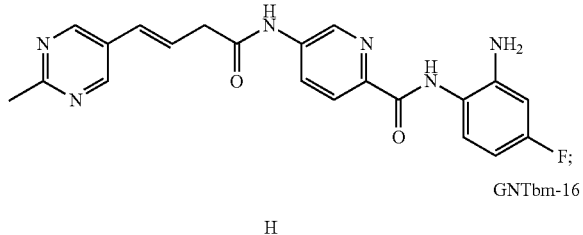
GNTbm-16
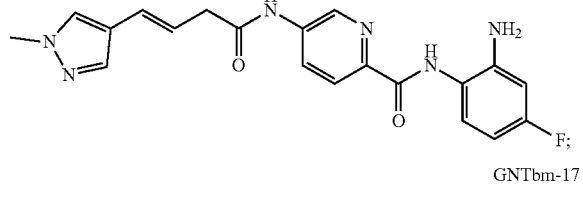
GNTbm-17
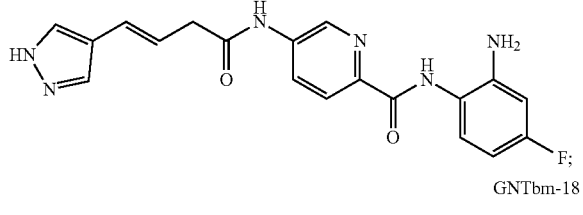
GNTbm-18
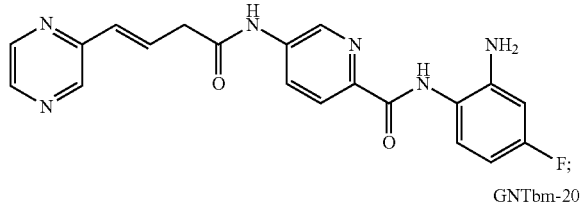
GNTbm-20
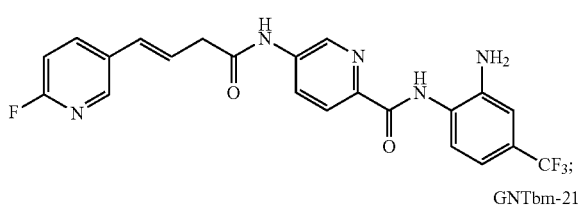
GNTbm-21
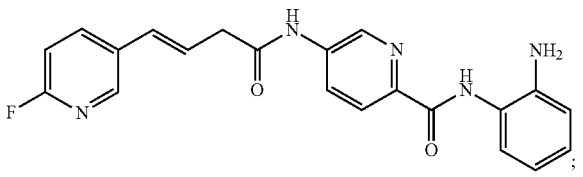

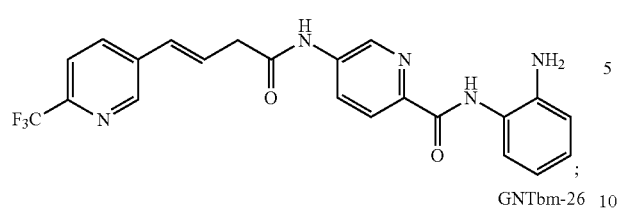
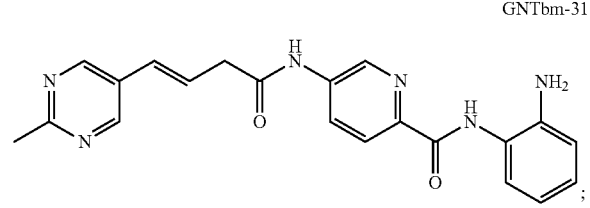
or a pharmaceutically acceptable salt, hydrate, stereoisomer or solvate thereof.
20. The method of claim 12, wherein one or more second agent can be further administered in combination with the compound of formula (I).
21. The method of claim 20, wherein the one or more second agent is an immune checkpoint inhibitor, an NSAID, a TKI or an anti-cancer agent or a combination thereof.
* * * * *